United States Patent
Hayashi et al.

(10) Patent No.: US 11,739,270 B2
(45) Date of Patent: *Aug. 29, 2023

(54) POLYMERIZABLE COMPOUND AS WELL AS LIQUID CRYSTAL COMPOSITION AND LIQUID CRYSTAL DISPLAY DEVICE EACH INCLUDING POLYMERIZABLE COMPOUND

(71) Applicant: DIC Corporation, Tokyo (JP)

(72) Inventors: Masanao Hayashi, Kita-adachi-gun (JP); Ayaki Hosono, Kita-adachi-gun (JP); Shota Kosaka, Kita-adachi-gun (JP)

(73) Assignee: DIC CORPORATION, Tokyo (JP)

(*) Notice: Subject to any disclaimer, the term of this patent is extended or adjusted under 35 U.S.C. 154(b) by 62 days.

This patent is subject to a terminal disclaimer.

(21) Appl. No.: 16/968,961

(22) PCT Filed: Feb. 14, 2019

(86) PCT No.: PCT/JP2019/005257
§ 371 (c)(1),
(2) Date: Aug. 11, 2020

(87) PCT Pub. No.: WO2019/167640
PCT Pub. Date: Sep. 6, 2019

(65) Prior Publication Data
US 2020/0399539 A1    Dec. 24, 2020

(30) Foreign Application Priority Data

Mar. 1, 2018  (JP) .................. 2018-036499

(51) Int. Cl.
| | | |
|---|---|---|
| G02F 1/1333 | (2006.01) |
| C09K 19/56 | (2006.01) |
| C07C 69/54 | (2006.01) |
| C07C 69/653 | (2006.01) |
| C09K 19/30 | (2006.01) |
| C09K 19/34 | (2006.01) |

(52) U.S. Cl.
CPC .............. C09K 19/56 (2013.01); C07C 69/54 (2013.01); C07C 69/653 (2013.01); C09K 19/3066 (2013.01); C09K 19/3402 (2013.01); *C09K 2019/3425* (2013.01)

(58) Field of Classification Search
CPC ............... C09K 19/56; C09K 19/3066; C09K 19/3402; C09K 19/38; C09K 19/54; C09K 2019/3425; C09K 2019/0448; C09K 2019/3004; C09K 2019/3016; C09K 2019/3025; C09K 2019/3027; G02F 1/1333; G02F 1/1337; G02F 1/139; C07C 69/54; C07C 69/653
See application file for complete search history.

(56) References Cited

U.S. PATENT DOCUMENTS

| | | |
|---|---|---|
| 3,210,327 A | 10/1965 | Graliano et al. |
| 3,280,078 A | 10/1966 | Hostettler et al. |
| 3,532,715 A | 10/1970 | Hostettler et al. |
| 3,755,420 A | 8/1973 | Stoffey et al. |
| 3,774,305 A | 11/1973 | Stoffey et al. |
| 4,962,163 A | 10/1990 | Hefner, Jr. et al. |
| 5,395,736 A | 3/1995 | Grasshoff et al. |
| 5,919,599 A | 7/1999 | Meador et al. |
| 5,998,499 A | 12/1999 | Klee et al. |
| 6,458,908 B1 | 10/2002 | Imai et al. |
| 6,906,116 B2 | 6/2005 | Nishikubo et al. |
| 7,541,071 B2 | 6/2009 | Shundo et al. |
| 9,458,264 B2 | 10/2016 | Aoshima et al. |

(Continued)

FOREIGN PATENT DOCUMENTS

| | | |
|---|---|---|
| CN | 1236115 A | 11/1999 |
| CN | 100341852 C | 10/2007 |

(Continued)

OTHER PUBLICATIONS

International Search Report dated Apr. 23, 2019, issued in counterpart International Application No. PCT/JP2019/005257 (3 pages).
International Search Report dated Aug. 28, 2018, issued in counterpart International Application No. PCT/JP2018/020478 (5 pages).
Nishikubo et al., "Synthesis of Photocrosslinkable Hyperbranched Polyesters with Terminal Methacryloyl Groups by the One-pot Polyaddition of Bis(oxetane)s with 1,3,5-Benzenetricarboxylic Acid and Methacrylic Acid", Polymer Journal (Tokyo, Japan), 2006, vol. 38, No. 5, pp. 447-456, ISSN:0032-3896, cited in ISR (10 pages).
Registry [online], US: American Chemical Society [retrieved on Jul. 9, 2018], Retrieved from: STN, CAS RN 2089601-61-4;2089601-60-3; 2089601-57-8; 2089601-55-6; 2089601-53-4; 2089601-51-2; 2089601-49-8; 2089601-47-6; 2089601-46-5;2089601-37-4, cited in ISR.

(Continued)

*Primary Examiner* — Geraldina Visconti
(74) *Attorney, Agent, or Firm* — Shuji Yoshizaki

(57) ABSTRACT

The present invention provides a compound represented by the general formula (i), which has a partial structure $K^{i1}$ represented by one of the general formulae (K-1) to (K-6) and has a ring B with at least one P-Sp- group and with at least one $R^{i2}$ ($R^{i2}$ denotes a linear or branched alkyl group having 2 to 10 carbon atoms or a linear or branched halogenated alkyl group having 2 to 10 carbon atoms, —$CH_2$— in the alkyl or halogenated alkyl group is optionally substituted with —CH=CH—, —O—, —COO—, or —OCO—, but —O— is not adjacent to another —O—). Thus, the compound in a liquid crystal composition adsorbs to substrates between which the liquid crystal composition (a liquid crystal layer) exists. The compound can hold vertically aligned liquid crystal molecules, can improve alignment stability, and can ensure low-temperature storage stability.

7 Claims, 2 Drawing Sheets

(56) References Cited

U.S. PATENT DOCUMENTS

| | | | |
|---|---|---|---|
| 9,725,590 B2 | 8/2017 | Chun et al. | |
| 9,809,748 B2 * | 11/2017 | Archetti | G02F 1/1337 |
| 10,190,050 B2 | 1/2019 | Lim et al. | |
| 10,927,300 B2 * | 2/2021 | Kimura | C07C 69/54 |
| 11,174,217 B2 * | 11/2021 | Hosono | C07F 7/081 |
| 11,312,906 B2 * | 4/2022 | Mamiya | C09K 19/32 |
| 11,390,811 B2 * | 7/2022 | Yamamoto | C09K 19/3405 |
| 11,415,840 B2 * | 8/2022 | Kurisawa | C09K 19/12 |
| 2006/0054859 A1 | 3/2006 | Shundo et al. | |
| 2009/0326186 A1 | 12/2009 | He et al. | |
| 2010/0296032 A1 | 11/2010 | Shin et al. | |
| 2014/0018517 A1 | 1/2014 | Busygin et al. | |
| 2014/0138581 A1 | 5/2014 | Archetti et al. | |
| 2014/0175342 A1 | 6/2014 | Uchikawa | |
| 2015/0252265 A1 | 9/2015 | Archetti et al. | |
| 2016/0137921 A1 | 5/2016 | Hayashi et al. | |
| 2016/0362606 A1 | 12/2016 | Tong et al. | |
| 2017/0158793 A1 | 6/2017 | Endo et al. | |
| 2017/0210994 A1 | 7/2017 | Lim et al. | |
| 2018/0002604 A1 | 1/2018 | Yoon et al. | |
| 2018/0045991 A1 | 2/2018 | Lan et al. | |
| 2018/0057743 A1 | 3/2018 | Archetti et al. | |
| 2018/0142152 A1 | 5/2018 | Archetti et al. | |
| 2019/0127376 A1 | 5/2019 | Wu et al. | |
| 2019/0264108 A1 | 8/2019 | Kimura et al. | |
| 2019/0292463 A1 | 9/2019 | Yano et al. | |
| 2019/0308926 A1 | 10/2019 | Lan | |
| 2019/0390076 A1 | 12/2019 | Isonaka et al. | |
| 2019/0391418 A1 | 12/2019 | Yamaguchi et al. | |
| 2020/0087240 A1 | 3/2020 | Hosono et al. | |
| 2020/0208054 A1 | 7/2020 | Yamamoto et al. | |
| 2020/0308488 A1 * | 10/2020 | Shimizu | G02F 1/1337 |
| 2020/0399539 A1 * | 12/2020 | Hayashi | C09K 19/56 |
| 2021/0026206 A1 | 1/2021 | Kurisawa et al. | |
| 2021/0214299 A1 * | 7/2021 | Hosono | C09K 19/3066 |

FOREIGN PATENT DOCUMENTS

| | | |
|---|---|---|
| CN | 105001879 A | 10/2015 |
| CN | 105061213 A | 11/2015 |
| CN | 105647547 A | 6/2016 |
| CN | 106397752 A | 2/2017 |
| CN | 107557024 A | 1/2018 |
| CN | 109195943 A | 1/2019 |
| CN | 110546176 A | 12/2019 |
| FR | 1434145 A | 4/1966 |
| JP | H02-173031 A | 7/1990 |
| JP | H02-232602 A | 9/1990 |
| JP | H02-240128 A | 9/1990 |
| JP | H03-244615 A | 10/1991 |
| JP | H04-4215 A | 1/1992 |
| JP | H04-316890 A | 11/1992 |
| JP | H07-92674 A | 4/1995 |
| JP | H07-206974 A | 8/1995 |
| JP | H09-157340 A | 6/1997 |
| JP | 2001-509128 A | 7/2001 |
| JP | 2002-502982 A | 1/2002 |
| JP | 2002-123921 A | 4/2002 |
| JP | 2002-145935 A | 5/2002 |
| JP | 2003-138223 A | 5/2003 |
| JP | 2005-206579 A | 8/2005 |
| JP | 2009-215189 A | 9/2009 |
| JP | 2011-514542 A | 5/2011 |
| JP | 2011-213790 A | 10/2011 |
| JP | 2012-008223 A | 1/2012 |
| JP | 2012-242701 A | 12/2012 |
| JP | 2013-542297 A | 11/2013 |
| JP | 2014-524951 A | 9/2014 |
| JP | 2015-155532 A | 8/2015 |
| JP | 2015-168826 A | 9/2015 |
| JP | 2015-535814 A | 12/2015 |
| JP | 2017-222709 A | 12/2017 |
| JP | 2018-16791 A | 2/2018 |
| JP | 2018-25752 A | 2/2018 |
| JP | 2018-90569 A | 6/2018 |
| KR | 10-2016-0115000 A | 10/2016 |
| WO | 2002/018313 A1 | 3/2002 |
| WO | 2002/064662 A1 | 8/2002 |
| WO | 2009/091225 A2 | 7/2009 |
| WO | 2013/047523 A1 | 4/2013 |
| WO | 2014/007361 A1 | 1/2014 |
| WO | 2014/106799 A2 | 7/2014 |
| WO | 2015/198915 A1 | 12/2015 |
| WO | 2017/041893 A1 | 3/2017 |
| WO | 2017/209161 A1 | 12/2017 |
| WO | 2018/079333 A1 | 5/2018 |
| WO | 2018/079528 A1 | 5/2018 |
| WO | 2018/105545 A1 | 6/2018 |
| WO | 2018/123821 A1 | 7/2018 |
| WO | 2018/159637 A1 | 9/2018 |
| WO | 2018/221236 A1 | 12/2018 |
| WO | 2018/230322 A1 | 12/2018 |
| WO | 2019/003935 A1 | 1/2019 |
| WO | 2019/049673 A1 | 3/2019 |

OTHER PUBLICATIONS

Fujisawa et al., "Mechanisms of Action of (Meth)acrylates in Hemolytic Activity, in Vivo Toxicity and Dipalmitoylphosphatidylcholine (DPPC) Liposomes Determined Using NMR Spectroscopy", Int. J. Mol. Sci. 2012, v.13, pp. 758-773 (16 pages).

Non-Final Office Action dated Dec. 9, 2020, issued in U.S. Appl. No. 16/615,503. (20 pages).

Final Office Action dated May 17, 2021, issued in U.S. Appl. No. 16/615,503. (11 pages).

Sun, Xiao-Hong et al., "Diffraction measurement and analysis of slanted holographic polymer dispersed liquid crystal", American Institute pf physics, 2005, vol. 98, pp. 043510-1 to 043510-5; cited in JP Office Action dated Jan. 14, 2020. (6 pages).

Notice of Allowance dated Sep. 14, 2021, issued in U.S. Appl. No. 16/615,503. (15 pages).

International Search Report dated Jan. 16, 2018, issued in counterpart International Application No. PCT/JP2017/037481. (3 pages).

"International Search Report (Form PCT/ISA/210) of PCT/JP2018/044883," dated Mar. 12, 2019, with English translation thereof. (6 pages).

Non-Final Office Action dated Jun. 16, 2022, issued in U.S. Appl. No. 16/770,067 (13 pages).

Non-Final Office Action dated Dec. 5, 2022, issued in U.S. Appl. No. 16/754,409. (26 pages).

International Search Report dated Jan. 8, 2019, issued in counterpart application No. PCT/JP2018/040671 (2 pages).

* cited by examiner

POLYMERIZABLE COMPOUND AS WELL AS LIQUID CRYSTAL COMPOSITION AND LIQUID CRYSTAL DISPLAY DEVICE EACH INCLUDING POLYMERIZABLE COMPOUND

TECHNICAL FIELD

The present invention relates to a polymerizable compound as well as a liquid crystal composition and a liquid crystal display device each including the polymerizable compound.

BACKGROUND ART

Vertical alignment (VA) liquid crystal displays have a polyimide alignment film (PI) layer on an electrode to induce vertical alignment of liquid crystal molecules when no voltage is applied and to achieve horizontal alignment of liquid crystal molecules when a voltage is applied. The formation of a PI layer, however, entails considerable cost. Thus, a method for aligning liquid crystal molecules without a PI layer have been investigated.

For example, Patent Literature 1 discloses a liquid crystal medium based on a polar compound mixture with negative dielectric anisotropy containing at least one spontaneously aligning additive agent. The liquid crystal medium is highly suitable for displays without an alignment layer. In Patent Literature 1, a specific compound with a hydroxy group is used as the spontaneously aligning additive agent.

CITATION LIST

Patent Literature

PTL 1: Japanese Unexamined Patent Application Publication (Translation of PCT Application) No. 2014-524951

SUMMARY OF INVENTION

Technical Problem

However, the present inventors found that the use of the spontaneously aligning additive agent described in Patent Literature 1 is unsatisfactory in terms of electro-optical characteristics, such as alignment regulating force that vertically aligns liquid crystal molecules and variations in alignment, and there is room for improvement in the storage stability of a liquid crystal composition containing the spontaneously aligning additive agent.

Accordingly, it is an object of the present invention to provide a polymerizable compound with a polar group that can be added to a liquid crystal composition to ensure storage stability and that can uniformly align liquid crystal molecules without a PI layer. It is another object of the present invention to provide a liquid crystal composition with high storage stability in which liquid crystal molecules can be vertically aligned without a PI layer and to provide a liquid crystal display device including the liquid crystal composition.

Solution to Problem

The present invention provides a compound represented by the general formula (i).

A compound represented by the general formula (i):

[Chem. 1]

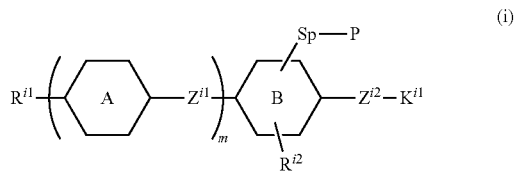

wherein $R^{i1}$ denotes a hydrogen atom, an alkyl group having 1 to 30 carbon atoms, or a halogenated alkyl group having 1 to 30 carbon atoms, —$CH_2$— in the alkyl or halogenated alkyl group is optionally substituted with —CH=CH—, —C≡C—, —O—, —NH—, —COO—, —OCO—, or —OCOO—, but —O— is not adjacent to another —O—, $R^{i2}$ denotes a linear or branched alkyl group having 2 to 10 carbon atoms or a linear or branched halogenated alkyl group having 2 to 10 carbon atoms, —$CH_2$— in the alkyl or halogenated alkyl group is optionally substituted with —CH=CH—, —O—, —COO—, or —OCO—, but —O— is not adjacent to another —O—, a ring A denotes a divalent aromatic group, a divalent alicyclic group, a divalent heterocyclic compound group, a divalent fused ring, or a divalent fused polycyclic ring, a hydrogen atom in these ring structures is optionally substituted with $L^{i1}$, $L^{i1}$ denotes a halogen atom, a cyano group, a nitro group, P-Sp-, a monovalent organic group having a group represented by a general formula $K^{i1}$, a linear or branched alkyl group having 1 to 10 carbon atoms, or a linear or branched halogenated alkyl group having 1 to 10 carbon atoms, —$CH_2$— in the alkyl or halogenated alkyl group is optionally substituted with —CH=CH—, —C≡C—, —O—, —NH—, —COO—, —OCO—, or —OCOO—, but —O— is not adjacent to another —O—, a ring B denotes a phenyl group or a naphthyl group, a hydrogen atom in the ring structure is optionally substituted with $L^{i2}$, $L^{i2}$ denotes a halogen atom, P-Sp-, a monovalent organic group having a group represented by the general formula $K^{i1}$, a linear or branched alkyl group having 1 to 10 carbon atoms, or a linear or branched halogenated alkyl group having 1 to 10 carbon atoms, —$CH_2$— in the alkyl or halogenated alkyl group is optionally substituted with —CH=CH—, —C≡C—, —O—, —COO—, or —OCO—, but —O— is not adjacent to another —O—, $Z^{i1}$ denotes a single bond, —O—, —CH=CH—, —CF=CF—, —C≡C—, —COO—, —OCO—, —OCOO—, —$CF_2$O—, —$OCF_2$—, —CH=CHCOO—, —OCOCH=CH—, —CH=C($CH_3$)COO—, —OCOC($CH_3$)=CH—, —$CH_2$—CH($CH_3$)COO—, —OCOCH($CH_3$)—$CH_2$—, —$OCH_2CH_2O$—, or an alkylene group having 1 to 10 carbon atoms, and one —$CH_2$— or two or more nonadjacent —$CH_2$— groups in the alkylene group are optionally substituted with —O—, —COO—, or —OCO—, $Z^{i2}$ denotes a single bond, —O—, —CH=CH—, —COO—, —OCO—, —OCOO—, —CH=CHCOO—, —OCOCH=CH—, —CH=C($CH_3$)COO—, —OCOC($CH_3$)=CH—, —$CH_2$—CH($CH_3$)COO—, —OCOCH($CH_3$)—$CH_2$—, or a linear or branched alkylene group having 1 to 20 carbon atoms, one —CH$_2$— or two or more nonadjacent —CH$_2$— groups in the alkylene group are optionally substituted with —O—, —COO—, or —OCO—, K$^{i1}$ denotes a group represented by one of the general formulae (K-1) to (K-6),

[Chem. 2]

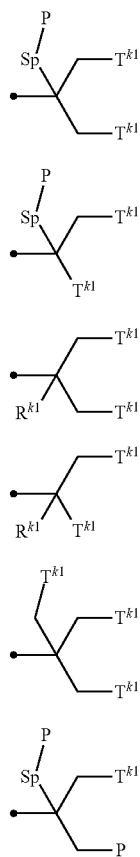

(K-1)
(K-2)
(K-3)
(K-4)
(K-5)
(K-6)

R$^{K1}$ denotes a hydrogen atom or a linear or branched alkyl group having 1 to 6 carbon atoms, and T$^{K1}$ independently denotes a group represented by one of the general formulae (T-1) to (T-6),

[Chem. 3]

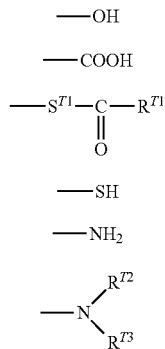

(T-1)
(T-2)
(T-3)
(T-4)
(T-5)
(T-6)

S$^{T1}$ denotes a single bond, a linear or branched alkylene group having 1 to 15 carbon atoms, or a linear or branched alkenylene group having 2 to 18 carbon atoms, —CH$_2$— in the alkylene or alkylene group is optionally substituted with —O—, —COO—, —C(=O)—, —C(=CH$_2$)—, or —OCO— such that oxygen atoms are not directly adjacent to each other, R$^{T1}$ denotes an alkyl group having 1 to 5 carbon atoms, —CH$_2$— in the alkyl group is optionally substituted with —O—, —COO—, —C(=O)—, —C(=CH$_2$)—, or —OCO— such that oxygen atoms are not directly adjacent to each other, and R$^{T2}$ and R$^{T3}$ independently denote a hydrogen atom or an alkyl group having 1 to 5 carbon atoms, and P denotes a polymerizable group, Sp denotes a spacer group or a single bond, m denotes an integer in the range of 1 to 4, a plurality of As, if present, may be the same or different, a plurality of Z$^{i1}$s, if present, may be the same or different, a plurality of Ps, if present, may be the same or different, and a plurality of Sps, if present, may be the same or different.

The present invention also provides a liquid crystal composition containing one or two or more compounds represented by the general formula (i).

Advantageous Effects of Invention

The present invention can provide a polymerizable compound and a liquid crystal composition that have high storage stability, contain liquid crystal molecules that can be vertically aligned without a PI layer, have no variation in display, and have high reliability with a stable tilt angle, and a liquid crystal display device including the liquid crystal composition. Due to the amount of additive smaller than in known compounds, there is little concern about a decrease in contrast caused by residual monomers after UV radiation and by a decrease in transmissivity.

DESCRIPTION OF EMBODIMENTS

Figure 1:
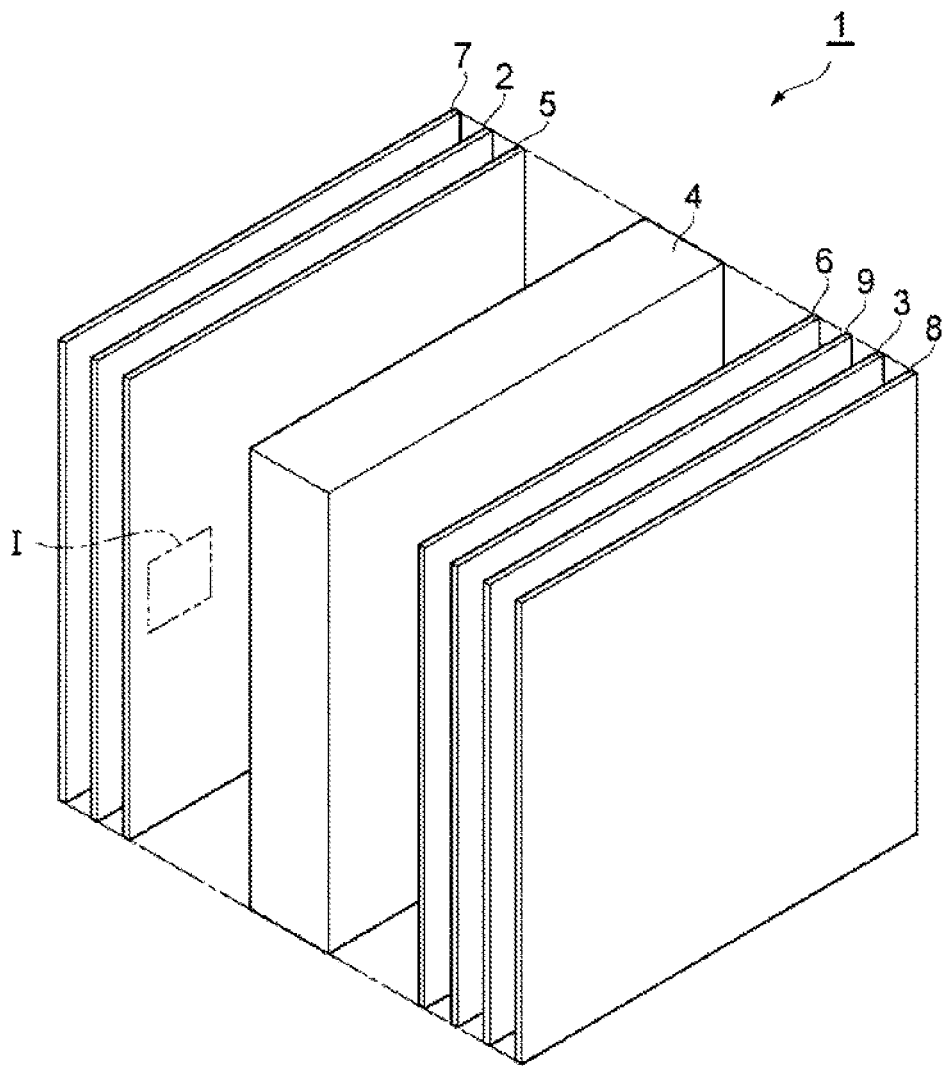
FIG. 1 is a schematic view of a liquid crystal display device according to an embodiment.

A polymerizable compound according to the present embodiment is a compound represented by the general formula (i).

[Chem. 4]

$$R^{i1}\left(\!\!\begin{array}{c}A\end{array}\!\!-Z^{i1}\right)_{\!\!m}\!\!\begin{array}{c}B\\\phantom{x}\\R^{i2}\end{array}\!\!-Z^{i2}-K^{i1}\begin{array}{c}\phantom{x}\\Sp\!\!-\!\!P\end{array}$$ (i)

K$^{i1}$ in the general formula (i) denotes a group represented by one of the following general formulae (K-1) to (K-6).

[Chem. 5]

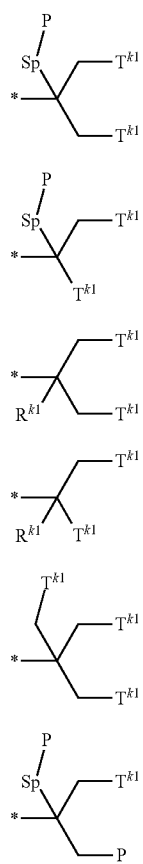

(K-1)

(K-2)

(K-3)

(K-4)

(K-5)

(K-6)

Particularly having a partial structure represented by one of the general formulae (K-1) to (K-5), a compound represented by the general formula (i) in a liquid crystal composition aligns on substrates between which the liquid crystal composition (a liquid crystal layer) exists and can hold vertically aligned liquid crystal molecules. In a liquid crystal composition containing the polymerizable compound according to the present embodiment, therefore, liquid crystal molecules can be aligned without a PI layer (induce vertical alignment of liquid crystal molecules when no voltage is applied and achieve horizontal alignment of liquid crystal molecules when a voltage is applied). Thus, a compound represented by the general formula (i) is suitably used to facilitate vertical alignment of liquid crystal molecules in a liquid crystal composition.

Furthermore, the present inventors found that a polymerizable compound represented by the general formula (i) according to the present embodiment, which has a partial structure represented by one of the general formulae (K-1) to (K-6) and has the ring B with a polymerizable group and with a substituent that is a linear or branched alkyl group having 2 to 10 carbon atoms or a linear or branched halogenated alkyl group having 2 to 10 carbon atoms, —CH$_2$— in the alkyl or halogenated alkyl group being optionally substituted with —CH=CH—, —O—, —COO—, or —OCO—, can not only align liquid crystal molecules but also improve alignment stability and ensure low-temperature storage stability.

From these perspectives, the polymerizable compound according to the present embodiment only need to have a partial structure represented by one of the general formulae (K-1) to (K-6) at a molecular end, preferably at an end of the main chain of the molecule, and have a structure having the ring B with a polymerizable group and with a substituent that is a linear or branched alkyl group having 2 to 10 carbon atoms or a linear or branched halogenated alkyl group having 2 to 10 carbon atoms, —CH$_2$— in the alkyl or halogenated alkyl group being optionally substituted with —CH=CH—, —O—, —COO—, or —OCO—, and may have another chemical structure that does not impair the function of the liquid crystal composition.

Having the polymerizable moiety and the substituent $R^{i2}$, the ring B, which denotes a phenylene group or a naphthylene group, in the formula (i) does not disturb vertical alignment in a polymerization reaction caused by UV radiation, can form a rigid polymer layer, and can improve low-temperature storage stability.

P in the general formula (i) preferably independently denotes a substituent selected from a group represented by the following general formulae (P-1) to (P-14). The formulae (P-1) and (P-2) are more preferred for convenience in handling and in terms of reactivity.

[Chem. 6]

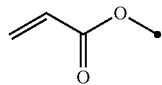

(P-1)

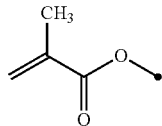

(P-2)

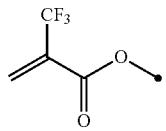

(P-3)

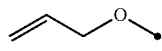

(P-4)

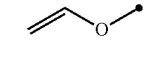

(P-5)

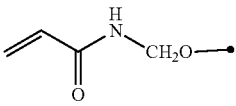

(P-6)

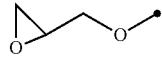

(P-7)

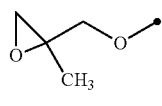

(P-8)

(P-9)

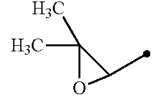

(P-10)

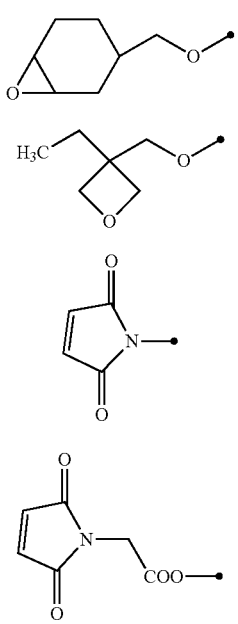

(P-11)

(P-12)

(P-13)

(P-14)

(In the formulae, each dark dot at the right end denotes a bonding arm.)

Sp in the formula (i) preferably denotes a linear alkylene group having 1 to 18 carbon atoms or a single bond, more preferably a linear alkylene group having 2 to 15 carbon atoms or a single bond, still more preferably a linear alkylene group having 2 to 8 carbon atoms or a single bond. —CH$_2$— in the alkyl group is optionally substituted with —CH=CH—, —O—, —COO—, or —OCO—, and a hydrogen in —CH$_2$— is optionally substituted with fluorine.

The partial structure represented by one of the general formulae (K-1) to (K-6) is preferably represented by the general formula (K-1) or (K-2) in terms of the pretilt stability of liquid crystal and is preferably represented by the general formula (K-5) in terms of alignment.

$T^{K1}$ independently denotes a group represented by one of the general formulae (T-1) to (T-6), preferably a group represented by the general formula (T-1), (T-3), or (T-4).

[Chem. 7]

—OH  (T-1)

—COOH  (T-2)

—S$^{T1}$—C(=O)—R$^{T1}$  (T-3)

—SH  (T-4)

—NH$_2$  (T-5)

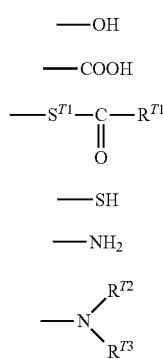

(T-6)

$S^{T1}$ in the general formula (T-3) preferably denotes a single bond, a linear or branched alkylene group having 1 to 10 carbon atoms, or a linear or branched alkenylene group having 2 to 10 carbon atoms, preferably a linear or branched alkyl group having 1 to 7 carbon atoms or a linear or branched alkenylene group having 2 to 7 carbon atoms, preferably a linear alkyl group having 1 to 3 carbon atoms, and —CH$_2$— in the alkyl or alkylene group is preferably substituted with —O—, —C(=O)—, or —C(=CH$_2$)— such that oxygen atoms are not directly adjacent to each other. $R^{T1}$ in the general formula (T-3) denotes a linear or branched alkyl group having 1 to 5 carbon atoms, and —CH$_2$— in the alkyl group is preferably substituted with —O—, —C(=O)—, —C(=CH$_2$)—, or —OCO— such that oxygen atoms are not directly adjacent to each other. $R^{T1}$ in the general formula (T-3) preferably denotes a linear alkyl group having 1 to 3 carbon atoms. In the general formula (T-3), at least two secondary carbon atoms preferably include —C(=O).

$R^{T2}$ and $R^{T3}$ in the general formula (T-6) independently denote a hydrogen atom or an alkyl group having 1 to 5 carbon atoms, preferably a hydrogen atom.

Preferred examples of the general formulae (K-1) to (K-5) include the following (K-1-1) to (K-1-4), (K-3-1), and (K-5-1) in terms of alignment and reactivity, particularly preferably the formulae (K-1-1), (K-1-3), and (K-3-1).

[Chem. 8]

(K-1-1)

(K-1-2)

(K-3-1)

(K-5-1)

(K-1-3)

-continued

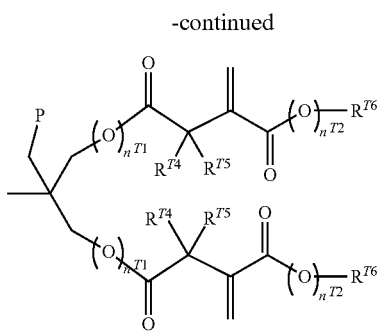

(K-1-4)

(In the formulae, P denotes a polymerizable group, $R^{T4}$, $R^{T5}$, and $R^{T6}$ independently denote a hydrogen atom or an alkyl group having 1 to 3 carbon atoms, $n^{T1}$ and $n^{T2}$ independently denote 0 or 1, $n^{T3}$ independently denotes an integer in the range of 0 to 3, a plurality of $R^{T4}$s may be the same or different, a plurality of $R^{T5}$s may be the same or different, a plurality of $R^{T6}$s may be the same or different, a plurality of $n^{T1}$s may be the same or different, a plurality of $n^{T2}$s may be the same or different, and a plurality of $n^{T3}$s may be the same or different.)

$Z^{i2}$ in the general formula (i) preferably denotes a single bond, —O—, —CH=CH—, —COO—, —OCO—, —OCOO—, —OOCO—, —CH=CHCOO—, —OCOCH=CH—, —CH=C(CH$_3$)COO—, —OCOC(CH$_3$)=CH—, —CH$_2$—CH(CH$_3$)COO—, —OCOCH(CH$_3$)—CH$_2$—, a linear alkylene group having 1 to 20 carbon atoms, or a branched alkylene group having 1 to 20 carbon atoms, and one —CH$_2$— or two or more nonadjacent —CH$_2$— groups in the alkylene group denote a group substituted with —O—, —COO—, or —OCO—. $Z^{i2}$ in the general formula (i) more preferably denotes —COO—, —OCO—, —OCH$_2$CH$_2$O—, a linear or branched alkylene group having 1 to 6 carbon atoms, an ethylene group in which one —CH$_2$— is substituted with —O— (—CH$_2$O—, —OCH$_2$—), or an ethylene group in which one —CH$_2$— is substituted with —COO— or —OCO— (—CH$_2$—CH$_2$COO—, —OCOCH$_2$—CH$_2$—).

$Z^{i2}$ preferably denotes —$Z^{i21}$—$S^{i1}$— ($Z^{i21}$— denotes —O—, —COO—, —OCO—, or an alkylene group having 1 to 6 carbon atoms, one —CH$_2$— or two or more nonadjacent —CH$_2$— groups in the alkylene group are optionally substituted with —O—, —COO—, or —OCO—, and $S^{i1}$ denotes an alkyl group having 1 to 6 carbon atoms).

$Z^{i1}$ in the formula (i) preferably denotes a single bond, —CH=CH—, —CF=CF—, —C≡C—, —COO—, —OCO—, —CF$_2$O—, —OCF$_2$—, —CH=CHCOO—, —OCOCH=CH—, —OCH$_2$CH$_2$O—, or an alkylene group having 1 to 10 carbon atoms, or a group in which one —CH$_2$— or two or more nonadjacent —CH$_2$— groups in the alkylene group is substituted with —O—, —COO—, or —OCO—, more preferably a single bond, —COO—, —OCO—, —CH=CHCOO—, —OCOCH=CH—, —OCH$_2$CH$_2$O—, a linear or branched alkylene group having 1 to 6 carbon atoms, or a group substituted with a group in which one —CH$_2$— or two or more nonadjacent —CH$_2$— groups in the alkylene group are substituted with —O—, —COO—, or —OCO—, still more preferably a single bond, —COO—, —OCO—, —OCH$_2$CH$_2$O—, an alkylene group having two carbon atoms (an ethylene group (—CH$_2$CH$_2$—)), an ethylene group in which one —CH$_2$— is substituted with —O— (—CH$_2$O—, —OCH$_2$—), or an ethylene group in which one —CH$_2$— is substituted with —COO— or —OCO— (—CH$_2$—CH$_2$COO—, —OCOCH$_2$—CH$_2$—).

$R^{i1}$ preferably denotes a hydrogen atom, an alkyl group having 1 to 20 carbon atoms, or a halogenated alkyl group, and —CH$_2$— in the alkyl group is optionally substituted with —CH=CH—, —C≡C—, —O—, —COO—, —OCO—, or —OCOO—, but —O— is not adjacent to another —O—. $R^{i1}$ more preferably denotes an alkyl group having 1 to 18 carbon atoms, and —CH$_2$— in the alkyl group is optionally substituted with —CH=CH—, —O—, or —OCO— (but —O— is not adjacent to another —O—). When $R^{i1}$ denotes an alkyl group, the alkyl group may be linear, branched, or cyclic, preferably linear or branched. To improve the alignment of the liquid crystal compound, the number of carbon atoms in $R^{i1}$ is preferably 3 or more, particularly preferably 5 or more.

$R^{i1}$ preferably denotes a linear or branched alkyl group having 2 to 10 carbon atoms or a linear or branched halogenated alkyl group having 2 to 10 carbon atoms, —CH$_2$— in the alkyl or halogenated alkyl group is optionally substituted with —O—, but —O— is not adjacent to another —O—. $R^{i2}$ more preferably denotes a linear or branched alkyl group having 2 to 8 carbon atoms.

The ring A denotes a divalent aromatic group, a divalent heteroaromatic group, a divalent alicyclic group, or a divalent heteroalicyclic group, a divalent aromatic group, a divalent heteroaromatic group, a divalent alicyclic group, or a divalent heteroalicyclic group. More specifically, preferred are a 1,4-phenylene group, a 1,4-cyclohexylene group, an anthracene-2,6-diyl group, a phenanthrene-2,7-diyl group, a pyridine-2,5-diyl group, a pyrimidine-2,5-diyl group, a naphthalene-2,6-diyl group, an indan-2,5-diyl group, a chroman-3,7-diyl, a 1,2,3,4-tetrahydronaphthalene-2,6-diyl group, a 1-cyclopentyl group, and 1,3-dioxane-2,5-diyl group. The ring structure is preferably unsubstituted or substituted with $L^{i1}$. $L^{i1}$ preferably denotes an alkyl group having 1 to 12 carbon atoms, a halogenated alkyl group having 1 to 12 carbon atoms, an alkoxy group having 1 to 12 carbon atoms, a halogenated alkoxy group having 1 to 12 carbon atoms, a halogen atom, a cyano group, a nitro group, or P-Sp-, preferably a group substituted with an alkyl group having 1 to 6 carbon atoms, an alkoxy group having 1 to 6 carbon atoms, or a halogen atom. When $L^{i1}$ denotes a monovalent organic group with a substituent represented by the general formula $K^{i1}$, $L^{i1}$ preferably denotes —$Z^{i3}$—$K^{i2}$ ($Z^{i3}$ and $K^{i2}$ have the same meaning as $Z^{i2}$ and $K^{i1}$, respectively, in the general formula (i)). The ring A more preferably denotes a 1,4-phenylene group, a 2,6-naphthalene group, or a 1,4-cyclohexyl group, optionally substituted with an alkyl group having 1 to 12 carbon atoms, a halogenated alkyl group having 1 to 12 carbon atoms, an alkoxy group having 1 to 12 carbon atoms, a halogen atom, or P-Sp-.

The ring B denotes a phenyl group or a naphthyl group, preferably a 1,4-phenylene group, and at least two hydrogen atoms are substituted with Sp-P and $R^{i2}$. Although the position of $R^{i2}$ on the ring B is not particularly limited, the following groups are preferred.

[Chem. 9]

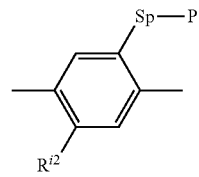

(B-1)

-continued

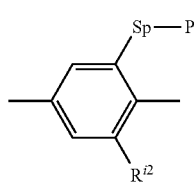
(B-2)

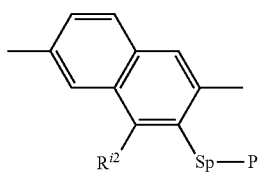
(B-3)

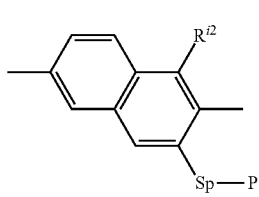
(B-4)

The ring B is optionally substituted with $L^{i2}$. $L^{i2}$ preferably denotes a halogen atom, P-Sp-, a monovalent organic group having a group represented by the general formula $K^{i1}$, a linear or branched alkyl group having 1 to 10 carbon atoms, or a linear or branched halogenated alkyl group having 1 to 10 carbon atoms, more preferably a halogen atom, a P-Sp- group, or a monovalent organic group having a group represented by the general formula $K^{i1}$.

The monovalent organic group having a group represented by the general formula $K^{i1}$ is a monovalent organic group including one of the general formulae (K-1) to (K-6) and preferably denotes a group represented by $—S^{i2}—K^{i1}$ ($K^{i1}$ denotes a group represented by one of the general formulae (K-1) to (K-6), $S^{i2}$ denotes a single bond, —O—, —CH=CH—, —COO—, —OCO—, —OCOO—, —CH=CHCOO—, —OCOCH=CH—, —CH=C(CH$_3$)COO—, —OCOC(CH$_3$)=CH—, —CH$_2$—CH(CH$_3$)COO—, —OCOCH(CH$_3$)—CH$_2$—, or a linear or branched alkylene group having 1 to 20 carbon atoms, and one —CH$_2$— or two or more nonadjacent —CH$_2$— groups in the alkylene group are optionally substituted with —O—, —COO—, or —OCO—).

m preferably denotes an integer in the range of 1 to 4, more preferably an integer in the range of 1 to 3. n denotes 0 or 1. A more preferred structure of the general formula (i) is represented by the general formula (i-1).

[Chem. 10]

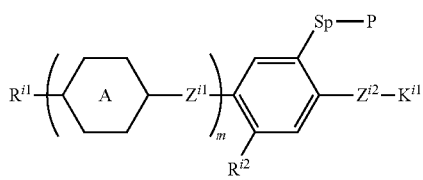
(i-1)

(In the formula, $R^{i1}$, $R^{i2}$, $Z^{i1}$, $Z^{i2}$, $K^{i1}$, Sp, P, and m have the same meaning as $R^{i1}$, $Z^{i1}$, $Z^{i2}$, $K^{i1}$, Sp, P, and m, respectively, in the general formula (i).)

$Z^{i2}$ preferably denotes $—Z^{i1}—S^{i1}—$, particularly preferably —OCH$_2$—, —COO—, or —CH$_2$CH$_2$—.

Specific examples of the general formula (i) include, but are not limited to, the following formulae (R-1-1) to (R-1-30).

[Chem. 11]

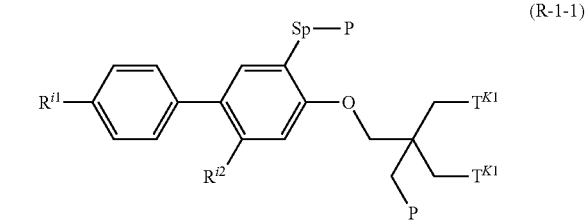
(R-1-1)

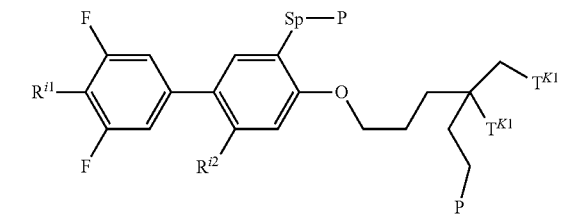
(R-1-2)

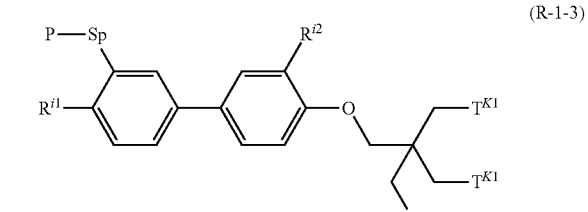
(R-1-3)

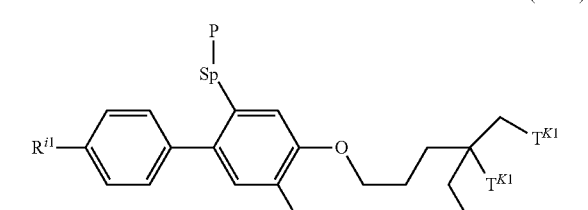
(R-1-4)

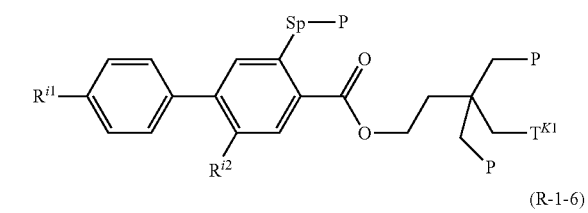
(R-1-5)

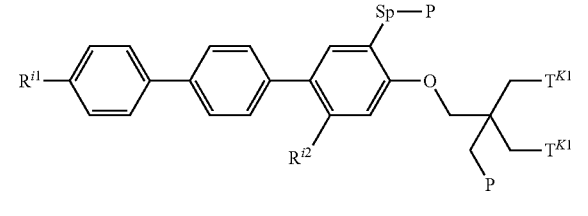
(R-1-6)

[Chem. 12]
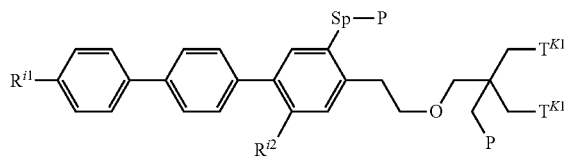 (R-1-7)
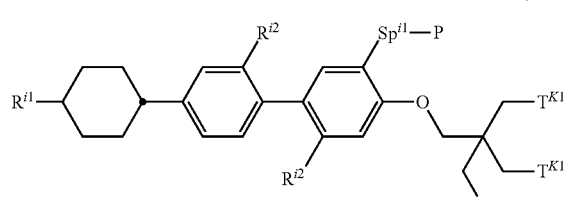 (R-1-8)
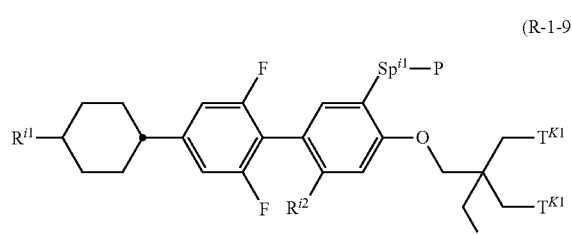 (R-1-9)
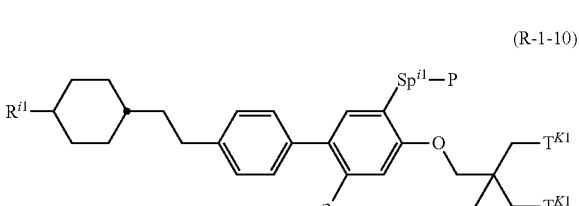 (R-1-10)
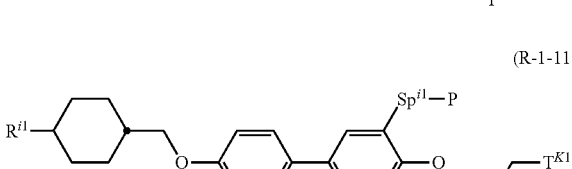 (R-1-11)
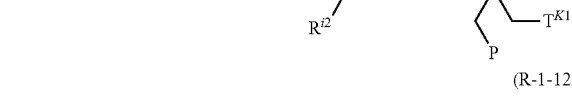 (R-1-12)
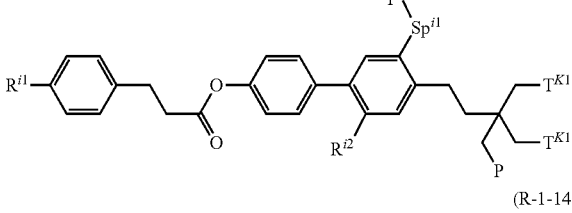 (R-1-13)
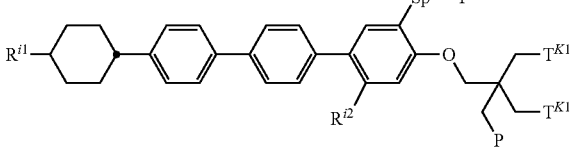 (R-1-14)
[Chem. 13]
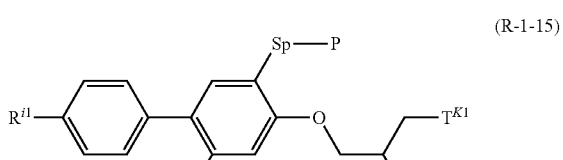 (R-1-15)
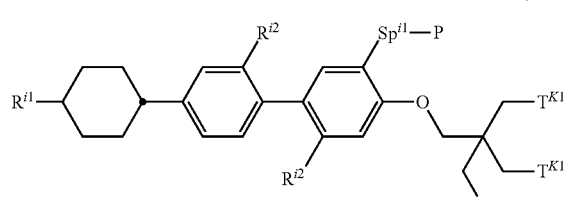 (R-1-16)
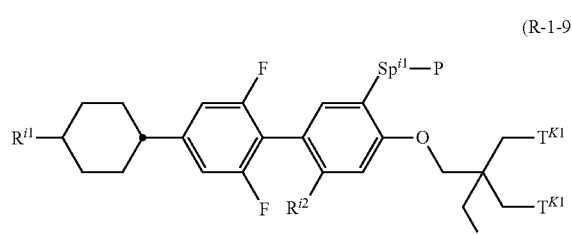 (R-1-17)
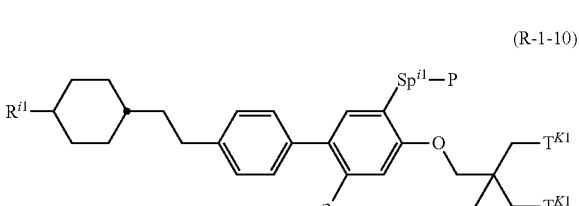 (R-1-18)
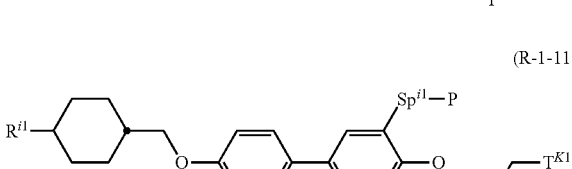 (R-1-19)
[Chem. 14]
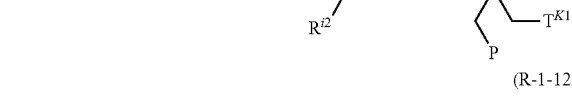 (R-1-20)
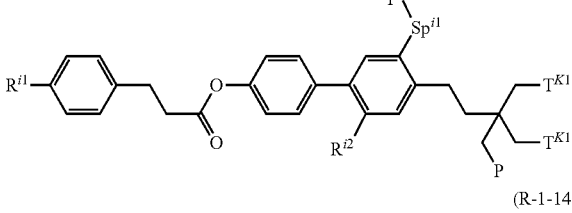 (R-1-21)
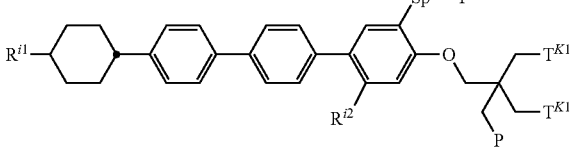 (R-1-22)

-continued (R-1-23)
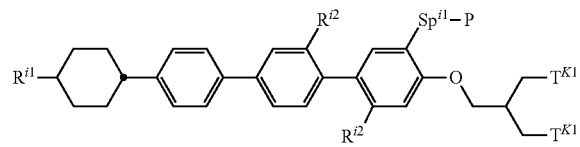

(R-1-24)

(R-1-25)

[Chem. 15]

(R-1-26)
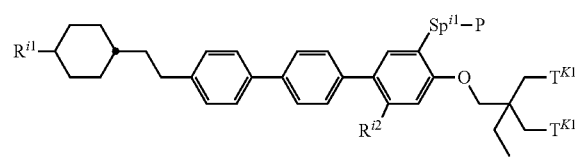

(R-1-27)
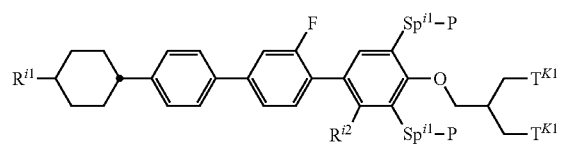

[Chem. 16]

-continued (R-1-28)
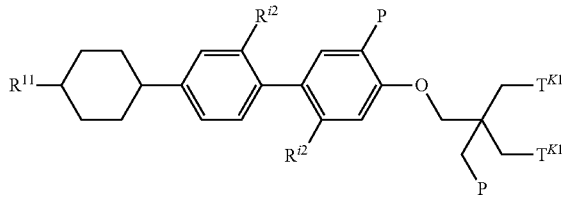

(R-1-29)

(R-1-30)
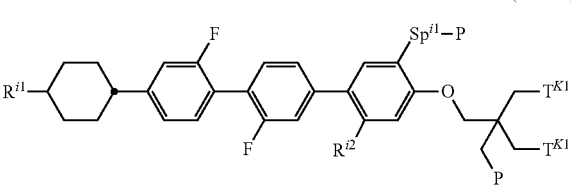

(In the formulae, $R^{i1}$, $R^{i2}$, $T^{K1}$, Sp, and P have the same meaning as $R^{i1}$, $R^{i2}$, $T^{K1}$, Sp, and P, respectively, in the general formula (i).)

In the general formulae (i-1) and (R-1-1) to (R-1-30), a preferred group of each of the reference numerals and letters is the same as in the general formula (i).

One or two or more of the compounds represented by the general formula (i) according to the present invention may be added to a liquid crystal composition. In addition to a compound represented by the general formula (i), a known polymerizable compound, a known antioxidant, and the like used in liquid crystal compositions may be contained. Examples of specific compounds of the compound (i) include the following (P-1-1) to (P-1-25).

(P-1-1)
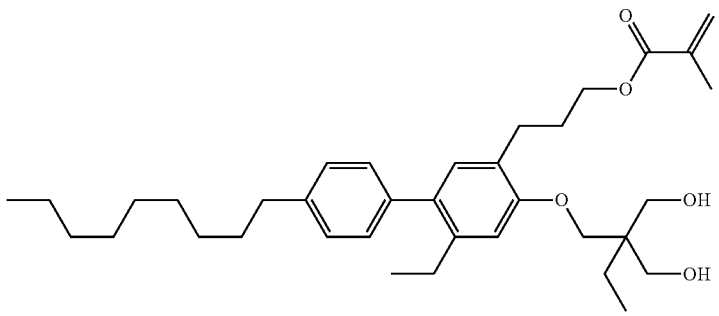

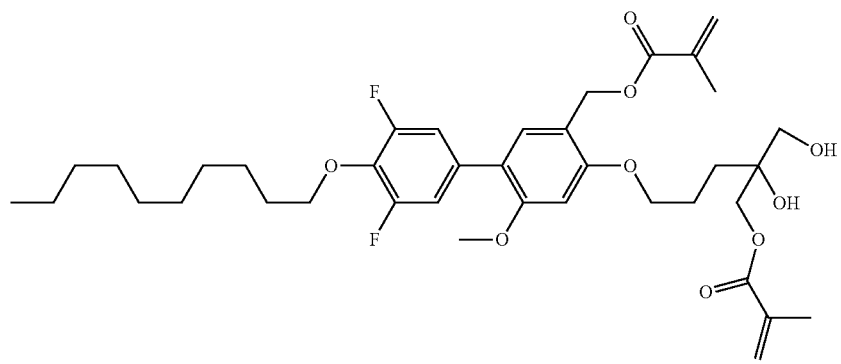
(P-1-2)
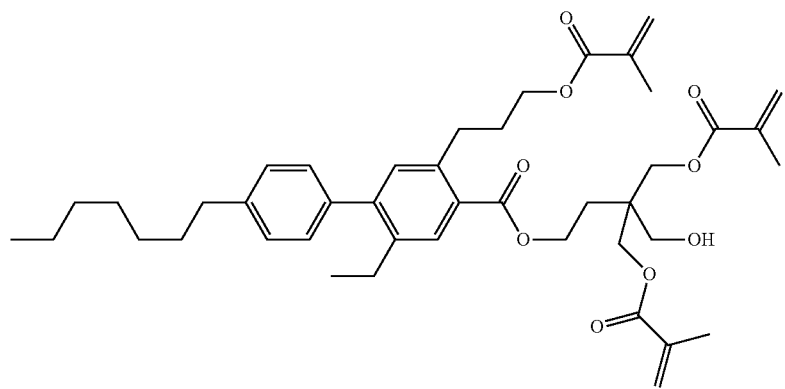
(P-1-3)
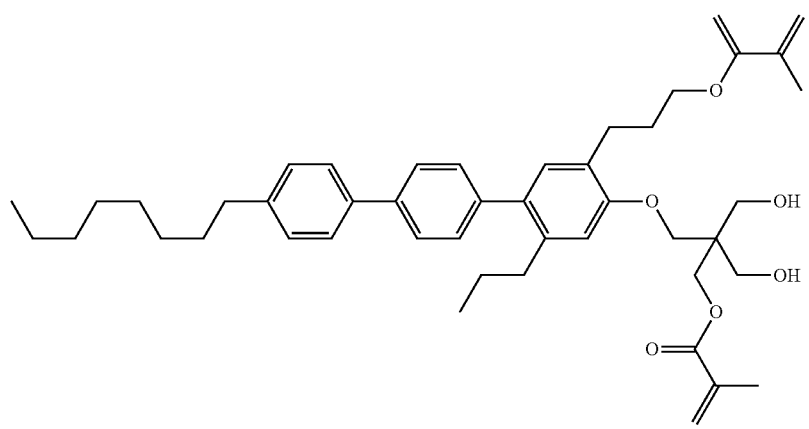
(P-1-4)
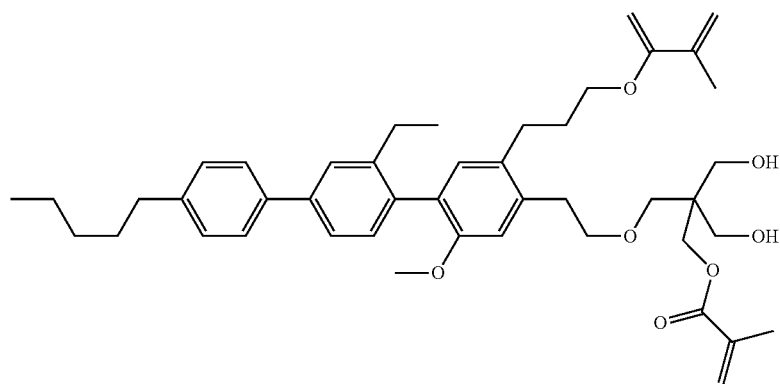
(P-1-5)

[Chem. 17]
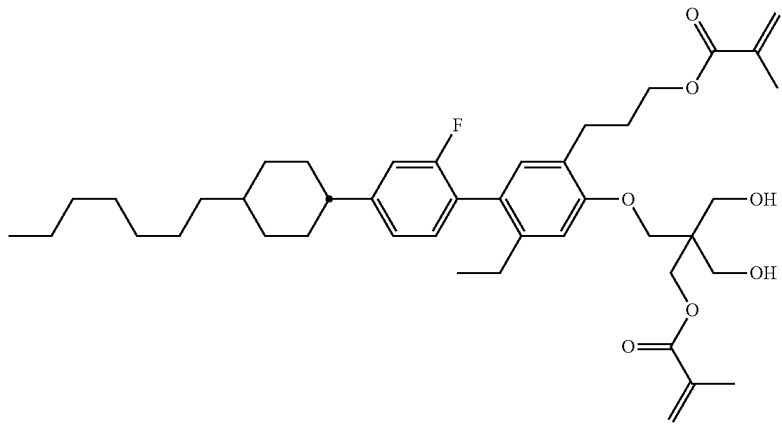
(P-1-6)
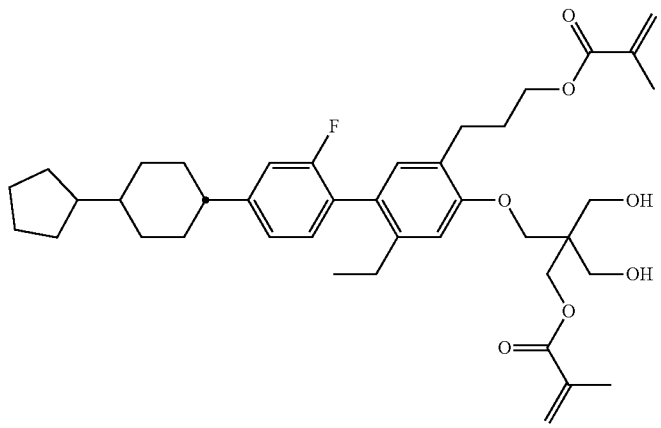
(P-1-7)
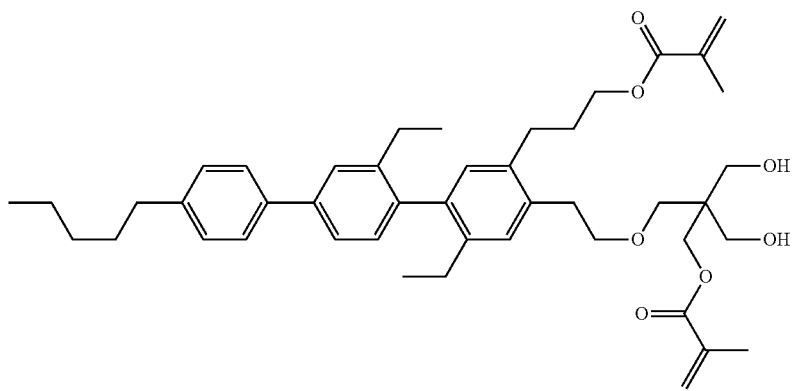
(P-1-8)

-continued
(P-1-9)
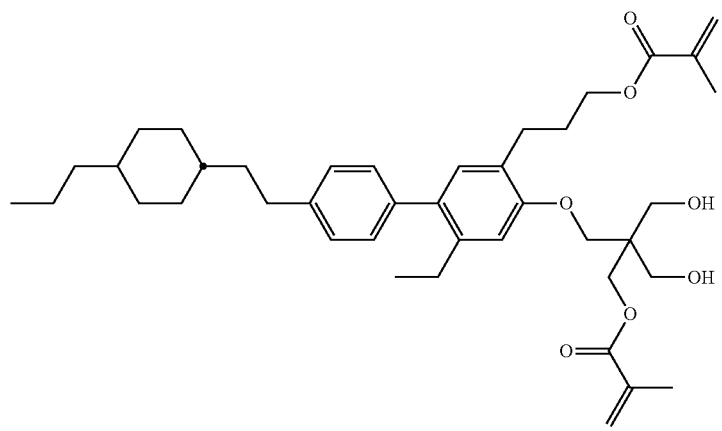
[Chem. 18]
(P-1-10)
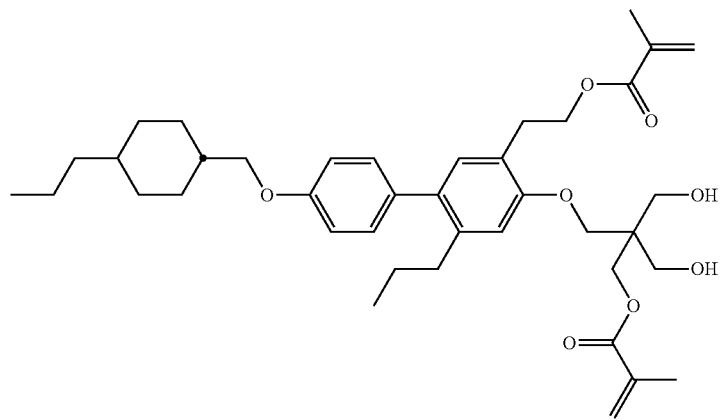
(P-1-11)
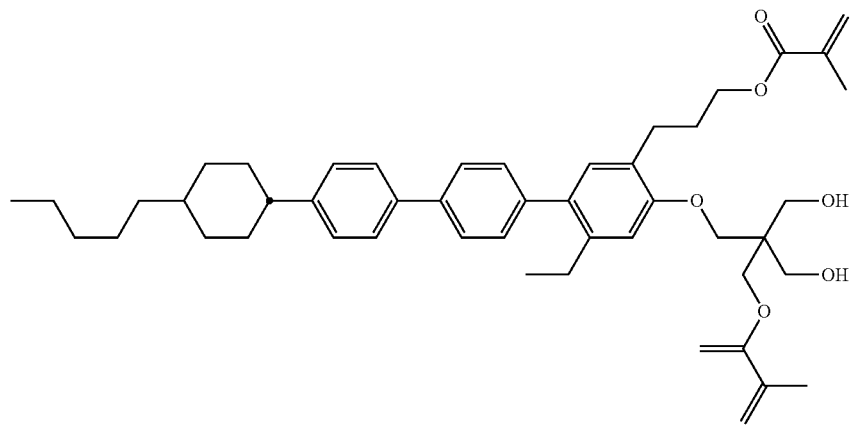

(P-1-12)
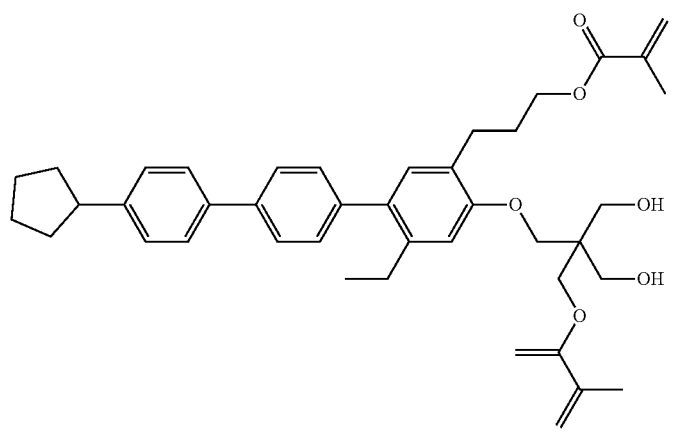
(P-1-13)
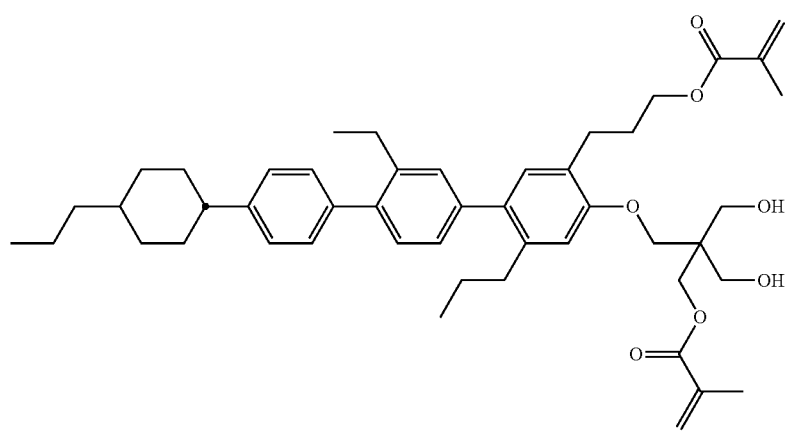
[Chem. 19]
(P-1-14)
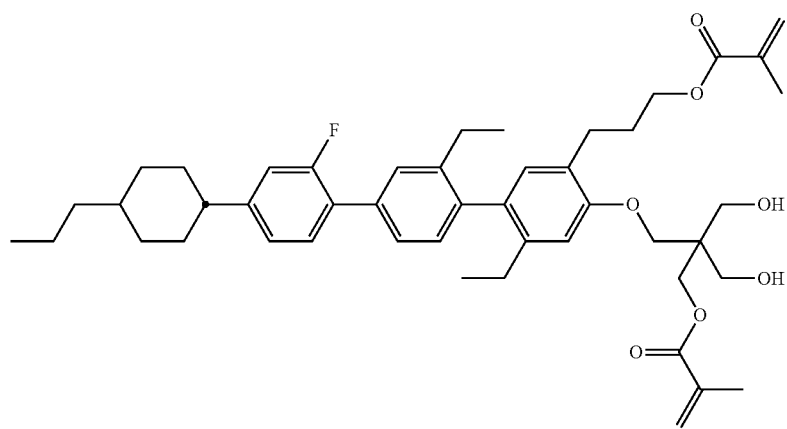

(P-1-15)
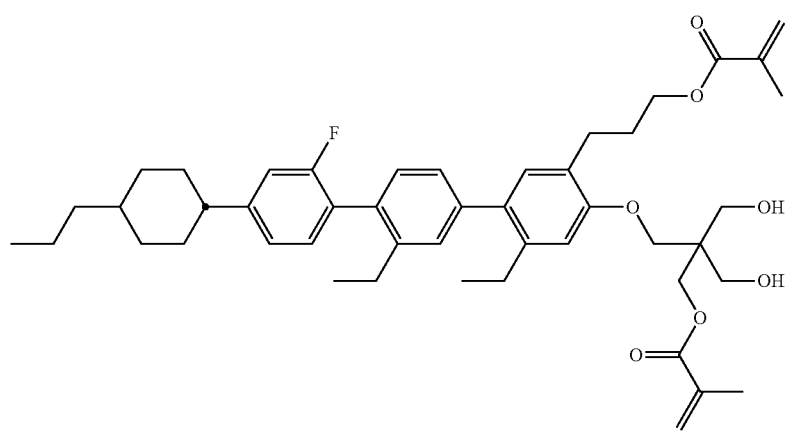
(P-1-16)
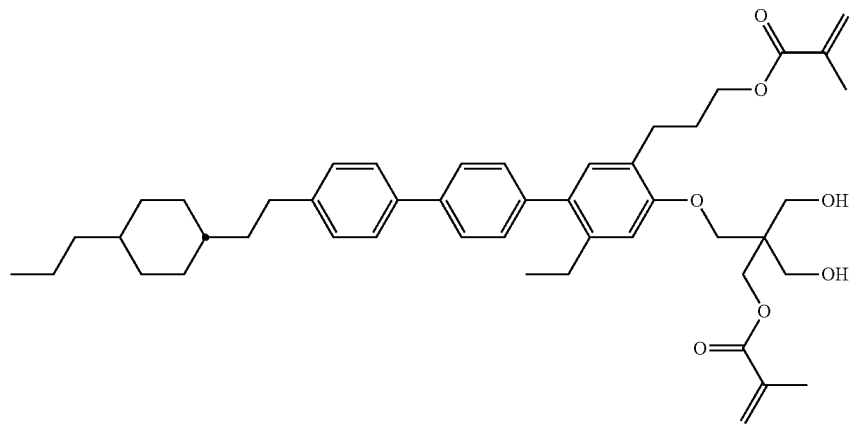
(P-1-17)
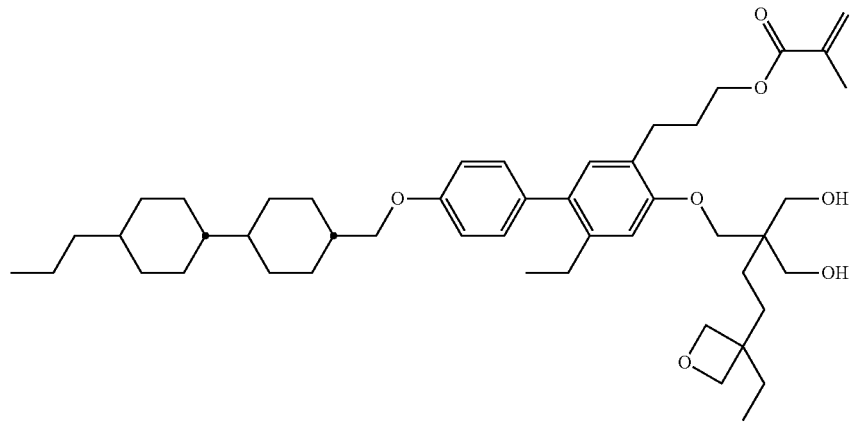
[Chem. 20]
(P-1-18)
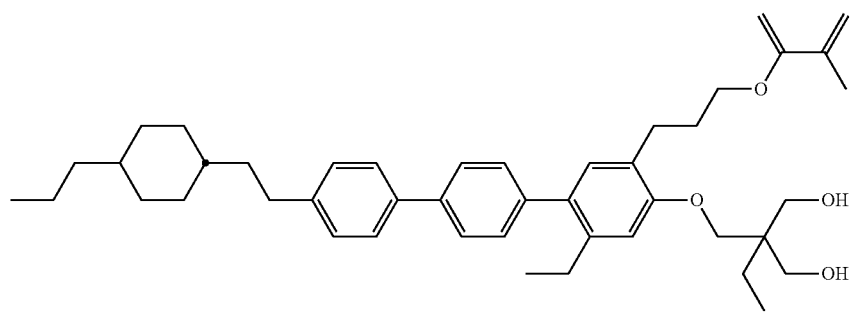

(P-1-19)
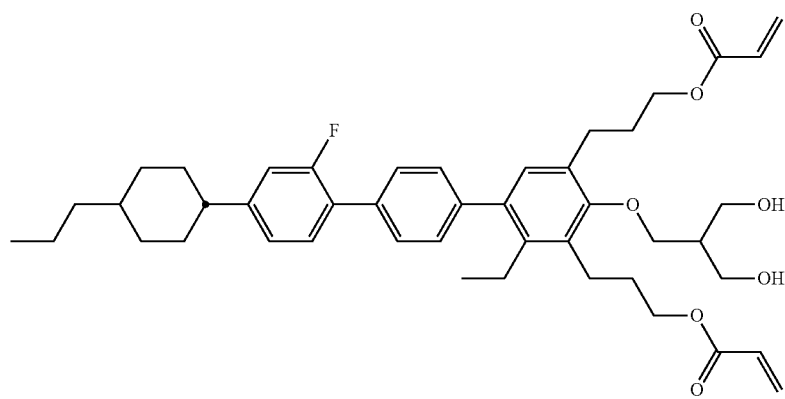
(P-1-20)
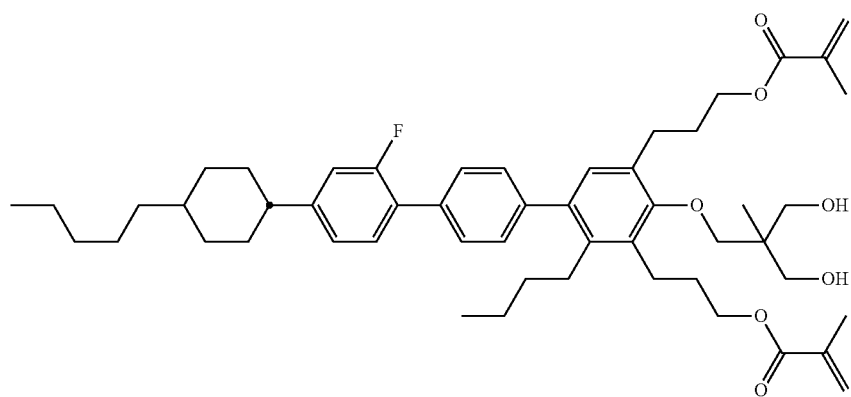
(P-1-21)
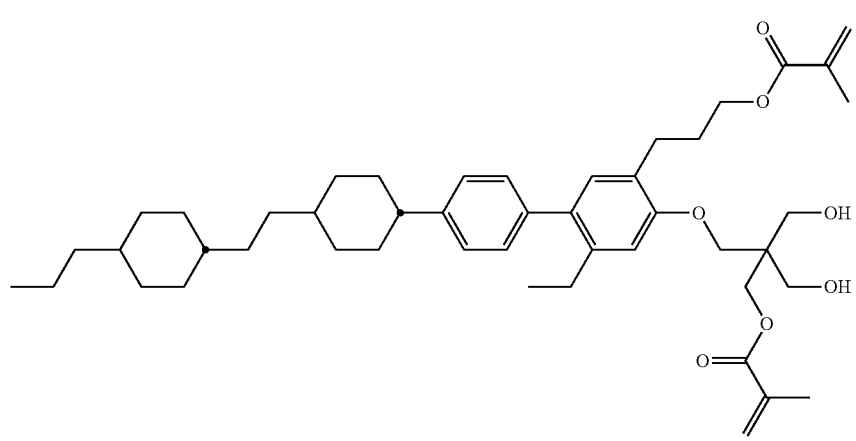

-continued
[Chem. 21]
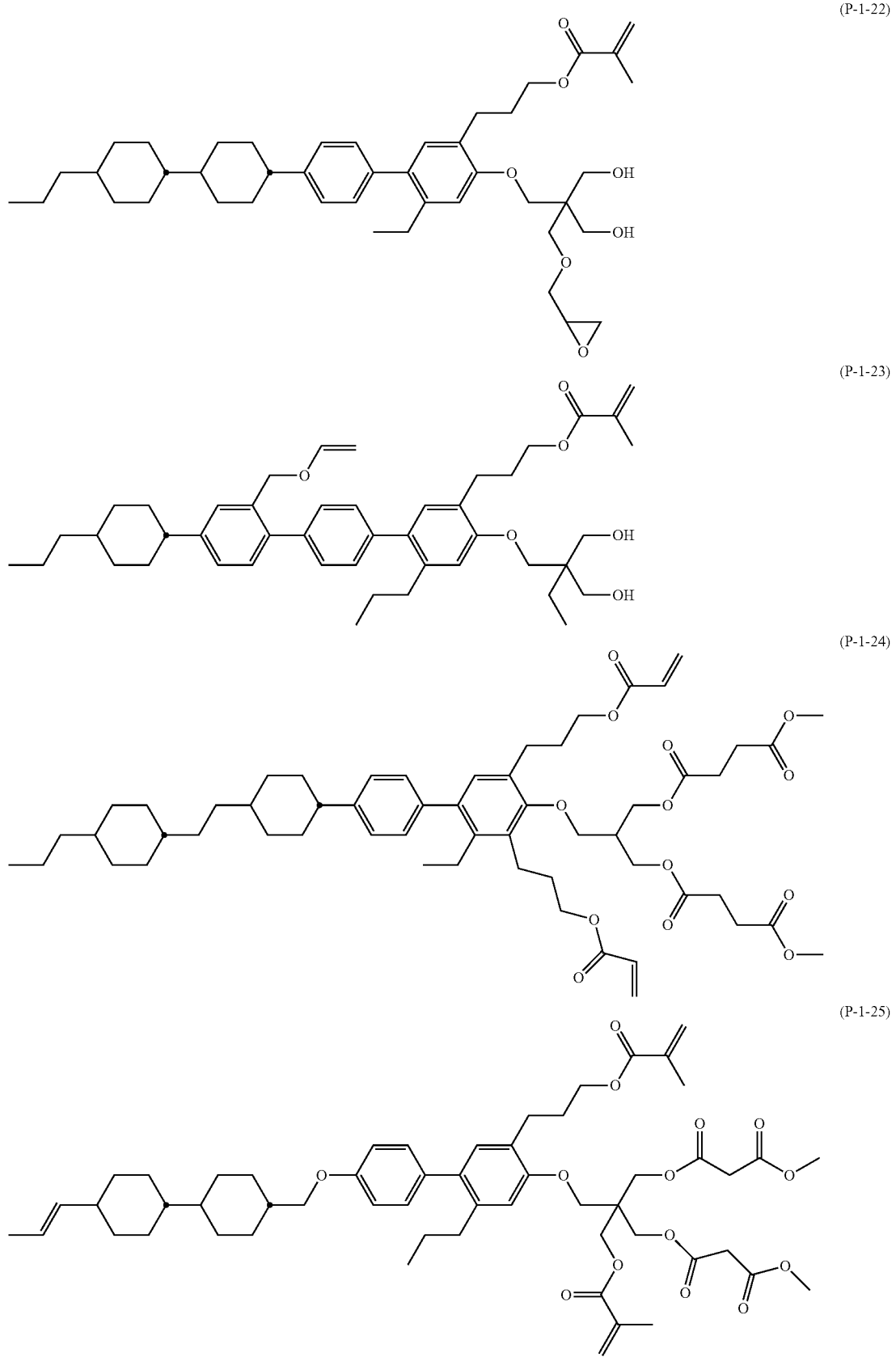
(P-1-22)
(P-1-23)
(P-1-24)
(P-1-25)

(Production Method 1) Production of Compound Represented by General Formula (P-1-1)

(S-1) is produced by a Suzuki coupling reaction between 4-nonylphenylboric acid and 4-bromo-5-ethyl-2-(3-hydroxypropyl)phenol in the presence of a palladium catalyst. (S-2) is then produced by an etherification reaction with (5-ethyl-2,2-dimethyl-1,3-dioxan-5-yl)methanol. Subsequently, a target product (P-1-1) can be produced by an esterification reaction with methacrylic acid and a pyran elimination reaction with hydrochloric acid.

[Chem. 22]

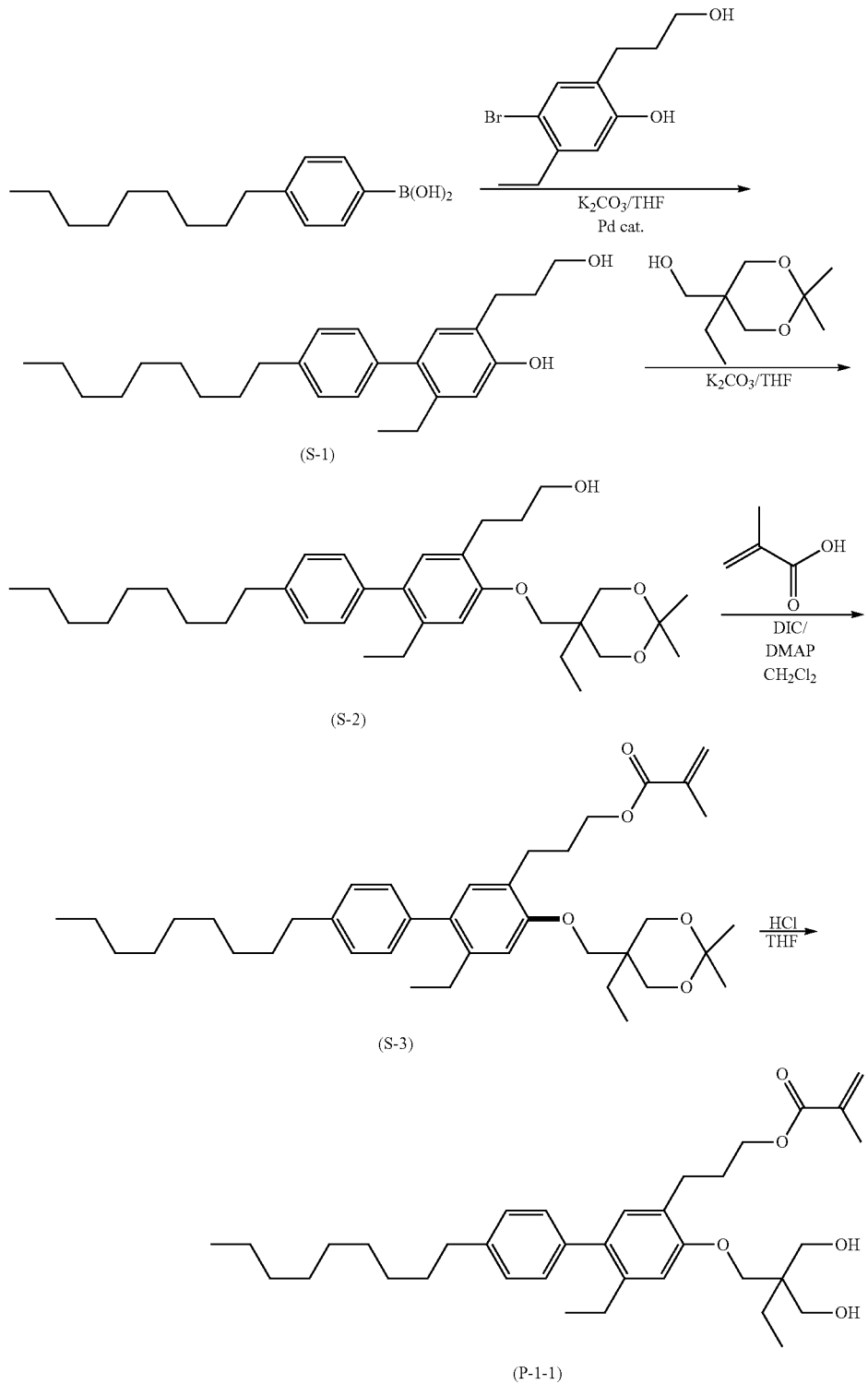

(Production Method 2) Production of Compound Represented By General Formula (P-1-8)

The following structure (S-3) is produced by protecting a phenol moiety of 2-(2-bromo-5-ethyl-4-hydroxyphenyl)acetic acid methyl with a tetrahydropyranyl group and then performing a Sonogashira reaction with propargyl alcohol. Subsequently, after the hydroxy group is protected with benzyl chloride, the tetrahydropyranyl group is eliminated with hydrochloric acid to produce a phenol compound, and methane sulfonyl chloride can be used to produce the following structure (S-4). (S-5) is then produced by a Suzuki coupling reaction between (S-4) and 2-(3-ethyl-4'-pentyl-[1,1'-biphenyl]-4-yl)-4,4,5,5,-tetramethyl-1,3,2-dioxabolane in the presence of a palladium catalyst. (S-6) is then produced by reduction with lithium aluminum hydride and by an etherification reaction with (5-ethyl-2,2-dimethyl-1,3-dioxan-5-yl)methanol. The following structure (S-7) is then produced by catalytic hydrogen reduction with palladium carbon. A target product (P-1-8) can then be produced by an esterification reaction with methacrylic acid and by deacetalization with hydrochloric acid.

[Chem. 23]

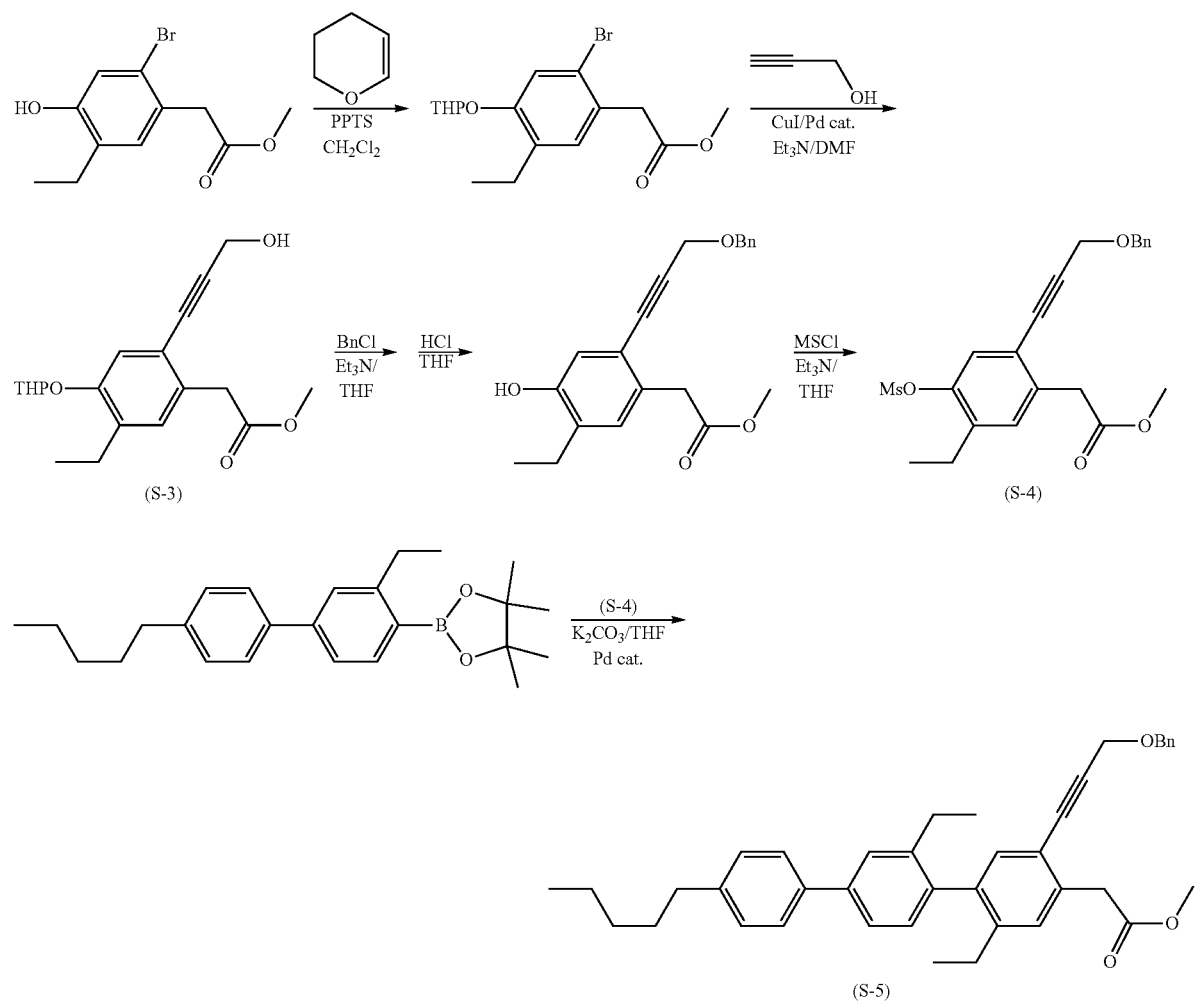

[Chem. 24]

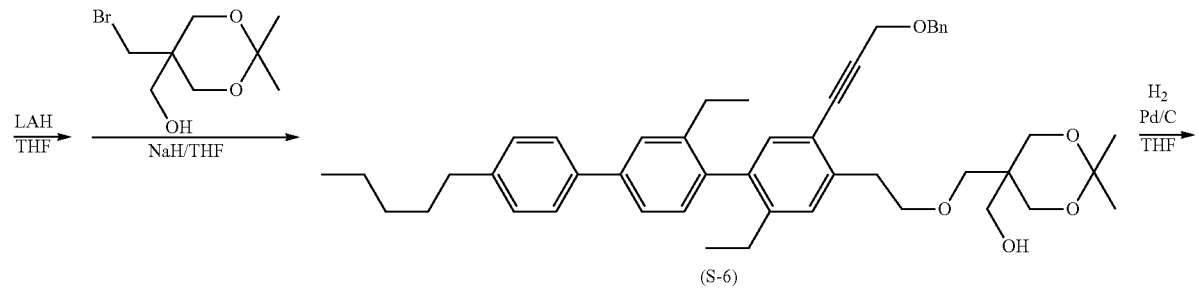

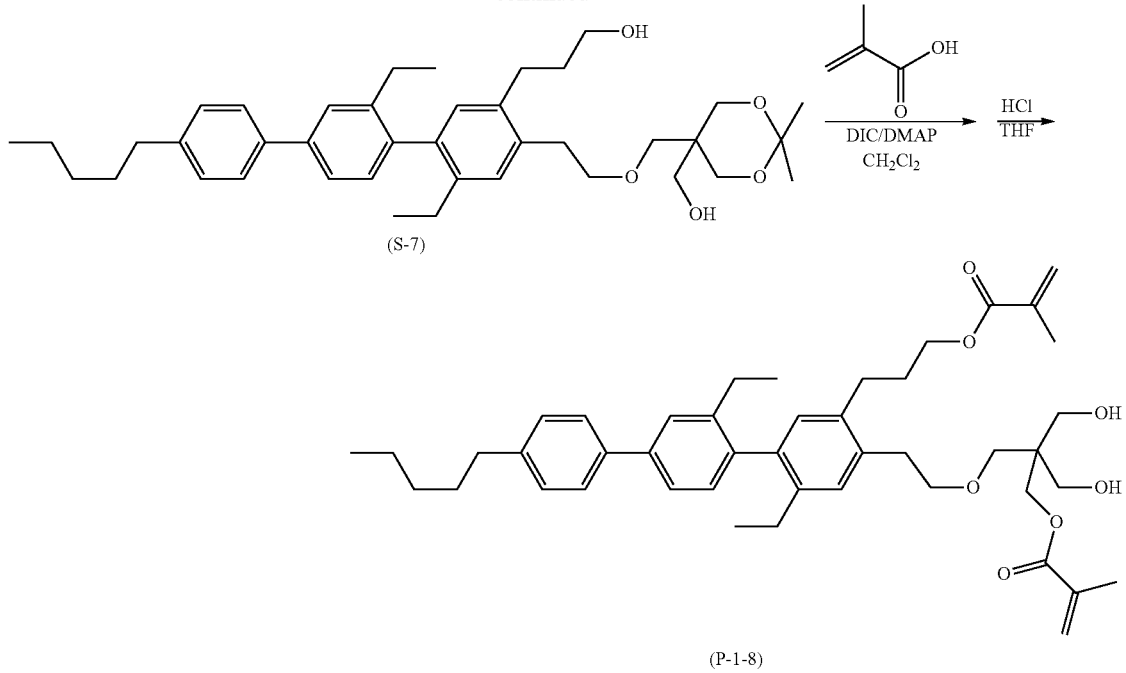

(Production Method 3) Production of Compound Represented By General Formula (P-1-10)

The following structure (S-8) is produced by etherification of 1-(bromomethyl)-4-propylcyclohexane and 4-bromophenol with potassium carbonate. The following borate esterified structure (S-9) is then produced by a coupling reaction with bis(pinacolato)diborane. The following structure (S-10) is then produced by a Suzuki coupling reaction with 4-bromo-5-propyl-2-(2-hydroxyethyl)phenol in the presence of a palladium catalyst. (S-11) is then produced by an etherification reaction with (5-ethyl-2,2-dimethyl-1,3-dioxan-5-yl)methanol. A target product (P-1-10) can then be produced by an esterification reaction with methacrylic acid and by deacetalization with hydrochloric acid.

[Chem. 25]

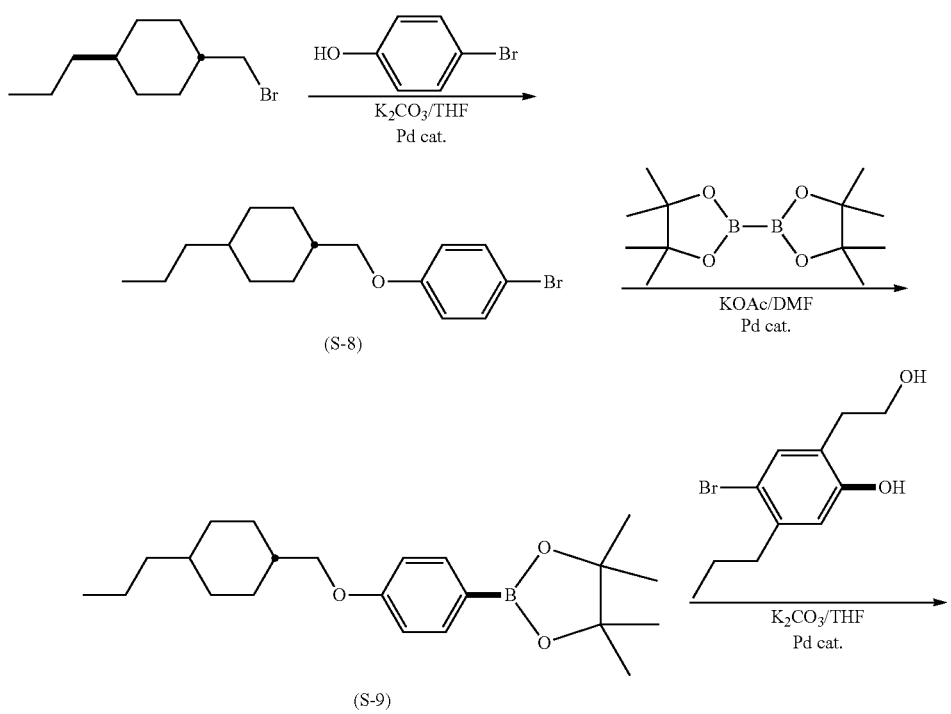

-continued

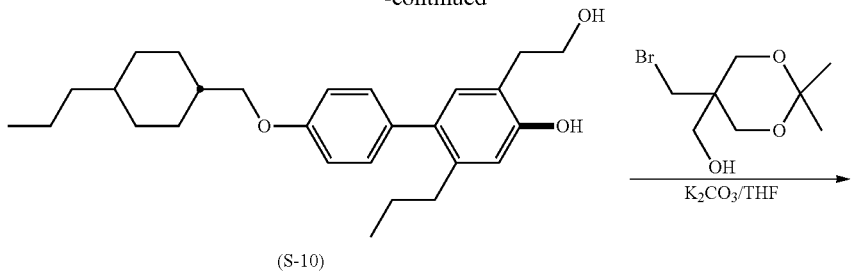

(S-10)

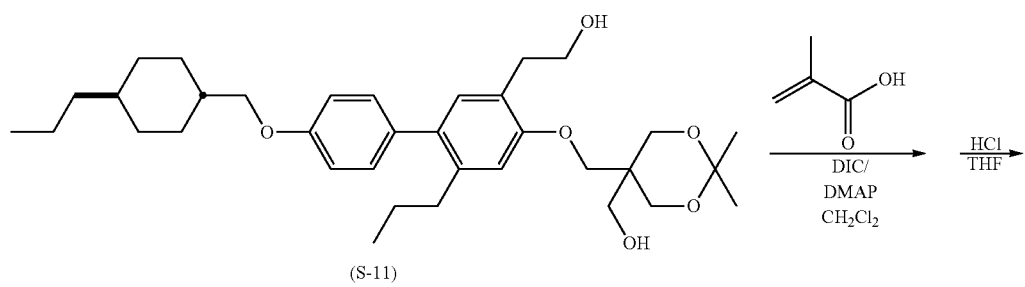

(S-11)

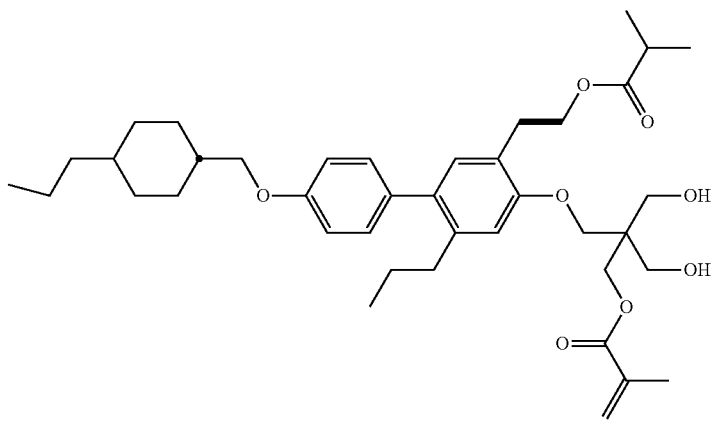

(P-1-10)

(Production Method 4) Production of Compound Represented By General Formula (P-1-25)

The following structure (S-12) is produced by an etherification reaction of 4-(chloromethyl)-4'-((E)-1-propenyl)-1,1'-bicyclohexane and 4-bromophenol with potassium carbonate. The following borate esterified structure (S-13) is then produced by a coupling reaction with bis(pinacolato)diborane. The following structure (S-14) is produced by a Suzuki coupling reaction with 4-bromo-5-propyl-2-(2-hydroxyethyl)phenol in the presence of a palladium catalyst. (S-15) is then produced by an etherification reaction with (5-ethyl-2,2-dimethyl-1,3-dioxan-5-yl)methanol and potassium carbonate. A target product (P-1-25) is then produced by benzyl protection of a hydroxy group with sodium hydride and benzyl chloride to synthesize (S-16), by a pyran elimination reaction with hydrochloric acid, by esterification with malonyl chloride, by an esterification reaction with hydrochloric acid methacrylic acid, by a pyran elimination reaction with hydrochloric acid, by catalytic hydrogen reduction with palladium carbon, and by esterification with methacrylic acid.

[Chem. 26]

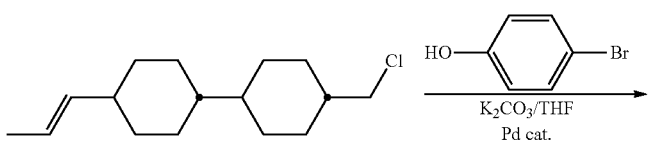

-continued
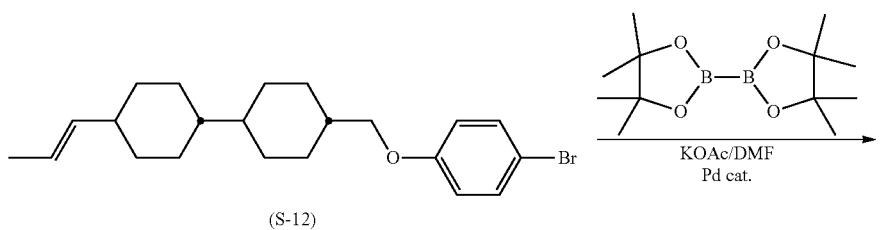
(S-12)
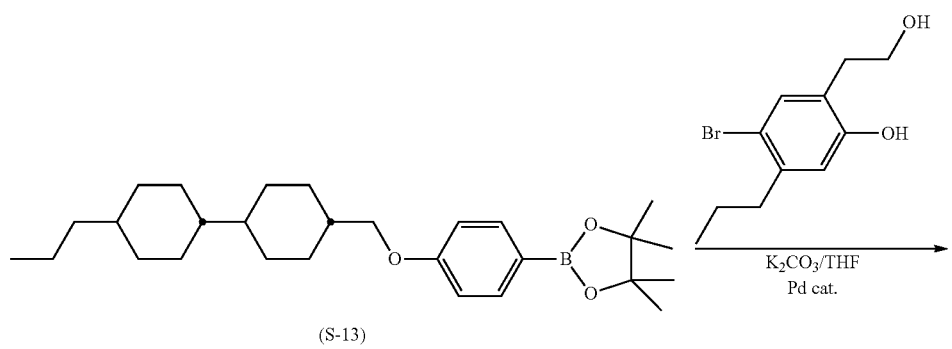
(S-13)
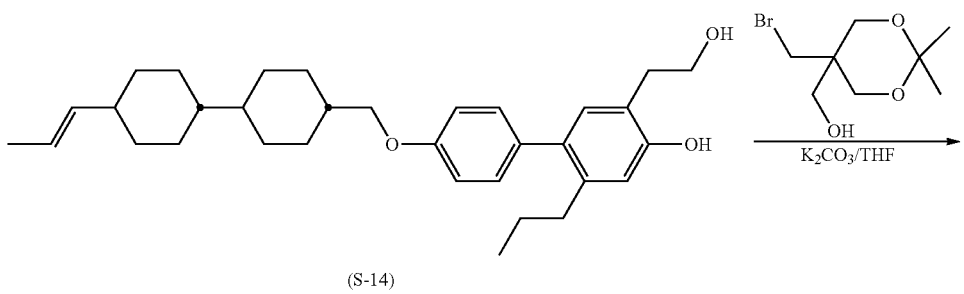
(S-14)
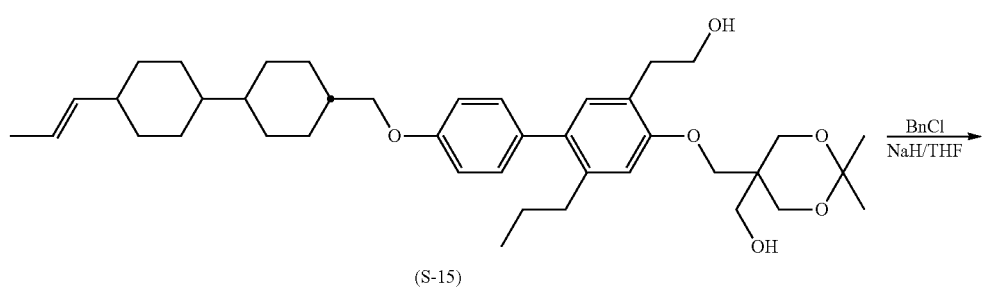
(S-15)
[Chem. 27]
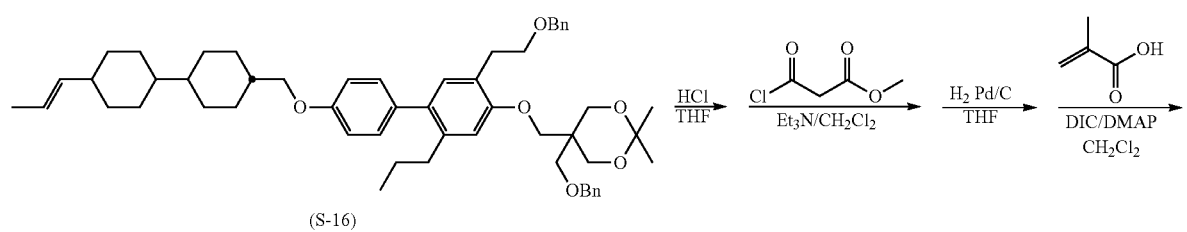
(S-16)

-continued

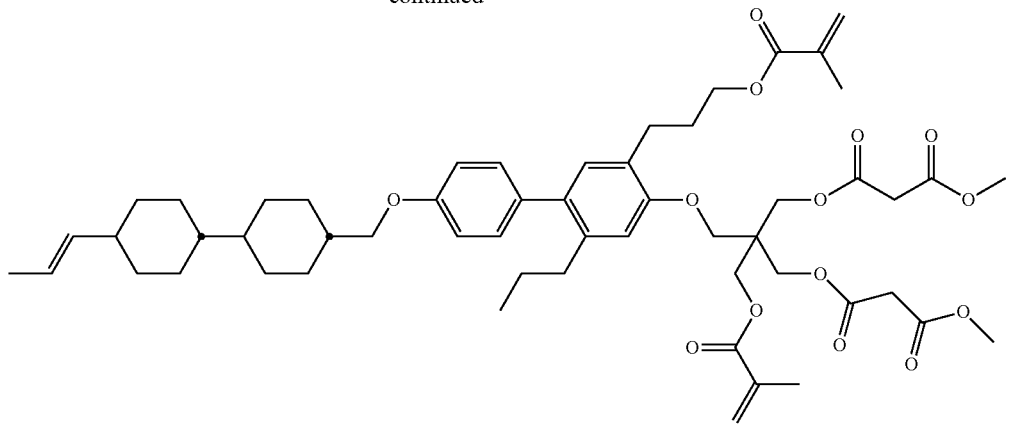

(P-1-25)

(Liquid Crystal Composition)

A liquid crystal composition according to the present embodiment contains one or two or more compounds with a partial structure represented by the general formula (i). The liquid crystal composition preferably has negative dielectric constant anisotropy (Δε). The compounds with a partial structure represented by the general formula (i) in the liquid crystal composition, including the compounds represented by the formulae (R-1-1) to (R-1-36), are the same as the compound (i) and are not described here.

The compound (i) content preferably ranges from 0.01% to 50% by mass, and the lower limit is preferably 0.01% or more by mass, 0.1% or more by mass, 0.5% or more by mass, 0.7% or more by mass, or 1% or more by mass of the total amount of the liquid crystal composition in order to further suitably align liquid crystal molecules. The upper limit of the compound (i) content is preferably 50% or less by mass, 30% or less by mass, 10% or less by mass, 7% or less by mass, 5% or less by mass, 4% or less by mass, or 3% or less by mass of the total amount of the liquid crystal composition in terms of response characteristics.

The liquid crystal composition may further contain as a nonpolymerizable liquid crystal compound a compound selected from the compound group represented by the general formulae (N-1), (N-2), and (N-3).

[Chem. 28]

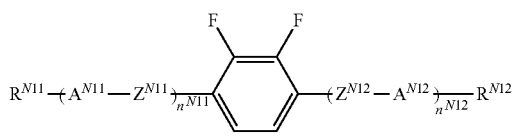
(N-1)

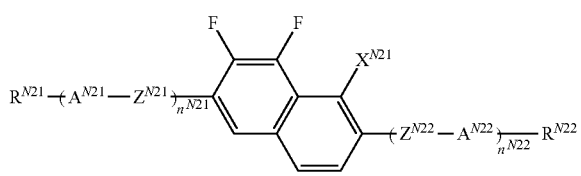
(N-2)

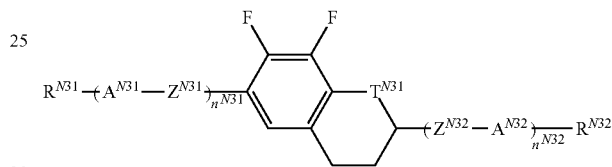
(N-3)

In the formulae (N-1), (N-2), and (N-3), $R^{N11}$, $R^{N12}$, $R^{N22}$, $R^{N22}$, $R^{N31}$, and $R^{N32}$ independently denote an alkyl group having 1 to 8 carbon atoms, and one —CH$_2$— or two or more nonadjacent —CH$_2$— groups in the alkyl group are independently optionally substituted with —CH=CH—, —C≡C—, —O—, —CO—, —COO—, or —OCO—, $A^{N11}$, $A^{N12}$, $A^{N21}$, $A^{N22}$, $A^{N31}$, and $A^{N32}$ independently denote a group selected from the group consisting of (a) a 1,4-cyclohexylene group (in which one —CH$_2$— or two or more nonadjacent —CH$_2$— groups are optionally substituted with —O—), (b) a 1,4-phenylene group (in which one —CH= or two or more nonadjacent —CH= groups are optionally substituted with —N=), (c) a naphthalene-2,6-diyl group, a 1,2,3,4-tetrahydronaphthalene-2,6-diyl group, or a decahydronaphthalene-2,6-diyl group (one —CH= or two or more nonadjacent —CH= groups in the naphthalene-2,6-diyl or 1,2,3,4-tetrahydronaphthalene-2,6-diyl group are optionally substituted with —N=), and (d) a 1,4-cyclohexenylene group.

The groups (a), (b), (c), and (d) are independently optionally substituted with a cyano group, a fluorine atom, or a chlorine atom, $Z^{N11}$, $Z^{N12}$, $Z^{N21}$, $Z^{N22}$, $Z^{N31}$, and $Z^{N32}$ independently denote a single bond, —CH$_2$CH$_2$—, —(CH$_2$)$_4$—, —OCH$_2$—, —CH$_2$O—, —COO—, —OCO—, —OCF$_2$—, —CF$_2$O—, —CH=N—N=CH—, —CH=CH—, —CF=CF—, or —C≡C—, $X^{N21}$ denotes a hydrogen atom or a fluorine atom, $T^{N31}$ denotes —CH$_2$— or an oxygen atom, $n^{N11}$, $n^{N12}$, $n^{N21}$, $n^{N22}$, $n^{N31}$, and $n^{N32}$ independently denote an integer in the range of 0 to 3, and $n^{N11}+n^{N12}$, $n^{N21}+n^{N22}$, and $n^{N31}+n^{N32}$ independently denote 1, 2, or 3, A plurality of $A^{N11}$s to $A^{N32}$s and $Z^{N11}$s to $Z^{N32}$s, if present, may be respectively the same or different.

A compound represented by the general formula (N-1), (N-2), or (N-3) preferably has a negative Δε with an absolute value of more than 3.

In the general formulae (N-1), (N-2), and (N-3), $R^{N11}$, $R^{N12}$, $R^{N21}$, $R^{N22}$, $R^{N31}$, and $R^{N32}$ independently denote an alkyl group having 1 to 8 carbon atoms, an alkoxy group having 1 to 8 carbon atoms, an alkenyl group having 2 to 8 carbon atoms, or an alkenyloxy group having 2 to 8 carbon atoms, preferably an alkyl group having 1 to 5 carbon atoms, an alkoxy group having 1 to 5 carbon atoms, an alkenyl group having 2 to 5 carbon atoms, or an alkenyloxy group having 2 to 5 carbon atoms, more preferably an alkyl group having 1 to 5 carbon atoms or an alkenyl group having 2 to 5 carbon atoms, still more preferably an alkyl group having 2 to 5 carbon atoms or an alkenyl group having 2 or 3 carbon atoms, particularly preferably an alkenyl group having 3 carbon atoms (a propenyl group).

If the ring structure to which it is bonded is a phenyl group (aromatic), then a linear alkyl group having 1 to 5 carbon atoms, a linear alkoxy group having 1 to 4 carbon atoms, and an alkenyl group having 4 or 5 carbon atoms are preferred. If the ring structure to which it is bonded is a saturated ring structure, such as cyclohexane, pyran, or dioxane, then a linear alkyl group having 1 to 5 carbon atoms, a linear alkoxy group having 1 to 4 carbon atoms, and a linear alkenyl group having 2 to 5 carbon atoms are preferred. To stabilize a nematic phase, the total number of carbon atoms and, if present, oxygen atoms is preferably 5 or less, and a straight chain is preferred.

The alkenyl group is preferably selected from the groups represented by the formulae (R1) to (R5) (the dark dot in each formula represents a bonding arm).

[Chem. 29]

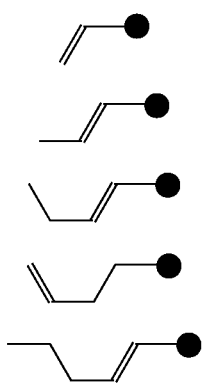

(R1)
(R2)
(R3)
(R4)
(R5)

$A^{N11}$, $A^{N12}$, $A^{N21}$, $A^{N22}$, $A^{N31}$, and $A^{N32}$ preferably independently denote an aromatic when an increase in Δn is desired, an aliphatic to improve the response speed, or a trans-1,4-cyclohexylene group, a 1,4-phenylene group, a 2-fluoro-1,4-phenylene group, a 3-fluoro-1,4-phenylene group, a 3,5-difluoro-1,4-phenylene group, a 2,3-difluoro-1,4-phenylene group, a 1,4-cyclohexenylene group, a 1,4-bicyclo[2.2.2]octylene group, a piperidine-1,4-diyl group, a naphthalene-2,6-diyl group, a decahydronaphthalene-2,6-diyl group, or a 1,2,3,4-tetrahydronaphthalene-2,6-diyl group, more preferably one of the following structures,

[Chem. 30]

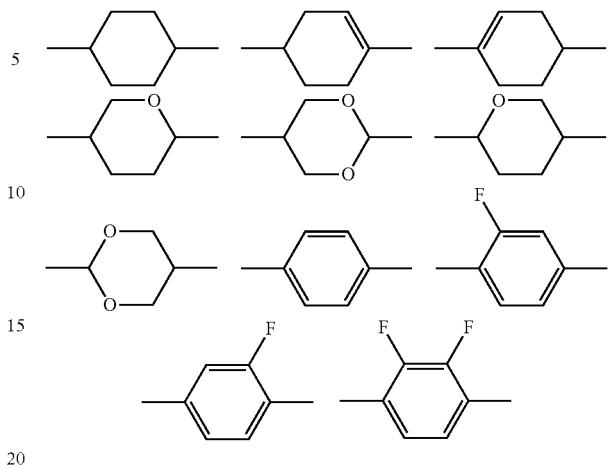

still more preferably a trans-1,4-cyclohexylene group, a 1,4-cyclohexenylene group, or a 1,4-phenylene group.

$Z^{N11}$, $Z^{N12}$, $Z^{N21}$, $Z^{N22}$, $Z^{N31}$, and $Z^{N32}$ preferably independently denote —CH$_2$O—, —CF$_2$O—, —CH$_2$CH$_2$—, —CF$_2$CF$_2$—, or a single bond, more preferably —CH$_2$O—, —CH$_2$CH$_2$—, or a single bond, particularly preferably —CH$_2$O— or a single bond.

$X^{N21}$ preferably denotes a fluorine atom.

$T^{N31}$ preferably denotes an oxygen atom.

$n^{N11}+n^{N12}$, $n^{N21}+n^{N22}$, and $n^{N31}+n^{N32}$ are preferably 1 or 2, and a combination of $n^{N11}=1$ and $n^{N12}=0$, a combination of $n^{N11}=2$ and $n^{N12}=0$, a combination of $n^{N11}=1$ and $n^{N12}=1$, a combination of $n^{N11}=2$ and $n^{N12}=1$, a combination of $n^{N21}=1$ and $n^{N22}=0$, a combination of $n^{N21}=2$ and $n^{N22}=0$, a combination of $n^{N31}=1$ and $n^{N32}=0$, and a combination of $n^{N31}=2$ and $n^{N32}=0$ are preferred.

The lower limit of the preferred amount of compound represented by the formula (N-1) is 1% or more by mass, 10% or more by mass, 20% or more by mass, 30% or more by mass, 40% or more by mass, 50% or more by mass, 55% or more by mass, 60% or more by mass, 65% or more by mass, 70% or more by mass, 75% or more by mass, or 80% or more by mass of the total amount of the composition according to the present embodiment. The upper limit of the preferred amount is 95% or less by mass, 85% or less by mass, 75% or less by mass, 65% or less by mass, 55% or less by mass, 45% or less by mass, 35% or less by mass, 25% or less by mass, or 20% or less by mass.

The lower limit of the preferred amount of compound represented by the formula (N-2) is 1% or more by mass, 10% or more by mass, 20% or more by mass, 30% or more by mass, 40% or more by mass, 50% or more by mass, 55% or more by mass, 60% or more by mass, 65% or more by mass, 70% or more by mass, 75% or more by mass, or 80% or more by mass of the total amount of the composition according to the present embodiment. The upper limit of the preferred amount is 95% or less by mass, 85% or less by mass, 75% or less by mass, 65% or less by mass, 55% or less by mass, 45% or less by mass, 35% or less by mass, 25% or less by mass, or 20% or less by mass.

The lower limit of the preferred amount of compound represented by the formula (N-3) is 1% or more by mass, 10% or more by mass, 20% or more by mass, 30% or more by mass, 40% or more by mass, 50% or more by mass, 55% or more by mass, 60% or more by mass, 65% or more by mass, 70% or more by mass, 75% or more by mass, or 80% or more by mass of the total amount of the composition according to the present embodiment. The upper limit of the preferred amount is 95% or less by mass, 85% or less by mass, 75% or less by mass, 65% or less by mass, 55% or less by mass, 45% or less by mass, 35% or less by mass, 25% or less by mass, or 20% or less by mass.

When a composition according to the present embodiment with a low viscosity and with a high response speed is required, the lower limit is preferably low, and the upper limit is preferably low. When a composition according to the present embodiment with a high Tni and with high temperature stability is required, the lower limit is preferably low, and the upper limit is preferably low. When dielectric constant anisotropy is increased to maintain a low drive voltage, the lower limit is preferably high, and the upper limit is preferably high.

The compounds represented by the general formula (N-1) include the compound group represented by the following general formulae (N-1a) to (N-1g).

[Chem. 31]

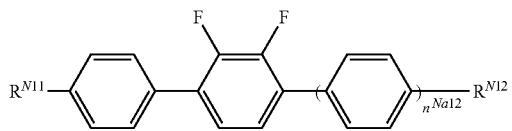
(N-1a)

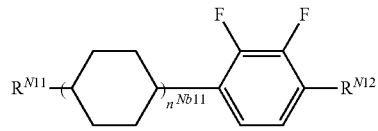
(N-1b)

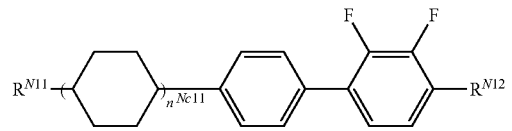
(N-1c)

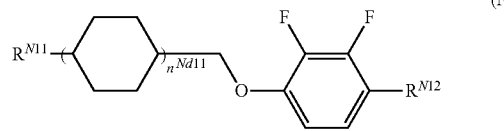
(N-1d)

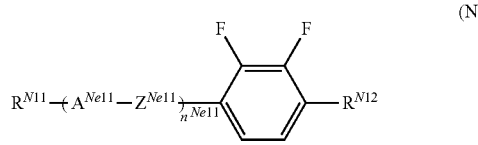
(N-1e)

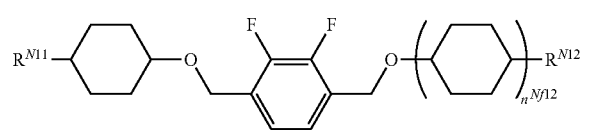
(N-1f)

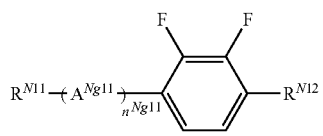
(N-1g)

(In the formulae, $R^{N11}$ and $R^{N12}$ have the same meaning as $R^{N11}$ and $R^{N12}$ in the general formula (N-1), $n^{Na11}$ denotes 0 or 1, $n^{Nb11}$ denotes 0 or 1 $n^{Nc11}$ denotes 0 or $n^{Nd11}$ denotes 0 or 1, $n^{Ne11}$ denotes 1 or 2, $n^{Nf11}$ denotes 1 or 2, $n^{Ng11}$ denotes 1 or 2, $A^{Ne11}$ denotes a trans-1,4-cyclohexylene group or a 1,4-phenylene group, $A^{Ng11}$ denotes a trans-1,4-cyclohexylene group, a 1,4-cyclohexenylene group, or a 1,4-phenylene group, at least one of $A^{Ng11}$s denotes a 1,4-cyclohexenylene group, $Z^{Ne11}$ denotes a single bond or ethylene, and at least one of $Z^{Ne11}$s denotes ethylene.)

More specifically, a compound represented by the general formula (N-1) is preferably a compound selected from the compound group represented by the general formulae (N-1-1) to (N-1-21).

A compound represented by the general formula (N-1-1) is the following compound.

[Chem. 32]

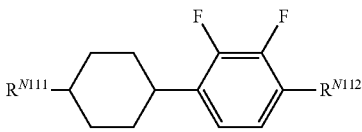
(N-1-1)

(In the formula, $R^{N111}$ and $R^{N112}$ have the same meaning as $R^{N11}$ and $R^{N12}$, respectively, in the general formula (N-1).)

$R^{N111}$ preferably denotes an alkyl group having 1 to 5 carbon atoms or an alkenyl group having 2 to 5 carbon atoms, preferably a propyl group, a pentyl group, or a vinyl group. $R^{N112}$ preferably denotes an alkyl group having 1 to 5 carbon atoms, an alkenyl group having 4 or 5 carbon atoms, or an alkoxy group having 1 to 4 carbon atoms, preferably an ethoxy group or a butoxy group.

The compounds represented by the general formula (N-1-1) may be used alone or as a combination of two or more thereof. Although compounds of any types may be combined, these compounds are appropriately combined in a manner that depends on the desired characteristics, such as solubility at low temperatures, transition temperature, electrical reliability, and birefringence index. For example, one, two, three, four, five, or more compounds are used in one embodiment of the present invention.

The amount is preferably set somewhat larger when improved Δε is regarded as important, is effectively set somewhat larger when solubility at low temperatures is regarded as important, and is effectively set somewhat smaller when $T_{NI}$ is regarded as important. The amount is preferably set in a medium range to reduce drop marks and improve image-sticking characteristics.

The lower limit of the preferred amount of a compound represented by the formula (N-1-1) is 5%, 10%, 13%, 15%, 17%, 20%, 23%, 25%, 27%, 30%, 33%, or 35% of the total amount of a composition according to the present invention. The upper limit of the preferred amount is 50%, 40%, 38%, 35%, 33%, 30%, 28%, 25%, 23%, 20%, 18%, 15%, 13%, 10%, 8%, 7%, 6%, 5%, or 3% of the total amount of a composition according to the present invention.

A compound represented by the general formula (N-1-1) is preferably a compound selected from the compound group represented by the formulae (N-1-1.1) to (N-1-1.23), preferably a compound represented by one of the formulae (N-1-1.1) to (N-1-1.4), preferably the compound represented by the formula (N-1-1.1) or (N-1-1.3).

[Chem. 33]

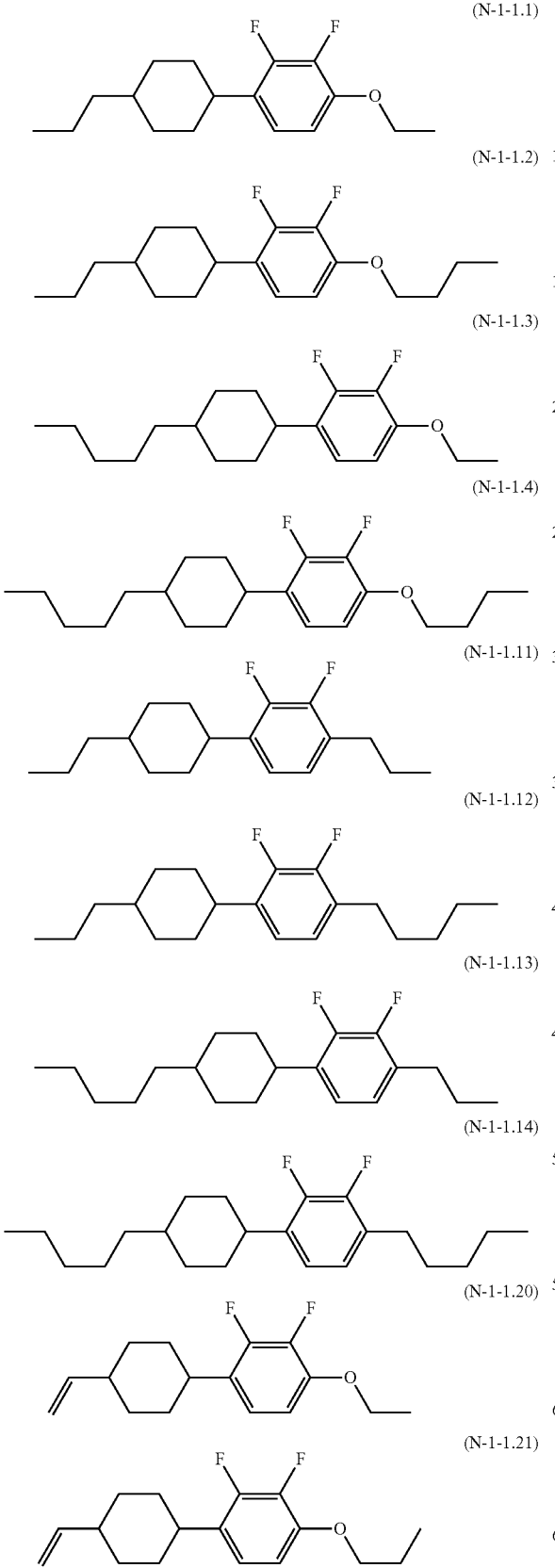

(N-1-1.1)
(N-1-1.2)
(N-1-1.3)
(N-1-1.4)
(N-1-1.11)
(N-1-1.12)
(N-1-1.13)
(N-1-1.14)
(N-1-1.20)
(N-1-1.21)

-continued

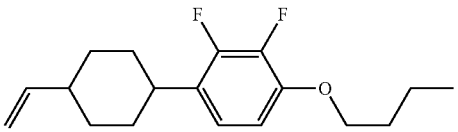

(N-1-1.22)

The compounds represented by the formulae (N-1-1.1) to (N-1-1.22) may be used alone or in combination. The lower limit of the preferred amount of each compound or these compounds is 5%, 10%, 13%, 15%, 17%, 20%, 23%, 25%, 27%, 30%, 33%, or 35% of the total amount of a composition according to the present invention. The upper limit of the preferred amount is 50%, 40%, 38%, 35%, 33%, 30%, 28%, 25%, 23%, 20%, 18%, 15%, 13%, 10%, 8%, 7%, 6%, 5%, or 3% of the total amount of a composition according to the present invention.

A compound represented by the general formula (N-1-2) is the following compound.

[Chem. 34]

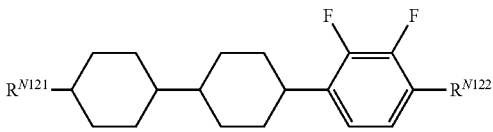

(N-1-2)

(In the formula, $R^{N121}$ and $R^{N122}$ have the same meaning as $R^{N11}$ and $R^{N12}$, respectively, in the general formula (N-1).)

$R^{N121}$ preferably denotes an alkyl group having 1 to 5 carbon atoms or an alkenyl group having 2 to 5 carbon atoms, preferably an ethyl group, a propyl group, a butyl group, or a pentyl group. $R^{N122}$ preferably denotes an alkyl group having 1 to 5 carbon atoms, an alkenyl group having 4 or 5 carbon atoms, or an alkoxy group having 1 to 4 carbon atoms, preferably a methyl group, a propyl group, a methoxy group, an ethoxy group, or a propoxy group.

The compounds represented by the general formula (N-1-2) may be used alone or as a combination of two or more thereof. Although compounds of any types may be combined, these compounds are appropriately combined in a manner that depends on the desired characteristics, such as solubility at low temperatures, transition temperature, electrical reliability, and birefringence index. For example, one, two, three, four, five, or more compounds are used in one embodiment of the present invention.

The amount is preferably set somewhat larger when improved Δε is regarded as important, is effectively set somewhat smaller when solubility at low temperatures is regarded as important, and is effectively set somewhat larger when $T_{NI}$ is regarded as important. The amount is preferably set in a medium range to reduce drop marks and improve image-sticking characteristics.

The lower limit of the preferred amount of a compound represented by the formula (N-1-2) is 5%, 7%, 10%, 13%, 15%, 17%, 20%, 23%, 25%, 27%, 30%, 33%, 35%, 37%, 40%, or 42% of the total amount of a composition according to the present invention. The upper limit of the preferred amount is 50%, 48%, 45%, 43%, 40%, 38%, 35%, 33%, 30%, 28%, 25%, 23%, 20%, 18%, 15%, 13%, 10%, 8%, 7%, 6%, or 5% of the total amount of a composition according to the present invention.

A compound represented by the general formula (N-1-2) is preferably a compound selected from the compound group represented by the formulae (N-1-2.1) to (N-1-2.22), preferably a compound represented by one of the formulae (N-1-2.3) to (N-1-2.7), (N-1-2.10), (N-1-2.11), (N-1-2.13), and (N-1-2.20), preferably a compound represented by one of the formulae (N-1-2.3) to (N-1-2.7) when improved Δε is regarded as important, preferably the compound represented by the formula (N-1-2.10), (N-1-2.1), or (N-1-2.13) when improved $T_{NI}$ is regarded as important, or preferably the compound represented by the formula (N-1-2.20) when an improved response speed is regarded as important.

[Chem. 35]

(N-1-2.1)

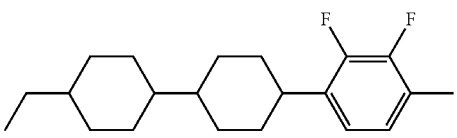

(N-1-2.2)

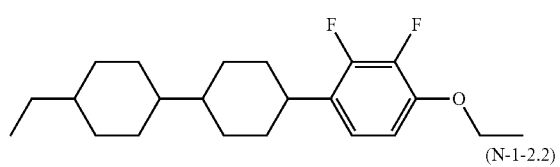

(N-1-2.3)

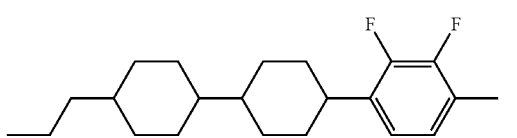

(N-1-2.4)

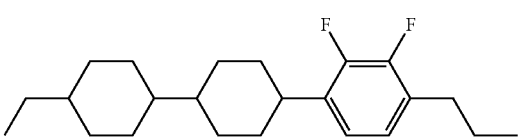

(N-1-2.5)

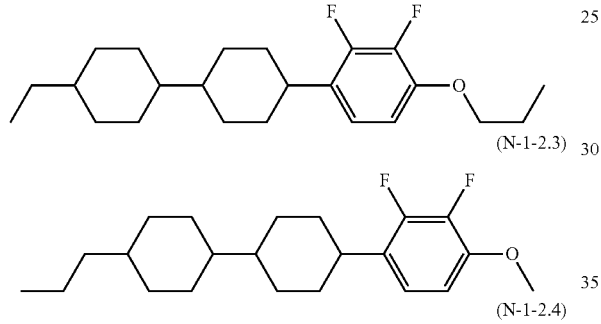

(N-1-2.6)

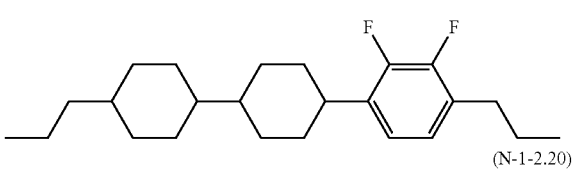

(N-1-2.7)

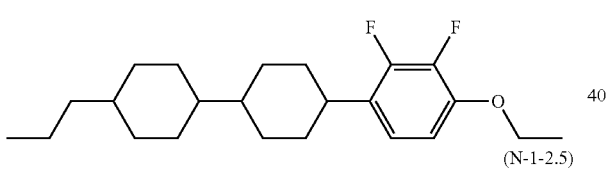

(N-1-2.8)

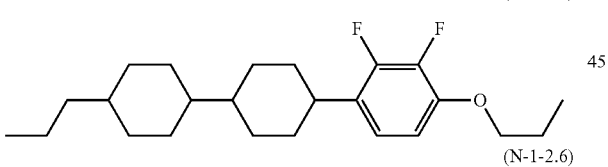

(N-1-2.10)

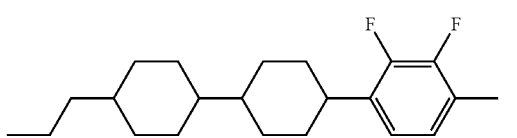

(N-1-2.11)

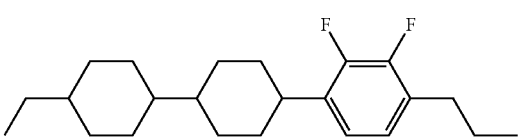

(N-1-2.12)

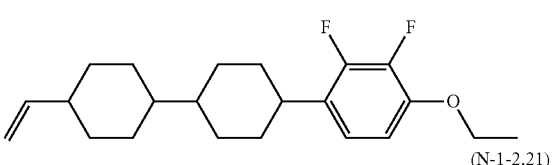

(N-1-2.13)

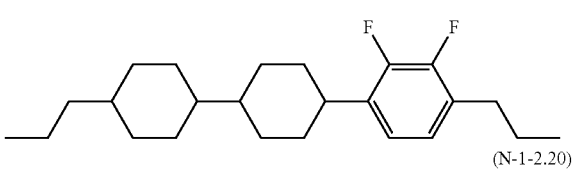

(N-1-2.20)

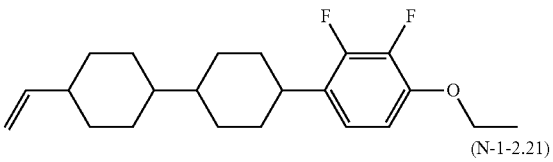

(N-1-2.21)

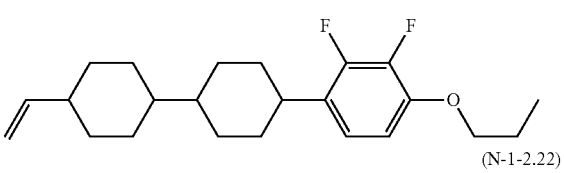

(N-1-2.22)

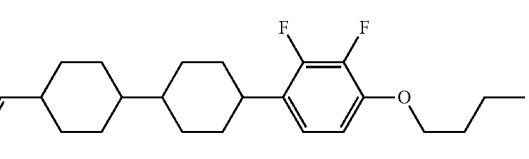

The compounds represented by the formulae (N-1-2.1) to (N-1-2.22) may be used alone or in combination. The lower limit of the preferred amount of each compound or these compounds is 5%, 10%, 13%, 15%, 17%, 20%, 23%, 25%, 27%, 30%, 33%, or 35% of the total amount of a composition according to the present invention. The upper limit of the preferred amount is 50%, 40%, 38%, 35%, 33%, 30%, 28%, 25%, 23%, 20%, 18%, 15%, 13%, 10%, 8%, 7%, 6%, 5%, or 3% of the total amount of a composition according to the present invention.

A compound represented by the general formula (N-1-3) is the following compound.

[Chem. 36]

(N-1-3)

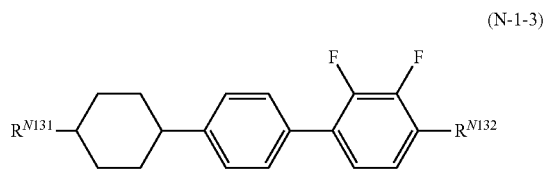

(In the formula, $R^{N131}$ and $R^{N132}$ have the same meaning as $R^{N11}$ and $R^{N12}$, respectively, in the general formula (N-1).)

$R^{N131}$ preferably denotes an alkyl group having 1 to 5 carbon atoms or an alkenyl group having 2 to 5 carbon atoms, preferably an ethyl group, a propyl group, or a butyl group. $R^{N132}$ preferably denotes an alkyl group having 1 to 5 carbon atoms, an alkenyl group having 3 to 5 carbon atoms, or an alkoxy group having 1 to 4 carbon atoms, preferably a 1-propenyl group, an ethoxy group, a propoxy group, or a butoxy group.

The compounds represented by the general formula (N-1-3) may be used alone or as a combination of two or more thereof. Although compounds of any types may be combined, these compounds are appropriately combined in a manner that depends on the desired characteristics, such as solubility at low temperatures, transition temperature, electrical reliability, and birefringence index. For example, one, two, three, four, five, or more compounds are used in one embodiment of the present invention.

The amount is preferably set somewhat larger when improved Δε is regarded as important, is effectively set somewhat larger when solubility at low temperatures is regarded as important, and is effectively set somewhat larger when $T_1$ is regarded as important. The amount is preferably set in a medium range to reduce drop marks and improve image-sticking characteristics.

The lower limit of the preferred amount of a compound represented by the formula (N-1-3) is 5%, 10%, 13%, 15%, 17%, or 20% of the total amount of a composition according to the present invention. The upper limit of the preferred amount is 35%, 30%, 28%, 25%, 23%, 20%, 18%, 15%, or 13% of the total amount of a composition according to the present invention.

A compound represented by the general formula (N-1-3) is preferably a compound selected from the compound group represented by the formulae (N-1-3.1) to (N-1-3.21), preferably a compound represented by one of the formulae (N-1-3.1) to (N-1-3.7) and (N-1-3.21), preferably the compound represented by the formula (N-1-3.1), (N-1-3.2), (N-1-3.3), (N-1-3.4), or (N-1-3.6).

[Chem. 37]

(N-1-3.1)

(N-1-3.2)

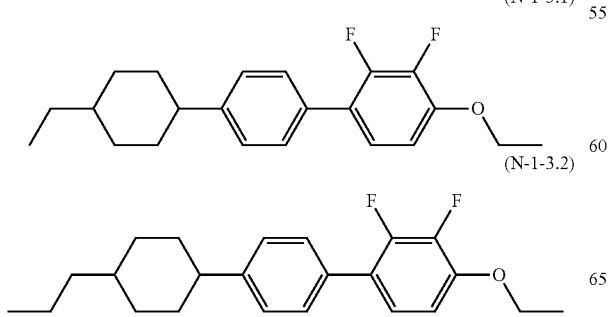

(N-1-3.3)

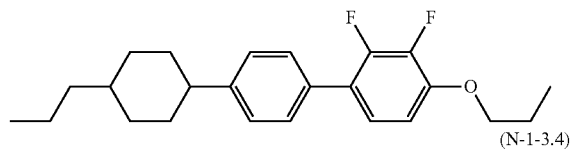

(N-1-3.4)

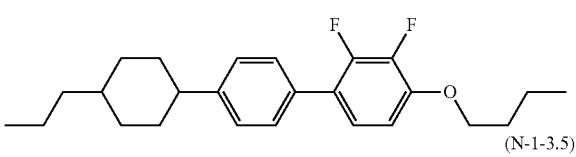

(N-1-3.5)

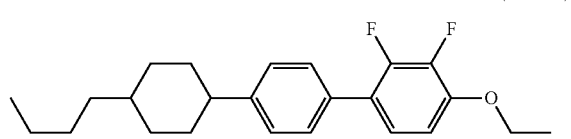

(N-1-3.5)

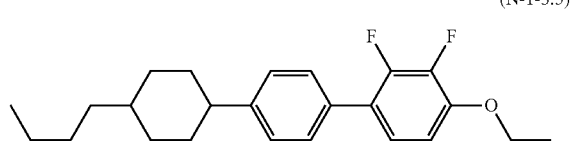

(N-1-3.6)

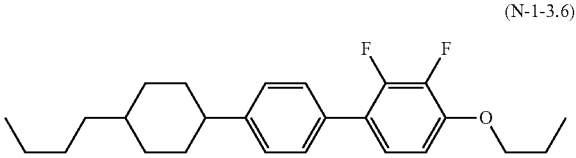

(N-1-3.7)

(N-1-3.10)

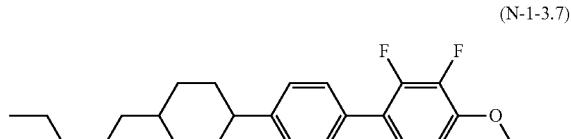

(N-1-3.11)

(N-1-3.20)

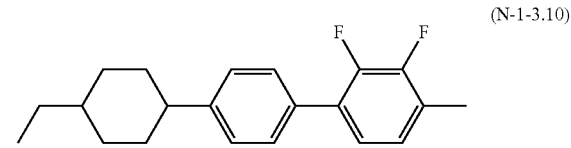

(N-1-3.21)

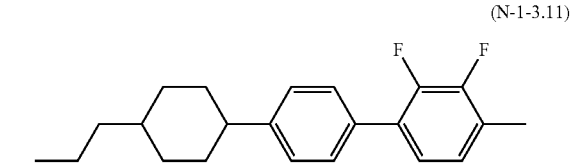

The compounds represented by the formulae (N-1-3.1) to (N-1-3.4), (N-1-3.6), and (N-1-3.21) may be used alone or in combination. A combination of the formula (N-1-3.1) and the formula (N-1-3.2) or a combination of two or three selected from the formulae (N-1-3.3), (N-1-3.4), and (N-1-3.6) is preferred. The lower limit of the preferred amount of each compound or these compounds is 5%, 10%, 13%, 15%, 17%, or 20% of the total amount of a composition according to the present invention. The upper limit of the preferred amount is 35%, 30%, 28%, 25%, 23%, 20%, 18%, 15%, or 13% of the total amount of a composition according to the present invention.

A compound represented by the general formula (N-1-4) is the following compound.

[Chem. 38]

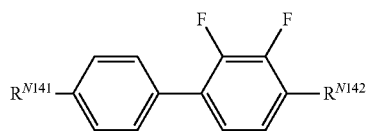

(N-1-4)

(In the formula, $R^{N141}$ and $R^{N142}$ have the same meaning as $R^{N11}$ and $R^{N12}$, respectively, in the general formula (N-1).)

$R^{N141}$ and $R^{N142}$ preferably independently denote an alkyl group having 1 to 5 carbon atoms, an alkenyl group having 4 or 5 carbon atoms, or an alkoxy group having 1 to 4 carbon atoms, preferably a methyl group, a propyl group, an ethoxy group, or a butoxy group.

The compounds represented by the general formula (N-1-4) may be used alone or as a combination of two or more thereof. Although compounds of any types may be combined, these compounds are appropriately combined in a manner that depends on the desired characteristics, such as solubility at low temperatures, transition temperature, electrical reliability, and birefringence index. For example, one, two, three, four, five, or more compounds are used in one embodiment of the present invention.

The amount is preferably set somewhat larger when improved $\Delta\varepsilon$ is regarded as important, is effectively set somewhat larger when solubility at low temperatures is regarded as important, and is effectively set somewhat smaller when $T_H$ is regarded as important. The amount is preferably set in a medium range to reduce drop marks and improve image-sticking characteristics.

The lower limit of the preferred amount of a compound represented by the formula (N-1-4) is 3%, 5%, 7%, 10%, 13%, 15%, 17%, or 20% of the total amount of a composition according to the present invention. The upper limit of the preferred amount is 35%, 30%, 28%, 25%, 23%, 20%, 18%, 15%, 13%, 11%, 10%, or 8% of the total amount of a composition according to the present invention.

A compound represented by the general formula (N-1-4) is preferably a compound selected from the compound group represented by the formulae (N-1-4.1) to (N-1-4.14), preferably a compound represented by one of the formulae (N-1-4.1) to (N-1-4.4), preferably the compound represented by the formula (N-1-4.1), (N-1-4.2), or (N-1-4.4).

[Chem. 39]

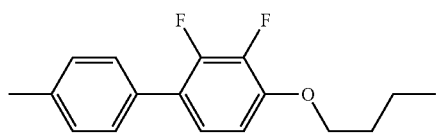

(N-1-4.1)

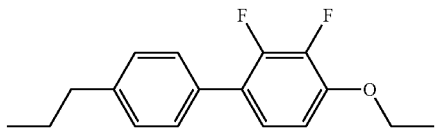

(N-1-4.2)

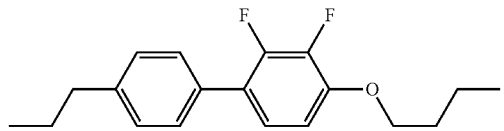

(N-1-4.3)

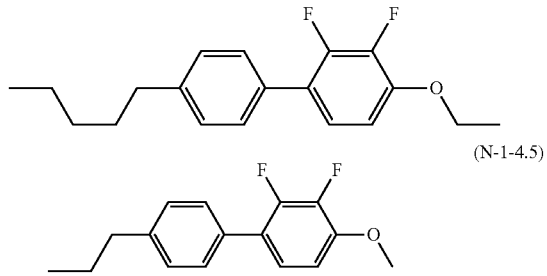

(N-1-4.4)

(N-1-4.5)

(N-1-4.6)

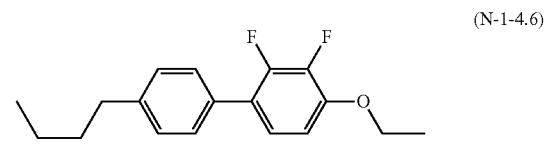

(N-1-4.11)

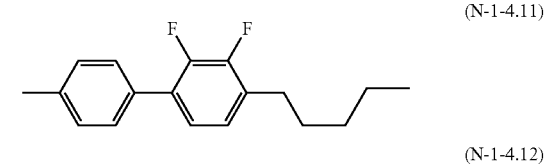

(N-1-4.12)

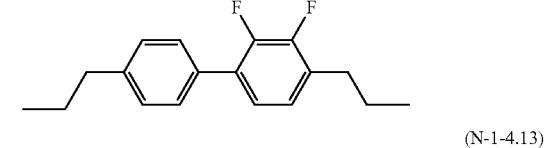

(N-1-4.13)

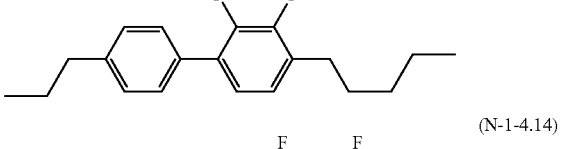

(N-1-4.14)

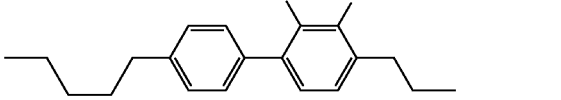

The compounds represented by the formulae (N-1-4.1) to (N-1-4.14) may be used alone or in combination. The lower limit of the preferred amount of each compound or these compounds is 3%, 5%, 7%, 10%, 13%, 15%, 17%, or 20% of the total amount of a composition according to the present invention. The upper limit of the preferred amount is 35%, 30%, 28%, 25%, 23%, 20%, 18%, 15%, 13%, 11%, 10%, or 8% of the total amount of a composition according to the present invention.

A compound represented by the general formula (N-1-5) is the following compound.

[Chem. 40]

(N-1-5)

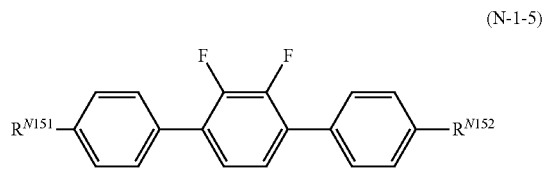

(In the formula, $R^{N151}$ and $R^{N152}$ have the same meaning as $R^{N11}$ and $R^{N12}$, respectively, in the general formula (N-1).)

$R^{N151}$ and $R^{N152}$ preferably independently denote an alkyl group having 1 to 5 carbon atoms, an alkenyl group having 4 or 5 carbon atoms, or an alkoxy group having 1 to 4 carbon atoms, preferably an ethyl group, a propyl group, or a butyl group.

The compounds represented by the general formula (N-1-5) may be used alone or as a combination of two or more thereof. Although compounds of any types may be combined, these compounds are appropriately combined in a manner that depends on the desired characteristics, such as solubility at low temperatures, transition temperature, electrical reliability, and birefringence index. For example, one, two, three, four, five, or more compounds are used in one embodiment of the present invention.

The amount is preferably set somewhat larger when improved Δε is regarded as important, is effectively set somewhat smaller when solubility at low temperatures is regarded as important, and is effectively set somewhat larger when $T_{NI}$ is regarded as important. The amount is preferably set in a medium range to reduce drop marks and improve image-sticking characteristics.

The lower limit of the preferred amount of a compound represented by the formula (N-1-5) is 5%, 8%, 10%, 13%, 15%, 17%, or 20% of the total amount of a composition according to the present invention. The upper limit of the preferred amount is 35%, 33%, 30%, 28%, 25%, 23%, 20%, 18%, 15%, or 13% of the total amount of a composition according to the present invention.

A compound represented by the general formula (N-1-5) is preferably a compound selected from the compound group represented by the formulae (N-1-5.1) to (N-1-5.6), preferably the compound represented by the formula (N-1-5.1), (N-1-5.2), or (N-1-5.4).

[Chem. 41]

(N-1-5.1)

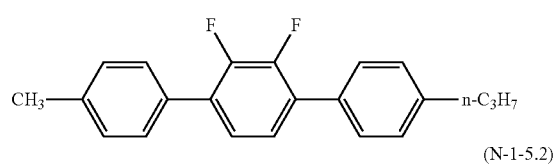

(N-1-5.2)

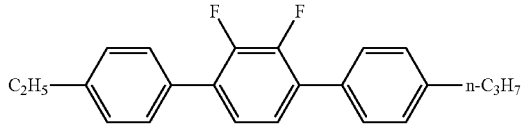

(N-1-5.3)

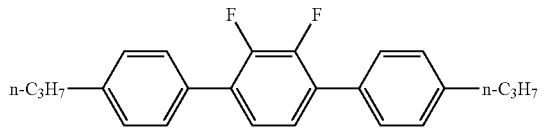

(N-1-5.4)

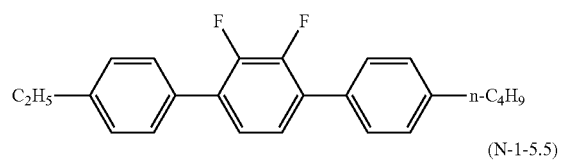

(N-1-5.5)

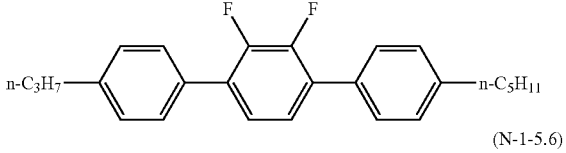

(N-1-5.6)

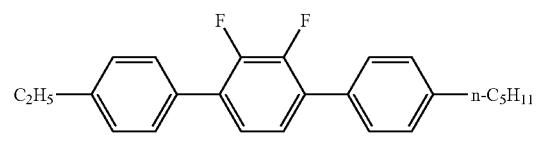

The compounds represented by the formulae (N-1-5.1), (N-1-5.2), and (N-1-5.4) may be used alone or in combination. The lower limit of the preferred amount of each compound or these compounds is 5%, 8%, 10%, 13%, 15%, 17%, or 20% of the total amount of a composition according to the present invention. The upper limit of the preferred amount is 35%, 33%, 30%, 28%, 25%, 23%, 20%, 18%, 15%, or 13% of the total amount of a composition according to the present invention.

A compound represented by the general formula (N-1-10) is the following compound.

[Chem. 42]

(N-1-10)

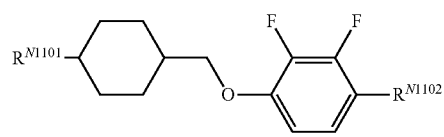

(In the formula, $R^{N1101}$ and $R^{N1102}$ have the same meaning as $R^{N11}$ and $R^{N12}$, respectively, in the general formula (N-1).)

$R^{N1101}$ preferably denotes an alkyl group having 1 to 5 carbon atoms or an alkenyl group having 2 to 5 carbon atoms, preferably an ethyl group, a propyl group, a butyl group, a vinyl group, or a 1-propenyl group. $R^{N1102}$ preferably denotes an alkyl group having 1 to 5 carbon atoms, an alkenyl group having 4 or 5 carbon atoms, or an alkoxy group having 1 to 4 carbon atoms, preferably an ethoxy group, a propoxy group, or a butoxy group.

The compounds represented by the general formula (N-1-10) may be used alone or as a combination of two or more thereof. Although compounds of any types may be combined, these compounds are appropriately combined in a manner that depends on the desired characteristics, such as solubility at low temperatures, transition temperature, electrical reliability, and birefringence index. For example, one, two, three, four, five, or more compounds are used in one embodiment of the present invention.

The amount is preferably set somewhat larger when improved Δε is regarded as important, is effectively set somewhat larger when solubility at low temperatures is regarded as important, and is effectively set somewhat smaller when $T_R$ is regarded as important. The amount is preferably set in a medium range to reduce drop marks and improve image-sticking characteristics.

The lower limit of the preferred amount of a compound represented by the formula (N-1-10) is 5%, 10%, 13%, 15%, 17%, or 20% of the total amount of a composition according to the present invention. The upper limit of the preferred amount is 35%, 30%, 28%, 25%, 23%, 20%, 18%, 15%, or 13% of the total amount of a composition according to the present invention.

A compound represented by the general formula (N-1-10) is preferably a compound selected from the compound group represented by the formulae (N-1-10.1) to (N-1-10.14), preferably a compound represented by one of the formulae (N-1-10.1) to (N-1-10.5), preferably the compound represented by the formula (N-1-10.1) or (N-1-10.2).

[Chem. 43]

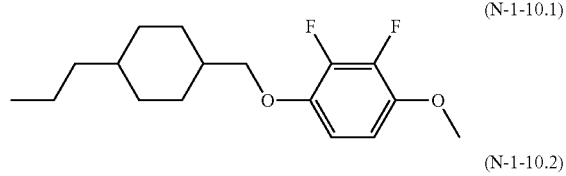
(N-1-10.1)

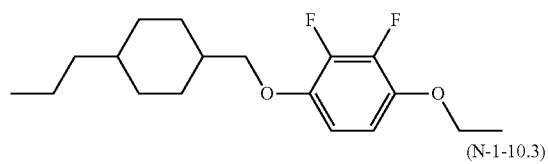
(N-1-10.2)

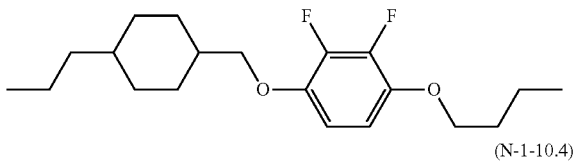
(N-1-10.3)

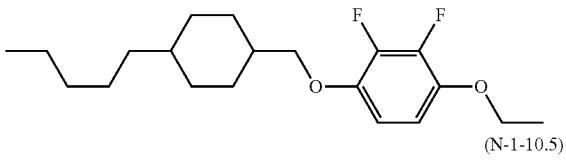
(N-1-10.4)

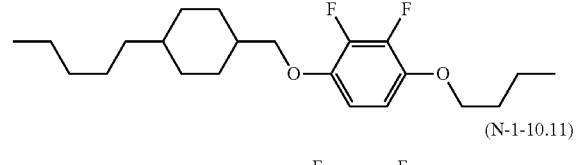
(N-1-10.5)

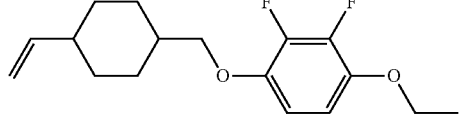
(N-1-10.11)

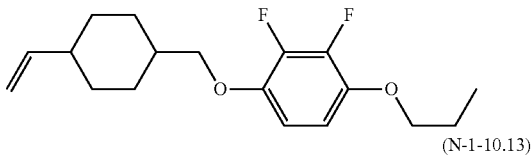
(N-1-10.12)

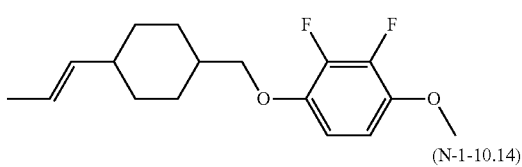
(N-1-10.13)

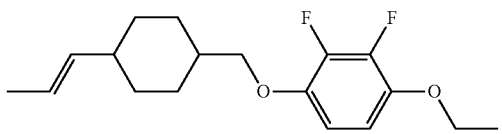
(N-1-10.14)

The compounds represented by the formulae (N-1-10.1) and (N-1-10.2) may be used alone or in combination. The lower limit of the preferred amount of each compound or these compounds is 5%, 10%, 13%, 15%, 17%, or 20% of the total amount of a composition according to the present invention. The upper limit of the preferred amount is 35%, 30%, 28%, 25%, 23%, 20%, 18%, 15%, or 13% of the total amount of a composition according to the present invention.

A compound represented by the general formula (N-1-11) is the following compound.

[Chem. 44]

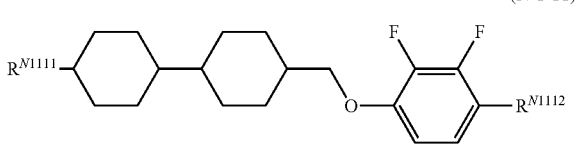
(N-1-11)

(In the formula, $R^{N1111}$ and $R^{N1112}$ have the same meaning as $R^{N11}$ and $R^{N12}$, respectively, in the general formula (N-1).)

$R^{N1111}$ preferably denotes an alkyl group having 1 to 5 carbon atoms or an alkenyl group having 2 to 5 carbon atoms, preferably an ethyl group, a propyl group, a butyl group, a vinyl group, or a 1-propenyl group. $R^{N1112}$ preferably denotes an alkyl group having 1 to 5 carbon atoms, an alkenyl group having 4 or 5 carbon atoms, or an alkoxy group having 1 to 4 carbon atoms, preferably an ethoxy group, a propoxy group, or a butoxy group.

The compounds represented by the general formula (N-1-11) may be used alone or as a combination of two or more thereof. Although compounds of any types may be combined, these compounds are appropriately combined in a manner that depends on the desired characteristics, such as solubility at low temperatures, transition temperature, electrical reliability, and birefringence index. For example, one, two, three, four, five, or more compounds are used in one embodiment of the present invention.

The amount is preferably set somewhat larger when improved Δε is regarded as important, is effectively set somewhat smaller when solubility at low temperatures is regarded as important, and is effectively set somewhat larger when $T_N$ is regarded as important. The amount is preferably set in a medium range to reduce drop marks and improve image-sticking characteristics.

The lower limit of the preferred amount of a compound represented by the formula (N-1-li) is 5%, 10%, 13%, 15%, 17%, or 20% of the total amount of a composition according to the present invention. The upper limit of the preferred amount is 35%, 30%, 28%, 25%, 23%, 20%, 18%, 15%, or 13% of the total amount of a composition according to the present invention.

A compound represented by the general formula (N-1-11) is preferably a compound selected from the compound group represented by the formulae (N-1-11.1) to (N-1-11.14), preferably a compound represented by one of the formulae (N-1-11.1) to (N-1-11.14), preferably a compound represented by one of the formulae (N-1-11.2 and (N-1-11.4).

[Chem. 45]

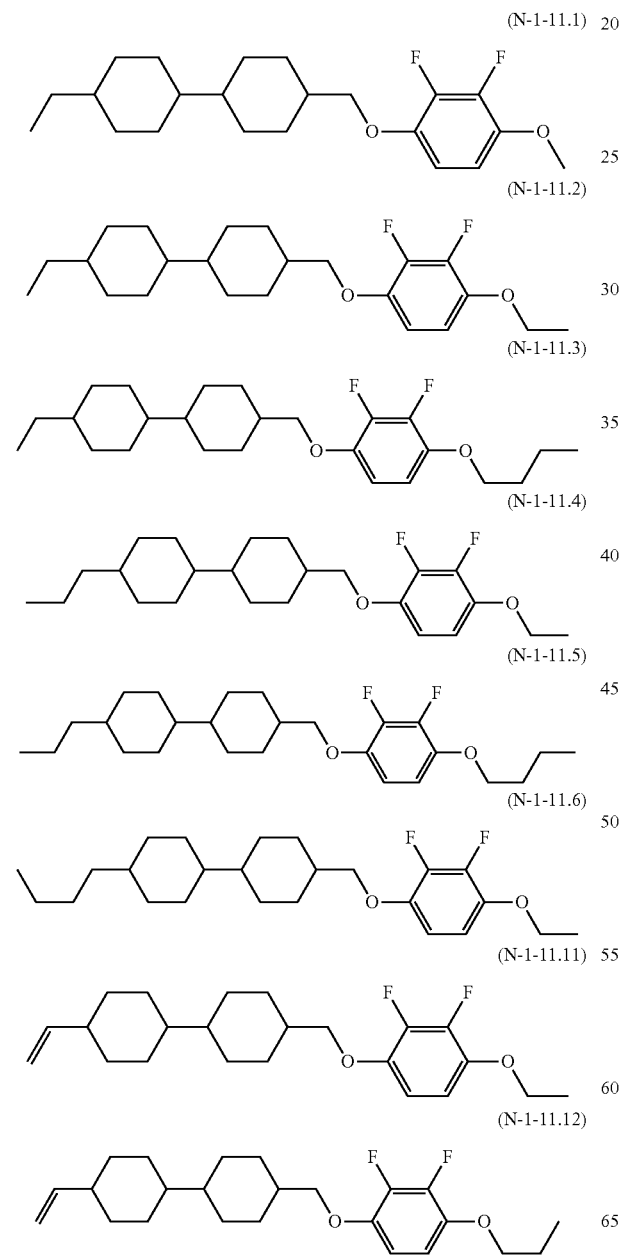
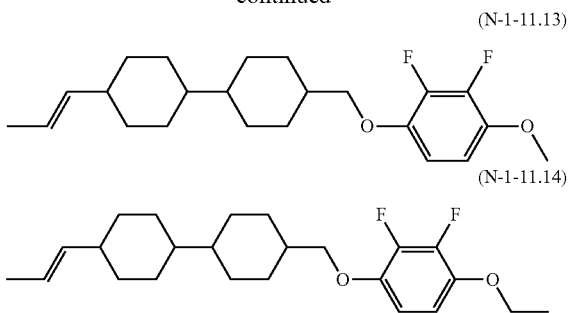

The compounds represented by the formulae (N-1-11.2) and (N-1-11.4) may be used alone or in combination. The lower limit of the preferred amount of each compound or these compounds is 5%, 10%, 13%, 15%, 17%, or 20% of the total amount of a composition according to the present invention. The upper limit of the preferred amount is 35%, 30%, 28%, 25%, 23%, 20%, 18%, 15%, or 13% of the total amount of a composition according to the present invention.

A compound represented by the general formula (N-1-12) is the following compound.

[Chem. 46]

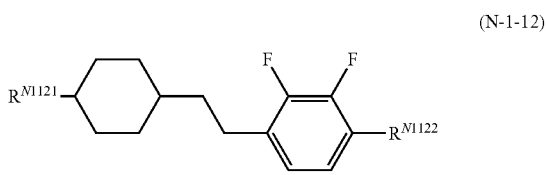

(In the formula, $R^{N1121}$ and $R^{N1122}$ have the same meaning as $R^{N11}$ and $R^{N12}$, respectively, in the general formula (N-1).)

$R^{N1112}$ preferably denotes an alkyl group having 1 to 5 carbon atoms or an alkenyl group having 2 to 5 carbon atoms, preferably an ethyl group, a propyl group, or a butyl group. $R^{N1122}$ preferably denotes an alkyl group having 1 to 5 carbon atoms, an alkenyl group having 4 or 5 carbon atoms, or an alkoxy group having 1 to 4 carbon atoms, preferably an ethoxy group, a propoxy group, or a butoxy group.

The compounds represented by the general formula (N-1-12) may be used alone or as a combination of two or more thereof. Although compounds of any types may be combined, these compounds are appropriately combined in a manner that depends on the desired characteristics, such as solubility at low temperatures, transition temperature, electrical reliability, and birefringence index. For example, one, two, three, four, five, or more compounds are used in one embodiment of the present invention.

The amount is preferably set somewhat larger when improved Δε is regarded as important, is effectively set somewhat larger when solubility at low temperatures is regarded as important, and is effectively set somewhat smaller when $T_{NI}$ is regarded as important. The amount is preferably set in a medium range to reduce drop marks and improve image-sticking characteristics.

The lower limit of the preferred amount of a compound represented by the formula (N-1-12) is 5%, 10%, 13%, 15%, 17%, or 20% of the total amount of a composition according to the present invention. The upper limit of the preferred amount is 35%, 30%, 28%, 25%, 23%, 20%, 18%, 15%, or 13% of the total amount of a composition according to the present invention.

A compound represented by the general formula (N-1-13) is the following compound.

[Chem. 47]

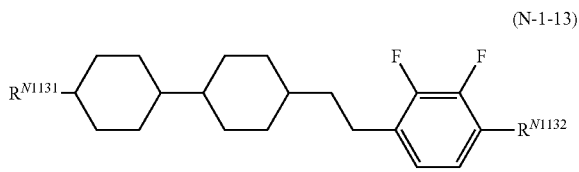

(N-1-13)

(In the formula, $R^{N1131}$ and $R^{N1132}$ have the same meaning as $R^{N11}$ and $R^{N12}$, respectively, in the general formula (N-1).)

$R^{N1131}$ preferably denotes an alkyl group having 1 to 5 carbon atoms or an alkenyl group having 2 to 5 carbon atoms, preferably an ethyl group, a propyl group, or a butyl group. $R^{N1132}$ preferably denotes an alkyl group having 1 to 5 carbon atoms, an alkenyl group having 4 or 5 carbon atoms, or an alkoxy group having 1 to 4 carbon atoms, preferably an ethoxy group, a propoxy group, or a butoxy group.

The compounds represented by the general formula (N-1-13) may be used alone or as a combination of two or more thereof. Although compounds of any types may be combined, these compounds are appropriately combined in a manner that depends on the desired characteristics, such as solubility at low temperatures, transition temperature, electrical reliability, and birefringence index. For example, one, two, three, four, five, or more compounds are used in one embodiment of the present invention.

The amount is preferably set somewhat larger when improved Δε is regarded as important, is effectively set somewhat larger when solubility at low temperatures is regarded as important, and is effectively set somewhat larger when $T_{NI}$ is regarded as important. The amount is preferably set in a medium range to reduce drop marks and improve image-sticking characteristics.

The lower limit of the preferred amount of a compound represented by the formula (N-1-13) is 5%, 10%, 13%, 15%, 17%, or 20% of the total amount of a composition according to the present invention. The upper limit of the preferred amount is 35%, 30%, 28%, 25%, 23%, 20%, 18%, 15%, or 13% of the total amount of a composition according to the present invention.

A compound represented by the general formula (N-1-14) is the following compound.

[Chem. 48]

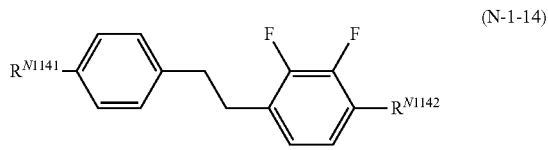

(N-1-14)

(In the formula, $R^{N1141}$ and $R^{N1142}$ have the same meaning as $R^{N11}$ and $R^{N12}$, respectively, in the general formula (N-1).)

$R^{N1141}$ preferably denotes an alkyl group having 1 to 5 carbon atoms or an alkenyl group having 2 to 5 carbon atoms, preferably an ethyl group, a propyl group, or a butyl group. $R^{N1142}$ preferably denotes an alkyl group having 1 to 5 carbon atoms, an alkenyl group having 4 or 5 carbon atoms, or an alkoxy group having 1 to 4 carbon atoms, preferably an ethoxy group, a propoxy group, or a butoxy group.

The compounds represented by the general formula (N-1-14) may be used alone or as a combination of two or more thereof. Although compounds of any types may be combined, these compounds are appropriately combined in a manner that depends on the desired characteristics, such as solubility at low temperatures, transition temperature, electrical reliability, and birefringence index. For example, one, two, three, four, five, or more compounds are used in one embodiment of the present invention.

The amount is preferably set somewhat larger when improved Δε is regarded as important, is effectively set somewhat larger when solubility at low temperatures is regarded as important, and is effectively set somewhat smaller when $T_{NI}$ is regarded as important. The amount is preferably set in a medium range to reduce drop marks and improve image-sticking characteristics.

The lower limit of the preferred amount of a compound represented by the formula (N-1-14) is 5%, 10%, 13%, 15%, 17%, or 20% of the total amount of a composition according to the present invention. The upper limit of the preferred amount is 35%, 30%, 28%, 25%, 23%, 20%, 18%, 15%, or 13% of the total amount of a composition according to the present invention.

A compound represented by the general formula (N-1-15) is the following compound.

[Chem. 49]

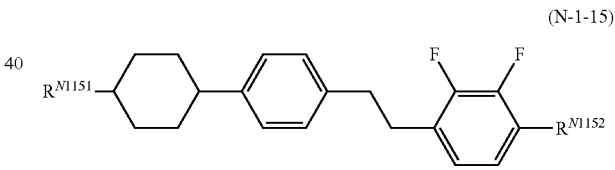

(N-1-15)

(In the formula, $R^{N1151}$ and $R^{N1152}$ have the same meaning as $R^{N11}$ and $R^{N12}$, respectively, in the general formula (N-1).)

$R^{N1151}$ preferably denotes an alkyl group having 1 to 5 carbon atoms or an alkenyl group having 2 to 5 carbon atoms, preferably an ethyl group, a propyl group, or a butyl group. $R^{N1152}$ preferably denotes an alkyl group having 1 to 5 carbon atoms, an alkenyl group having 4 or 5 carbon atoms, or an alkoxy group having 1 to 4 carbon atoms, preferably an ethoxy group, a propoxy group, or a butoxy group.

The compounds represented by the general formula (N-1-15) may be used alone or as a combination of two or more thereof. Although compounds of any types may be combined, these compounds are appropriately combined in a manner that depends on the desired characteristics, such as solubility at low temperatures, transition temperature, electrical reliability, and birefringence index. For example, one, two, three, four, five, or more compounds are used in one embodiment of the present invention.

The amount is preferably set somewhat larger when improved Δε is regarded as important, is effectively set somewhat larger when solubility at low temperatures is regarded as important, and is effectively set somewhat larger when $T_N$ is regarded as important. The amount is preferably set in a medium range to reduce drop marks and improve image-sticking characteristics.

The lower limit of the preferred amount of a compound represented by the formula (N-1-15) is 5%, 10%, 13%, 15%, 17%, or 20% of the total amount of a composition according to the present invention. The upper limit of the preferred amount is 35%, 30%, 28%, 25%, 23%, 20%, 18%, 15%, or 13% of the total amount of a composition according to the present invention.

A compound represented by the general formula (N-1-16) is the following compound.

[Chem. 50]

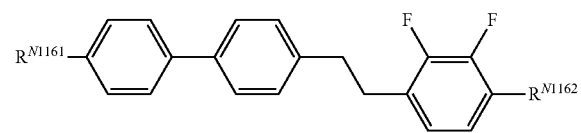

(N-1-16)

(In the formula, $R^{N1161}$ and $R^{N1162}$ have the same meaning as $R^{N11}$ and $R^{N12}$, respectively, in the general formula (N-1).)

$R^{N1161}$ preferably denotes an alkyl group having 1 to 5 carbon atoms or an alkenyl group having 2 to 5 carbon atoms, preferably an ethyl group, a propyl group, or a butyl group. $R^{N1162}$ preferably denotes an alkyl group having 1 to 5 carbon atoms, an alkenyl group having 4 or 5 carbon atoms, or an alkoxy group having 1 to 4 carbon atoms, preferably an ethoxy group, a propoxy group, or a butoxy group.

The compounds represented by the general formula (N-1-16) may be used alone or as a combination of two or more thereof. Although compounds of any types may be combined, these compounds are appropriately combined in a manner that depends on the desired characteristics, such as solubility at low temperatures, transition temperature, electrical reliability, and birefringence index. For example, one, two, three, four, five, or more compounds are used in one embodiment of the present invention.

The amount is preferably set somewhat larger when improved Δε is regarded as important, is effectively set somewhat larger when solubility at low temperatures is regarded as important, and is effectively set somewhat larger when $T_1$ is regarded as important. The amount is preferably set in a medium range to reduce drop marks and improve image-sticking characteristics.

The lower limit of the preferred amount of a compound represented by the formula (N-1-16) is 5%, 10%, 13%, 15%, 17%, or 20% of the total amount of a composition according to the present invention. The upper limit of the preferred amount is 35%, 30%, 28%, 25%, 23%, 20%, 18%, 15%, or 13% of the total amount of a composition according to the present invention.

A compound represented by the general formula (N-1-17) is the following compound.

[Chem. 51]

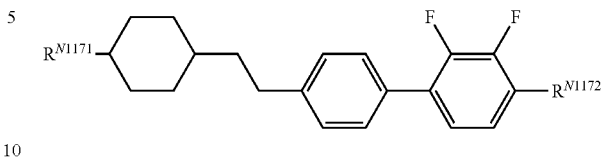

(N-1-17)

(In the formula, $R^{N1171}$ and $R^{N1172}$ have the same meaning as $R^{N11}$ and $R^{N12}$, respectively, in the general formula (N-1).)

$R^{N1171}$ preferably denotes an alkyl group having 1 to 5 carbon atoms or an alkenyl group having 2 to 5 carbon atoms, preferably an ethyl group, a propyl group, or a butyl group. $R^{N1172}$ preferably denotes an alkyl group having 1 to 5 carbon atoms, an alkenyl group having 4 or 5 carbon atoms, or an alkoxy group having 1 to 4 carbon atoms, preferably an ethoxy group, a propoxy group, or a butoxy group.

The compounds represented by the general formula (N-1-17) may be used alone or as a combination of two or more thereof. Although compounds of any types may be combined, these compounds are appropriately combined in a manner that depends on the desired characteristics, such as solubility at low temperatures, transition temperature, electrical reliability, and birefringence index. For example, one, two, three, four, five, or more compounds are used in one embodiment of the present invention.

The amount is preferably set somewhat larger when improved Δε is regarded as important, is effectively set somewhat larger when solubility at low temperatures is regarded as important, and is effectively set somewhat larger when $T_{NI}$ is regarded as important. The amount is preferably set in a medium range to reduce drop marks and improve image-sticking characteristics.

The lower limit of the preferred amount of a compound represented by the formula (N-1-17) is 5%, 10%, 13%, 15%, 17%, or 20% of the total amount of a composition according to the present invention. The upper limit of the preferred amount is 35%, 30%, 28%, 25%, 23%, 20%, 18%, 15%, or 13% of the total amount of a composition according to the present invention.

A compound represented by the general formula (N-1-18) is the following compound.

[Chem. 52]

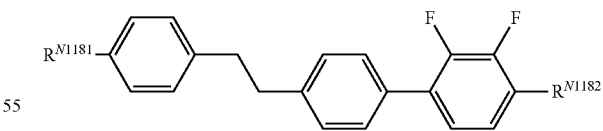

(N-1-18)

(In the formula, $R^{N1181}$ and $R^{N1182}$ have the same meaning as $R^{N11}$ and $R^{N1}$, respectively, in the general formula (N-1).)

$R^{N1181}$ preferably denotes an alkyl group having 1 to 5 carbon atoms or an alkenyl group having 2 to 5 carbon atoms, preferably a methyl group, an ethyl group, a propyl group, or a butyl group. $R^{N1182}$ preferably denotes an alkyl group having 1 to 5 carbon atoms, an alkenyl group having 4 or 5 carbon atoms, or an alkoxy group having 1 to 4 carbon atoms, preferably an ethoxy group, a propoxy group, or a butoxy group.

The compounds represented by the general formula (N-1-18) may be used alone or as a combination of two or more thereof. Although compounds of any types may be combined, these compounds are appropriately combined in a manner that depends on the desired characteristics, such as solubility at low temperatures, transition temperature, electrical reliability, and birefringence index. For example, one, two, three, four, five, or more compounds are used in one embodiment of the present invention.

The amount is preferably set somewhat larger when improved Δε is regarded as important, is effectively set somewhat larger when solubility at low temperatures is regarded as important, and is effectively set somewhat larger when $T_{NI}$ is regarded as important. The amount is preferably set in a medium range to reduce drop marks and improve image-sticking characteristics.

The lower limit of the preferred amount of a compound represented by the formula (N-1-18) is 5%, 10%, 13%, 15%, 17%, or 20% of the total amount of a composition according to the present invention. The upper limit of the preferred amount is 35%, 30%, 28%, 25%, 23%, 20%, 18%, 15%, or 13% of the total amount of a composition according to the present invention.

A compound represented by the general formula (N-1-18) is preferably a compound selected from the compound group represented by the formulae (N-1-18.1) to (N-1-18.5), preferably a compound represented by one of the formulae (N-1-18.1) to (N-1-11.3), preferably a compound represented by the formula (N-1-18.2 or (N-1-18.3).

[Chem. 53]

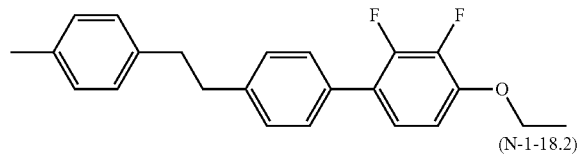
(N-1-18.1)

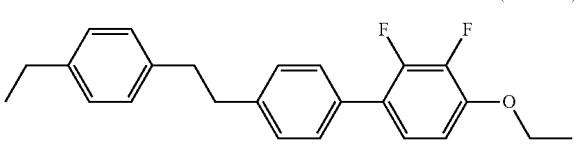
(N-1-18.2)

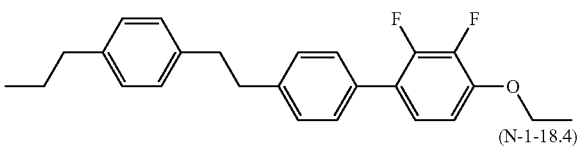
(N-1-18.3)

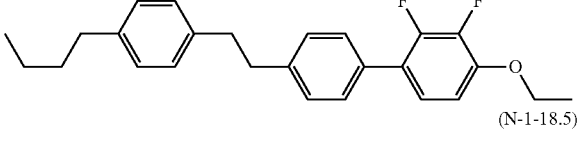
(N-1-18.4)

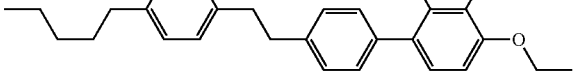
(N-1-18.5)

A compound represented by the general formula (N-1-20) is the following compound.

[Chem. 54]

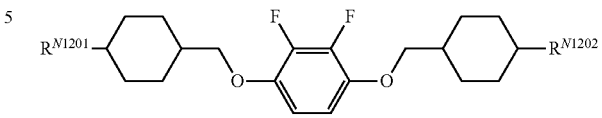
(N-1-20)

(In the formula, $R^{N1201}$ and $R^{N1202}$ have the same meaning as $R^{N11}$ and $R^{N12}$, respectively, in the general formula (N-1).)

$R^{N1201}$ and $R^{N1202}$ preferably independently denote an alkyl group having 1 to 5 carbon atoms or an alkenyl group having 2 to 5 carbon atoms, preferably an ethyl group, a propyl group, or a butyl group.

The compounds represented by the general formula (N-1-20) may be used alone or as a combination of two or more thereof. Although compounds of any types may be combined, these compounds are appropriately combined in a manner that depends on the desired characteristics, such as solubility at low temperatures, transition temperature, electrical reliability, and birefringence index. For example, one, two, three, four, five, or more compounds are used in one embodiment of the present invention.

The amount is preferably set somewhat larger when improved Δε is regarded as important, is effectively set somewhat larger when solubility at low temperatures is regarded as important, and is effectively set somewhat larger when $T_{NI}$ is regarded as important. The amount is preferably set in a medium range to reduce drop marks and improve image-sticking characteristics.

The lower limit of the preferred amount of a compound represented by the formula (N-1-20) is 5%, 10%, 13%, 15%, 17%, or 20% of the total amount of a composition according to the present invention. The upper limit of the preferred amount is 35%, 30%, 28%, 25%, 23%, 20%, 18%, 15%, or 13% of the total amount of a composition according to the present invention.

A compound represented by the general formula (N-1-21) is the following compound.

[Chem. 55]

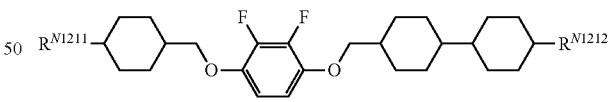
(N-1-21)

(In the formula, $R^{N1211}$ and $R^{N1212}$ have the same meaning as $R^{N11}$ and $R^{N12}$, respectively, in the general formula (N-1).)

$R^{N1211}$ and $R^{N1212}$ preferably independently denote an alkyl group having 1 to 5 carbon atoms or an alkenyl group having 2 to 5 carbon atoms, preferably an ethyl group, a propyl group, or a butyl group.

The compounds represented by the general formula (N-1-21) may be used alone or as a combination of two or more thereof. Although compounds of any types may be combined, these compounds are appropriately combined in a manner that depends on the desired characteristics, such as solubility at low temperatures, transition temperature, electrical reliability, and birefringence index. For example, one, two, three, four, five, or more compounds are used in one embodiment of the present invention.

The amount is preferably set somewhat larger when improved Δε is regarded as important, is effectively set somewhat larger when solubility at low temperatures is regarded as important, and is effectively set somewhat larger when $T_{NI}$ is regarded as important. The amount is preferably set in a medium range to reduce drop marks and improve image-sticking characteristics.

The lower limit of the preferred amount of a compound represented by the formula (N-1-21) is 5%, 10%, 13%, 15%, 17%, or 20% of the total amount of a composition according to the present invention. The upper limit of the preferred amount is 35%, 30%, 28%, 25%, 23%, 20%, 18%, 15%, or 13% of the total amount of a composition according to the present invention.

A compound represented by the general formula (N-1-22) is the following compound.

[Chem. 56]

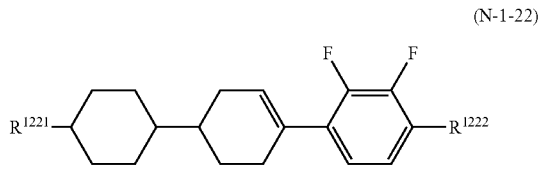

(N-1-22)

(In the formula, $R^{N1221}$ and $R^{N1222}$ have the same meaning as $R^{N11}$ and $R^{N12}$, respectively, in the general formula (N-1).)

$R^{N1221}$ and $R^{N1222}$ preferably independently denote an alkyl group having 1 to 5 carbon atoms or an alkenyl group having 2 to 5 carbon atoms, preferably an ethyl group, a propyl group, or a butyl group.

The compounds represented by the general formula (N-1-22) may be used alone or as a combination of two or more thereof. Although compounds of any types may be combined, these compounds are appropriately combined in a manner that depends on the desired characteristics, such as solubility at low temperatures, transition temperature, electrical reliability, and birefringence index. For example, one, two, three, four, five, or more compounds are used in one embodiment of the present invention.

The amount is preferably set somewhat larger when improved Δε is regarded as important, is effectively set somewhat larger when solubility at low temperatures is regarded as important, and is effectively set somewhat larger when $T_{NI}$ is regarded as important. The amount is preferably set in a medium range to reduce drop marks and improve image-sticking characteristics.

The lower limit of the preferred amount of a compound represented by the formula (N-1-21) is 1%, 5%, 10%, 13%, 15%, 17%, or 20% of the total amount of a composition according to the present invention. The upper limit of the preferred amount is 35%, 30%, 28%, 25%, 23%, 20%, 18%, 15%, 13%, 10%, or 5% of the total amount of a composition according to the present invention.

A compound represented by the general formula (N-1-22) is preferably a compound selected from the compound group represented by the formulae (N-1-22.1) to (N-1-22.12), preferably a compound represented by one of the formulae (N-1-22.1) to (N-1-22.5), preferably a compound represented by one of the formulae (N-1-22.1) to (N-1-22.4).

[Chem. 57]

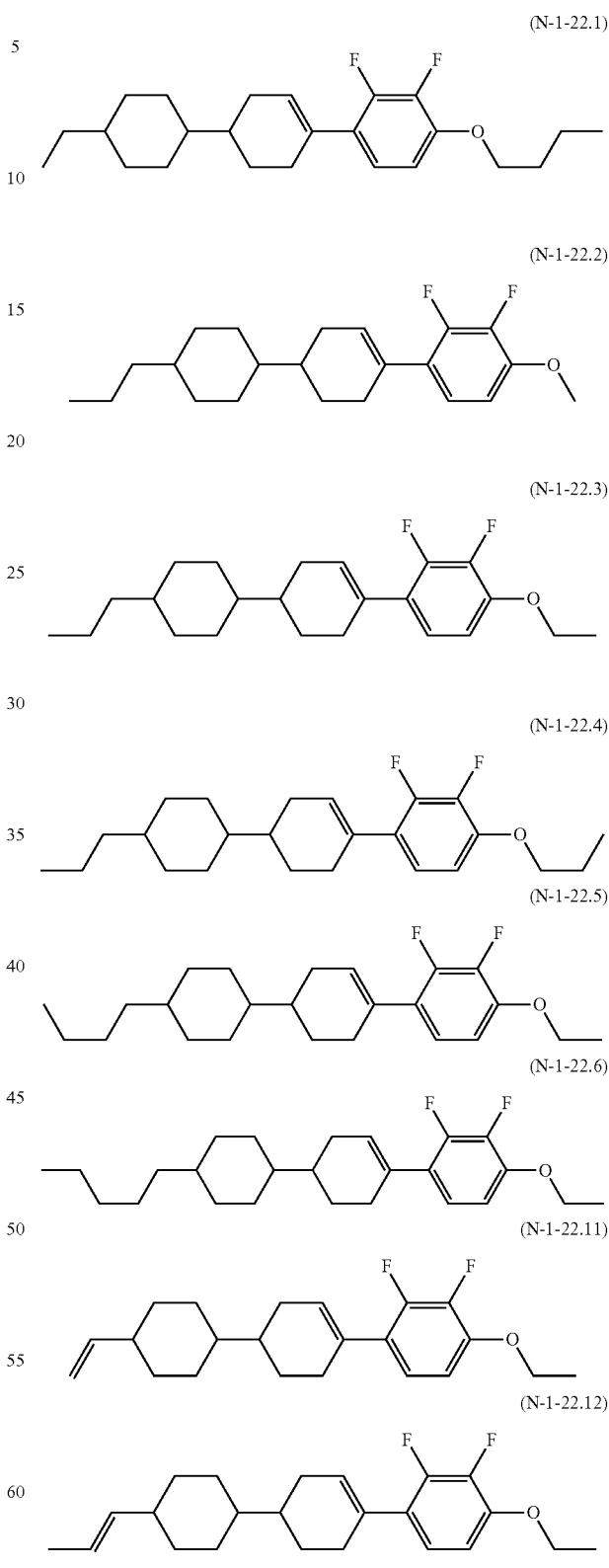

A compound represented by the general formula (N-3) is preferably a compound selected from the compound group represented by the general formula (N-3-2).

[Chem. 58]

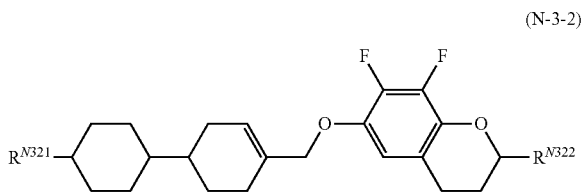
(N-3-2)

[Chem. 59]

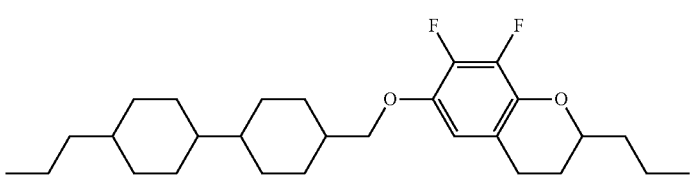
(N-3-2.1)

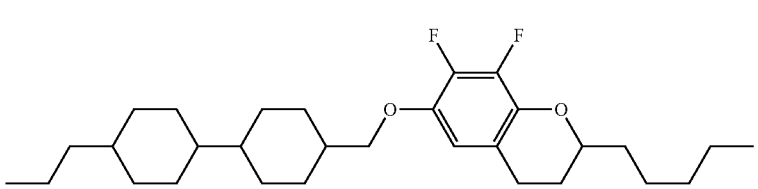
(N-3-2.2)

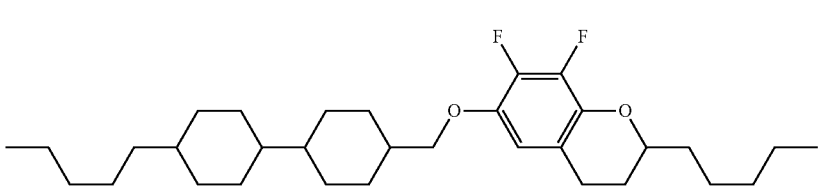
(N-3-2.3)

(In the formula, $R^{N321}$ and $R^{N322}$ have the same meaning as $R^{N11}$ and $R^{N12}$, respectively, in the general formula (N-3).)

$R^{N321}$ and $R^{K322}$ preferably denote an alkyl group having 1 to 5 carbon atoms or an alkenyl group having 2 to 5 carbon atoms, preferably a propyl group or a pentyl group.

The compounds represented by the general formula (N-3-2) may be used alone or as a combination of two or more thereof. Although compounds of any types may be combined, these compounds are appropriately combined in a manner that depends on the desired characteristics, such as solubility at low temperatures, transition temperature, electrical reliability, and birefringence index. For example, one, two, three, four, five, or more compounds are used in one embodiment of the present invention.

The amount is preferably set somewhat larger when improved Δε is regarded as important, is effectively set somewhat larger when solubility at low temperatures is regarded as important, and is effectively set somewhat larger when $T_{NI}$ is regarded as important. The amount is preferably set in a medium range to reduce drop marks and improve image-sticking characteristics.

The lower limit of the preferred amount of a compound represented by the formula (N-3-2) is 3%, 5%, 10%, 13%, 15%, 17%, 20%, 23%, 25%, 27%, 30%, 33%, or 35% of the total amount of a composition according to the present invention. The upper limit of the preferred amount is 50%, 40%, 38%, 35%, 33%, 30%, 28%, 25%, 23%, 20%, 18%, 15%, 13%, 10%, 8%, 7%, 6%, or 5% of the total amount of a composition according to the present invention.

A compound represented by the general formula (N-3-2) is preferably a compound selected from the compound group represented by the formulae (N-3-2.1) to (N-3-2.3).

In compounds represented by the general formulae (N-1), (N-2), and (N-3) in a liquid crystal composition, the total amount of compounds in which $Z^{N11}$, $Z^{N12}$, $Z^{N21}$, $Z^{N22}$, $Z^{N31}$, and $Z^{N32}$ are single bonds preferably ranges from 5% to 50% by mass of the total amount of compounds represented by the general formulae (N-1), (N-2), and (N-3). In a compound represented by the general formula (N-1) in a liquid crystal composition, the total amount of compounds in which $Z^{N11}$, $Z^{N12}$, $Z^{N21}$, $Z^{N22}$, $Z^{N31}$, and $Z^{N32}$ are single bonds preferably ranges from 5% to 50% by mass of the total amount of compounds represented by the general formulae (N-1), (N-2), and (N-3).

A compound represented by the general formula (N-1) in which $Z^{N11}$ and $Z^{N12}$ are single bonds is preferably a compound represented by the general formula (N-1a), (N-1b), (N-1c), or (N-1g), preferably a compound represented by (N-1a), (N-1b), or (N-1c).

A compound represented by the general formula (N-1-1), (N-1-2), (N-1-3), (N-1-4), (N-1-5), or (N-1-22) is also preferred. A compound represented by the general formula (N-1-1), (N-1-2), (N-1-3), (N-1-4), or (N-1-5) is also preferred.

The total amount of compounds represented by the general formulae (N-1), (N-2), and (N-3) is preferably 80% or more, 85% or more, 87% or more, 90% or more, 93% or more, 96% or more, 98% or more, or substantially 100% or more of the total amount of compounds with negative dielectric constant anisotropy. The term "substantially", as used herein, means that incidental inclusions, such as impurities in the production, are excluded.

In compounds represented by the general formulae (N-1), (N-2), and (N-3) in a liquid crystal composition, the total amount of compounds in which $Z^{N11}$, $Z^{N12}$, $Z^{N21}$, $Z^{N22}$, $Z^{N31}$, and $Z^{N32}$ are single bonds preferably ranges from 50% to 100%, 60% to 100%, 65% to 95%, or 70% to 90% of the total amount of compounds represented by the general formulae (N-1), (N-2), and (N-3).

In a compound represented by the general formula (N-1) in a liquid crystal composition, the total amount of compounds in which $Z^{N11}$ and $Z^{N12}$ are single bonds preferably ranges from 50% to 100%, 60% to 100%, 65% to 95%, or 70% to 90% of the total amount of compounds represented by the general formulae (N-1), (N-2), and (N-3).

The total amount of compounds represented by the general formulae (N-1a), (N-1b), (N-1c), and (N-1g) in a liquid crystal composition preferably ranges from 50% to 100%, 60% to 100%, 65% to 95%, or 70% to 90% of the total amount of compounds represented by the general formulae (N-1), (N-2), and (N-3).

The total amount of compounds represented by the general formulae (N-1-1), (N-1-2), (N-1-3), and (N-1-4) in a liquid crystal composition preferably ranges from 50% to 100%, 60% to 100%, 65% to 95%, or 70% to 90% of the total amount of compounds represented by the general formulae (N-1), (N-2), and (N-3).

Preferred lower limits of the amount of compounds represented by the general formulae (N-1), (N-2), and (N-3) in which $Z^{N11}$, $Z^{N12}$, $Z^{N21}$, $Z^{N22}$, $Z^{N31}$, and $Z^{N32}$ are single bonds, the amount of compound represented by the general formula (N-1) in which $Z^{N11}$ and $Z^{N12}$ are single bonds, the amount of compounds represented by the general formulae (N-1a), (N-1b), (N-1c), and (N-1g), and the amount of compounds represented by the general formulae (N-1-1), (N-1-2), (N-1-3), and (N-1-4) are 50%, 60%, 65%, or 70% of the total amount of compounds represented by the general formulae (N-1), (N-2), and (N-3). Likewise, preferred upper limits are 100%, 98%, 95%, 93%, 91%, or 90%.

When these amounts are adjusted to produce a liquid crystal display device from a liquid crystal composition according to the present invention, a liquid crystal composition according to the present invention preferably contains one or two or more compounds represented by the general formula (L). A compound represented by the general formula (L) corresponds to a dielectrically nearly neutral compound (with Δε in the range of −2 to 2). Thus, the number of polar groups, such as halogen, in each molecule is preferably two or less, one or less, or zero.

[Chem. 60]

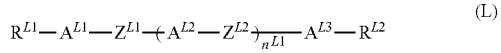

(L)

(In the formula, $R^{L1}$ and $R^{L2}$ independently denote an alkyl group having 1 to 8 carbon atoms, and one —CH$_2$— or two or more nonadjacent —CH$_2$— groups in the alkyl group are independently optionally substituted with —CH=CH—, —C≡C—, —O—, —CO—, —COO—, or —OCO—, $n^{L1}$ denotes 0, 1, 2, or 3, $A^{L1}$, $A^{L2}$, and $A^{L3}$ independently denote a group selected from the group consisting of (a) a 1,4-cyclohexylene group (in which one —CH$_2$— or two or more nonadjacent —CH$_2$— groups are optionally substituted with —O—), (b) a 1,4-phenylene group (in which one —CH= or two or more nonadjacent —CH= groups are optionally substituted with —N=), and (c) a naphthalene-2,6-diyl group, a 1,2,3,4-tetrahydronaphthalene-2,6-diyl group, or a decahydronaphthalene-2,6-diyl group (one —CH= or two or more nonadjacent —CH= groups in the naphthalene-2,6-diyl or 1,2,3,4-tetrahydronaphthalene-2,6-diyl group are optionally substituted with —N=).

The groups (a), (b), and (c) are independently optionally substituted with a cyano group, a fluorine atom, or a chlorine atom, $Z^{L1}$ and $Z^{L2}$ independently denote a single bond, —CH$_2$CH$_2$—, —(CH$_2$)$_4$—, —OCH$_2$—, —CH$_2$O—, —COO—, —OCO—, —OCF$_2$—, —CF$_2$O—, —CH=N—N=CH—, —CH=CH—, —CF=CF—, or —C≡C—, and if $n^{L1}$ is 2 or 3, a plurality of $A^{L2}$s may be the same or different, and if $n^{L1}$ is 2 or 3, a plurality of $Z^{L3}$s may be the same or different, but compounds represented by the general formulae (N-1), (N-2), and (N-3) are excluded.)

The compounds represented by the general formula (L) may be used alone or in combination. Although compounds of any types may be combined, these compounds are appropriately combined in a manner that depends on the desired characteristics, such as solubility at low temperatures, transition temperature, electrical reliability, and birefringence index. For example, one compound is used in one embodiment of the present invention. Two, three, four, five, six, seven, eight, nine, ten, or more compounds are used in another embodiment of the present invention.

The amount of a compound represented by the general formula (L) in a composition according to the present invention should be appropriately adjusted in a manner that depends on the desired characteristics, such as solubility at low temperatures, transition temperature, electrical reliability, birefringence index, process compatibility, drop marks, image-sticking, and dielectric constant anisotropy.

The lower limit of the preferred amount of compound represented by the formula (L) is 1%, 10%, 20%, 30%, 40%, 50%, 55%, 60%, 65%, 70%, 75%, or 80% of the total amount of a composition according to the present invention. The upper limit of the preferred amount is 95%, 85%, 75%, 65%, 55%, 45%, 35%, or 25%.

When a composition according to the present invention with a low viscosity and with a high response speed is required, the lower limit is preferably high, and the upper limit is preferably high. When a composition according to the present invention with a high Tni and with high temperature stability is required, the lower limit is preferably high, and the upper limit is preferably high. When dielectric constant anisotropy is increased to maintain a low drive voltage, the lower limit is preferably low, and the upper limit is preferably low.

When reliability is regarded as important, both $R^{L1}$ and $R^{L2}$ preferably denote an alkyl group. When lower volatility of the compound is regarded as important, both $R^{L1}$ and $R^{L2}$ preferably denote an alkoxy group. When lower viscosity is regarded as important, at least one of $R^{L1}$ and $R^{L2}$ preferably denotes an alkenyl group.

The number of halogen atoms in the molecule is preferably 0, 1, 2, or 3, preferably 0 or 1, or preferably 1 when compatibility with another liquid crystal molecule is regarded as important.

When the ring structure to which $R^{L1}$ and $R^{L2}$ are bonded is a phenyl group (aromatic), $R^{L1}$ and $R^{L2}$ preferably denote a linear alkyl group having 1 to 5 carbon atoms, a linear alkoxy group having 1 to 4 carbon atoms, or an alkenyl group having 4 or 5 carbon atoms. When the ring structure to which $R^{L1}$ and $R^{L2}$ are bonded is a saturated ring structure, such as cyclohexane, pyran, or dioxane, $R^{L1}$ and $R^{L2}$ preferably denote a linear alkyl group having 1 to 5 carbon atoms, a linear alkoxy group having 1 to 4 carbon atoms, or a linear alkenyl group having 2 to 5 carbon atoms. To stabilize a nematic phase, the total number of carbon atoms and, if present, oxygen atoms is preferably 5 or less, and a straight chain is preferred.

The alkenyl group is preferably selected from the groups represented by the formulae (R1) to (R5). (The dark dot in each formula represents a carbon atom in the ring structure.)

[Chem. 61]

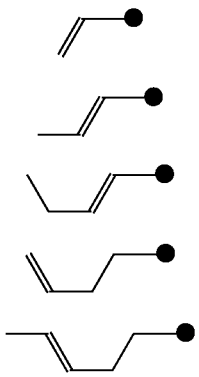

(R1)
(R2)
(R3)
(R4)
(R5)

When the response speed is regarded as important, $n^{L1}$ is preferably 0. To improve the upper limit temperature of a nematic phase, $n^{L1}$ is preferably 2 or 3. To achieve the balance therebetween, $n^{L1}$ is preferably 1. To satisfy the characteristics required for the composition, compounds with different $n^{L1}$s are preferably combined.

$A^{L1}$, $A^{L2}$, and $A^{L3}$ preferably denote an aromatic when an increase in Δn is desired, preferably denote an aliphatic to improve the response speed, preferably independently denote a trans-1,4-cyclohexylene group, a 1,4-phenylene group, a 2-fluoro-1,4-phenylene group, a 3-fluoro-1,4-phenylene group, a 3,5-difluoro-1,4-phenylene group, a 1,4-cyclohexenylene group, a 1,4-bicyclo[2.2.2]octylene group, a piperidine-1,4-diyl group, a naphthalene-2,6-diyl group, a decahydronaphthalene-2,6-diyl group, or a 1,2,3,4-tetrahydronaphthalene-2,6-diyl group, more preferably denote one of the following structures,

[Chem. 62]

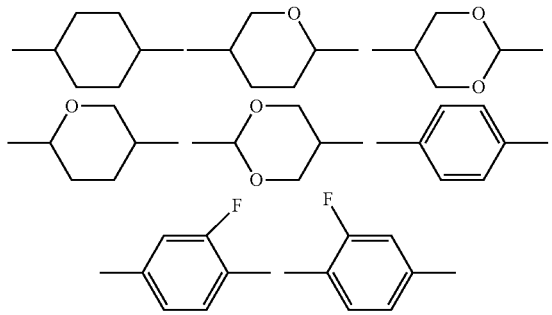

and still more preferably denotes a trans-1,4-cyclohexylene group or a 1,4-phenylene group.

When the response speed is regarded as important, $Z^{L1}$ and $Z^{L2}$ preferably denote a single bond.

The number of halogen atoms per molecule of a compound represented by the general formula (L) is preferably 0 or 1.

A compound represented by the general formula (L) is preferably a compound selected from the compound group represented by the general formulae (L-1) to (L-7).

A compound represented by the general formula (L-1) is the following compound.

[Chem. 63]

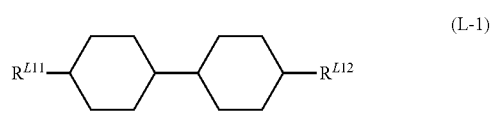

(L-1)

(In the formula, $R^{L11}$ and $R^{L12}$ have the same meaning as $R^{L1}$ and $R^{L2}$, respectively, in the general formula (L).)

$R^{L11}$ and $R^{L22}$ preferably denote a linear alkyl group having 1 to 5 carbon atoms, a linear alkoxy group having 1 to 4 carbon atoms, or a linear alkenyl group having 2 to 5 carbon atoms.

The compounds represented by the general formula (L-1) may be used alone or as a combination of two or more thereof. Although compounds of any types may be combined, these compounds are appropriately combined in a manner that depends on the desired characteristics, such as solubility at low temperatures, transition temperature, electrical reliability, and birefringence index. For example, one, two, three, four, five, or more compounds are used in one embodiment of the present invention.

The lower limit of the preferred amount is 1%, 2%, 3%, 5%, 7%, 10%, 15%, 20%, 25%, 30%, 35%, 40%, 45%, 50%, or 55% of the total amount of a composition according to the present invention. The upper limit of the preferred amount is 95%, 90%, 85%, 80%, 75%, 70%, 65%, 60%, 55%, 50%, 45%, 40%, 35%, 30%, or 25% of the total amount of a composition according to the present invention.

When a composition according to the present invention with a low viscosity and with a high response speed is required, the lower limit is preferably high, and the upper limit is preferably high. When a composition according to the present invention with a high Tni and high temperature stability is required, the lower limit is preferably medium, and the upper limit is preferably medium. When the dielectric constant anisotropy is increased to maintain a low driving voltage, the lower limit is preferably low, and the upper limit is preferably low.

A compound represented by the general formula (L-1) is preferably a compound selected from the compound group represented by the general formula (L-1-1).

[Chem. 64]

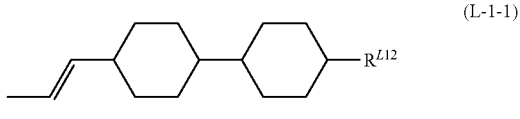

(L-1-1)

(In the formula, $R^{L12}$ has the same meaning as in the general formula (L-1).)

A compound represented by the general formula (L-1-1) is preferably a compound selected from the compound group represented by the formulae (L-1-1.1) to (L-1-1.3), preferably a compound represented by the formula (L-1-1.2) or (L-1-1.3), particularly preferably the compound represented by the formula (L-1-1.3).

[Chem. 65]

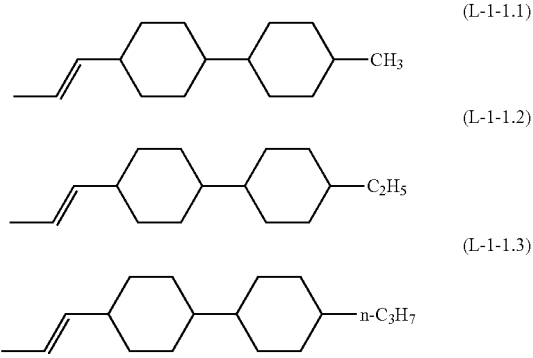

(L-1-1.1)
(L-1-1.2)
(L-1-1.3)

The lower limit of the preferred amount of the compound represented by the formula (L-1-1.3) is 1%, 2%, 3%, 5%, 7%, or 10% of the total amount of a composition according to the present invention. The upper limit of the preferred amount is 20%, 15%, 13%, 10%, 8%, 7%, 6%, 5%, or 3% of the total amount of a composition according to the present invention.

A compound represented by the general formula (L-1) is preferably a compound selected from the compound group represented by the general formula (L-1-2).

[Chem. 66]

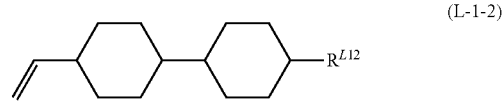

(L-1-2)

(In the formula, $R^{L12}$ has the same meaning as in the general formula (L-1).)

The lower limit of the preferred amount of a compound represented by the formula (L-1-2) is 1%, 5%, 10%, 15%, 17%, 20%, 23%, 25%, 27%, 30%, or 35% of the total amount of a composition according to the present invention. The upper limit of the preferred amount is 60%, 55%, 50%, 45%, 42%, 40%, 38%, 35%, 33%, or 30% of the total amount of a composition according to the present invention.

A compound represented by the general formula (L-1-2) is preferably a compound selected from the compound group represented by the formulae (L-1-2.1) to (L-1-2.4), preferably a compound represented by one of the formulae (L-1-2.2) to (L-1-2.4). In particular, the compound represented by the formula (L-1-2.2) is preferred to particularly improve the response speed of a composition according to the present invention. A compound represented by the formula (L-1-2.3) or (L-1-2.4) is preferably used to increase Tni rather than the response speed. To improve solubility at low temperatures, it is undesirable that the amount of a compound represented by the formula (L-1-2.3) or (L-1-2.4) be 30% or more.

[Chem. 67]

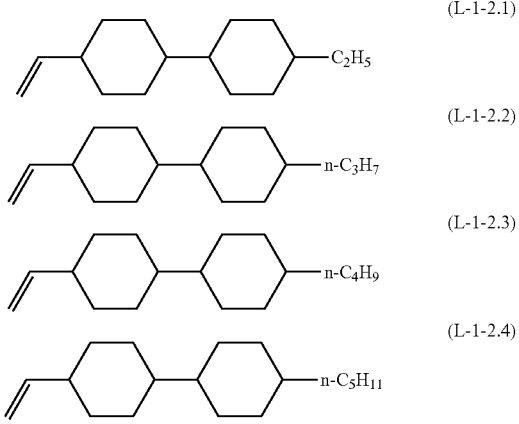

(L-1-2.1)
(L-1-2.2)
(L-1-2.3)
(L-1-2.4)

The lower limit of the preferred amount of the compound represented by the formula (L-1-2.2) is 10%, 15%, 18%, 20%, 23%, 25%, 27%, 30%, 33%, 35%, 38%, or 40% of the total amount of a composition according to the present invention. The upper limit of the preferred amount is 60%, 55%, 50%, 45%, 43%, 40%, 38%, 35%, 32%, 30%, 27%, 25%, or 22% of the total amount of a composition according to the present invention.

The lower limit of the preferred total amount of the compound represented by the formula (L-1-1.3) and the compound represented by the formula (L-1-2.2) is 10%, 15%, 20%, 25%, 27%, 30%, 35%, or 40% of the total amount of a composition according to the present invention. The upper limit of the preferred amount is 60%, 55%, 50%, 45%, 43%, 40%, 38%, 35%, 32%, 30%, 27%, 25%, or 22% of the total amount of a composition according to the present invention.

A compound represented by the general formula (L-1) is preferably a compound selected from the compound group represented by the general formula (L-1-3).

[Chem. 68]

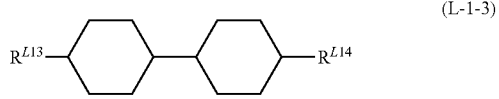

(L-1-3)

(In the formula, $R^{L13}$ and $R^{L14}$ independently denote an alkyl group having 1 to 8 carbon atoms or an alkoxy group having 1 to 8 carbon atoms.)

$R^{L13}$ and $R^{L14}$ preferably denote a linear alkyl group having 1 to 5 carbon atoms, a linear alkoxy group having 1 to 4 carbon atoms, or a linear alkenyl group having 2 to 5 carbon atoms.

The lower limit of the preferred amount of a compound represented by the formula (L-1-3) is 1%, 5%, 10%, 13%, 15%, 17%, 20%, 23%, 25%, or 30% of the total amount of a composition according to the present invention. The upper limit of the preferred amount is 60%, 55%, 50%, 45%, 40%, 37%, 35%, 33%, 30%, 27%, 25%, 23%, 20%, 17%, 15%, 13%, or 10% of the total amount of a composition according to the present invention. A compound represented by the general formula (L-1-3) is preferably a compound selected from the compound group represented by the formulae (L-1-3.1) to (L-1-3.13), preferably a compound represented by the formula (L-1-3.1), (L-1-3.3), or (L-1-3.4). In particular, the compound represented by the formula (L-1-3.1) is preferred to particularly improve the response speed of a composition according to the present invention. A compound represented by the formula (L-1-3.3), (L-1-3.4), (L-1-3.11), or (L-1-3.12) is preferably used to increase Tni rather than the response speed. To improve solubility at low temperatures, it is undesirable that the total amount of compounds represented by the formulae (L-1-3.3), (L-1-3.4), (L-1-3.11), and (L-1-3.13) be 20% or more.

[Chem. 69]

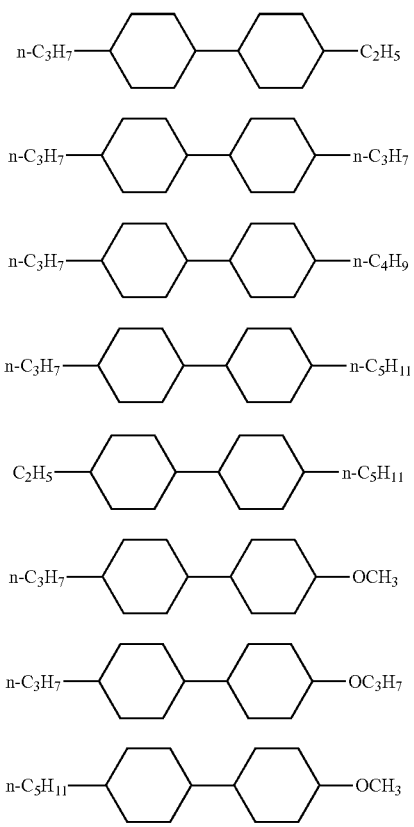

The lower limit of the preferred amount of the compound represented by the formula (L-1-3.1) is 1%, 2%, 3%, 5%, 7%, 10%, 13%, 15%, 18%, or 20% of the total amount of a composition according to the present invention. The upper limit of the preferred amount is 20%, 17%, 15%, 13%, 10%, 8%, 7%, or 6% of the total amount of a composition according to the present invention.

A compound represented by the general formula (L-1) is preferably a compound selected from the compound group represented by the general formulae (L-1-4) and/or (L-1-5).

[Chem. 70]

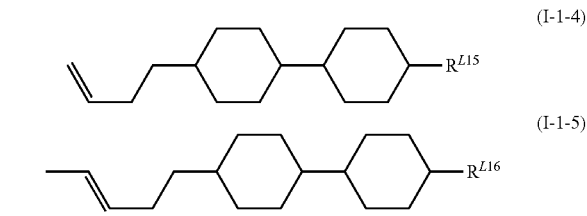

(In the formula, $R^{L15}$ and $R^{L16}$ independently denote an alkyl group having 1 to 8 carbon atoms or an alkoxy group having 1 to 8 carbon atoms.)

$R^{L15}$ and $R^{L16}$ preferably denote a linear alkyl group having 1 to 5 carbon atoms, a linear alkoxy group having 1 to 4 carbon atoms, or a linear alkenyl group having 2 to 5 carbon atoms.

The lower limit of the preferred amount of a compound represented by the formula (L-1-4) is 1%, 5%, 10%, 13%, 15%, 17%, or 20% of the total amount of a composition according to the present invention. The upper limit of the preferred amount is 25%, 23%, 20%, 17%, 15%, 13%, or 10% of the total amount of a composition according to the present invention.

The lower limit of the preferred amount of a compound represented by the formula (L-1-5) is 1%, 5%, 10%, 13%, 15%, 17%, or 20% of the total amount of a composition according to the present invention. The upper limit of the preferred amount is 25%, 23%, 20%, 17%, 15%, 13%, or 10% of the total amount of a composition according to the present invention.

The compounds represented by the general formulae (L-1-4) and (L-1-5) are preferably compounds selected from the compound group represented by the formulae (L-1-4.1) to (L-1-5.3), preferably a compound represented by the formula (L-1-4.2) or (L-1-5.2).

[Chem. 71]

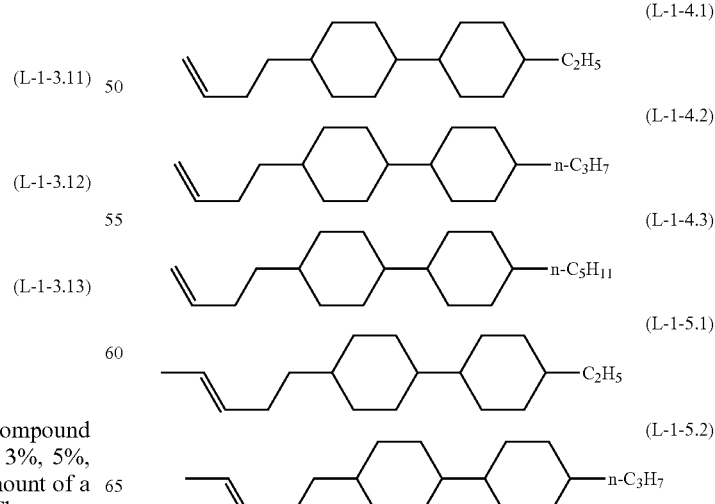

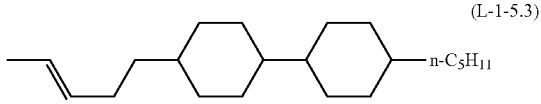
(L-1-5.3)

The lower limit of the preferred amount of the compound represented by the formula (L-1-4.2) is 1%, 2%, 3%, 5%, 7%, 10%, 13%, 15%, 18%, or 20% of the total amount of a composition according to the present invention. The upper limit of the preferred amount is 20%, 17%, 15%, 13%, 10%, 8%, 7%, or 6% of the total amount of a composition according to the present invention.

Two or more compounds selected from the compounds represented by the formulae (L-1-1.3), (L-1-2.2), (L-1-3.1), (L-1-3.3), (L-1-3.4), (L-1-3.11), and (L-1-3.12) are preferably combined. Two or more compounds selected from the compounds represented by the formulae (L-1-1.3), (L-1-2.2), (L-1-3.1), (L-1-3.3), (L-1-3.4), and (L-1-4.2) are preferably combined. The lower limit of the preferred total amount of these compounds is 1%, 2%, 3%, 5%, 7%, 10%, 13%, 15%, 18%, 20%, 23%, 25%, 27%, 30%, 33%, or 35% of the total amount of a composition according to the present invention. The upper limit is 80%, 70%, 60%, 50%, 45%, 40%, 37%, 35%, 33%, 30%, 28%, 25%, 23%, or 20% of the total amount of a composition according to the present invention. When the reliability of the composition is regarded as important, two or more compounds selected from the compounds represented by the formulae (L-1-3.1), (L-1-3.3), and (L-1-3.4)) are preferably combined. When the response speed of the composition is regarded as important, two or more compounds selected from the compounds represented by the formulae (L-1-1.3) and (L-1-2.2) are preferably combined.

A compound represented by the general formula (L-1) is preferably a compound selected from the compound group represented by the general formula (L-1-6).

[Chem. 72]

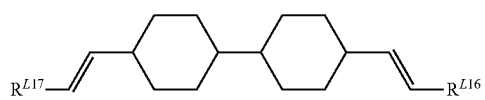
(L-1-6)

(In the formula, $R^{L17}$ and $R^{L18}$ independently denote a methyl group or a hydrogen atom.)

The lower limit of the preferred amount of a compound represented by the formula (L-1-6) is 1%, 5%, 10%, 15%, 17%, 20%, 23%, 25%, 27%, 30%, or 35% of the total amount of a composition according to the present invention. The upper limit of the preferred amount is 60%, 55%, 50%, 45%, 42%, 40%, 38%, 35%, 33%, or 30% of the total amount of a composition according to the present invention.

A compound represented by the general formula (L-1-6) is preferably a compound selected from the compound group represented by the formulae (L-1-6.1) to (L-1-6.3).

[Chem. 73]

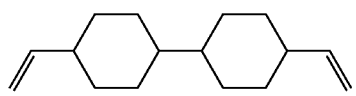
(L-1-6.1)

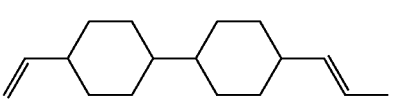
(L-1-6.2)

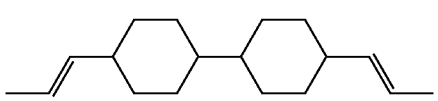
(L-1-6.3)

A compound represented by the general formula (L-2) is the following compound.

[Chem. 74]

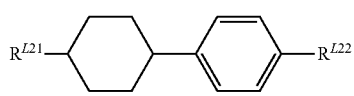
(L-2)

(In the formula, $R^{L21}$ and $R^{L22}$ have the same meaning as $R^{L1}$ and $R^{L2}$, respectively, in the general formula (L).)

$R^{L21}$ preferably denotes an alkyl group having 1 to 5 carbon atoms or an alkenyl group having 2 to 5 carbon atoms, and $R^{L22}$ preferably denotes an alkyl group having 1 to 5 carbon atoms, an alkenyl group having 4 or 5 carbon atoms, or an alkoxy group having 1 to 4 carbon atoms.

The compounds represented by the general formula (L-2) may be used alone or as a combination of two or more thereof. Although compounds of any types may be combined, these compounds are appropriately combined in a manner that depends on the desired characteristics, such as solubility at low temperatures, transition temperature, electrical reliability, and birefringence index. For example, one, two, three, four, five, or more compounds are used in one embodiment of the present invention.

The amount is effectively set somewhat larger when solubility at low temperatures is regarded as important and is effectively set somewhat smaller when the response speed is regarded as important. The amount is preferably set in a medium range to reduce drop marks and improve image-sticking characteristics.

The lower limit of the preferred amount of a compound represented by the formula (L-2) is 1%, 2%, 3%, 5%, 7%, or 10% of the total amount of a composition according to the present invention. The upper limit of the preferred amount is 20%, 15%, 13%, 10%, 8%, 7%, 6%, 5%, or 3% of the total amount of a composition according to the present invention.

A compound represented by the general formula (L-2) is preferably a compound selected from the compound group represented by the formulae (L-2.1) to (L-2.6), preferably a compound represented by the formula (L-2.1), (L-2.3), (L-2.4), or (L-2.6).

[Chem. 75]

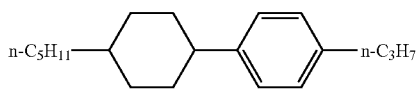
(L-2.1)

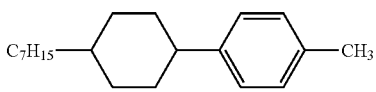
(L-2.2)

-continued

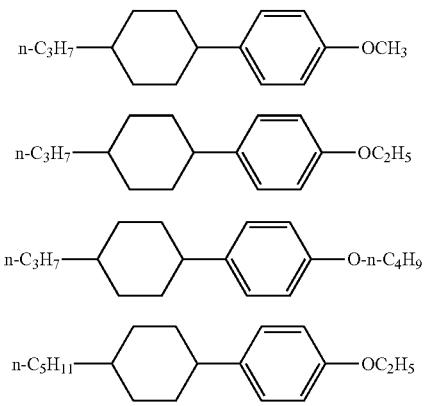

(L-2.3)
(L-2.4)
(L-2.5)
(L-2.6)

A compound represented by the general formula (L-3) is the following compound.

[Chem. 76]

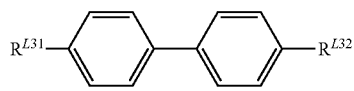

(L-3)

(In the formula, $R^{L31}$ and $R^{L32}$ have the same meaning as $R^{L1}$ and $R^{L2}$, respectively, in the general formula (L).)

$R^{L31}$ and $R^{L32}$ preferably independently denote an alkyl group having 1 to 5 carbon atoms, an alkenyl group having 4 or 5 carbon atoms, or an alkoxy group having 1 to 4 carbon atoms.

The compounds represented by the general formula (L-3) may be used alone or as a combination of two or more thereof. Although compounds of any types may be combined, these compounds are appropriately combined in a manner that depends on the desired characteristics, such as solubility at low temperatures, transition temperature, electrical reliability, and birefringence index. For example, one, two, three, four, five, or more compounds are used in one embodiment of the present invention.

The lower limit of the preferred amount of a compound represented by the formula (L-3) is 1%, 2%, 3%, 5%, 7%, or 10% of the total amount of a composition according to the present invention. The upper limit of the preferred amount is 20%, 15%, 13%, 10%, 8%, 7%, 6%, 5%, or 3% of the total amount of a composition according to the present invention.

The amount is effectively set somewhat larger to achieve a high birefringence index and is effectively set somewhat smaller when a high Tni is regarded as important. The amount is preferably set in a medium range to reduce drop marks and improve image-sticking characteristics.

A compound represented by the general formula (L-3) is preferably a compound selected from the compound group represented by the formulae (L-3.1) to (L-3.7), preferably a compound represented by one of the formulae (L-3.2) to (L-3.5).

[Chem. 77]

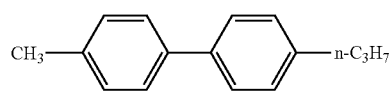

(L-3.1)

-continued

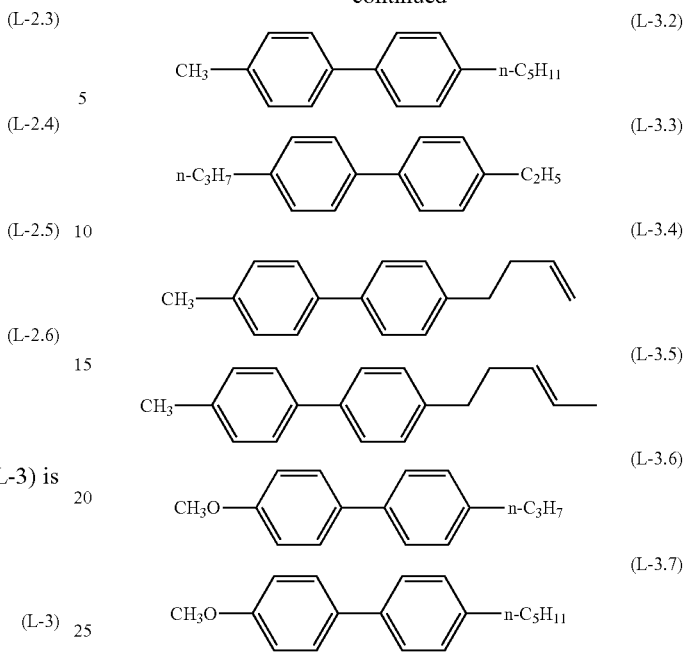

(L-3.2)
(L-3.3)
(L-3.4)
(L-3.5)
(L-3.6)
(L-3.7)

A compound represented by the general formula (L-4) is the following compound.

[Chem. 78]

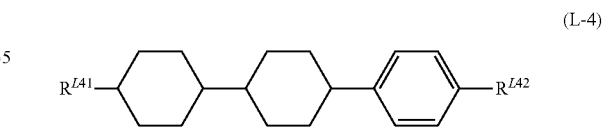

(L-4)

(In the formula, $R^{L41}$ and $R^{L42}$ have the same meaning as $R^{L1}$ and $R^{L2}$, respectively, in the general formula (L).)

$R^{L41}$ preferably denotes an alkyl group having 1 to 5 carbon atoms or an alkenyl group having 2 to 5 carbon atoms, and $R^{L42}$ preferably denotes an alkyl group having 1 to 5 carbon atoms, an alkenyl group having 4 or 5 carbon atoms, or an alkoxy group having 1 to 4 carbon atoms.)

The compounds represented by the general formula (L-4) may be used alone or as a combination of two or more thereof. Although compounds of any types may be combined, these compounds are appropriately combined in a manner that depends on the desired characteristics, such as solubility at low temperatures, transition temperature, electrical reliability, and birefringence index. For example, one, two, three, four, five, or more compounds are used in one embodiment of the present invention.

The amount of a compound represented by the general formula (L-4) in a composition according to the present invention should be appropriately adjusted in a manner that depends on the desired characteristics, such as solubility at low temperatures, transition temperature, electrical reliability, birefringence index, process compatibility, drop marks, image-sticking, and dielectric constant anisotropy.

The lower limit of the preferred amount of the compound represented by the formula (L-4) is 1%, 2%, 3%, 5%, 7%, 10%, 14%, 16%, 20%, 23%, 26%, 30%, 35%, or 40% of the total amount of a composition according to the present invention. The upper limit of the preferred amount of a compound represented by the formula (L-4) is 50%, 40%, 35%, 30%, 20%, 15%, 10%, or 5% of the total amount of a composition according to the present invention.

A compound represented by the general formula (L-4) is preferably a compound represented by one of the formulae (L-4.1) to (L-4.3), for example.

[Chem. 79]

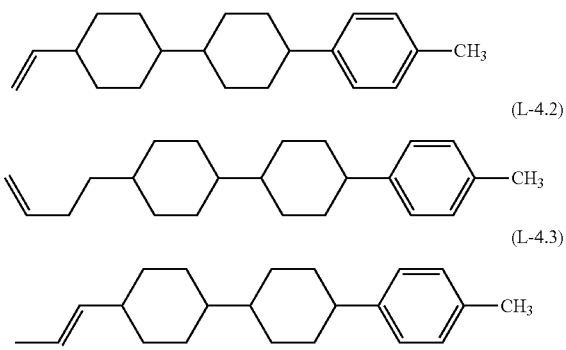

Depending on the desired characteristics, such as solubility at low temperatures, transition temperature, electrical reliability, and birefringence index, the compound represented by the formula (L-4.1), the compound represented by the formula (L-4.2), or both the compound represented by the formula (L-4.1) and the compound represented by the formula (L-4.2) may be contained, or all the compounds represented by the formulae (L-4.1) to (L-4.3) may be contained. The lower limit of the preferred amount of the compound represented by the formula (L-4.1) or (L-4.2) is 3%, 5%, 7%, 9%, 11%, 12%, 13%, 18%, or 21% of the total amount of a composition according to the present invention, and the preferred upper limit thereof is 45, 40%, 35%, 30%, 25%, 23%, 20%, 18%, 15%, 13%, 10%, or 8%.

When both the compound represented by the formula (L-4.1) and the compound represented by the formula (L-4.2) are contained, the lower limit of the preferred amount of both compounds is 15%, 19%, 24%, or 30% of the total amount of a composition according to the present invention, and the preferred upper limit thereof is 45, 40%, 35%, 30%, 25%, 23%, 20%, 18%, 15%, or 13%.

A compound represented by the general formula (L-4) is preferably a compound represented by one of the formulae (L-4.4) to (L-4.6), preferably the compound represented by the formula (L-4.4), for example.

[Chem. 80]

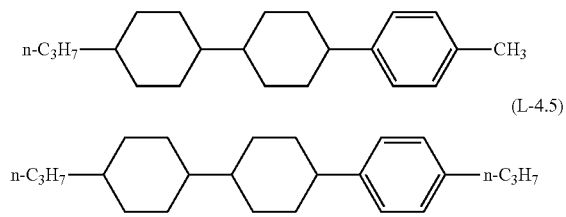

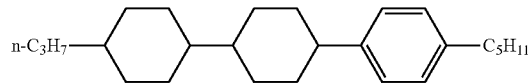

Depending on the desired characteristics, such as solubility at low temperatures, transition temperature, electrical reliability, and birefringence index, the compound represented by the formula (L-4.4), the compound represented by the formula (L-4.5), or both the compound represented by the formula (L-4.4) and the compound represented by the formula (L-4.5) may be contained.

The lower limit of the preferred amount of the compound represented by the formula (L-4.4) or (L-4.5) is 3%, 5%, 7%, 9%, 11%, 12%, 13%, 18%, or 21% of the total amount of a composition according to the present invention. The preferred upper limit is 45, 40%, 35%, 30%, 25%, 23%, 20%, 18%, 15%, 13%, 10%, or 8%.

When both the compound represented by the formula (L-4.4) and the compound represented by the formula (L-4.5) are contained, the lower limit of the preferred amount of both compounds is 15%, 19%, 24%, or 30% of the total amount of a composition according to the present invention, and the preferred upper limit thereof is 45, 40%, 35%, 30%, 25%, 23%, 20%, 18%, 15%, or 13%.

A compound represented by the general formula (L-4) is preferably a compound represented by one of the formulae (L-4.7) to (L-4.10), particularly preferably the compound represented by the formula (L-4.9).

[Chem. 81]

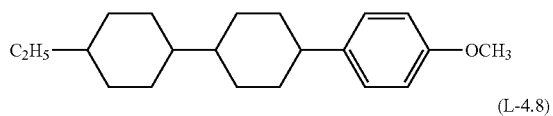

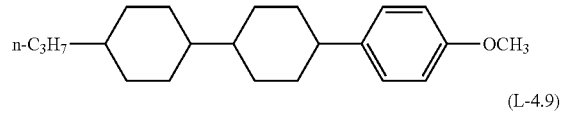

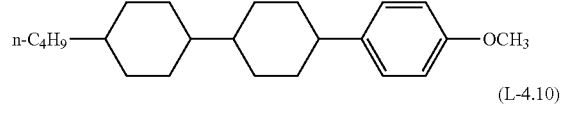

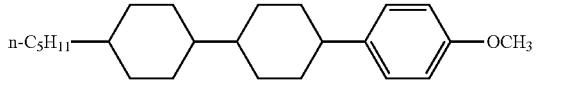

A compound represented by the general formula (L-5) is the following compound.

[Chem. 82]

(In the formula, $R^{L51}$ and $R^{L52}$ have the same meaning as $R^{L1}$ and $R^{L2}$, respectively, in the general formula (L).)

$R^{L51}$ preferably denotes an alkyl group having 1 to 5 carbon atoms or an alkenyl group having 2 to 5 carbon atoms, and $R^{L52}$ preferably denotes an alkyl group having 1 to 5 carbon atoms, an alkenyl group having 4 or 5 carbon atoms, or an alkoxy group having 1 to 4 carbon atoms.

The compounds represented by the general formula (L-5) may be used alone or as a combination of two or more thereof. Although compounds of any types may be combined, these compounds are appropriately combined in a manner that depends on the desired characteristics, such as solubility at low temperatures, transition temperature, electrical reliability, and birefringence index. For example, one, two, three, four, five, or more compounds are used in one embodiment of the present invention.

The amount of a compound represented by the general formula (L-5) in a composition according to the present invention should be appropriately adjusted in a manner that depends on the desired characteristics, such as solubility at low temperatures, transition temperature, electrical reliability, birefringence index, process compatibility, drop marks, image-sticking, and dielectric constant anisotropy.

The lower limit of the preferred amount of the compound represented by the formula (L-5) is 1%, 2%, 3%, 5%, 7%, 10%, 14%, 16%, 20%, 23%, 26%, 30%, 35%, or 40% of the total amount of a composition according to the present invention. The upper limit of the preferred amount of a compound represented by the formula (L-5) is 50%, 40%, 35%, 30%, 20%, 15%, 10%, or 5% of the total amount of a composition according to the present invention.

A compound represented by the general formula (L-5) is preferably the compound represented by the formula (L-5.1) or (L-5.2), particularly preferably the compound represented by the formula (L-5.1).

The lower limit of the preferred amount of these compounds is 1%, 2%, 3%, 5%, or 7% of the total amount of a composition according to the present invention. The upper limit of the preferred amount of these compounds is 20%, 15%, 13%, 10%, or 9%.

[Chem. 83]

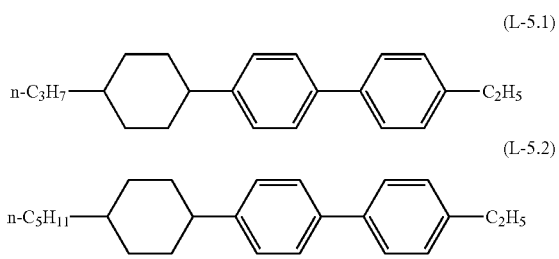

(L-5.1)

(L-5.2)

A compound represented by the general formula (L-5) is preferably the compound represented by the formula (L-5.3) or (L-5.4).

The lower limit of the preferred amount of these compounds is 1%, 2%, 3%, 5%, or 7% of the total amount of a composition according to the present invention. The upper limit of the preferred amount of these compounds is 20%, 15%, 13%, 10%, or 9%.

[Chem. 84]

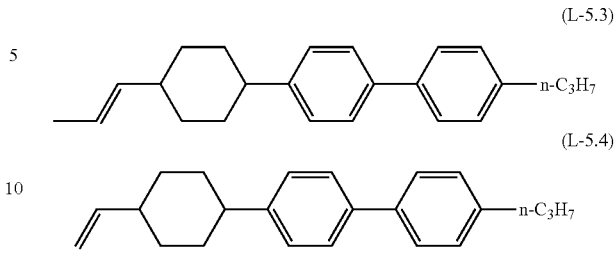

(L-5.3)

(L-5.4)

A compound represented by the general formula (L-5) is preferably a compound selected from the compound group represented by the formulae (L-5.5) to (L-5.7), particularly preferably the compound represented by the formula (L-5.7).

The lower limit of the preferred amount of these compounds is 1%, 2%, 3%, 5%, or 7% of the total amount of a composition according to the present invention. The upper limit of the preferred amount of these compounds is 20%, 15%, 13%, 10%, or 9%.

[Chem. 85]

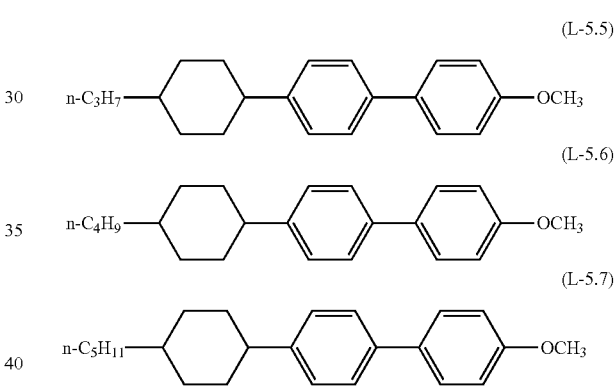

(L-5.5)

(L-5.6)

(L-5.7)

A compound represented by the general formula (L-6) is the following compound.

[Chem. 86]

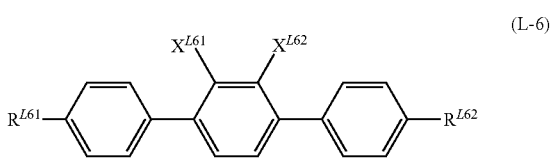

(L-6)

(In the formula, $R^{L61}$ and $R^{L62}$ have the same meaning as $R^{L1}$ and $R^{L2}$, respectively, in the general formula (L), and $X^{L61}$ and $X^{L62}$ independently denote a hydrogen atom or a fluorine atom.)

$R^{L61}$ and $R^{L62}$ preferably independently denote an alkyl group having 1 to 5 carbon atoms or an alkenyl group having 2 to 5 carbon atoms. One of $X^{L61}$ and $X^{L62}$ preferably denotes a fluorine atom, and the other preferably denotes a hydrogen atom.

The compounds represented by the general formula (L-6) may be used alone or as a combination of two or more thereof. Although compounds of any types may be combined, these compounds are appropriately combined in a manner that depends on the desired characteristics, such as solubility at low temperatures, transition temperature, electrical reliability, and birefringence index. For example, one, two, three, four, five, or more compounds are used in one embodiment of the present invention.

The lower limit of the preferred amount of the compound represented by the formula (L-6) is 1%, 2%, 3%, 5%, 7%, 10%, 14%, 16%, 20%, 23%, 26%, 30%, 35%, or 40% of the total amount of a composition according to the present invention. The upper limit of the preferred amount of a compound represented by the formula (L-6) is 50%, 40%, 35%, 30%, 20%, 15%, 10%, or 5% of the total amount of a composition according to the present invention. When an increased Δn is regarded as important, the amount is preferably increased, and when precipitation at low temperatures is regarded as important, the amount is preferably decreased.

A compound represented by the general formula (L-6) is preferably a compound represented by one of the formulae (L-6.1) to (L-6.9).

[Chem. 87]

(L-6.1)
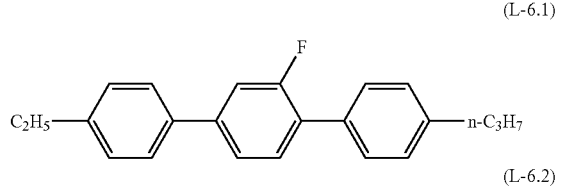

(L-6.2)
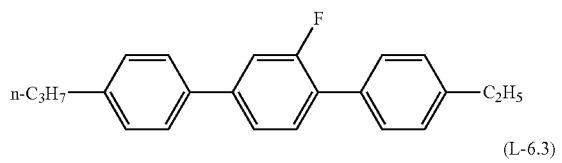

(L-6.3)
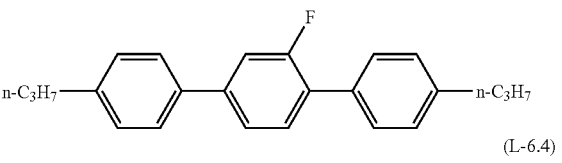

(L-6.4)
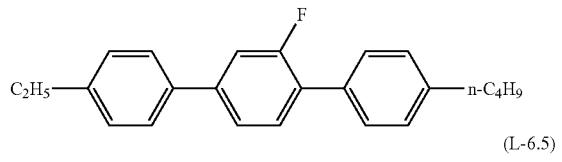

(L-6.5)
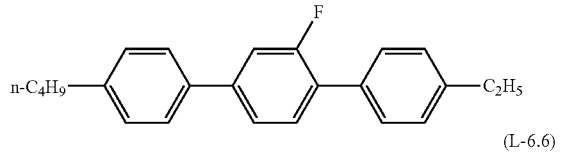

(L-6.6)
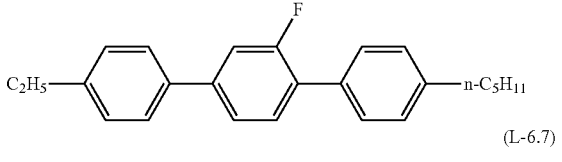

(L-6.7)
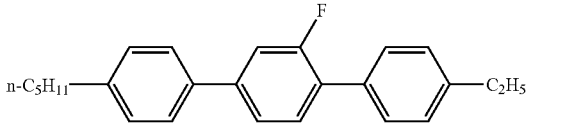

-continued (L-6.8)
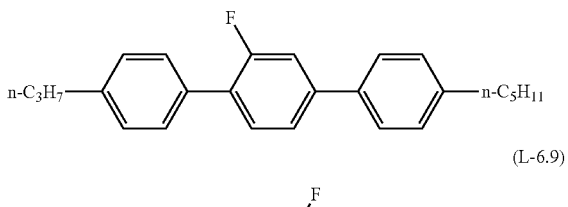

(L-6.9)
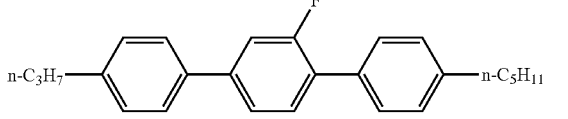

Although compounds of any types may be combined, one to three of these compounds are preferably contained, and one to four of these compounds are more preferably contained. Because a broad molecular weight distribution of a compound to be selected is also effective for solubility, for example, one compound represented by the formula (L-6.1) or (L-6.2), one compound represented by the formula (L-6.4) or (L-6.5), one compound represented by the formula (L-6.6) or (L-6.7), and one compound represented by the formula (L-6.8) or (L-6.9) are preferably appropriately combined. Among these, the compounds represented by the formulae (L-6.1), (L-6.3), (L-6.4), (L-6.6), and (L-6.9) are preferably contained.

A compound represented by the general formula (L-6) is preferably, for example, a compound represented by one of the formulae (L-6.10) to (L-6.17) and is, among these, preferably the compound represented by the formula (L-6.11).

[Chem. 88]

(L-6.10)
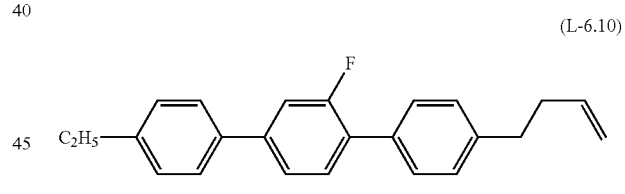

(L-6.11)
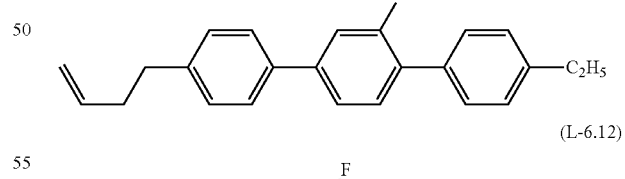

(L-6.12)
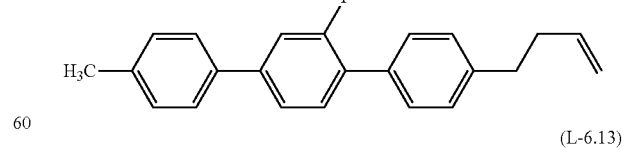

(L-6.13)
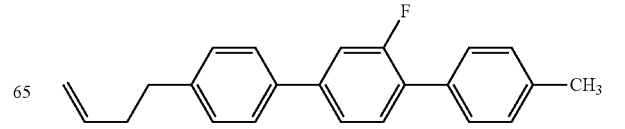

-continued

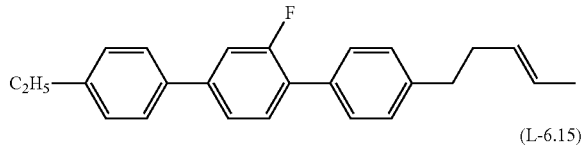
(L-6.14)

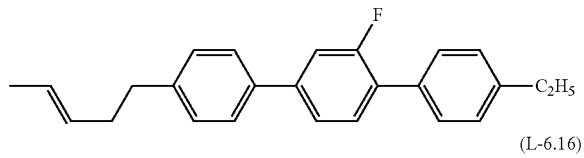
(L-6.15)

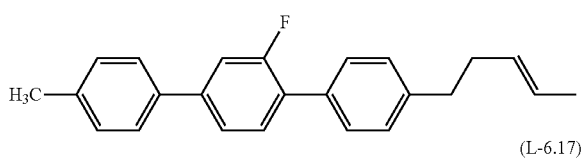
(L-6.16)

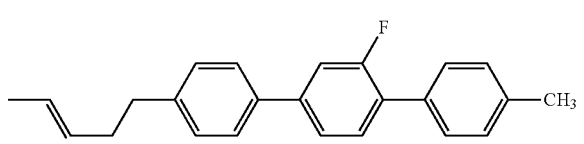
(L-6.17)

The lower limit of the preferred amount of these compounds is 1%, 2%, 3%, 5%, or 7% of the total amount of a composition according to the present invention. The upper limit of the preferred amount of these compounds is 20%, 15%, 13%, 10%, or 9%.

A compound represented by the general formula (L-7) is the following compound.

[Chem. 89]

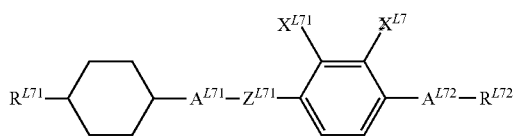
(L-7)

(In the formula, $R^{L71}$ and $R^{L72}$ have the same meaning as $R^{L1}$ and $R^{L2}$, respectively, in the general formula (L), $A^{L71}$ and $A^{L72}$ have the same meaning as $A^{L2}$ and $A^{L3}$, respectively, in the general formula (L), a hydrogen atom of $A^{L71}$ and $A^{L72}$ is optionally substituted with a fluorine atom, $Z^{L71}$ has the same meaning as $Z^{L2}$ in the general formula (L), and $X^{L71}$ and $X^{L72}$ independently denote a fluorine atom or a hydrogen atom.)

In the formula, $R^{L71}$ and $R^{L72}$ preferably independently denote an alkyl group having 1 to 5 carbon atoms, an alkenyl group having 2 to 5 carbon atoms, or an alkoxy group having 1 to 4 carbon atoms, $A^{L71}$ and $A^{L72}$ preferably independently denote a 1,4-cyclohexylene group or a 1,4-phenylene group, a hydrogen atom of $A^{L71}$ and $A^{L72}$ is optionally substituted with a fluorine atom, $Z^{L71}$ preferably denotes a single bond or COO—, preferably a single bond, and $X^{L71}$ and $X^{L72}$ preferably denote a hydrogen atom.

Although compounds of any types may be combined, these compounds are combined in a manner that depends on the desired characteristics, such as solubility at low temperatures, transition temperature, electrical reliability, and birefringence index. For example, one, two, three, or four compounds are used in one embodiment of the present invention.

The amount of a compound represented by the general formula (L-7) in a composition according to the present invention should be appropriately adjusted in a manner that depends on the desired characteristics, such as solubility at low temperatures, transition temperature, electrical reliability, birefringence index, process compatibility, drop marks, image-sticking, and dielectric constant anisotropy.

The lower limit of the preferred amount of the compound represented by the formula (L-7) is 1%, 2%, 3%, 5%, 7%, 10%, 14%, 16%, or 20% of the total amount of a composition according to the present invention. The upper limit of the preferred amount of a compound represented by the formula (L-7) is 30%, 25%, 23%, 20%, 18%, 15%, 10%, or 5% of the total amount of a composition according to the present invention.

In an embodiment in which a composition according to the present invention is desired to have a high Tni, the amount of a compound represented by the formula (L-7) is preferably somewhat larger. In an embodiment in which a low viscosity is desired, the amount is preferably somewhat smaller.

A compound represented by the general formula (L-7) is preferably a compound represented by one of the formulae (L-7.1) to (L-7.4), preferably the compound represented by the formula (L-7.2).

[Chem. 90]

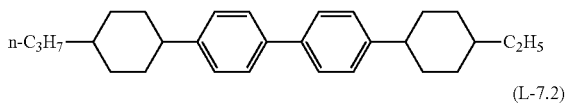
(L-7.1)

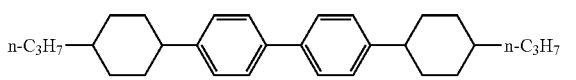
(L-7.2)

(L-7.3)

(L-7.4)

A compound represented by the general formula (L-7) is preferably a compound represented by one of the formulae (L-7.11) to (L-7.13), preferably the compound represented by the formula (L-7.11).

[Chem. 91]

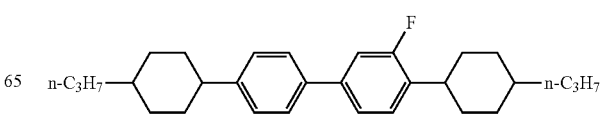
(L-7.11)

(L-7.12)
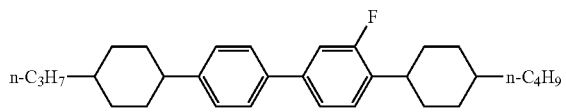

(L-7.13)
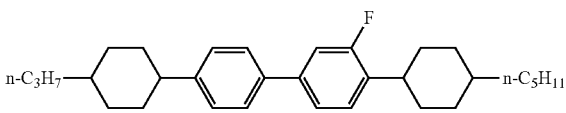

A compound represented by the general formula (L-7) is a compound represented by one of the formulae (L-7.21) to (L-7.23). The compound represented by the formula (L-7.21) is preferred.

[Chem. 92]

(L-7.21)
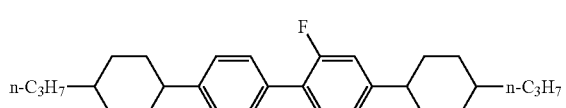

(L-7.22)
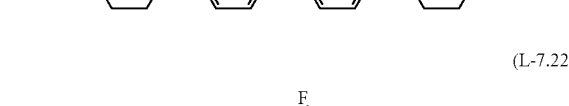

(L-7.23)
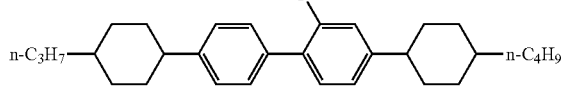

A compound represented by the general formula (L-7) is preferably a compound represented by one of the formulae (L-7.31) to (L-7.34), preferably a compound represented by the formula (L-7.31) and/or (L-7.32).

[Chem. 93]

(L-7.31)
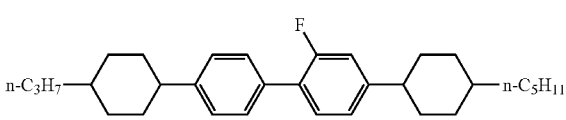

(L-7.32)
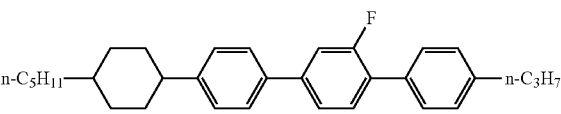

(L-7.33)
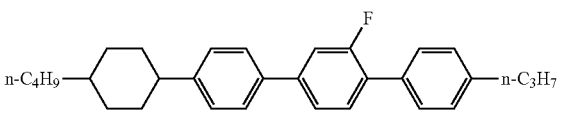

(L-7.34)
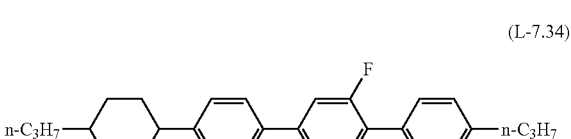

A compound represented by the general formula (L-7) is preferably a compound represented by one of the formulae (L-7.41) to (L-7.44), preferably a compound represented by the formula (L-7.41) and/or (L-7.42).

[Chem. 94]

(L-7.41)
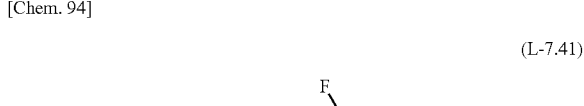

(L-7.42)
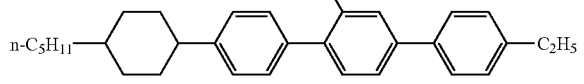

(L-7.43)
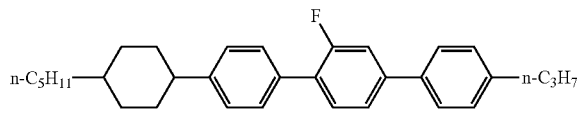

(L-7.44)
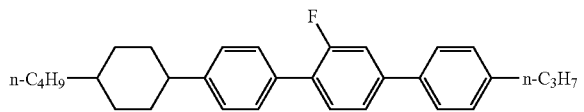

A compound represented by the general formula (L-7) is preferably a compound represented by one of the formulae (L-7.51) to (L-7.53).

[Chem. 95]

(L-7.51)
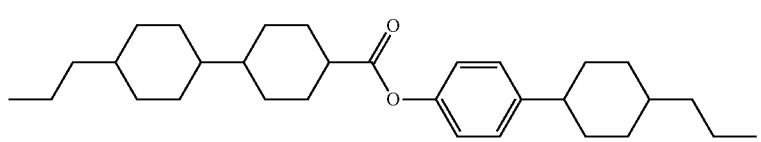

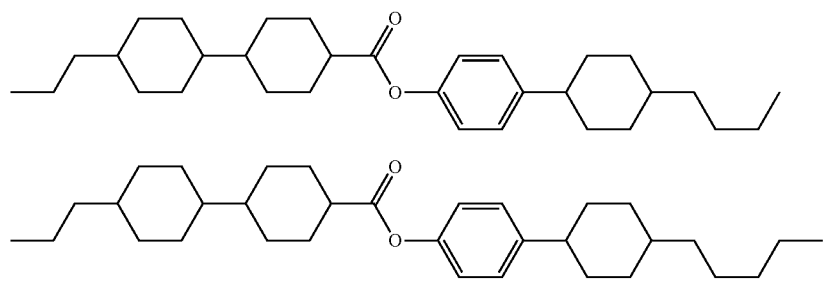

(L-7.52)

(L-7.53)

The lower limit of the preferred total amount of compounds represented by the general formulae (i), (ii), (L), and (N) is 80%, 85%, 88%, 90%, 92%, 93%, 94%, 95%, 96%, 97%, 98%, 99%, or 100% of the total amount of a composition according to the present invention. The upper limit of the preferred amount is 100%, 99%, 98%, or 95%.

The lower limit of the preferred total amount of compounds represented by the general formulae (i), (ii), (L-1) to (L-7), and (M-1) to (M-8) is 80%, 85%, 88%, 90%, 92%, 93%, 94%, 95%, 96%, 97%, 98%, 99%, or 100% of the total amount of a composition according to the present invention. The upper limit of the preferred amount is 100%, 99%, 98%, or 95%.

A composition according to the present invention preferably contains no compound with a structure in which oxygen atoms are bonded together, such as a peroxy (—CO—OO—) structure, in its molecules.

When the reliability and long-term stability of a composition are regarded as important, the amount of compound or compounds with a carbonyl group is preferably 5% or less, more preferably 3% or less, still more preferably 1% or less, most preferably substantially zero percent, of the total mass of the composition.

When stability under UV radiation is regarded as important, the amount of compound or compounds substituted with a chlorine atom is preferably 15% or less, 10% or less, 8% or less, more preferably 5% or less, preferably 3% or less, more preferably substantially zero percent, of the total mass of the composition.

The amount of compound in which all the ring structures of its molecules are 6-membered rings is preferably increased. The amount of compound in which all the ring structures of its molecules are 6-membered rings is preferably 80% or more, more preferably 90% or more, still more preferably 95% or more, of the total mass of the composition. Most preferably, a composition is composed substantially solely of a compound in which all the ring structures of its molecules are 6-membered rings.

To suppress the oxidative degradation of a composition, the amount of compound having a cyclohexenylene group as a ring structure is preferably decreased. The amount of compound with a cyclohexenylene group is preferably 10% or less, preferably 8% or less, more preferably 5% or less, preferably 3% or less, still more preferably substantially zero percent, of the total mass of the composition.

When improved viscosity and Tni are regarded as important, the amount of compound having a 2-methylbenzene-1,4-diyl group in its molecules in which a hydrogen atom is optionally substituted with a halogen is preferably decreased, and the amount of compound having a 2-methylbenzene-1,4-diyl group in its molecules is preferably 10% or less, preferably 8% or less, more preferably 5% or less, preferably 3% or less, still more preferably substantially zero percent, of the total mass of the composition.

The phrase "substantially zero percent", as used herein, refers to zero percent except for incidental inclusions.

When a compound in a composition according to a first embodiment of the present invention has an alkenyl group as a side chain, and the alkenyl group is bonded to cyclohexane, the alkenyl group preferably has 2 to 5 carbon atoms. When the alkenyl group is bonded to benzene, the alkenyl group preferably has 4 or 5 carbon atoms, and an unsaturated bond of the alkenyl group is preferably not directly bonded to benzene.

A liquid crystal composition for use in the present invention preferably has an average elastic constant ($K_{AVG}$) in the range of 10 to 25. The lower limit of the average elastic constant ($K_{AVG}$) is preferably 10, 10.5, 11, 11.5, 12, 12.3, 12.5, 12.8, 13, 13.3, 13.5, 13.8, 14, 14.3, 14.5, 14.8, 15, 15.3, 15.5, 15.8, 16, 16.3, 16.5, 16.8, 17, 17.3, 17.5, 17.8, or 18. The upper limit of the average elastic constant ($K_{AVG}$) is preferably 25, 24.5, 24, 23.5, 23, 22.8, 22.5, 22.3, 22, 21.8, 21.5, 21.3, 21, 20.8, 20.5, 20.3, 20, 19.8, 19.5, 19.3, 19, 18.8, 18.5, 18.3, 18, 17.8, 17.5, 17.3, or 17. When a reduction in power consumption is regarded as important, the light amount of a backlight is effectively decreased, the light transmittance of a liquid crystal display device is preferably improved, and for that purpose $K_{AVG}$ is preferably set somewhat lower. When improved response speed is regarded as important, $K_{AVG}$ is preferably set somewhat higher.

A polymerizable compound according to the present invention is preferably represented by the following general formula (P).

[Chem. 96]

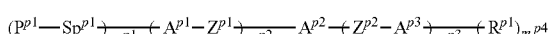

(P)

(In the general formula (P), $R^{p1}$ denotes a hydrogen atom, a fluorine atom, a cyano group, a hydrogen atom, an alkyl group having 1 to 15 carbon atoms in which a hydrogen atom is optionally substituted with a halogen atom, an alkoxy group having 1 to 15 carbon atoms in which a hydrogen atom is optionally substituted with a halogen atom, an alkenyl group having 1 to 15 carbon atoms in which a hydrogen atom is optionally substituted with a halogen atom, an alkenyloxy group having 1 to 15 carbon atoms in which a hydrogen atom is optionally substituted with a halogen atom, or -$Sp^{p2}$-$P^{p2}$, $P^{p1}$ and $P^{p2}$ are independently represented by one of the general formulae ($P^{p1}$-1) to ($P^{p1}$-9),

[Chem. 97]

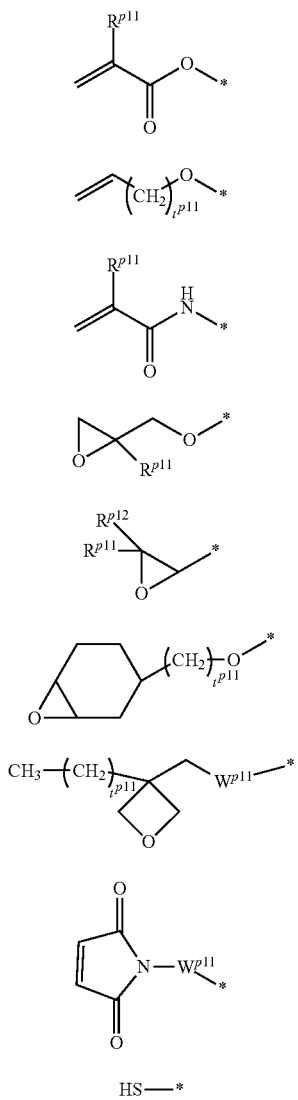

(wherein $R^{p11}$ and $R^{p12}$ independently denote a hydrogen atom, an alkyl group having 1 to 5 carbon atoms, or a halogenated alkyl group having 1 to 5 carbon atoms, $W^{p11}$ denotes a single bond, —O—, —COO—, or a methylene group, $t^{p11}$ denotes 0, 1, or 2, a plurality of $R^{p11}$s, if present, in the molecule may be the same or different, a plurality of $R^{p12}$s, if present, in the molecule may be the same or different, a plurality of $W^{p11}$s, if present, in the molecule may be the same or different, and/or a plurality of $t^{p11}$s, if present, in the molecule may be the same or different)

$Sp^{p1}$ and $Sp^{p2}$ independently denote a single bond or a spacer group, $Z^{p1}$ and $Z^{p2}$ independently denote a single bond, —O—, —S—, —CH$_2$—, —OCH$_2$—, —CH$_2$O—, —CO—, —C$_2$H$_4$—, —COO—, —OCO—, —OCOOCH$_2$—, —CH$_2$OCOO—, —OCH$_2$CH$_2$O—, —CO—NR$^{ZP1}$—, —NR$^{ZP1}$—CO—, —SCH$_2$—, —CH$_2$S—,
—CH=CR$^{ZP1}$—COO—, —CH=CR$^{ZP1}$—OCO—, —COO—CR$^{ZP1}$=CH—, —OCO—CR$^{ZP1}$=CH—, —COO—CR$^{ZP1}$=CH—COO—, —COO—CR$^{ZP1}$=CH—OCO—, —OCO—CR$^{ZP1}$=CH—COO—, —OCO—CR$^{ZP1}$=CH—OCO—, —(CH$_2$)$_z$—COO—, —(CH$_2$)$_2$—OCO—, —OCO—(CH$_2$)$_2$—, —(C=O)—O—(CH$_2$)$_2$—, —CH=CH—, —CF=CF—, —CF=CH—, —CH=CF—, —CF$_2$—, —CF$_2$O—, —OCF$_2$—, —CF$_2$CH$_2$—, —CH$_2$CF$_2$—, —CF$_2$CF$_2$—, or —C≡C— (wherein $R^{ZP1}$ independently denotes a hydrogen atom or an alkyl group having 1 to 4 carbon atoms, and a plurality of $R^{ZP1}$s, if present, in the molecule may be the same or different)

$A^{p2}$ denotes a 1,4-phenylene group, a 1,4-cyclohexylene group, an anthracene-2,6-diyl group, a phenanthrene-2,7-diyl group, a pyridine-2,5-diyl group, a pyrimidine-2,5-diyl group, a naphthalene-2,6-diyl group, an indan-2,5-diyl group, a 1,2,3,4-tetrahydronaphthalene-2,6-diyl group, or a 1,3-dioxane-2,5-diyl group, and $A^{p2}$ is unsubstituted or optionally substituted with an alkyl group having 1 to 12 carbon atoms, a halogenated alkyl group having 1 to 12 carbon atoms, an alkoxy group having 1 to 12 carbon atoms, a halogenated alkoxy group having 1 to 12 carbon atoms, a halogen atom, a cyano group, a nitro group, or -Sp$^{p2}$-P$^{p2}$, $A^{p1}$ denotes a group represented by one of the formulae ($A^{p1}$-11) to ($A^{p1}$-19),

[Chem. 98]

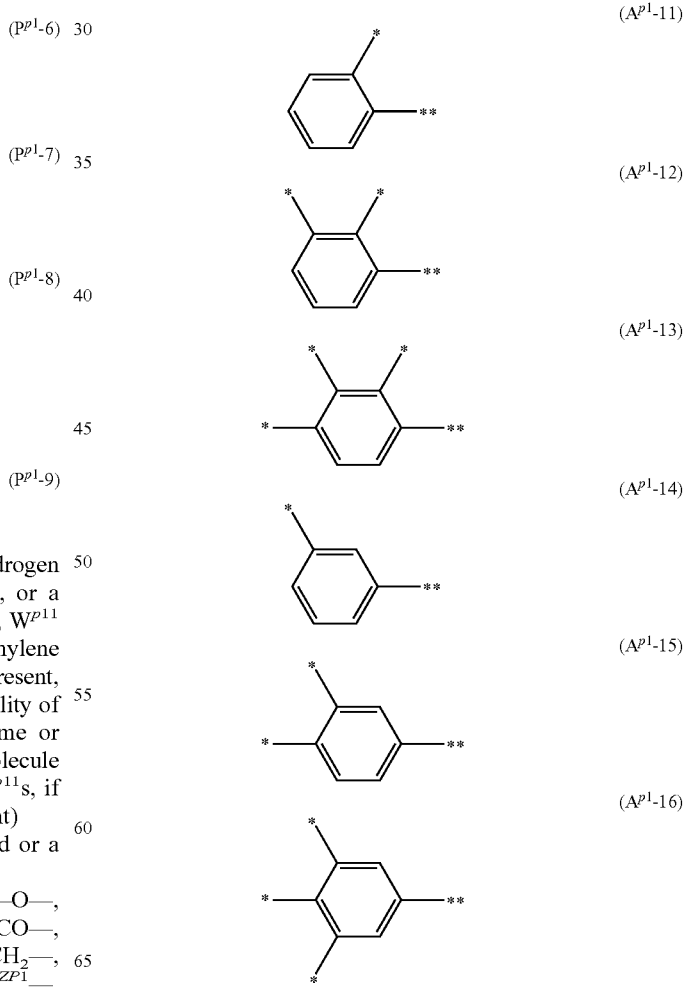

97

-continued (A^{p1}-17)

(A^{p1}-18)

(A^{p1}-19)

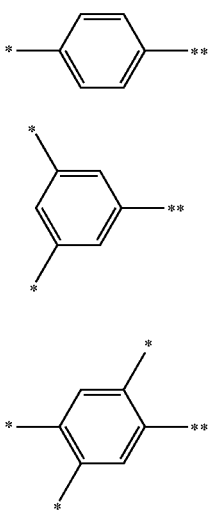

(wherein * is bonded to $Sp^{p1}$ or, when $m^{p1}$ is 2 or 3, to $p^{p1}$ or $Z^{p1}$, and ** is bonded to $Z^{p1}$, and 1 or 2 or more hydrogen atoms in the structure are optionally substituted with an alkyl group having 1 to 12 carbon atoms, a halogenated alkyl group having 1 to 12 carbon atoms, an alkoxy group having 1 to 12 carbon atoms, a halogenated alkoxy group having 1 to 12 carbon atoms, a halogen atom, a cyano group, or a nitro group), $A^{p3}$ denotes a group represented by one of the formulae $(A^{p3}-11)$ to $(A^{p3}-19)$, and

[Chem. 99]

(A^{p3}-11)

(A^{p3}-12)

(A^{p3}-13)

(A^{p3}-14)

(A^{p3}-15)

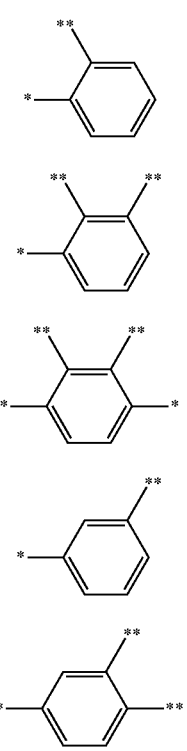

98

-continued (A^{p3}-16)

(A^{p3}-17)

(A^{p3}-18)

(A^{p3}-19)

(wherein * is bonded to $Z^{p2}$, and ** is bonded to $R^{p1}$ or, when $m^{p3}$ is 2 or 3, to $R^{p1}$ or $Z^{p2}$, and 1 or 2 or more hydrogen atoms in the structure are optionally substituted with an alkyl group having 1 to 12 carbon atoms, a halogenated alkyl group having 1 to 12 carbon atoms, an alkoxy group having 1 to 12 carbon atoms, a halogenated alkoxy group having 1 to 12 carbon atoms, a halogen atom, a cyano group, or a nitro group), $m^{p2}$ and $m^{p3}$ independently denote 0, 1, 2, or 3, $m^{p1}$ and $m^{p4}$ independently denote 1, 2, or 3, a plurality of $P^{p1}$s, if present, in the molecule may be the same or different, a plurality of $Sp^{p1}$s, if present, in the molecule may be the same or different, a plurality of APs, if present, in the molecule may be the same or different, a plurality of $Z^{p1}$s, if present, in the molecule may be the same or different, a plurality of $Z^{p2}$s, if present, in the molecule may be the same or different, a plurality of $A^{p3}$s, if present, in the molecule may be the same or different, and/or a plurality of $R^{p1}$s, if present, in the molecule may be the same or different.) One or two or more of the polymerizable monomers are preferably contained.

In the general formula (P) according to the present invention, $R^{p1}$ preferably denotes $-Sp^{p2}-P^{p2}$.

$P^{p1}$ and $P^{p2}$ are preferably independently represented by one of the formulae $(P^{p1}-1)$ to $(P^{p1}-3)$, preferably $(P^{p1}-1)$.

$R^{p11}$ and $R^{p12}$ preferably independently denote a hydrogen atom or a methyl group.

$m^{p1}+m^{p4}$ is preferably 2 or more, preferably 2 or 3.

$Z^{p1}$ and $Z^{p2}$ preferably independently denote a single bond, —OCH$_2$—, —CH$_2$O—, —CO—, —C$_2$H$_4$—, —COO—, —OCO—, —COOC$_2$H$_4$—, —OCOC$_2$H$_4$—, —C$_2$H$_4$OCO—, —C$_2$H$_4$COO—, —CH=CH—, —CF$_2$—, —CF$_2$O—, —(CH$_2$)$_2$—COO—, —(CH$_2$)$_2$—OCO—, —OCO—(CH$_2$)$_2$—, —CH=CH—COO—, —COO—CH=CH—, —OCOCH=CH—, —COO—(CH$_2$)$_2$—, —OCF$_2$—, or —C≡C—, preferably a single bond, —OCH$_2$—, —CH$_2$O—, —C$_2$H$_4$—, —COO—, —OCO—, —COOC$_2$H$_4$—, —OCOC$_2$H$_4$—, —C$_2$H$_4$OCO—, —C$_2$H$_4$COO—, —CH=CH—, —(CH$_2$)$_2$—COO—, —(CH$_2$)$_2$—OCO—, —OCO—(CH$_2$)$_2$—, —CH=CH—COO—, —COO—CH=CH—, —OCOCH=CH—, —COO—(CH$_2$)$_2$—, or —C≡C—. Preferably, only one of $Z^{p1}$s and $Z^{p2}$s in the molecule denotes —OCH$_2$—, —CH$_2$O—, —C$_2$H$_4$—, —COO—, —OCO—, —COOC$_2$H$_4$—, —OCOC$_2$H$_4$—, —C—H$_4$OCO—, —C$_2$H$_4$COO—, —CH=CH—, —(CH$_2$)$_2$—COO—, —(CH$_2$)$_2$—OCO—, —OCO—(CH$_2$)$_2$—, —CH=CH—COO—, —COO—CH=CH—, —OCOCH=CH—, —COO—(CH$_2$)$_2$—, or —C≡C—, and the others denote a single bond. Preferably, only one of $Z^{p1}$s and $Z^{p2}$s in the molecule denotes —OCH$_2$—, —CH$_2$O—, —C$_2$H$_4$—, —COO—, or —OCO—, and the others denote a single bond. Preferably, all $Z^{p1}$s and $Z^{p2}$s denote a single bond.

Preferably, only one of $Z^{p1}$s and $Z^{p2}$s in the molecule denotes a linking group selected from the group consisting of —CH=CH—COO—, —COO—CH=CH—, —(CH$_2$)$_2$—COO—, —(CH$_2$)$_2$—OCO—, —O—CO—(CH$_2$)$_2$—, and —COO—(CH$_2$)—, and the others denote a single bond.

$Sp^{p1}$ and $Sp^{p2}$ independently denote a single bond or an alkylene group having 1 to 30 carbon atoms, —CH$_2$— in the alkylene group is optionally substituted with —O—, —CO—, —COO—, —OCO—, —CH=CH—, or —C≡C—, provided that oxygen atoms are not bonded together, and a hydrogen atom in the alkylene group is optionally substituted with a halogen atom. $Sp^{p1}$ and $Sp^{p2}$ preferably independently denote a linear alkylene group having 1 to 10 carbon atoms or a single bond.

$A^{p2}$ preferably denotes a 1,4-phenylene group, a 1,4-cyclohexylene group, an anthracene-2,6-diyl group, a phenanthrene-2,7-diyl group, or a naphthalene-2,6-diyl group, preferably a 1,4-phenylene group, a 1,4-cyclohexylene group, a phenanthrene-2,7-diyl group, or a naphthalene-2,6-diyl group, preferably a phenanthrene-2,7-diyl group when m$^{p2}$+m$^{p3}$ is 0, or preferably a 1,4-phenylene group or a 1,4-cyclohexylene group when m$^{p2}$+m$^{p3}$ is 1, 2, or 3. To improve compatibility with a liquid crystal compound, 1 or 2 or more hydrogen atoms in the structure of $A^{p2}$ is optionally substituted with a methyl group, an ethyl group, a methoxy group, an ethoxy group, or a fluorine atom.

$A^{p1}$ is preferably represented by the formula ($A^{p1}$-15), ($A^{p1}$-16), ($A^{p1}$-17), or ($A^{p1}$-18). To improve compatibility with a liquid crystal compound, 1 or 2 or more hydrogen atoms in the structure of $A^{p1}$ is optionally substituted with a methyl group, an ethyl group, a methoxy group, an ethoxy group, or a fluorine atom.

$A^{p3}$ is preferably represented by the formula ($A^{p1}$-14), ($A^{p1}$-15), ($A^{p1}$-16), ($A^{p1}$-17), or ($A^{p1}$-18). To improve compatibility with a liquid crystal compound, 1 or 2 or more hydrogen atoms in the structure of $A^3$ is optionally substituted with a methyl group, an ethyl group, a methoxy group, an ethoxy group, or a fluorine atom.

m$^{p2}$+m$^{p3}$ is preferably 0, 1, 2, or 3, preferably 1 or 2.

The total amount of a compound represented by the general formula (P) preferably ranges from 0.05% to 10%, 0.1% to 8%, 0.1% to 5%, 0.1% to 3%, 0.2% to 2%, 0.2% to 1.3%, 0.2% to 1%, or 0.2% to 0.56% of a composition containing the compound represented by the general formula (P) in the present application.

The preferred lower limit of the total amount of a compound represented by the general formula (P) is 0.01%, 0.03%, 0.05%, 0.08%, 0.1%, 0.15%, 0.2%, 0.25%, or 0.3% of a composition containing the compound represented by the general formula (P) in the present application.

The preferred upper limit of the total amount of a compound represented by the general formula (P) is 10%, 8%, 5%, 3%, 1.5%, 1.2%, 1%, 0.8%, or 0.5% of a composition containing the compound represented by the general formula (P) in the present application.

A small amount of a compound represented by the general formula (P) is less likely to produce its effects and results in a liquid crystal composition with small or gradually decreasing alignment regulating force. An excessively large amount of a compound represented by the general formula (P) results in a large remaining amount after curing, a longer curing time, or a liquid crystal with low reliability. Thus, the amount is determined in consideration of the balance of them.

A compound represented by the general formula (P) is preferably a compound represented by the general formula (P-1), (P-2), (P-3), or (P-4).

[Chem. 100]

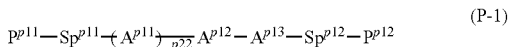
(P-1)

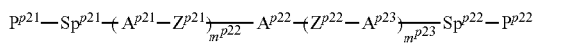
(P-2)

(P-3)

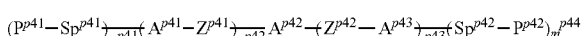

(P-4)

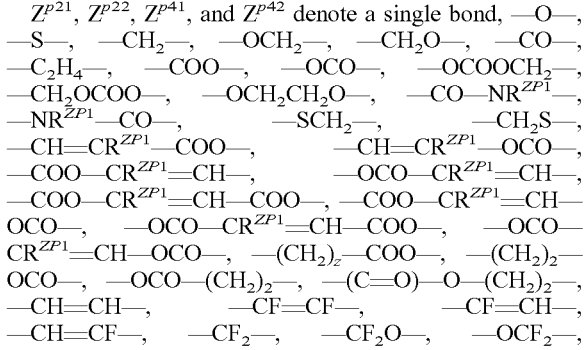

(In the formula, $P^{p11}$, $P^{p12}$, $P^{p21}$, $P^{p22}$, $P^{p31}$, $P^{p32}$, $P^{p41}$, and $P^{p42}$ independently have the same meaning as $P^{p1}$ in the general formula (P), $Sp^{p11}$, $Sp^{p12}$, $Sp^{p21}$, $Sp^{p22}$, $Sp^{p31}$, $Sp^{p32}$, $Sp^{p41}$, and $Sp^{p42}$ independently have the same meaning as $Sp^{p1}$ in the general formula (P), $A^{p11}$, $A^{p12}$, $A^{p13}$, $A^{p21}$, $A^{p22}$, $A^{p23}$, $A^{p31}$, and $A^{p42}$ independently denote a 1,4-phenylene group, a 1,4-cyclohexylene group, an anthracene-2,6-diyl group, a phenanthrene-2,7-diyl group, a pyridine-2,5-diyl group, a pyrimidine-2,5-diyl group, a naphthalene-2,6-diyl group, an indan-2,5-diyl group, a 1,2,3,4-tetrahydronaphthalene-2,6-diyl group, or a 1,3-dioxane-2,5-diyl group; $A^{p11}$, $A^{p12}$, $A^{p13}$, $A^{p21}$, $A^{p22}$, $A^{p23}$, $A^{p32}$, and $A^{p42}$ is independently unsubstituted or optionally substituted with an alkyl group having 1 to 12 carbon atoms, a halogenated alkyl group having 1 to 12 carbon atoms, an alkoxy group having 1 to 12 carbon atoms, a halogenated alkoxy group having 1 to 12 carbon atoms, a halogen atom, a cyano group, or a nitro group, or with -$Sp^2$-$P^{p2}$ in the general formula (P), $A^{p41}$ has the same meaning as $A^{p1}$ in the general formula (P), $A^{p43}$ has the same meaning as $A^{p3}$ in the general formula (P), and $Z^{p21}$, $Z^{p22}$, $Z^{p41}$, and $Z^{p42}$ denote a single bond, —O—, —S—, —CH$_2$—, —OCH$_2$—, —CH$_2$O—, —CO—, —C$_2$H$_4$—, —COO—, —OCO—, —OCOOCH$_2$—, —CH$_2$OCOO—, —OCH$_2$CH$_2$O—, —CO—NR$^{ZP1}$—, —NR$^{ZP1}$—CO—, —SCH$_2$—, —CH$_2$S—, —CH=CR$^{ZP1}$—COO—, —CH=CR$^{ZP1}$—OCO—, —COO—CR$^{ZP1}$=CH—, —OCO—CR$^{ZP1}$=CH—, —COO—CR$^{ZP1}$=CH—COO—, —COO—CR$^{ZP1}$=CH—OCO—, —OCO—CR$^{ZP1}$=CH—COO—, —OCO—CR$^{ZP1}$=CH—OCO—, —(CH$_2$)$_z$—COO—, —(CH$_2$)$_2$—OCO—, —OCO—(CH$_2$)$_2$—, —(C=O)—O—(CH$_2$)$_2$—, —CH=CH—, —CF=CF—, —CF=CH—, —CH=CF—, —CF$_2$—, —CF$_2$O—, —OCF$_2$—, —CF$_2$CH$_2$—, —CH$_2$CF$_2$—, —CF$_2$CF$_2$—, or —C≡C— (wherein R$^{ZP1}$ independently denotes a hydrogen atom or an alkyl group having 1 to 4 carbon atoms, and a plurality of R$^{ZP1}$s, if present, in the molecule may be the same or different), and at least one of Z$^{p21}$s and Z$^{p22}$s in the molecule is not a single bond.)

P$^{p11}$, P$^{p12}$, P$^{p21}$, P$^{p22}$, P$^{p31}$, P$^{p32}$, P$^{p41}$, and P$^{p42}$ are preferably independently represented by one of the formulae (P$^{p1}$-1) to (P$^{p1}$-3), preferably (P$^{p1}$-1), as in P$^{p1}$ in the general formula (P). R$^{p11}$ and R$^{p12}$ preferably independently denote a hydrogen atom or a methyl group.

Sp$^{p11}$, Sp$^{p12}$, Sp$^{p21}$, Sp$^{p22}$, Sp$^{p31}$, Sp$^{p32}$, Sp$^{p41}$, and Sp$^{p42}$ independently denote a single bond or an alkylene group having 1 to 30 carbon atoms, —CH$_2$— in the alkylene group is optionally substituted with —O—, —CO—, —COO—, —OCO—, —CH=CH—, or —C≡C—, provided that oxygen atoms are not bonded together, and a hydrogen atom in the alkylene group is optionally substituted with a halogen atom. Sp$^{p11}$, Sp$^{p12}$, Sp$^{p21}$, Sp$^{p22}$, Sp$^{p31}$, Sp$^{p32}$, Sp$^{p41}$, and Sp$^{p42}$ preferably independently denote a linear alkylene group having 1 to 10 carbon atoms or a single bond.

A$^{p11}$, A$^{p12}$, A$^{p13}$, A$^{p21}$, A$^{p22}$, A$^{p23}$, A$^{p32}$, and A$^{p42}$ independently denote a 1,4-phenylene group, a 1,4-cyclohexylene group, an anthracene-2,6-diyl group, a phenanthrene-2,7-diyl group, or a naphthalene-2,6-diyl group, preferably a 1,4-phenylene group, a 1,4-cyclohexylene group, a phenanthrene-2,7-diyl group, or a naphthalene-2,6-diyl group. In the general formulae (P-1) and (P-2), a 1,4-phenylene group or a 1,4-cyclohexylene group is independently preferred. To improve compatibility with a liquid crystal compound, 1 or 2 or more hydrogen atoms in the structure are optionally substituted with a methyl group, an ethyl group, a methoxy group, an ethoxy group, or a fluorine atom. In the general formula (P-3), a phenanthrene-2,7-diyl group is preferred. To improve compatibility with a liquid crystal compound, 1 or 2 or more hydrogen atoms in the structure is optionally substituted with a methyl group, an ethyl group, a methoxy group, an ethoxy group, or a fluorine atom.

Z$^{p21}$ preferably denotes a single bond, —OCH$_2$—, —CH$_2$O—, —CO—, —C$_2$H$_4$—, —COO—, —OCO—, —COOC$_2$H$_4$—, —OCOC$_2$H$_4$—, —C$_2$H$_4$OCO—, —C$_2$H$_4$COO—, —CH=CH—, —CF$_2$—, —CF$_2$O—, —(CH$_2$)$_2$—COO—, —(CH$_2$)$_2$—OCO—, —OCO—(CH$_2$)$_2$—, —CH=CH—COO—, —COO—CH=CH—, —OCOCH=CH—, —COO—(CH$_2$)$_2$—, —OCF$_2$—, or —C≡C—, preferably a single bond, —OCH$_2$—, —CH$_2$O—, —C$_2$H$_4$—, —COO—, —OCO—, —COOC$_2$H$_4$—, —OCOC$_2$H$_4$—, —C$_2$H$_4$OCO—, —C$_2$H$_4$COO—, —CH=CH—, —(CH$_2$)$_2$—COO—, —(CH$_2$)$_2$—OCO—, —OCO—(CH$_2$)$_2$—, —CH=CH—COO—, —COO—CH=CH—, —OCOCH=CH—, —COO—(CH$_2$)$_2$—, or —C≡C—. Preferably, only one of Z$^{p21}$s in the molecule denotes —OCH$_2$—, —CH$_2$O—, —C$_2$H$_4$—, —COO—, —OCO—, —COOC$_2$H$_4$—, —OCOC$_2$H$_4$—, —C$_2$H$_4$OCO—, —C$_2$H$_4$COO—, —CH=CH—, —(CH$_2$)$_2$—COO—, —(CH$_2$)$_2$—OCO—, —OCO—(CH$_2$)$_2$—, —CH=CH—COO—, —COO—CH=CH—, —OCOCH=CH—, —COO—(CH$_2$)$_2$—, or —C≡C—, and the others denote a single bond. Preferably, only one of Z$^{p21}$s in the molecule denotes —OCH$_2$—, —CH$_2$O—, —C$_2$H$_4$—, —COO—, or —OCO—, and the others denote a single bond. Preferably, all Z$^{p21}$s denote a single bond.

Preferably, only one of Z$^{p21}$s in the molecule denotes a linking group selected from the group consisting of —(CH$_2$)$_2$—COO—, —(CH$_2$)$_2$—OCO—, —O—CO—(CH$_2$)$_2$—, and —COO—(CH$_2$)$_2$—, and the others denote a single bond.

A preferred example of a compound represented by the general formula (P-1) according to the present invention may be a polymerizable compound represented by one of the following formulae (P-1-1) to (P-1-46).

[Chem. 101]

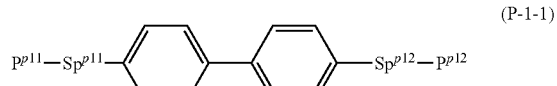
(P-1-1)

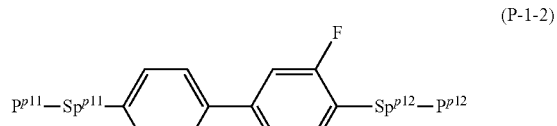
(P-1-2)

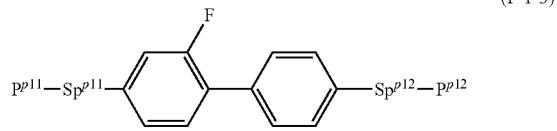
(P-1-3)

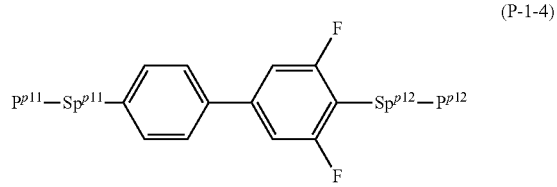
(P-1-4)

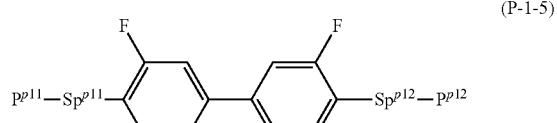
(P-1-5)

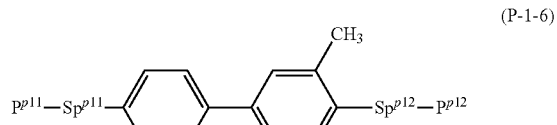
(P-1-6)

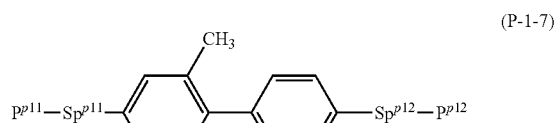
(P-1-7)

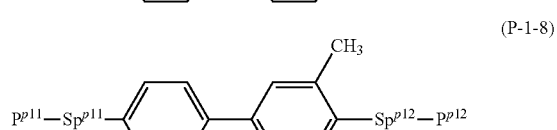
(P-1-8)

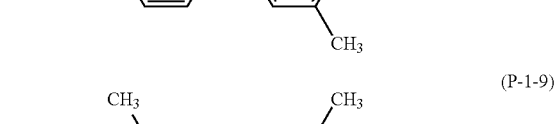
(P-1-9)

[Chem. 102]
(P-1-10)
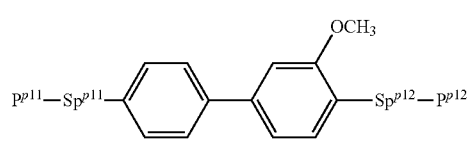
(P-1-11)
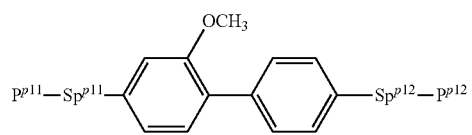
(P-1-12)
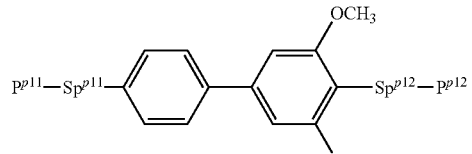
(P-1-13)
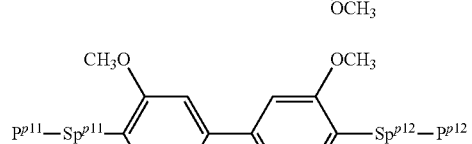
[Chem. 103]
(P-1-21)
(P-1-22)
(P-1-23)
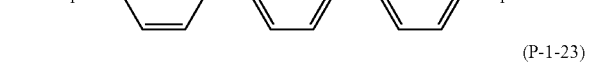
(P-1-24)
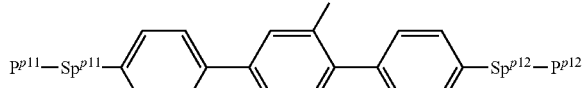
(P-1-25)
(P-1-26)
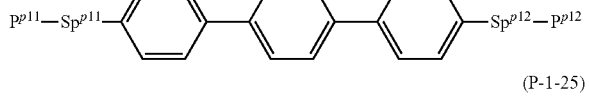
(P-1-27)
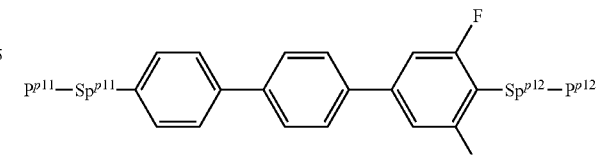
[Chem. 104]
(P-1-31)
(P-1-32)
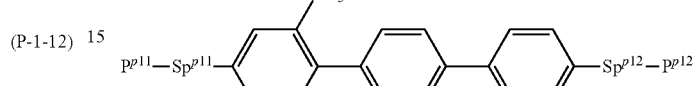
(P-1-33)
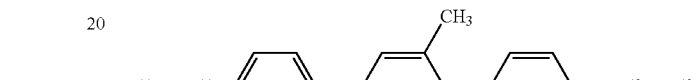
(P-1-34)
(P-1-35)
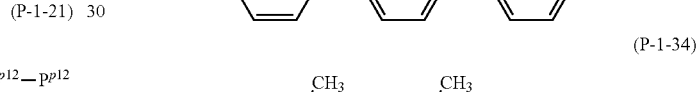
(P-1-36)
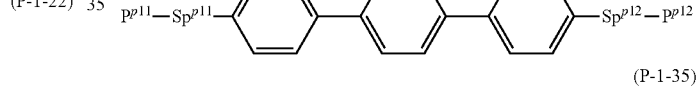
[Chem. 105]
(P-1-41)
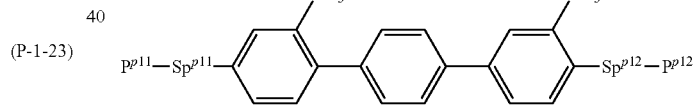
(P-1-42)

(P-1-43)
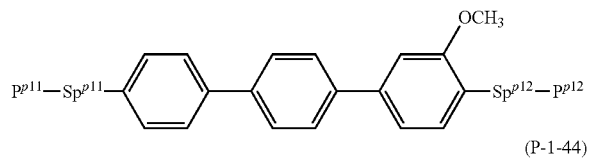
(P-1-44)
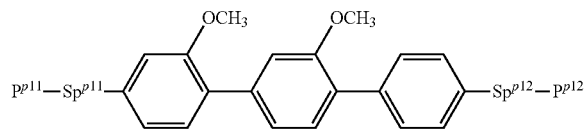
(P-1-45)
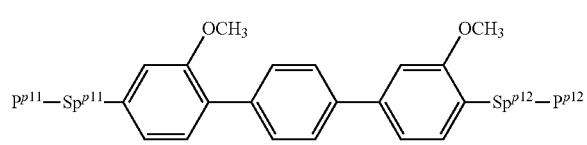
(P-1-46)
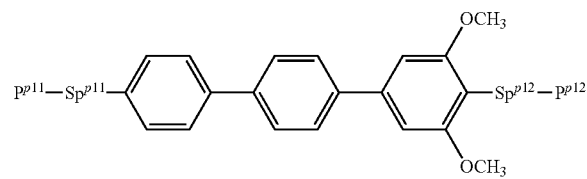
(In the formulae, $P^{p11}$, $P^{p12}$, $Sp^{p11}$, and $Sp^{p12}$ have the same meaning as $P^{p11}$, $P^{p12}$, $Sp^{p11}$, and $Sp^{p12}$ in the general formula (P-1).)
A preferred example of a compound represented by the general formula (P-2) according to the present invention may be a polymerizable compound represented by one of the following formulae (P-2-1) to (P-2-12).
[Chem. 106]
(P-2-1)
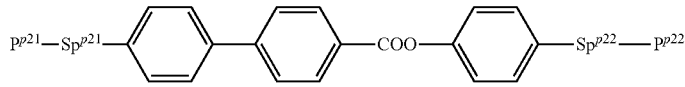
(P-2-2)
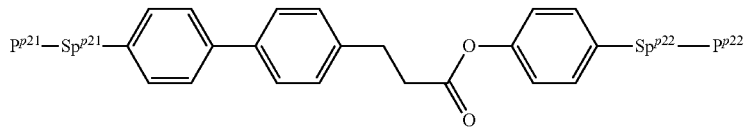
(P-2-3)
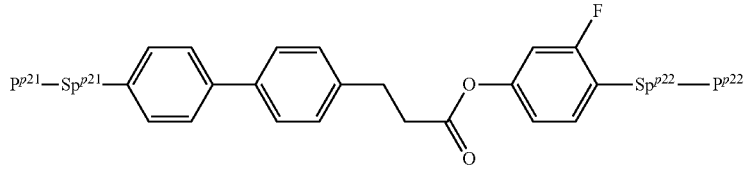
(P-2-4)
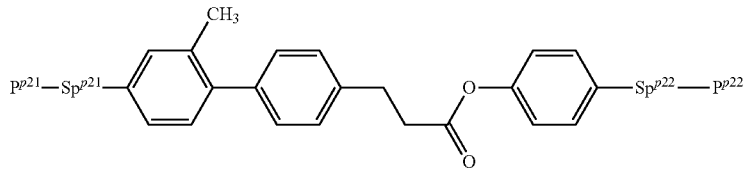
(P-2-5)
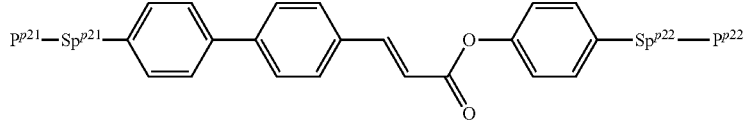
(P-2-6)
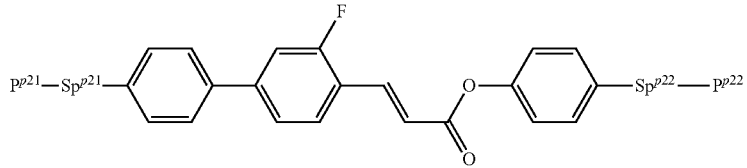

(P-2-7)
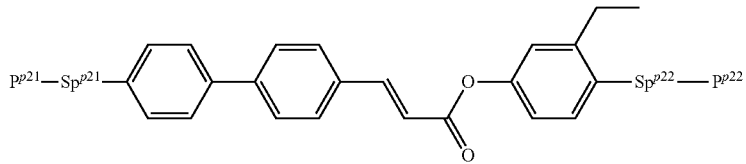
(P-2-8)
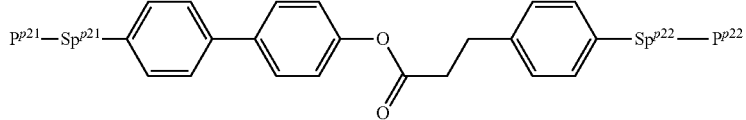
(P-2-9)
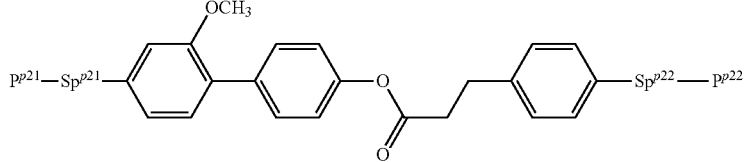
(P-2-10)
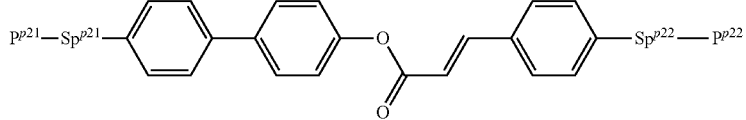
(P-2-11)
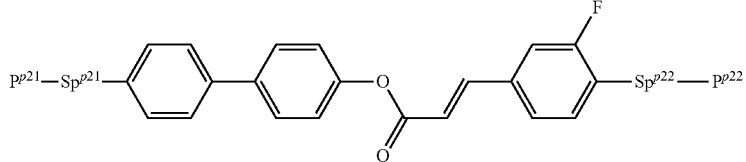
(P-2-12)
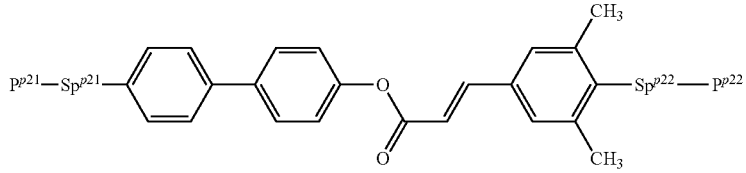
(In the formulae, $P^{p21}$, $P^{p22}$, $Sp^{p21}$, and $Sp^{p22}$ have the same meaning as $P^{p21}$, $P^{p22}$, $Sp^{p21}$, and $Sp^{p22}$ in the general formula (P-2).)
A preferred example of a compound represented by the general formula (P-3) according to the present invention may be a polymerizable compound represented by one of the following formulae (P-3-1) to (P-3-15).
[Chem. 107]
(P-3-1)
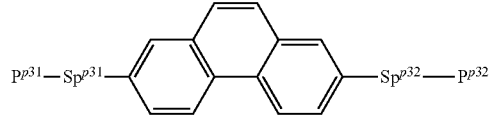
(P-3-2)
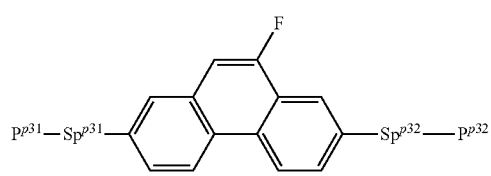
-continued
(P-3-3)
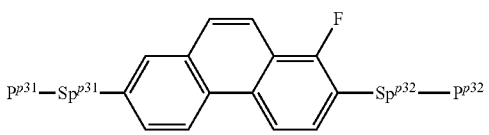
(P-3-4)
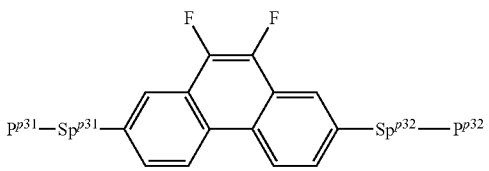
(P-3-5)
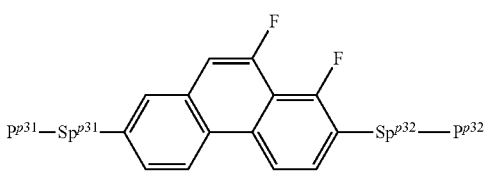

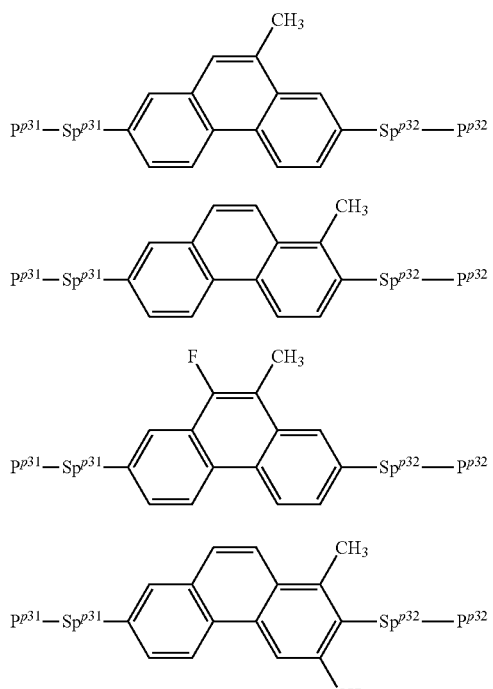
(P-3-6)
(P-3-7)
(P-3-8)
(P-3-9)
[Chem. 108]
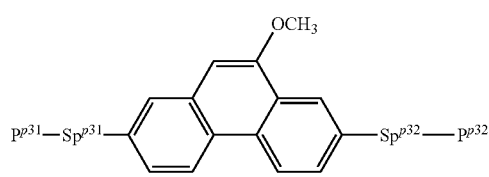
(P-3-11)
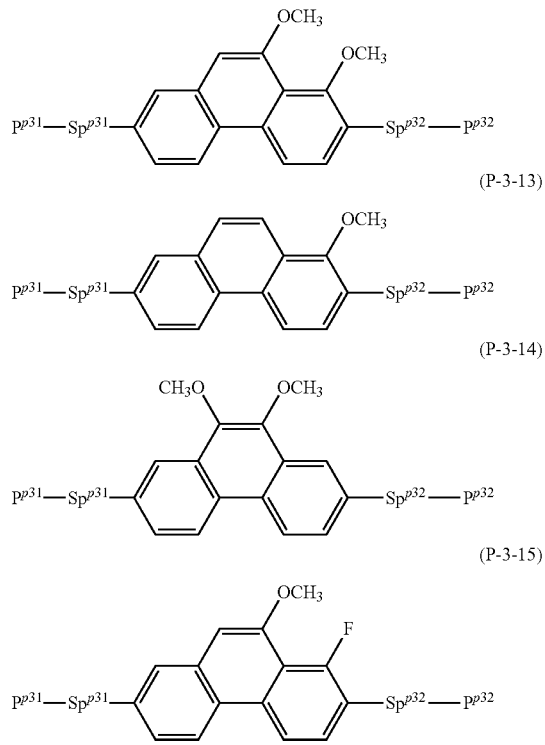
(P-3-12)
(P-3-13)
(P-3-14)
(P-3-15)
(In the formulae, $P^{p31}$, $P^{p32}$, $Sp^{p31}$, and $Sp^{p32}$ have the same meaning as $P^{p33}$, $P^{p32}$, $Sp^{p31}$, and $Sp^{p32}$ in the general formula (P-3).)
A preferred example of a compound represented by the general formula (P-4) according to the present invention may be a polymerizable compound represented by one of the following formulae (P-4-1) to (P-4-15).
[Chem. 109]
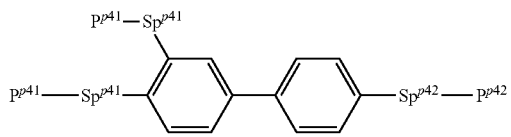
(P-4-1)
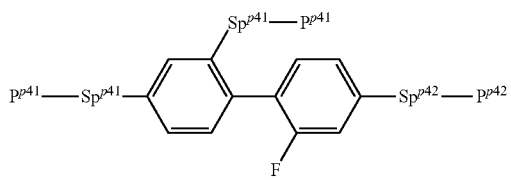
(P-4-2)
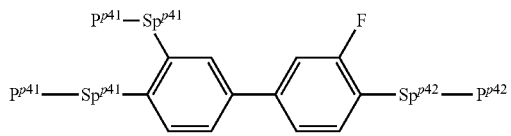
(P-4-3)

-continued
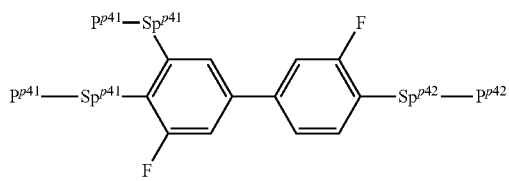
(P-4-4)
[Chem. 110]
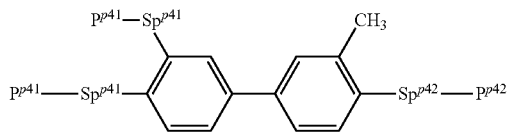
(P-4-5)
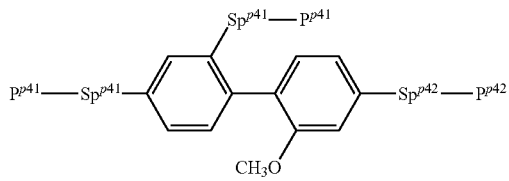
(P-4-6)
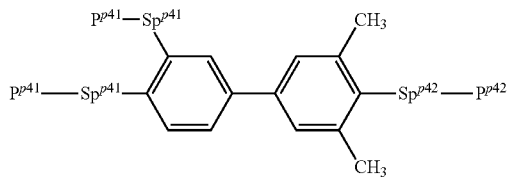
(P-4-7)
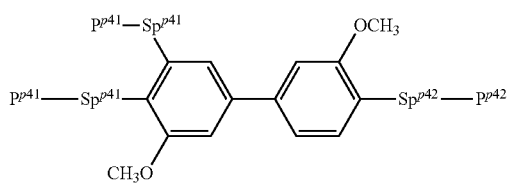
(P-4-8)
[Chem. 111]
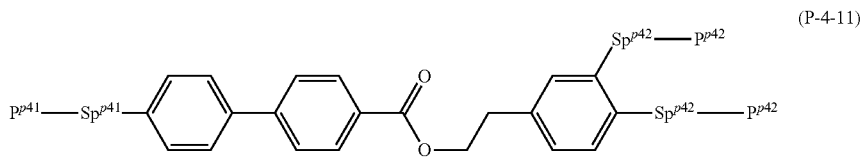
(P-4-11)
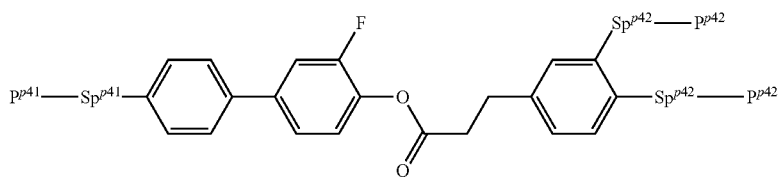
(P-4-12)
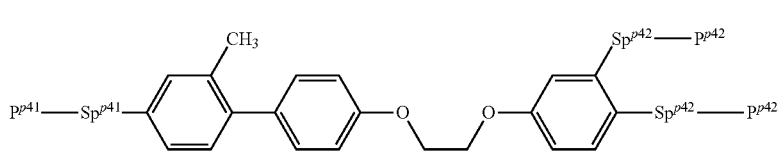
(P-4-13)
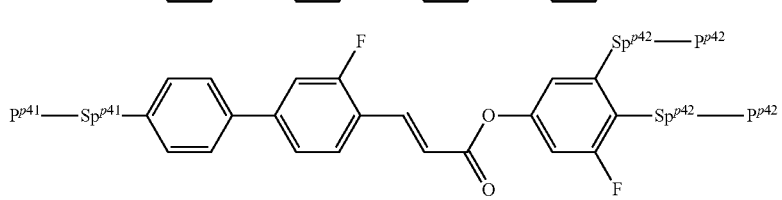
(P-4-14)

-continued
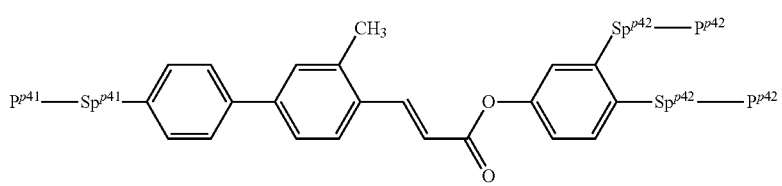
(P-4-15)
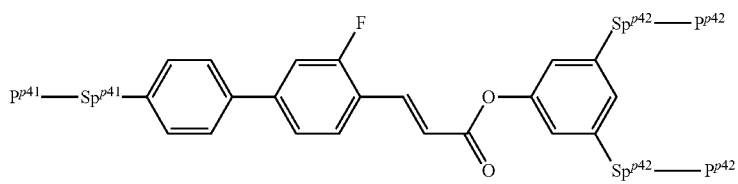
[Chem. 112]
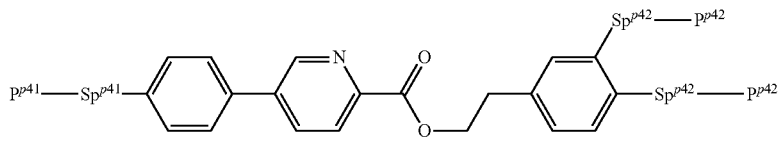
(P-4-17)
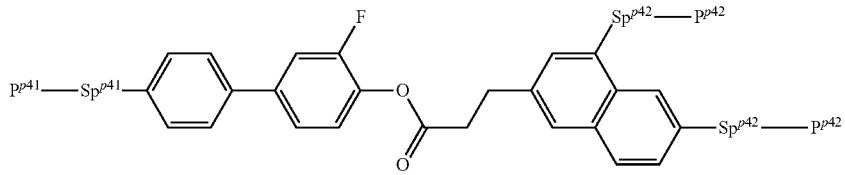
(P-4-18)
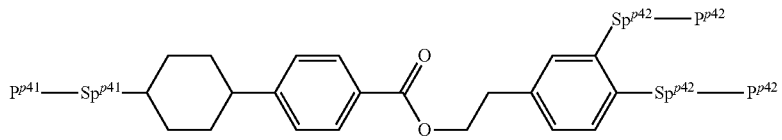
(P-4-17)
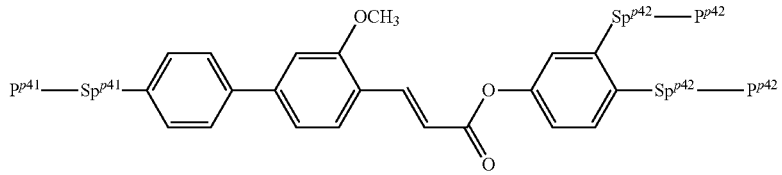
(P-4-18)
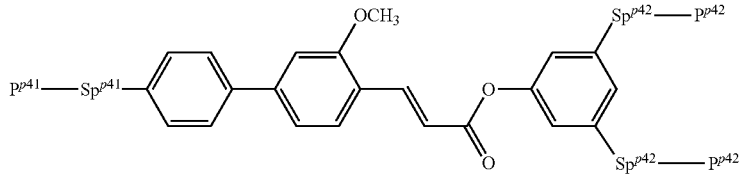
(P-4-19)
(In the formulae, $P^{p41}$, $P^{p42}$, $Sp^{p41}$, and $Sp^{p42}$ have the same meaning as $P^{p41}$, $P^{p42}$, $Sp^{p41}$, and $Sp^{p42}$ in the general formula (P-4).) A composition according to the present invention may further contain one or two or more compounds (Q) as an additive agent to improve reliability. The compounds (Q) preferably have the following structures.

[Chem. 113]

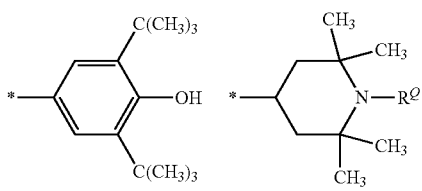

(In the formulae, $R^Q$ denotes a hydroxy group, a hydrogen atom, a linear or branched alkyl group having 1 to 22 carbon atoms, one or two or more $CH_2$ groups in the alkyl group are optionally substituted with —O—, —CH=CH—, —CO—, —OCO—, —COO—, —C≡C—, —CF$_2$O—, or —OCF$_2$— such that oxygen atoms are not directly adjacent to each other, and * is bonded to another structure.)

$R^Q$ denotes a linear or branched alkyl group having 1 to 22 carbon atoms. One or two or more $CH_2$ groups in the alkyl group are optionally substituted with —O—, —CH=CH—, —CO—, —OCO—, —COO—, —C≡C—, —CF$_2$O—, or —OCF$_2$— such that oxygen atoms are not directly adjacent to each other. $R^Q$ preferably denotes a linear alkyl group having 1 to 10 carbon atoms, a linear alkoxy group, a linear alkyl group in which one $CH_2$ group is substituted with —OCO— or —COO—, a branched alkyl group, a branched alkoxy group, or a branched alkyl group in which one $CH_2$ group is substituted with —OCO— or —COO—, more preferably a linear alkyl group having 1 to 20 carbon atoms, a linear alkyl group in which one $CH_2$ group is substituted with —OCO— or —COO—, a branched alkyl group, a branched alkoxy group, or a branched alkyl group in which one $CH_2$ group is substituted with —OCO— or —COO—. MQ denotes a trans-1,4-cyclohexylene group, a 1,4-phenylene group, or a single bond, preferably a trans-1,4-cyclohexylene group or a 1,4-phenylene group.

More specifically, the compounds (Q) are preferably the compounds represented by the general formulae (Q-a) to (Q-d).

[Chem. 114]

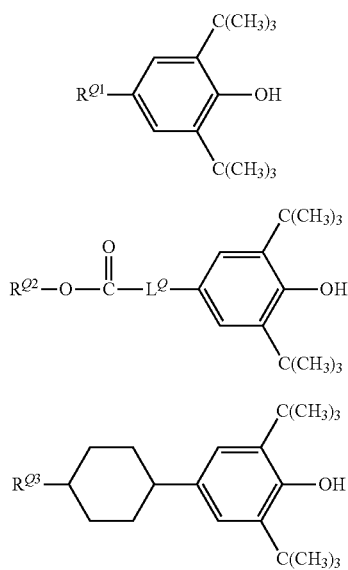

In these formulae, $R^{Q1}$ is preferably a linear or branched alkyl group having 1 to 10 carbon atoms, $R^{Q2}$ is preferably a linear or branched alkyl group having 1 to 20 carbon atoms, $R^{Q3}$ is preferably a linear alkyl group, a branched alkyl group, a linear alkoxy group, or a branched alkoxy group each having 1 to 8 carbon atoms, and $L^Q$ is preferably a linear or branched alkylene group having 1 to 8 carbon atoms. Among the compounds represented by the general formulae (Q-a) to (Q-d), more preferred are compounds represented by the general formulae (Q-c) and (Q-d).

A composition according to the present invention preferably contains one or two, more preferably one to five, compounds represented by the general formula (Q). The amount of compound(s) represented by the general formulae (Q) in a composition according to the present invention preferably ranges from 0.001% to 1%, more preferably 0.001% to 0.1%, particularly preferably 0.001% to 0.05%.

More specifically, the compounds represented by the following (Q-1) to (Q-44) are preferred as antioxidants or light stabilizers for use in the present invention.

[Chem. 115]

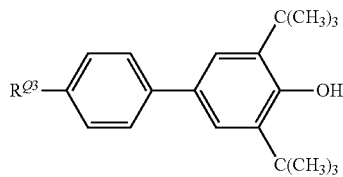

(Q-4)
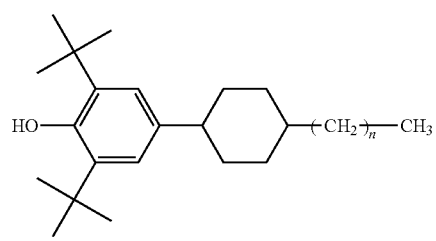
(Q-5)
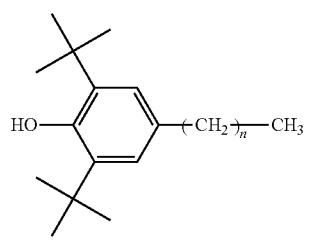
(Q-6)
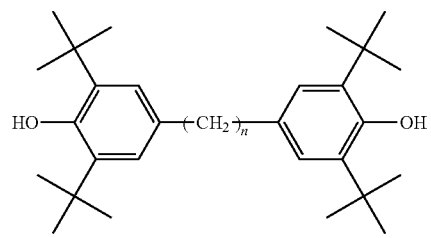
(Q-7)
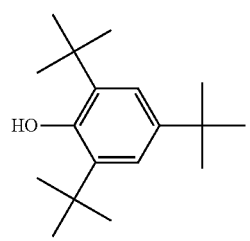
(Q-8)
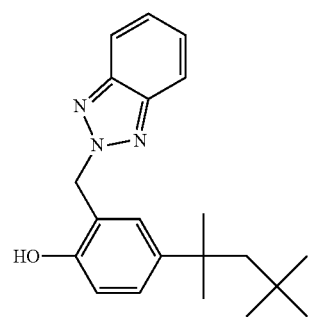
(Q-9)
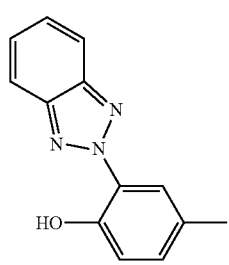
(Q-10)
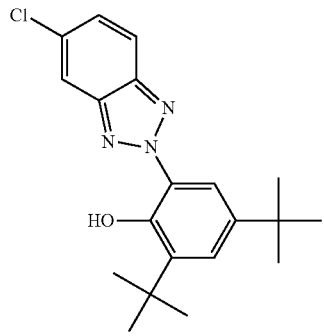
[Chem. 116]
(Q-11)
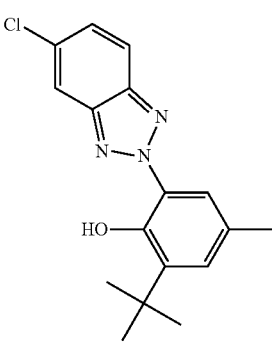
(Q-12)
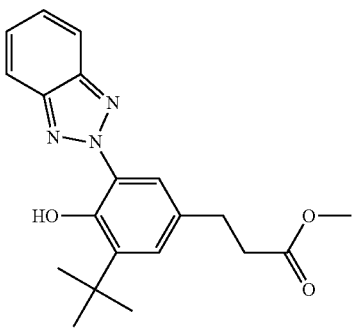
(Q-13)
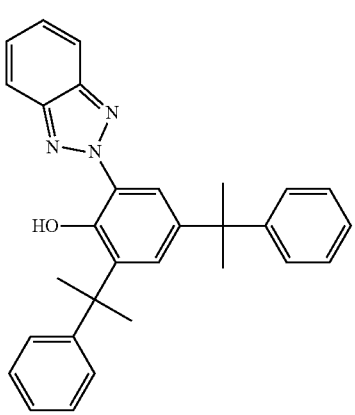

-continued
(Q-14)
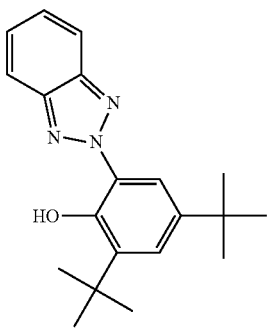
(Q-19)
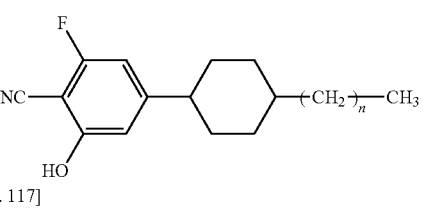
(Q-15)
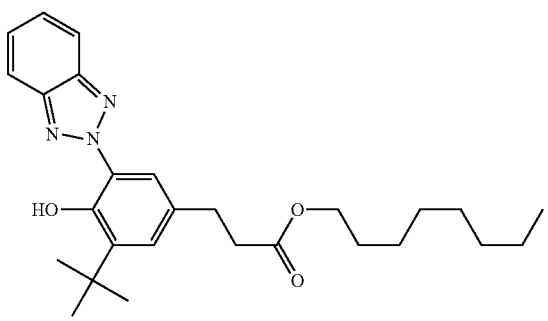
(Q-20)
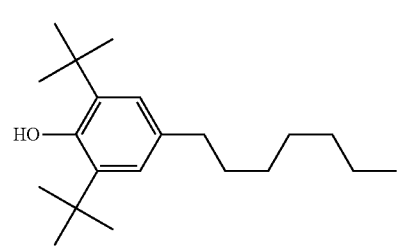
[Chem. 117]
(Q-21)
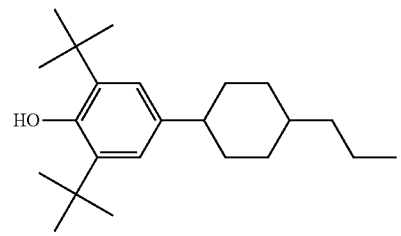
(Q-16)
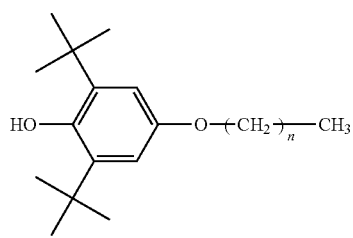
(Q-22)
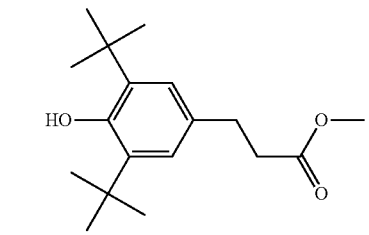
(Q-17)
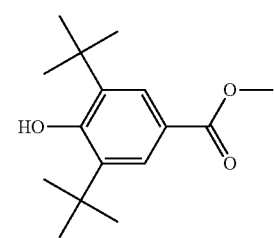
(Q-23)
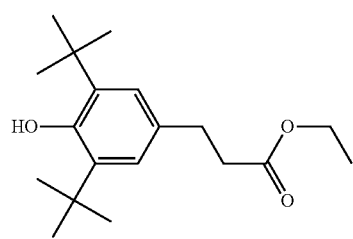
(Q-18)
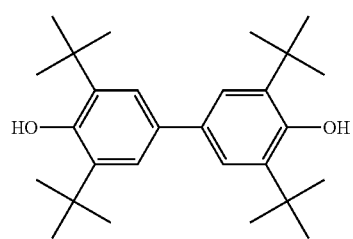
(Q-24)
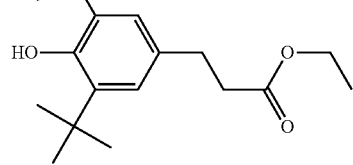

(Q-25)
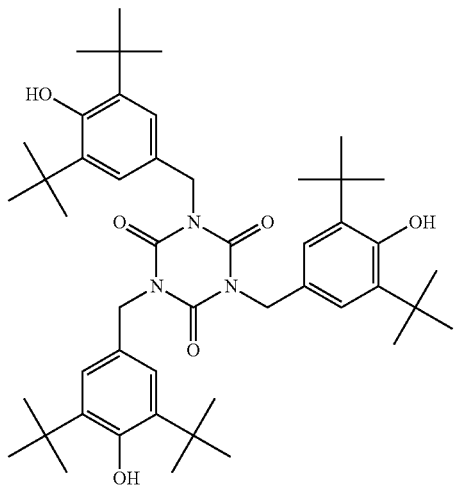
(Q-26)
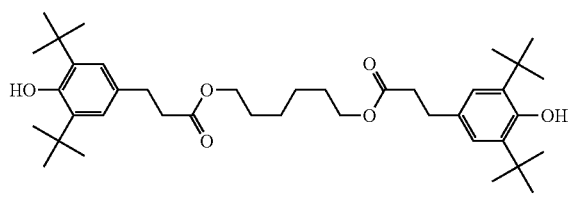
(Q-27)
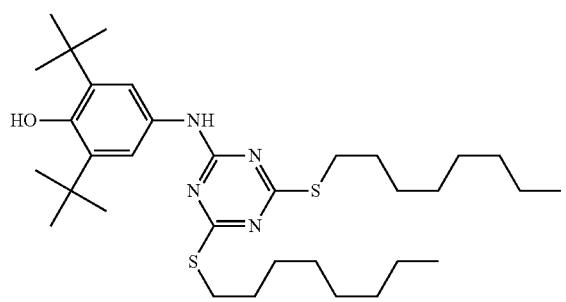
(Q-28)
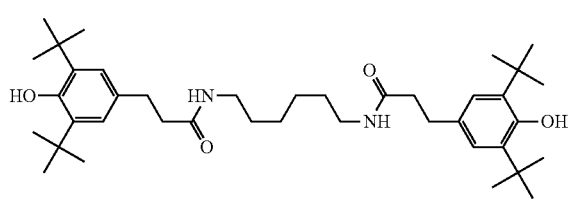
[Chem. 118]
(Q-29)
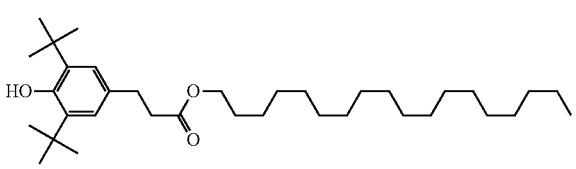
(Q-30)
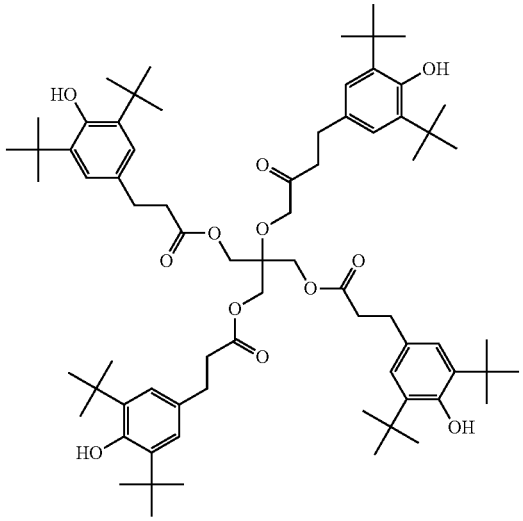
(Q-31)
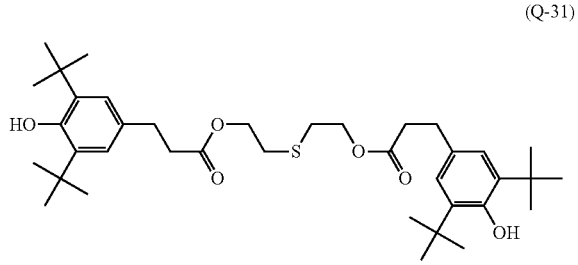
(Q-32)
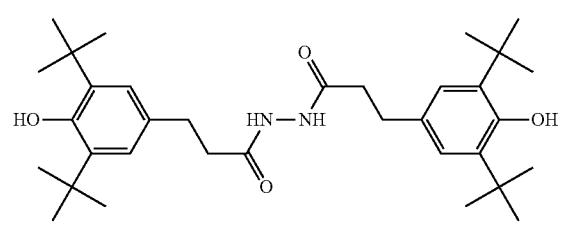
(Q-33)
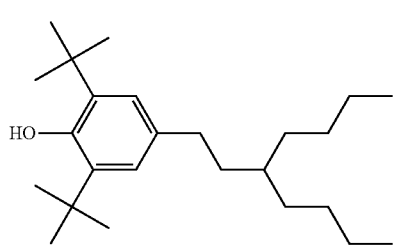

(Q-34)
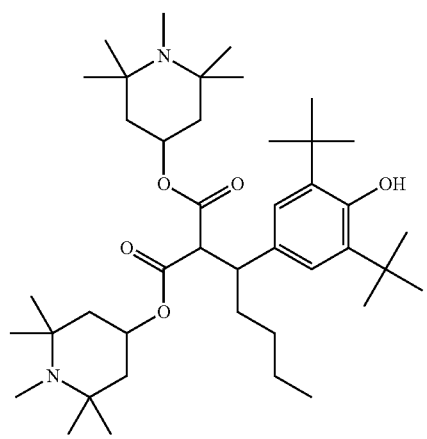
(Q-35)
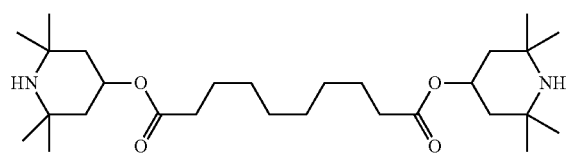
(Q-36)
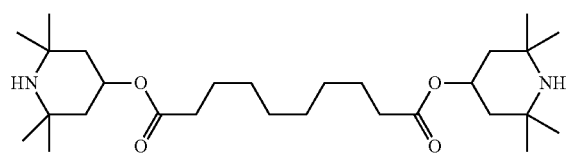
[Chem. 119]
(Q-37)
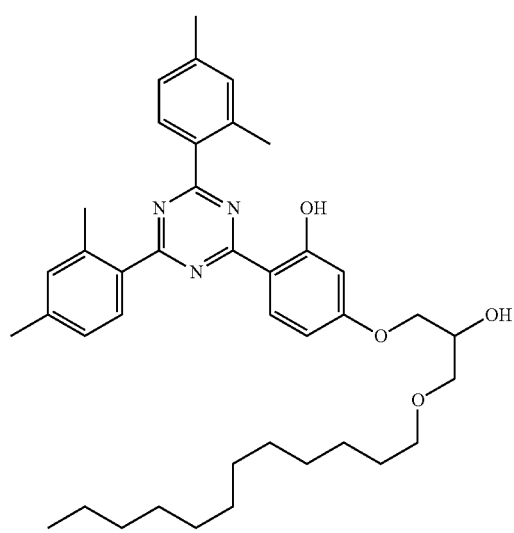
(Q-38)
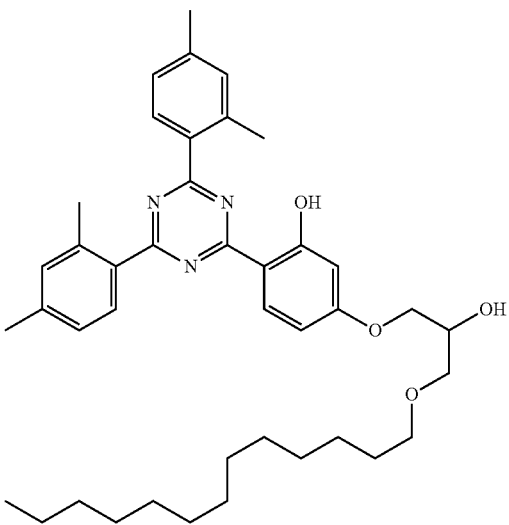
(Q-39)
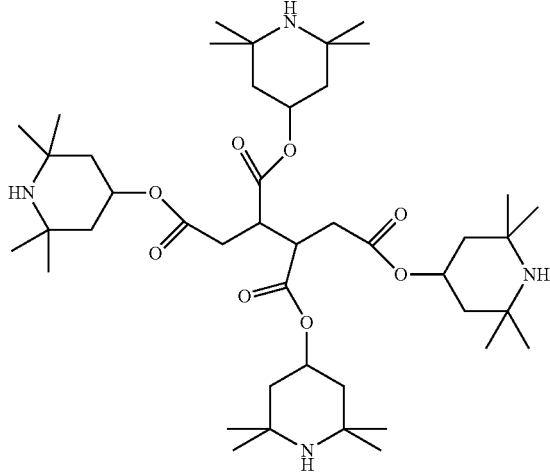
(Q-40)
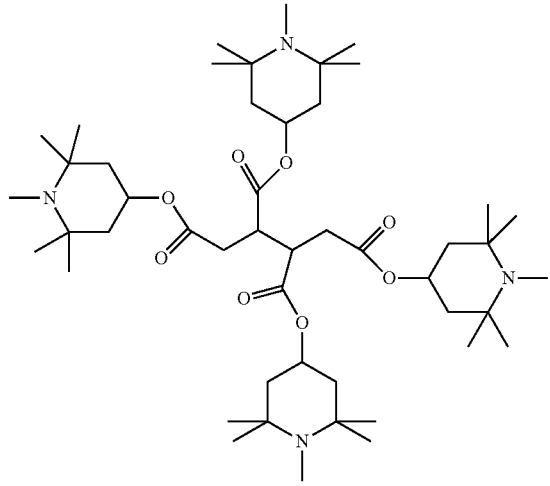

(Q-41)

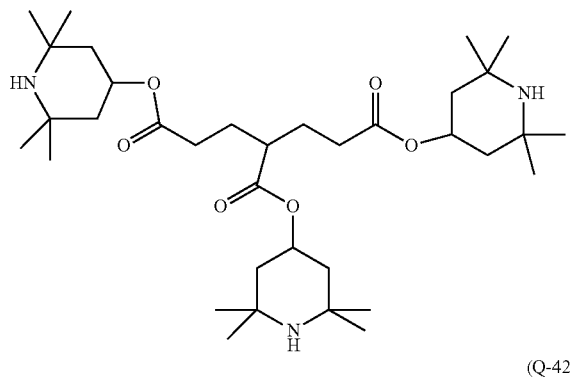

(Q-42)

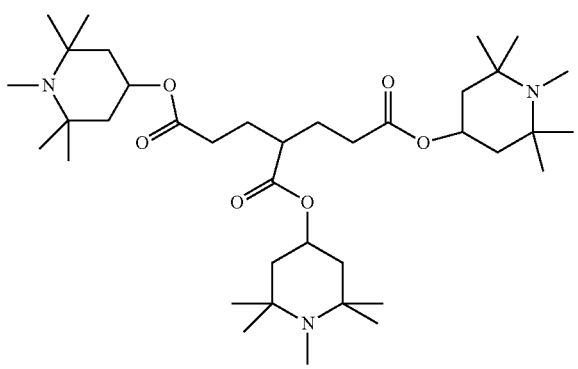

(Q-43)

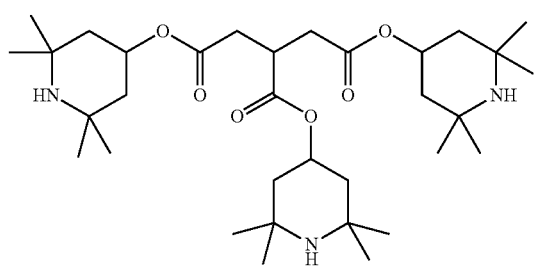

(Q-44)

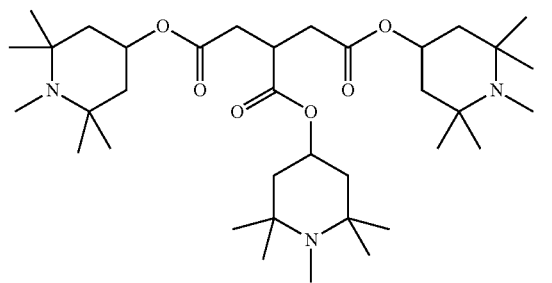

(In the formula, n denotes an integer in the range of 0 to 20.)

A liquid crystal composition according to the present embodiment is used for a liquid crystal display device. A liquid crystal display device according to the present embodiment is described below with reference to FIGS. 1 and 2.

FIG. 1 is a schematic view of a liquid crystal display device. FIG. 1 illustrates each component separately for convenience of description. As illustrated in FIG. 1, a liquid crystal display device 1 according to the present embodiment includes a first substrate 2 and a second substrate 3 facing each other and a liquid crystal layer 4 located between the first substrate 2 and the second substrate 3. The liquid crystal layer 4 is formed of a liquid crystal composition according to the present embodiment.

A pixel electrode layer 5 is formed on a surface of the first substrate 2 facing the liquid crystal layer 4. A common electrode layer 6 is formed on a surface of the second substrate 3 facing the liquid crystal layer 4. The first substrate 2 and the second substrate 3 may be held between a pair of polarizers 7 and 8. A color filter 9 may also be located on the surface of the second substrate 3 facing the liquid crystal layer 4.

Thus, the liquid crystal display device 1 according to the present embodiment includes the first polarizer 7, the first substrate 2, the pixel electrode layer 5, the liquid crystal layer 4 containing the liquid crystal composition, the common electrode layer 6, the color filter 9, the second substrate 3, and the second polarizer 8 stacked in this order.

The first substrate 2 and the second substrate 3 are formed of glass or a flexible material, such as plastic, for example. At least one of the first substrate 2 and the second substrate 3 is formed of a transparent material, and the other may be formed of a transparent material or an opaque material, such as metal or silicon. The first substrate 2 and the second substrate 3 are bonded together via a sealing material and a sealant, such as an epoxy thermosetting composition, located on the peripheral region. The distance between the substrates may be maintained, for example, with a granular spacer, such as glass particles, plastic particles, or alumina particles, or with a resin spacer column formed by photolithography.

In the first polarizer 7 and the second polarizer 8, the polarization axis of each polarizer can be adjusted to improve the viewing angle and contrast. The first polarizer 7 and the second polarizer 8 preferably have orthogonal transmission axes such that the transmission axis of each polarizer can operate in the normally black mode. In particular, one of the first polarizer 7 and the second polarizer 8 is preferably placed so as to have a transmission axis parallel to the alignment direction of liquid crystal molecules during no voltage application.

The color filter 9 preferably forms a black matrix to prevent light leakage. The black matrix (not shown) is preferably formed in a portion corresponding to the thin-film transistor.

The black matrix, together with a color filter, may be placed on a substrate opposite an array substrate or on the array substrate side. Alternatively, the black matrix may be placed on an array substrate, and a color filter may be placed on the other substrate. The black matrix may be separated from a color filter, or different color filters may be stacked to decrease transmittance.

Figure 2:
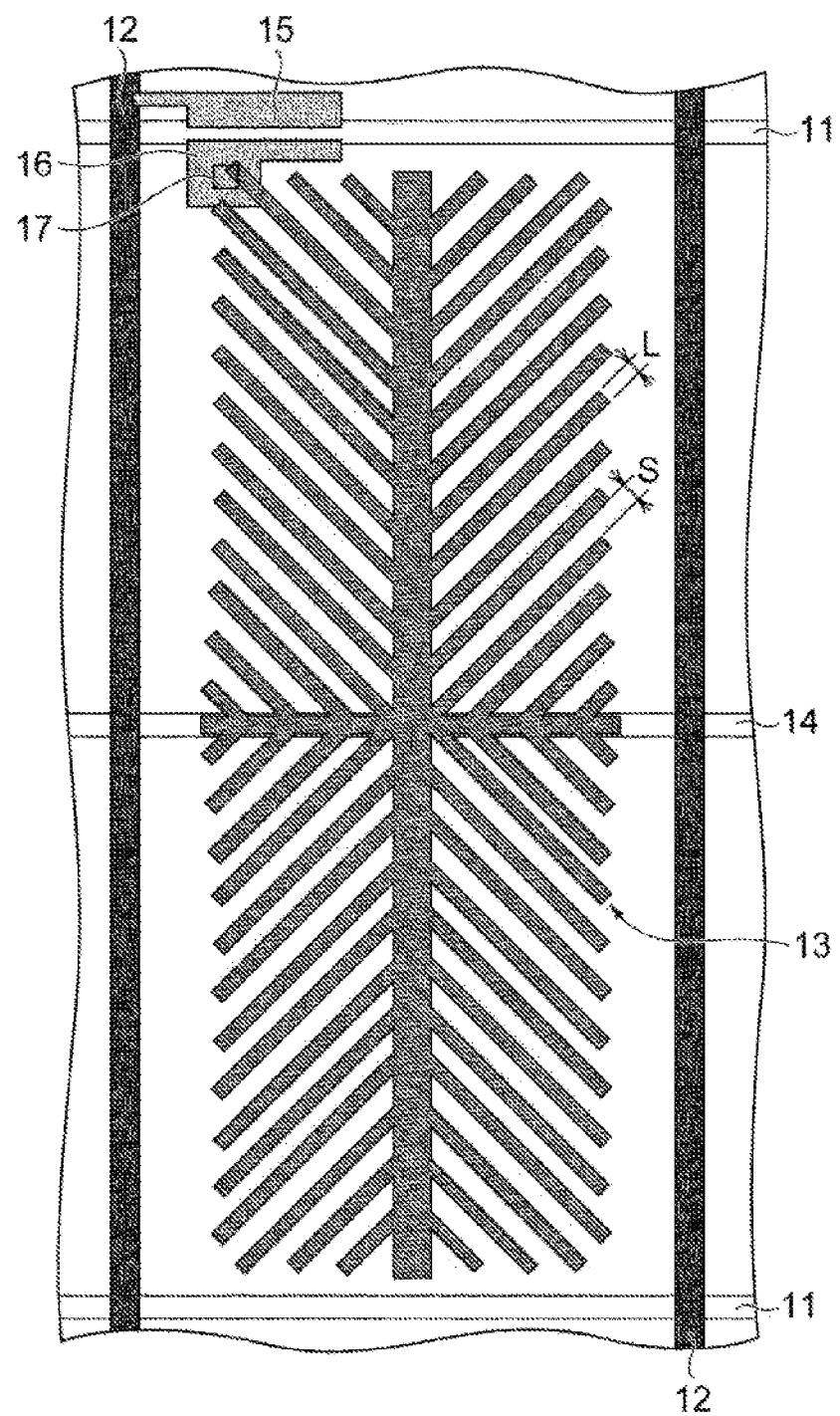
FIG. 2 is an enlarged plan view of a region within the line I of FIG. 1.

FIG. 2 is an enlarged plan view of a region within the line I in the pixel electrode layer 5 formed on the first substrate 2 in FIG. 1. As illustrated in FIG. 2, the pixel electrode layer 5 including a thin-film transistor formed on the first substrate 2 includes a matrix of a plurality of gate bus lines 11 and a plurality of data bus lines 12 crossing each other. The gate bus lines 11 relay scanning signals. The data bus lines 12 relay display signals. FIG. 2 illustrates only a pair of gate bus lines 11, 11 and a pair of data bus lines 12, 12.

A region surrounded by the gate bus lines 11 and the data bus lines 12 forms a unit pixel of a liquid crystal display device. A pixel electrode 13 is formed in the unit pixel. The pixel electrode 13 has a so-called fishbone structure including two trunks crossing at right angles and a plurality of branches extending from each trunk. A Cs electrode 14 approximately parallel to the gate bus lines 11 is located between the pair of gate bus lines 11, 11. A thin-film transistor that includes a source electrode 15 and a drain electrode 16 is located near an intersecting portion at which the gate bus line 11 and the data bus line 12 cross each other. The drain electrode 16 has a contact hole 17.

The gate bus lines 11 and the data bus lines 12 are preferably formed of a metal film, more preferably Al, Cu, Au, Ag, Cr, Ta, Ti, Mo, W, Ni, or an alloy thereof, still more preferably Mo, Al, or an alloy thereof.

The pixel electrode 13 is preferably a transparent electrode to improve transmissivity. Such a transparent electrode can be formed of an oxide semiconductor (ZnO, InGaZnO, SiGe, GaAs, indium zinc oxide (IZO), indium tin oxide (ITO), SnO, TiO, AZTO (AlZnSnO), etc.) by sputtering. The transparent electrode may have a thickness in the range of 10 to 200 nm. To decrease electrical resistance, an amorphous ITO film may be baked to form a polycrystalline ITO film as a transparent electrode.

In the liquid crystal display device according to the present embodiment, for example, the pixel electrode layer 5 and the common electrode layer 6 can be formed by forming a wire of a metallic material, such as Al or an alloy thereof, on the first substrate 2 and the second substrate 3 by sputtering. The color filter 9 can be formed, for example, by a pigment dispersion method, a printing method, an electrodeposition method, or a staining method. For example, in a method for forming a color filter by a pigment dispersion method, a curable coloring composition for a color filter is applied to a transparent substrate, is patterned, and is cured by heating or light irradiation. This process is repeatedly performed for three colors red, green, and blue to produce pixel units for color filters. The color filter 9 may be placed near a substrate having a TFT.

The first substrate 2 faces the second substrate 3 such that the pixel electrode layer 5 and the common electrode layer 6 are interposed therebetween. The distance between the first substrate 2 and the second substrate 3 may be adjusted with a spacer. The distance is preferably adjusted such that the liquid crystal layer 4 has a thickness in the range of 1 to 100 μm, for example.

When the polarizers 7 and 8 are used, the product of the refractive index anisotropy Δn of the liquid crystal layer 4 and the thickness of the liquid crystal layer 4 is preferably adjusted to maximize the contrast. When the two polarizers 7 and 8 are used, the polarization axis of each polarizer may be adjusted to improve the viewing angle or contrast. A retardation film for increasing the viewing angle may also be used. Subsequently, a sealant, such as a thermosetting epoxy composition, is applied to a substrate by screen printing such that a liquid crystal inlet is formed. The substrates are then joined and heated to cure the sealant.

A composition can be placed between the two substrates 2 and 3 by a conventional vacuum injection or one drop fill (ODF) method. Although the vacuum injection method causes no drop marks, the vacuum injection method has a problem of leaving an injection mark. In the present embodiment, a display device is preferably produced by the ODF method. In a process of producing a liquid crystal display device by the ODF method, a light and heat curable epoxy sealant is applied in a closed-loop bank shape to a back or front plane substrate using a dispenser. A predetermined amount of a composition is dropped inside the closed-loop bank while degassing is performed. The front plane and the back plane are then joined to produce the liquid crystal display device. In the present embodiment, the ODF method can reduce the occurrence of drop marks resulting from dropping of a liquid crystal composition on a substrate. Drop marks are defined as a phenomenon in which marks of dropping of a liquid crystal composition appear white in black display.

In a process of manufacturing a liquid crystal display device by the ODF method, the amount of liquid crystal to be injected must be optimized according to the size of the liquid crystal display device. A liquid crystal composition according to the present embodiment has a little influence on a sudden pressure change in a dropping apparatus or an impact during dropping of the liquid crystal, for example, and a liquid crystal can be stably dropped for extended periods. This can maintain a high yield of the liquid crystal display device. In particular, in small liquid crystal display devices frequently used in recent popular smartphones, due to a small optimum amount of liquid crystal to be injected, it is difficult to control the deviation from the optimum value within a certain range. However, the use of a liquid crystal composition according to the present embodiment allows a liquid crystal material to be ejected in a proper amount even in small liquid crystal display devices.

In order to achieve high liquid crystal alignment capability, an appropriate rate of polymerization is desirable. Thus, for a liquid crystal composition according to the present embodiment containing a polymerizable compound, the polymerizable compound is preferably polymerized by irradiation with an active energy beam, such as ultraviolet light or an electron beam, alone, in combination, or in sequence. When ultraviolet light is used, a polarized or unpolarized light source may be used. For polymerization of a composition containing a polymerizable compound between two substrates, at least the substrate to be irradiated must be transparent to an active energy beam. Only a particular portion may be polymerized using a mask during light irradiation, and then the condition such as an electric field, a magnetic field, or temperature may be altered to change the alignment state of an unpolymerized portion, which is then polymerized by irradiation with an active energy beam. In particular, for ultraviolet exposure, a composition containing a polymerizable compound is preferably exposed to ultraviolet light in an alternating electric field. The alternating electric field preferably has a frequency in the range of 10 Hz to 10 kHz, more preferably 60 Hz to 10 kHz. The voltage depends on the desired pretilt angle of a liquid crystal display device. Thus, the pretilt angle of a liquid crystal display device can be controlled by the voltage to be applied. A transverse electric field MVA mode liquid crystal display device preferably has a pretilt angle in the range of 80 to 89.9 degrees in terms of alignment stability and contrast.

The irradiation temperature is preferably in such a range that the composition according to the present embodiment can retain its liquid crystal state. The polymerization temperature is preferably close to room temperature, typically in the range of 15° C. to 35° C. Examples of lamps for generating ultraviolet light include metal halide lamps, high-pressure mercury lamps, and ultrahigh-pressure mercury lamps. The wavelength of ultraviolet light is preferably outside the absorption wavelength range of the composition. Ultraviolet light is preferably filtered as required. The ultraviolet radiation intensity preferably ranges from 0.1 mW/cm$^2$ to 100 W/cm$^2$, more preferably 2 mW/cm$^2$ to 50 W/cm$^2$. The ultraviolet light energy can be appropriately determined and preferably ranges from 10 mJ/cm$^2$ to 500 J/cm$^2$, more preferably 100 mJ/cm$^2$ to 200 J/cm$^2$. During ultraviolet radiation, the ultraviolet radiation intensity may be changed. The ultraviolet radiation time depends on the ultraviolet radiation intensity and preferably ranges from 10 to 3600 seconds, more preferably 10 to 600 seconds.

In a liquid crystal composition according to the present embodiment, the compound (i) does not inhibit the polymerization reaction of the polymerizable compound, the polymerizable compound is suitably polymerized, and an unreacted polymerizable compound remaining in the liquid crystal composition can be decreased.

When the compound (ii) is used as a polymerizable compound, the liquid crystal display device 1 includes the two substrates 2 and 3 and the liquid crystal layer 4 located between the two substrates 2 and 3. The liquid crystal layer 4 contains a liquid crystal composition and a polymer of a compound represented by the general formula (ii). In this case, the polymer of the compound represented by the general formula (ii) in the liquid crystal layer 4 is localized near the substrates 2 and 3.

The liquid crystal display device 1 may be an active-matrix drive liquid crystal display device. The liquid crystal display device 1 may be a PSA, PSVA, VA, IPS, FFS, or ECB liquid crystal display device, preferably a PSA liquid crystal display device.

In the liquid crystal display device according to the present embodiment, the use of the liquid crystal composition containing the compound (i) obviates the need for an alignment film, such as a polyimide alignment film, between the first substrate 2 or the second substrate 3 and the liquid crystal layer 4. In other words, in the liquid crystal display device according to the present embodiment, at least one of the two substrates does not have an alignment film, such as a polyimide alignment film.

EXAMPLES

Although the present invention is more specifically described in the following examples, the present invention is not limited to these examples.

Example 1

29 g of 4-(4-pentylcyclohexyl)phenyl boric acid, 18 g of bromophenol, 22 g of potassium carbonate, 200 mg of tetrakis(triphenylphosphine)palladium, and 200 ml of ethanol were charged into a reaction vessel equipped with a stirrer, a cooler, and a thermometer in a nitrogen atmosphere and were allowed to react at 80° C. for 5 hours. After the completion of the reaction and cooling, 300 ml of acid ethyl was added to the product, the organic layer was washed with water and saturated saline, the solvent was evaporated, and the product was recrystallized with toluene. 27 g of a compound represented by (1) was produced.

[Chem. 120]

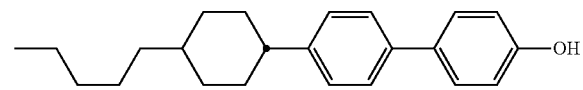

(1)

27 g of the compound (1), 10 g of pyridine, and 200 ml of dichloromethane were then charged into a reaction vessel equipped with a stirrer, a dropping funnel, and a thermometer in a nitrogen atmosphere and were cooled to 10° C. or less. 28 g of trifluoromethanesulfonic acid anhydride was slowly added dropwise to the mixture. After the completion of dropwise addition, the reaction vessel was warmed to room temperature, and the mixture was allowed to react for 2 hours. After the completion of the reaction, the organic layer was washed with water and saturated saline, and the solvent was evaporated. 35 g of a reaction product was obtained. 35 g of a reaction concentrate, 200 ml of dichloromethane, 26 g of potassium acetate, 25 g of bis(pinacolato)diborane, 350 ml of N,N-dimethylformamide, and 1.5 g of PdCl$_2$ (dppf) were then charged into a reaction vessel equipped with a stirrer, a dropping funnel, and a thermometer in a nitrogen atmosphere and were allowed to react at 80° C. for 5 hours. After the completion of the reaction and cooling, 300 ml of acid ethyl was added to the product, the organic layer was washed with water and saturated saline, the solvent was evaporated, and the product was purified in a silica gel column. 32 g of a compound represented by (2) was produced.

[Chem. 121]

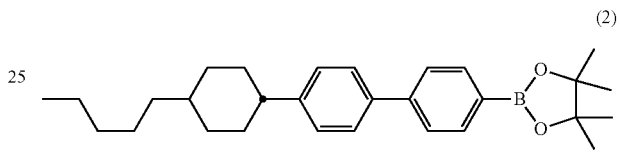

(2)

32 g of the compound (2), 18 g of 4-bromo-2-(3-hydroxypropyl)-5-methoxyphenol, 15 g of potassium carbonate, 300 mg of tetrakis(triphenylphosphine)palladium, and 200 ml of ethanol were then charged into a reaction vessel equipped with a stirrer, a cooler, and a thermometer in a nitrogen atmosphere and were allowed to react at 80° C. for 5 hours. After the completion of the reaction and cooling, 300 ml of acid ethyl was added to the product, the organic layer was washed with water and saturated saline, the solvent was evaporated, and the product was recrystallized with toluene. 29.5 g of a compound represented by (1) was produced.

[Chem. 121]

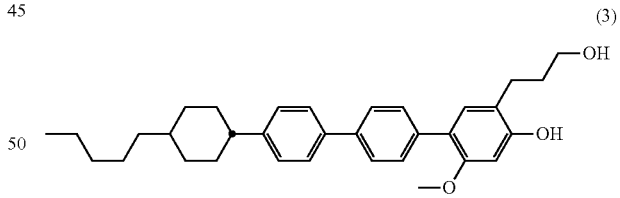

(3)

Subsequently, 29.5 g of the compound (3), 14 g of potassium carbonate, 24 g of (5-ethyl-2,2'-dimethyl-1,3-dioxan-5-yl)methanol, and 200 ml of N,N-dimethylformamide were charged into a reaction vessel equipped with a stirrer, a cooler, and a thermometer and were allowed to react at 90° C. for 5 hours. After the completion of the reaction and cooling, 300 ml of ethyl acetate was added to the product, the organic layer was washed with water and saturated saline, and the solvent was evaporated. The product was then dispersed in and washed with toluene and was purified in an alumina column. 31 g of a compound represented by the formula (4) was obtained.

[Chem. 123]

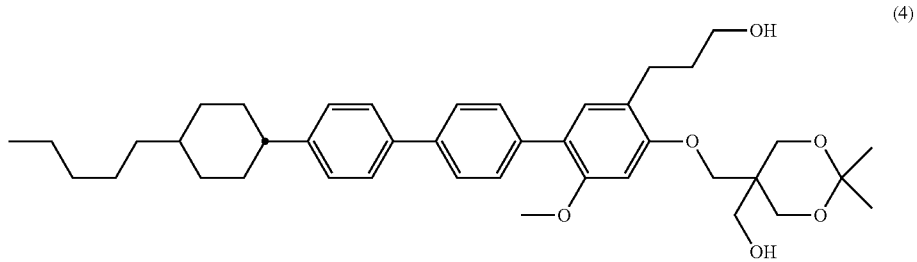

(4)

A reaction vessel equipped with a stirrer, a dropping funnel, and a thermometer was charged with 31 g of the compound (4), 10 g of methacrylic acid, 300 mg of dimethylaminopyridine, and 200 ml of dichloromethane and was cooled to 10° C. or less. Subsequently, 15 g of diisopropylcarbodiimide was slowly added dropwise. After the completion of dropwise addition, the reaction vessel was warmed to room temperature, and the mixture was allowed to react for 3 hours. After the completion of the reaction, water was slowly added to the product, and the product was washed with 100 ml of dichloromethane, water, and saturated saline. After the solvent was evaporated, purification in an alumina column yielded 33 g of a compound represented by the formula (5).

[Chem. 124]

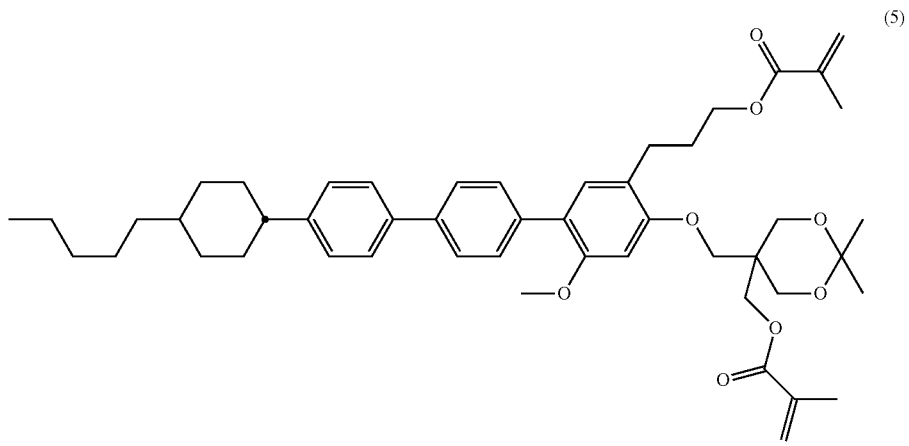

(5)

33 g of the compound (5) and 150 ml of tetrahydrofuran were charged into a reaction vessel equipped with a stirrer, a dropping funnel, and a thermometer and were stirred. 20 ml of 2 N hydrochloric acid was added to the mixture at room temperature, and the mixture was stirred for 6 hours. After the completion of the reaction, 200 ml of ethyl acetate was added to the product, the product was washed with water and saturated saline, and the solvent was evaporated. The concentrate was purified in a silica gel column with dichloromethane/ethyl acetate, and 26 g of a target compound represented by (P-1-24) was obtained.

[Chem. 125]

(P-1-26)

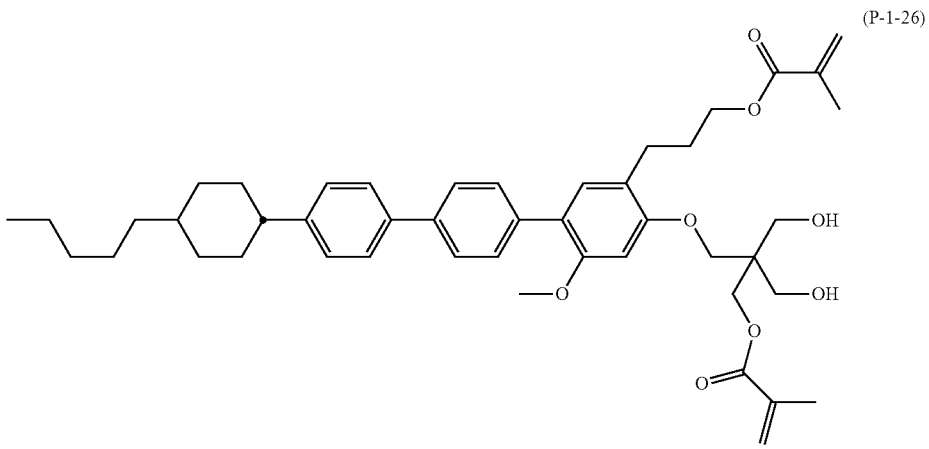

(Physical Properties)

¹H-NMR (solvent: deuteriochloroform): δ: 0.88 (t, 3H), 1.22 (m, 2H), 1.28-1.48 (m, 9H), 1.50-1.54 (m, 2H), 1.87-2.02 (m, 12H), 2.49 (m, 1H), 2.70 (t, 2H), 3.81-3.89 (m, 7H), 4.17 (s, 2H), 4.21 (t, 2H), 4.39 (s, 1H), 5.38 (d, 2H), 6.10 (d, 2H), 6.56 (s, 1H), 7.15 (s, 1H), 7.25-7.30 (m, 2H), 7.53-7.61 (m, 6H)

¹³C-NMR (solvent: deuteriochloroform): δ: 14.2, 18.3, 18.4, 22.8, 26.3, 26.7, 29.3, 32.3, 33.7, 34.4, 37.4, 44.4, 45.4, 56.0, 63.3, 63.4, 64.8, 66.8, 96.5, 121.7, 122.8, 125.7, 126.6, 126.7, 127.0, 129.7, 132.1, 135.9, 136.3, 136.9, 138.6, 139.4, 147.0, 155.9, 156.5, 167.9

Example 2

29 g of 4-(4-pentylcyclohexyl)phenyl boric acid, 19 g of 4-bromo-2-fluorophenol, 22 g of potassium carbonate, 200 mg of tetrakis(triphenylphosphine)palladium, and 200 ml of ethanol were charged into a reaction vessel equipped with a stirrer, a cooler, and a thermometer in a nitrogen atmosphere and were allowed to react at 80° C. for 5 hours. After the completion of the reaction and cooling, 300 ml of acid ethyl was added to the product, the organic layer was washed with water and saturated saline, the solvent was evaporated, and the product was recrystallized with toluene. 27 g of a compound represented by (6) was produced.

[Chem. 126]

(6)

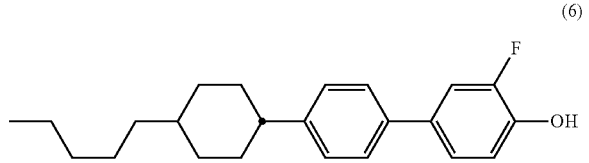

27 g of the compound (6), 9.5 g of pyridine, and 200 ml of dichloromethane were then charged into a reaction vessel equipped with a stirrer, a dropping funnel, and a thermometer in a nitrogen atmosphere and were cooled to 10° C. or less. 27 g of trifluoromethanesulfonic acid anhydride was slowly added dropwise to the mixture. After the completion of dropwise addition, the reaction vessel was warmed to room temperature, and the mixture was allowed to react for 2 hours. After the completion of the reaction, the organic layer was washed with water and saturated saline, and the solvent was evaporated. 35 g of a reaction product was obtained. 35 g of a reaction concentrate, 22 g of potassium acetate, 23 g of bis(pinacolato)diborane, 350 ml of N,N-dimethylformamide, and 1.5 g of PdCl₂ (dppf) were then charged into a reaction vessel equipped with a stirrer, a dropping funnel, and a thermometer in a nitrogen atmosphere and were allowed to react at 80° C. for 5 hours. After the completion of the reaction and cooling, 300 ml of acid ethyl was added to the product, the organic layer was washed with water and saturated saline, the solvent was evaporated, and the product was purified in a silica gel column. 32 g of a compound represented by (7) was produced.

[Chem. 127]

(7)

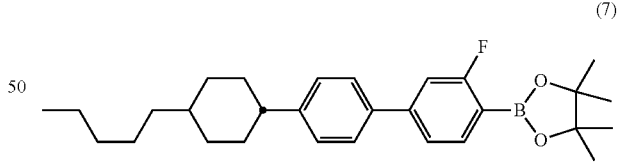

32 g of the compound (7), 17.5 g of 4-bromo-5-ethyl-2-(3-hydroxypropyl)phenol, 15 g of potassium carbonate, 300 mg of tetrakis(triphenylphosphine)palladium, and 200 ml of ethanol were then charged into a reaction vessel equipped with a stirrer, a cooler, and a thermometer in a nitrogen atmosphere and were allowed to react at 80° C. for 5 hours. After the completion of the reaction and cooling, 300 ml of acid ethyl was added to the product, the organic layer was washed with water and saturated saline, the solvent was evaporated, and the product was recrystallized with toluene. 32 g of a compound represented by (8) was produced.

[Chem. 128]

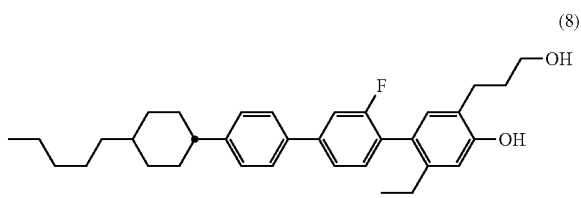

(8)

32 g of the compound (8), 13 g of potassium carbonate, 25 g of (5-ethyl-2,2'-dimethyl-1,3-dioxan-5-yl)methanol, and 200 ml of N,N-dimethylformamide were charged into a reaction vessel equipped with a stirrer, a cooler, and a thermometer and were allowed to react at 90° C. for 5 hours. After the completion of the reaction and cooling, 300 ml of ethyl acetate was added to the product, the organic layer was washed with water and saturated saline, and the solvent was evaporated. The product was then dispersed in and washed with toluene and was purified in an alumina column. 34.5 g of a compound represented by the formula (9) was obtained.

[Chem. 129]

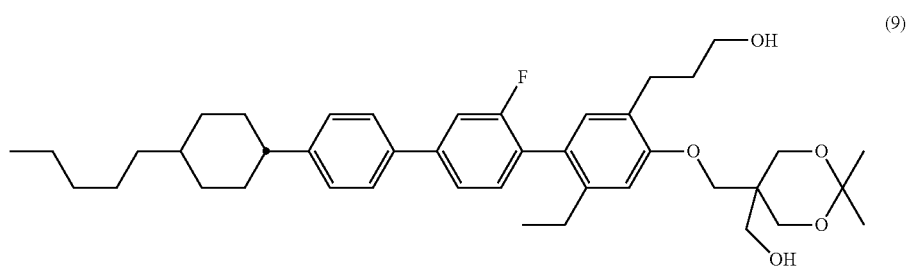

(9)

A reaction vessel equipped with a stirrer, a dropping funnel, and a thermometer was charged with 34.5 g of the compound (9), 11 g of methacrylic acid, 300 mg of dimethylaminopyridine, and 200 ml of dichloromethane and was cooled to 10° C. or less. Subsequently, 16 g of diisopropylcarbodiimide was slowly added dropwise. After the completion of dropwise addition, the reaction vessel was warmed to room temperature, and the mixture was allowed to react for 3 hours. After the completion of the reaction, water was slowly added to the product, and the product was washed with 100 ml of dichloromethane, water, and saturated saline. After the solvent was evaporated, purification in an alumina column yielded 33 g of a compound represented by the formula (10).

[Chem. 130]

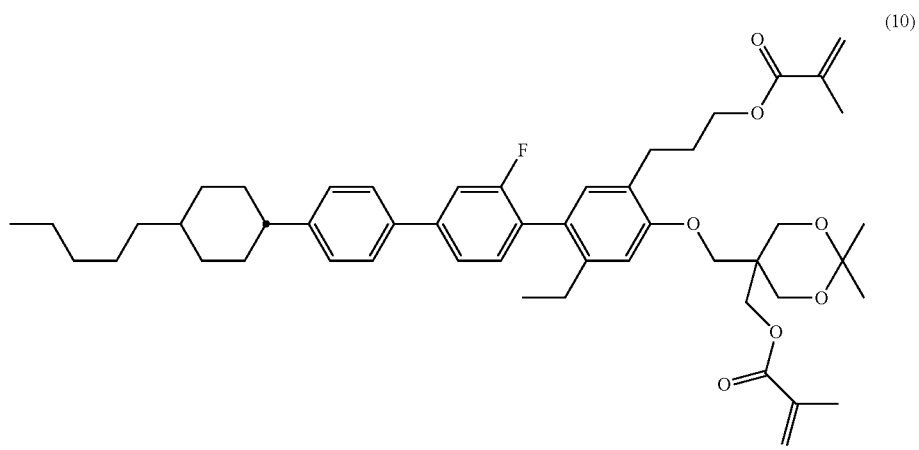

(10)

33 g of the compound (10) and 150 ml of tetrahydrofuran were charged into a reaction vessel equipped with a stirrer, a dropping funnel, and a thermometer and were stirred. 20 ml of 2 N hydrochloric acid was added to the mixture at room temperature, and the mixture was stirred for 6 hours. After the completion of the reaction, 200 ml of ethyl acetate was added to the product, the product was washed with water and saturated saline, and the solvent was evaporated. The concentrate was purified in a silica gel column with dichloromethane/ethyl acetate, and 26 g of a target compound represented by (P-1-25) was obtained.

[Chem. 131]

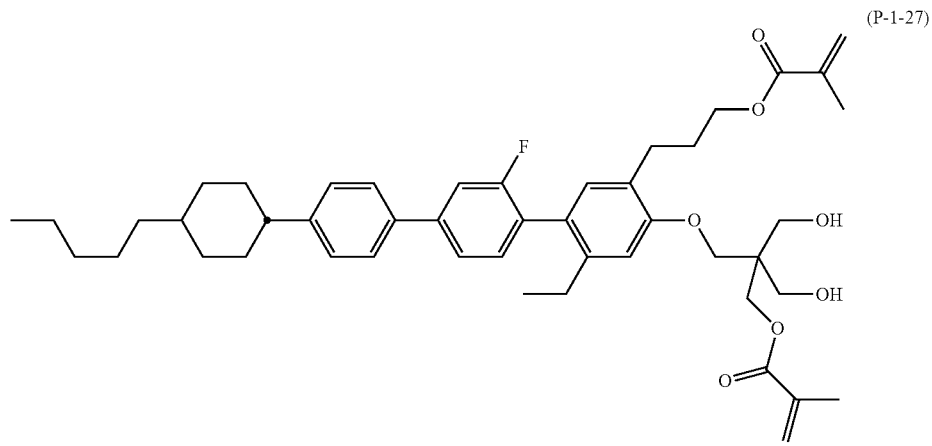

(P-1-27)

Melting point 53° C.

(Physical Properties)

$^1$H-NMR (solvent: deuteriochloroform): δ: 0.88 (t, 3H), 1.14-1.22 (m, 5H), 1.28-1.48 (m, 9H), 1.50-1.54 (m, 2H), 1.87-2.02 (m, 12H), 2.49-2.57 (m, 3H), 2.70 (t, 2H), 3.81-3.89 (m, 4H), 4.17 (s, 2H), 4.21 (t, 2H), 4.39 (s, 1H), 5.38 (d, 2H), 6.10 (d, 2H), 6.80 (s, 1H), 7.00 (s, 1H), 7.22-7.26 (m, 2H), 7.31-7.40 (m, 3H), 7.56 (d, 2H)

$^{13}$C-NMR (solvent: deuteriochloroform): δ: 14.1, 15.3, 18.3, 22.7, 26.4, 26.5, 28.6, 32.1, 33.5, 34.4, 37.3, 41.1, 43.0, 44.3, 56.0, 63.3, 63.4, 64.8, 66.8, 110.8, 113.5, 113.8, 122.2, 125.2, 126.3, 126.8, 127.1, 127.6, 131.9, 132.1, 135.6, 136.3, 137.1, 142.0, 142.2, 147.7, 155.9, 156.5, 167.9

Example 3

32 g of 2-fluoro-4-(4-pentylcyclohexyl)phenyl boric acid, 17 g of 4-bromophenol, 22 g of potassium carbonate, 200 mg of tetrakis(triphenylphosphine)palladium, and 200 ml of ethanol were charged into a reaction vessel equipped with a stirrer, a cooler, and a thermometer in a nitrogen atmosphere and were allowed to react at 80° C. for 5 hours. After the completion of the reaction and cooling, 300 ml of acid ethyl was added to the product, the organic layer was washed with water and saturated saline, the solvent was evaporated, and the product was recrystallized with toluene. 29 g of a compound represented by (11) was produced.

[Chem. 132]

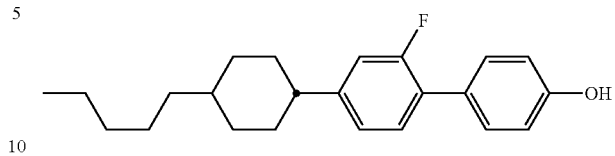

(11)

27 g of the compound (6), 10 g of pyridine, and 200 ml of dichloromethane were then charged into a reaction vessel equipped with a stirrer, a dropping funnel, and a thermometer in a nitrogen atmosphere and were cooled to 10° C. or less. 29 g of trifluoromethanesulfonic acid anhydride was slowly added dropwise to the mixture. After the completion of dropwise addition, the reaction vessel was warmed to room temperature, and the mixture was allowed to react for 2 hours. After the completion of the reaction, the organic layer was washed with water and saturated saline, and the solvent was evaporated. 38 g of a reaction product was obtained. 38 g of a reaction concentrate, 24 g of potassium acetate, 24 g of bis(pinacolato)diborane, 350 ml of N,N-dimethylformamide, and 1.5 g of PdCl$_2$ (dppf) were then charged into a reaction vessel equipped with a stirrer, a dropping funnel, and a thermometer in a nitrogen atmosphere and were allowed to react at 80° C. for 5 hours. After the completion of the reaction and cooling, 300 ml of acid ethyl was added to the product, the organic layer was washed with water and saturated saline, the solvent was evaporated, and the product was purified in a silica gel column. 34 g of a compound represented by (12) was produced.

[Chem. 133]

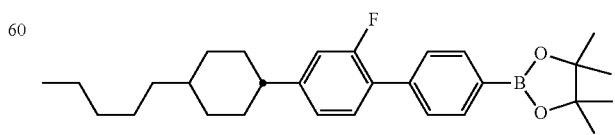

(12)

34 g of the compound (12), 21.5 g of 4-bromo-5-ethyl-2-(3-hydroxypropyl)phenol, 15.5 g of potassium carbonate, 300 mg of tetrakis(triphenylphosphine)palladium, and 200 ml of ethanol were then charged into a reaction vessel equipped with a stirrer, a cooler, and a thermometer in a nitrogen atmosphere and were allowed to react at 80° C. for 5 hours. After the completion of the reaction and cooling, 300 ml of acid ethyl was added to the product, the organic layer was washed with water and saturated saline, the solvent was evaporated, and the product was recrystallized with toluene. 33 g of a compound represented by (13) was produced.

[Chem. 134]

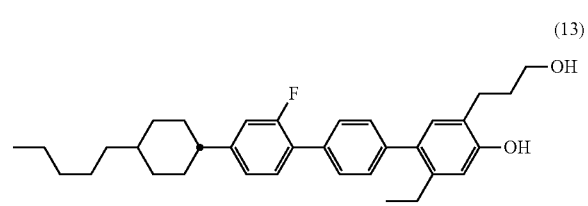

(13)

A reaction vessel equipped with a stirrer, a dropping funnel, and a thermometer was charged with 33 g of the compound (13), 1.4 g of isopropylamine, and 200 ml of dichloromethane and was cooled to 10° C. or less. A solution of 16.3 g of N-iodosuccinimide in 100 ml of acetonitrile was slowly added dropwise while the temperature was maintained at 10° C. or less. After the completion of dropwise addition, the reaction vessel was warmed to room temperature, and the mixture was allowed to react for 3 hours. After the completion of the reaction, 200 ml of 10% sodium hydrogen sulfite solution was added. After separation, the organic layer was washed with water and saturated saline. The solvent was evaporated. Purification in a silica gel column yielded 37 g of a compound represented by (14).

[Chem. 135]

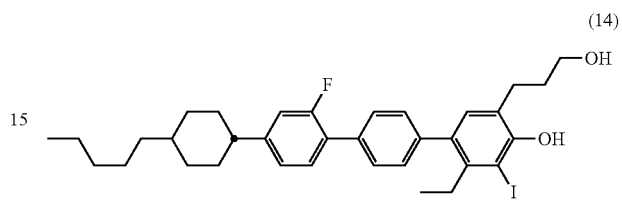

(14)

Subsequently, 37 g of the compound (14), 12 g of potassium carbonate, 16 g of (2,2-dimethyl-1,3-dioxan-5-yl) methyl methanesulfonate, and 200 ml of N,N-dimethylformamide were charged into a reaction vessel equipped with a stirrer, a cooler, and a thermometer and were allowed to react at 90° C. for 5 hours. After the completion of the reaction and cooling, 300 ml of ethyl acetate was added to the product, the organic layer was washed with water and saturated saline, and the solvent was evaporated. Subsequently, purification in an alumina column yielded 34.5 g of a compound represented by the formula (15).

[Chem. 136]

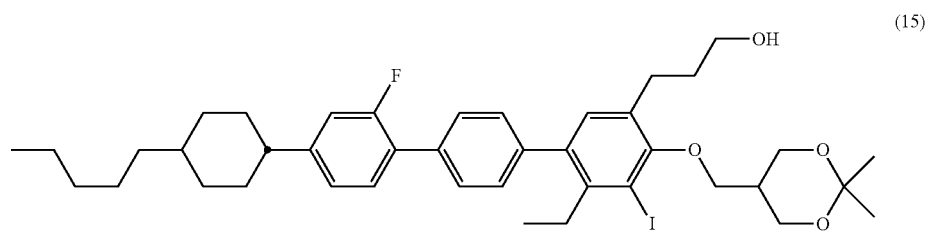

(15)

34.5 g of the compound (15), 0.9 g of copper iodide, 2.6 g of tetrakis(triphenylphosphine)palladium, 150 ml of tetrahydrofuran, and 20 ml of water were charged into a reaction vessel equipped with a stirrer, a cooler, and a thermometer and were stirred at room temperature. Subsequently, 30 ml of ethanolamine was added, and the reactor was then heated to 65° C. 3 g of propargyl alcohol was slowly added dropwise. After the completion of dropwise addition, the reaction was performed for 1 hour. After the completion of the reaction and cooling, 100 ml of toluene was added, the organic layer was washed with a saturated ammonium chloride solution, water, and saturated saline, and the solvent was evaporated. Subsequently, 300 ml of tetrahydrofuran and 30 ml of ethanol were added, and the mixture was charged in an autoclave. 4 g of 5% (hydrated) palladium carbon was added, and a catalytic hydrogen reduction was performed at a hydrogen pressure of 0.5 kPa. After the completion of the reaction, the palladium carbon was filtered off, and purification in a silica gel column yielded 24 g of a compound represented by the formula (16).

[Chem. 137]

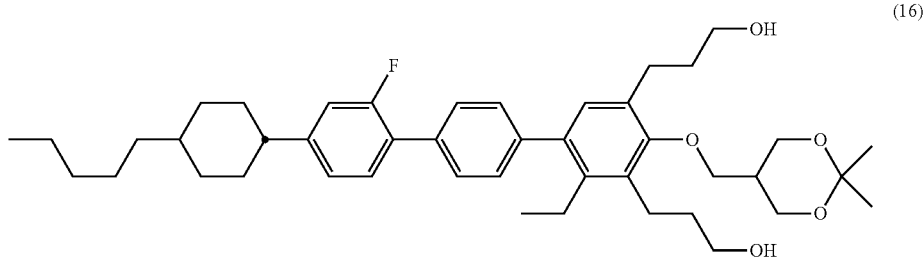

(16)

A reaction vessel equipped with a stirrer, a dropping funnel, and a thermometer was charged with 24 g of the compound (16), 7.2 g of methacrylic acid, 600 mg of dimethylaminopyridine, and 100 ml of dichloromethane and was cooled to 10° C. or less. Subsequently, 10.5 g of diisopropylcarbodiimide was slowly added dropwise. After the completion of dropwise addition, the reaction vessel was warmed to room temperature, and the mixture was allowed to react for 3 hours. After the completion of the reaction, water was slowly added to the product, and the product was washed with 100 ml of dichloromethane, water, and saturated saline. After the solvent was evaporated, the product was dissolved in 100 ml of tetrahydrofuran, 20 ml of 2 N hydrochloric acid was added at room temperature, and the product was stirred for 6 hours. After the completion of the reaction, 200 ml of ethyl acetate was added to the product, the product was washed with water and saturated saline, and the solvent was evaporated. The concentrate was purified in a silica gel column with dichloromethane/ethyl acetate, and 25 g of a compound represented by the formula (17) was obtained.

[Chem. 138]

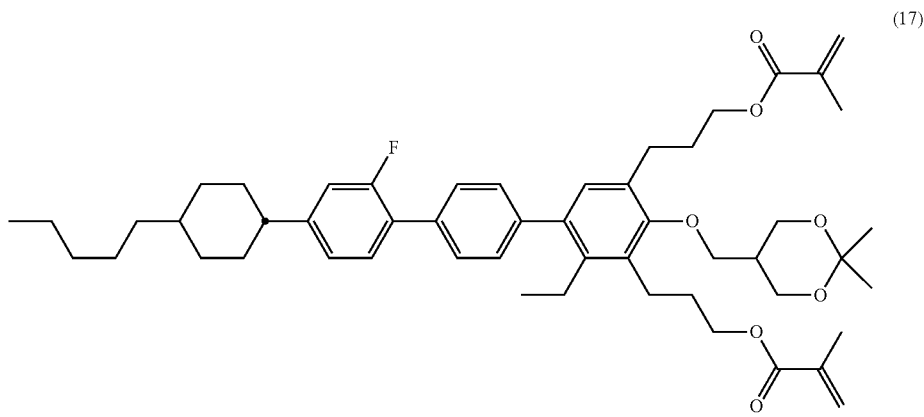

(17)

25 g of the compound (17) and 150 ml of tetrahydrofuran were charged into a reaction vessel equipped with a stirrer, a dropping funnel, and a thermometer and were stirred. 20 ml of 2 N hydrochloric acid was added to the mixture at room temperature, and the mixture was stirred for 6 hours. After the completion of the reaction, 200 ml of ethyl acetate was added to the product, the product was washed with water and saturated saline, and the solvent was evaporated. The concentrate was purified in a silica gel column with dichloromethane/ethyl acetate, and 21 g of a target compound represented by (P-1-26) was obtained.

[Chem. 139]
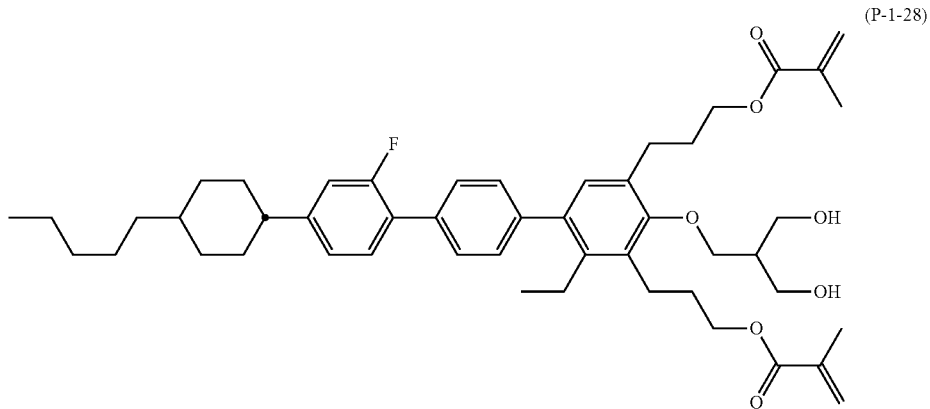
(Physical Properties)
Melting point 53° C.
(Physical Properties)
¹H-NMR (solvent: deuteriochloroform): δ: 0.88 (t, 3H), 1.14-1.22 (m, 5H), 1.28-1.48 (m, 9H), 1.50-1.54 (m, 2H), 1.87-2.06 (m, 15H), 2.49-2.61 (m, 3H), 2.67-2.72 (m, 4H), 3.61-3.72 (m, 4H), 4.17 (t, 4H), 4.21 (m, 2H), 5.38 (d, 2H), 6.10 (d, 2H), 7.22-7.26 (m, 4H), 7.31-7.40 (m, 2H), 7.46-7.56 (m, 2H)
¹³C-NMR (solvent: deuteriochloroform): δ: 14.3, 15.3, 18.3, 22.7, 26.4, 26.5, 28.6, 31.6, 32.1, 33.5, 34.4, 37.3, 41.1, 44.3, 56.0, 63.3, 63.4, 64.8, 66.8, 113.5, 113.8, 122.2, 124.1, 125.2, 126.3, 126.8, 127.1, 127.6, 131.9, 132.1, 135.6, 136.3, 137.1, 142.0, 142.2, 147.7, 155.9, 156.5, 167.9
Example 4
The following compounds (P-1-29) and (P-1-30) were synthesized in the same way.
[Chem. 140]
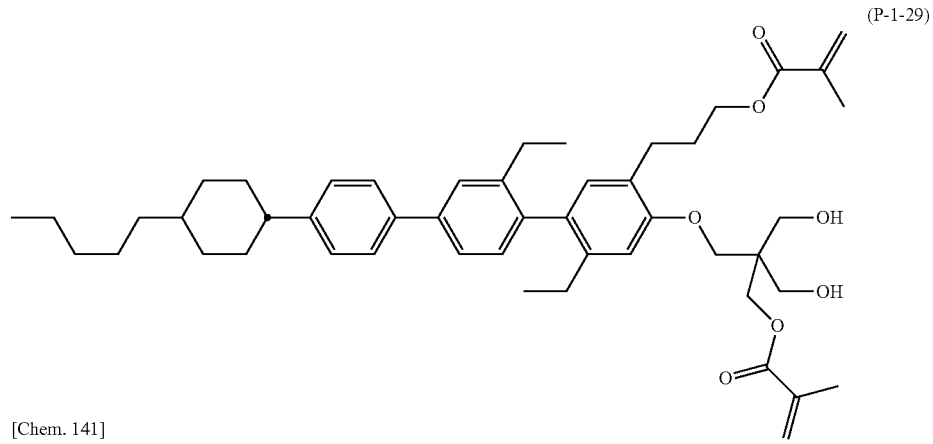
[Chem. 141]
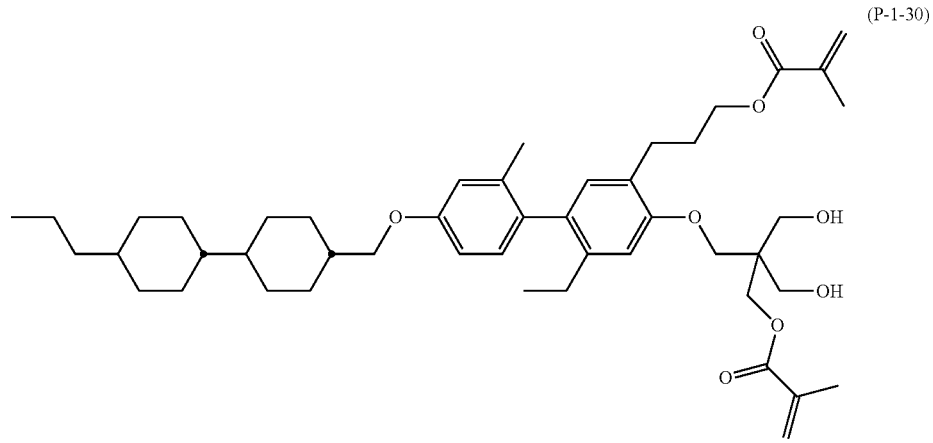

Example 5

A composition LC-1 contained 100 parts by mass of a composition composed of the following compounds at the following mixing ratios and 0.3 parts by mass of the following polymerizable compound (R-1-0).

[Chem.142]

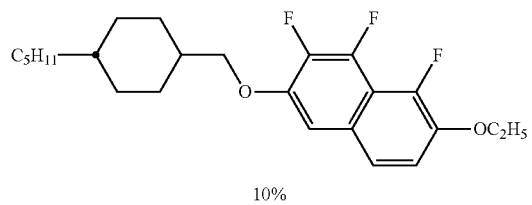

10%

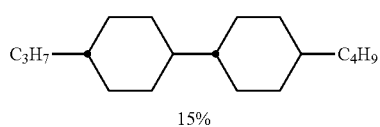

15%

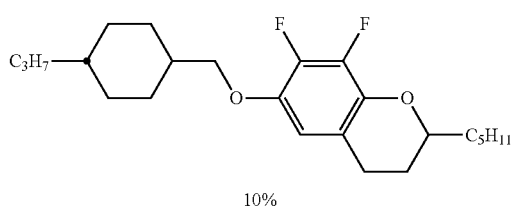

10%

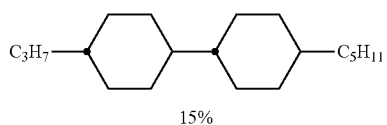

15%

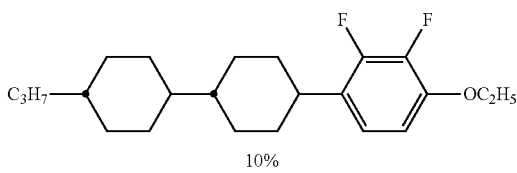

10%

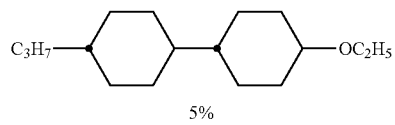

5%

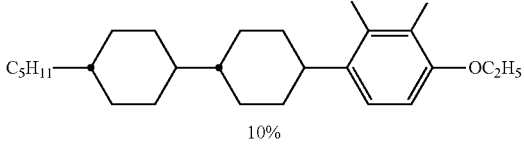

10%

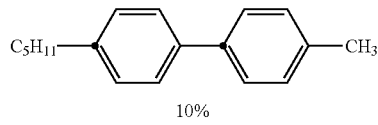

10%

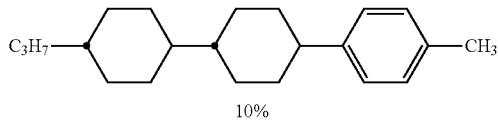

10%

[Chem. 143]

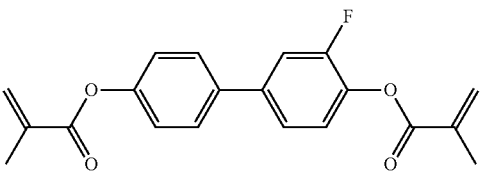

(R-1-0)

LC-1 had a nematic phase-isotropic liquid phase transition temperature (TNI) of 81° C., a solid phase-nematic phase transition temperature (TCN) of −54° C., a refractive index anisotropy (Δn) of 0.11, a dielectric constant anisotropy (Δε) of −3.0, and a rotational viscosity (γ1) of 95 mPa·s. The refractive index anisotropy (Δn), dielectric constant anisotropy (Δε), and rotational viscosity (γ1) were measured at 25° C. (the same applies hereinafter).

0.6 parts by mass of the compound (P-1-26) synthesized in Example 1 was added to 100 parts by mass of (LC-1) to prepare a liquid crystal composition (LC-1M1). The liquid crystal composition (LC-1M1) was then subjected to the following evaluation test.

(Low-Temperature Storage Stability Evaluation Test)

The liquid crystal composition was passed through a membrane filter (manufactured by Agilent Technologies, PTFE 13 mm-0.2 μm) and was left standing in a vacuum for 15 minutes to remove dissolved air. The liquid crystal composition was washed with acetone. 0.5 g of the liquid crystal composition in a thoroughly dried vial was left standing at −25° C. for 10 days. After that, the liquid crystal composition was visually inspected for precipitation and was rated in the following three grades.

A: No precipitation is observed.
B: An infinitesimal amount of precipitate is observed.
C: Precipitation is observed.

(Vertical Alignment Evaluation Test)

A first substrate (a common electrode substrate) and a second substrate (a pixel electrode substrate) were produced. The first substrate had a transparent electrode layer compose of a transparent common electrode and had no alignment film. The second substrate had a color filter protective film and the transparent electrode layer and had no alignment film. A liquid crystal composition was dropped onto the first substrate and was held between the first substrate and the second substrate. A sealing material was cured at atmospheric pressure and at 110° C. for 2 hours. Thus, a liquid crystal cell with a cell gap of 3.2 μm was formed. Vertical alignment and variations in alignment, such as drop marks, were examined with a polarizing microscope and were rated in the following four grades.

A: Uniform vertical alignment over the entire surface.
B: Acceptable alignment defects around the sealant.
C: Unacceptable alignment defects to the central portion.
D: Very poor alignment.

(Pretilt Angle Formation and Stability Evaluation Test)

A liquid crystal composition was applied at a cell gap of 3.5 μm to a polyimide alignment film that can induce vertical alignment, and then the polyimide alignment film was injected into a liquid crystal cell including a rubbed ITO-coated substrate by a vacuum injection method. The vertical alignment film was made of a material JALS2096 manufactured by JSR.

Subsequently, while a voltage of 10 V was applied at a frequency of 100 Hz to the liquid crystal cell into which the liquid crystal composition containing the polymerizable compound had been injected, the liquid crystal cell was irradiated with ultraviolet light from a high-pressure mercury lamp through a filter that can eliminate ultraviolet light of 325 nm or less. More specifically, the liquid crystal cell was irradiated with ultraviolet light at an illuminance of 100 mW/cm² measured at a center wavelength of 365 nm, and the integrated amount of light was 7 J/cm². These ultraviolet irradiation conditions are referred to as the irradiation conditions 1. The liquid crystal molecules in the liquid crystal cell have a pretilt angle under the irradiation conditions 1. The liquid crystal cell was then irradiated with ultraviolet light emitted from a fluorescent UV lamp at an illuminance of 3 mW/cm² measured at a center wavelength of 313 nm. The integrated amount of light was 10 J/cm². A liquid crystal display device was thus produced. These ultraviolet irradiation conditions are referred to as the irradiation conditions 2. The amount of residual polymerizable compound unreacted under the irradiation conditions 1 in the liquid crystal cell was reduced under the irradiation conditions 2.

After ultraviolet irradiation, a display defect due to a change in pretilt angle (image-sticking) was examined. First, the pretilt angle of the liquid crystal display device was measured as a pretilt angle (initial). In the present invention, the pretilt angle was measured by a rotating analyzer. While a voltage of 30 V was applied to the liquid crystal display device at a frequency of 100 Hz, the liquid crystal display device was irradiated with backlight for 24 hours. The pretilt angle was then measured as a pretilt angle (after test). The pretilt angle (after test) was subtracted from the pretilt angle (initial) to determine the amount of change in pretilt angle (=the absolute value of a change in pretilt angle) [degrees]. The pretilt angle was measured with OPTIPRO manufactured by Shintech Inc. An amount of change in pretilt angle closer to 0 [degrees] results in a lower probability of display defects due to a change in pretilt angle, and an amount of change in pretilt angle of 1.0 [degree] or more results in display defects due to a change in pretilt angle.

Example 6

Adjustment of Liquid Crystal Composition 0.6 parts by mass of the compound represented by the compound (P-1-27) synthesized in Example 2 was added to 100 parts by mass of the liquid crystal composition (LC-1) to prepare a liquid crystal composition (LC-1M2).

The liquid crystal composition (LC-1M2) was subjected to the evaluation test described in Example 5.

Example 7

Adjustment of Liquid Crystal Composition 0.6 parts by mass of the compound represented by the compound (P-1-28) synthesized in Example 3 was added to 100 parts by mass of the liquid crystal composition (LC-1) to prepare a liquid crystal composition (LC-1M3).

The liquid crystal composition (LC-1M3) was subjected to the evaluation test described in Example 5.

Example 8

Adjustment of Liquid Crystal Composition 0.6 parts by mass of the compound represented by the compound (P-1-29) synthesized in Example 4 was added to 100 parts by mass of the liquid crystal composition (LC-1) to prepare a liquid crystal composition (LC-1M4). The liquid crystal composition (LC-1M4) was subjected to the evaluation test described in Example 5.

Example 9

Adjustment of Liquid Crystal Composition 0.6 parts by mass of the compound represented by the compound (P-1-30) synthesized in Example 4 was added to 100 parts by mass of the liquid crystal composition (LC-1) to prepare a liquid crystal composition (LC-1M5).

The liquid crystal composition (LC-1M5) was subjected to the evaluation test described in Example 5.

Example 10

Adjustment of Liquid Crystal Composition

A composition LC-2 contained 100 parts by mass of a composition composed of the following compounds at the following mixing ratios and 0.3 parts by mass of the polymerizable compound (R-1-0).

[Chem. 144]

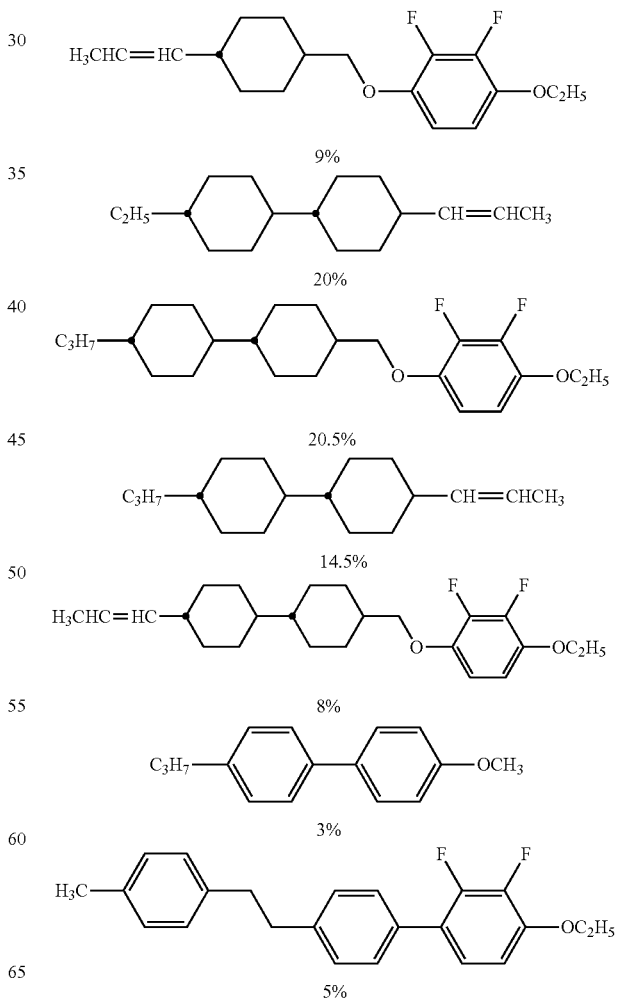

-continued

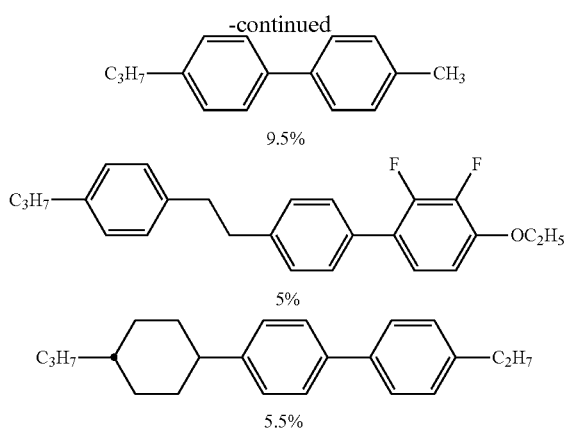

9.5%

5%

5.5%

LC-2 had a nematic phase-isotropic liquid phase transition temperature (TNI) of 75° C., a solid phase-nematic phase transition temperature (TCN) of −33° C., a refractive index anisotropy (Δn) of 0.11, a dielectric constant anisotropy (Δε) of −2.8, and a rotational viscosity (γ1) of 98 mPa·s.

0.6 parts by mass of the compound (P-1-27) synthesized in Example 2 was added to 100 parts by mass of (LC-2) to prepare a liquid crystal composition (LC-2M2).

The liquid crystal composition (LC-2M2) was subjected to the evaluation test described in Example 5.

Example 11

Adjustment of Liquid Crystal Composition 0.6 parts by mass of the compound represented by the compound (P-1-29) synthesized in Example 4 was added to 100 parts by mass of the liquid crystal composition (LC-2) to prepare a liquid crystal composition (LC-2M4).

The liquid crystal composition (LC-2M4) was subjected to the evaluation test described in Example 5.

Comparative Example 1

0.6 parts by mass of a compound represented by the following formula (18) was added to 100 parts by mass of the liquid crystal composition (LC-1) to prepare a liquid crystal composition (LC-1M6).

[Chem. 145]

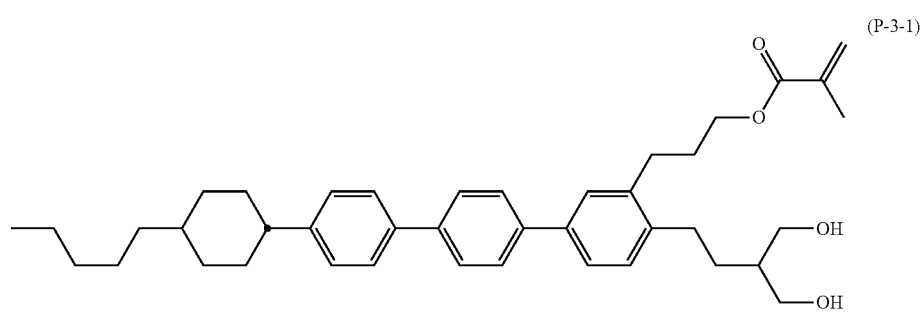

(P-3-1)

The liquid crystal composition (LC-1M6) was subjected to the evaluation test described in Example 5.

Comparative Example 2

0.6 parts by mass of a compound represented by the following formula (19) was added to 100 parts by mass of the liquid crystal composition (LC-1) to prepare a liquid crystal composition (LC-1M7).

[Chem. 146]

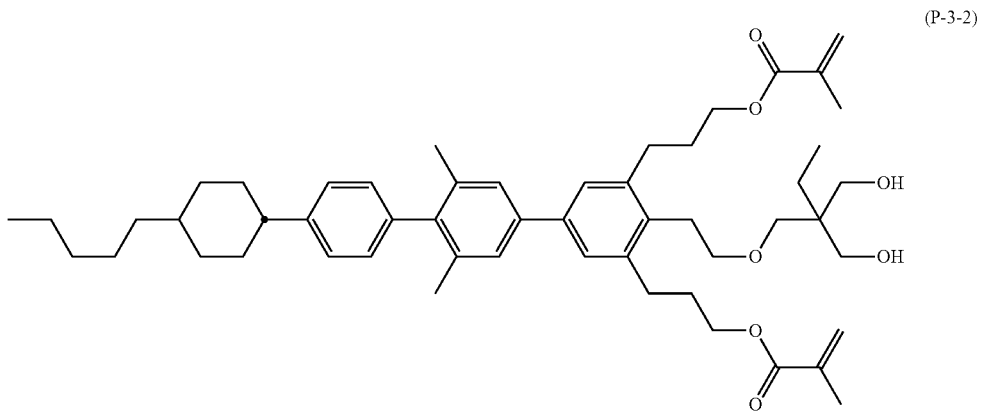

(P-3-2)

The liquid crystal composition (LC-1M7) was subjected to the evaluation test described in Example 5.

Comparative Example 3

0.6 parts by mass of a compound represented by the following formula (20) was added to 100 parts by mass of the liquid crystal composition (LC-1) to prepare a liquid crystal composition (LC-1M8), which, however, precipitated at room temperature and could not be evaluated.

[Chem. 147]

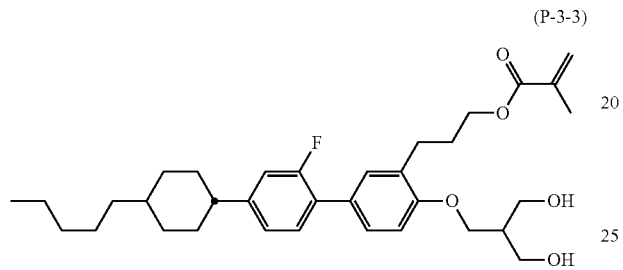

(P-3-3)

the liquid crystal composition (LC-1) to prepare a liquid crystal composition (LC-1M9).

[Chem. 148]

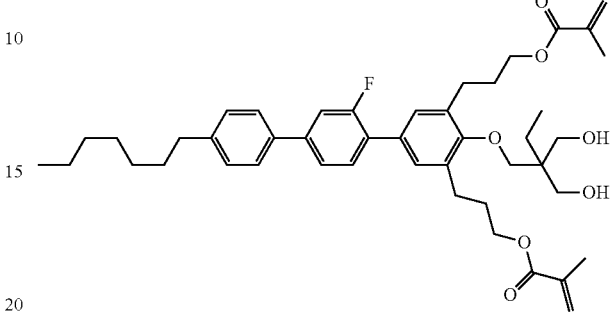

(P-3-4)

The liquid crystal composition (LC-1M9) was subjected to the evaluation test described in Example 5.

Comparative Example 5

0.6 parts by mass of the compound represented by the formula (21) was added to 100 parts by mass of the liquid crystal composition (LC-2) to prepare a liquid crystal composition (LC-2M9).

Comparative Example 4

0.6 parts by mass of a compound represented by the following formula (21) was added to 100 parts by mass of

TABLE 1

| Example | Liquid crystal composon | Additive compound | Additive amount (%) | Low-temperature storage stability | Vertical alignment | Pretilt angle formation (°) |
|---|---|---|---|---|---|---|
| Example 5 | LC-1 | P-1-26 | 0.6 | B | A | 3 |
| Example 6 | LC-1 | P-1-27 | 0.6 | A | A | 0.2 |
| Example 7 | LC-1 | P-1-28 | 0.6 | A | A | 0.4 |
| Example 8 | LC-1 | P-1-29 | 0.6 | A | A | 0.2 |
| Example 9 | LC-1 | P-1-230 | 0.6 | A | B | 0.3 |
| Example 10 | LC-2 | P-1-27 | 0.6 | A | A | 0.3 |
| Example 11 | LC-2 | P-1-29 | 0.6 | B | A | 0.5 |
| Comparative example 1 | LC-1 | P-3-1 | 0.6 | C | B | 1.4 |
| Comparative example 2 | LC-1 | P-3-2 | 0.6 | A | B | 0.8 |
| Comparative example 3 | LC-1 | P-3-3 | 0.6 | C | C | 1.6 |
| Comparative example 4 | LC-1 | P-3-4 | 0.6 | B | B | 0.8 |
| Comparative example 5 | LC-2 | P-3-4 | 0.6 | B | B | 0.9 |

The unit "%" with respect to compositions in the following examples and comparative examples refers to "% by mass". The following abbreviations are used to describe the liquid crystal compounds in the examples.

(Ring Structures)

[Chem. 149]

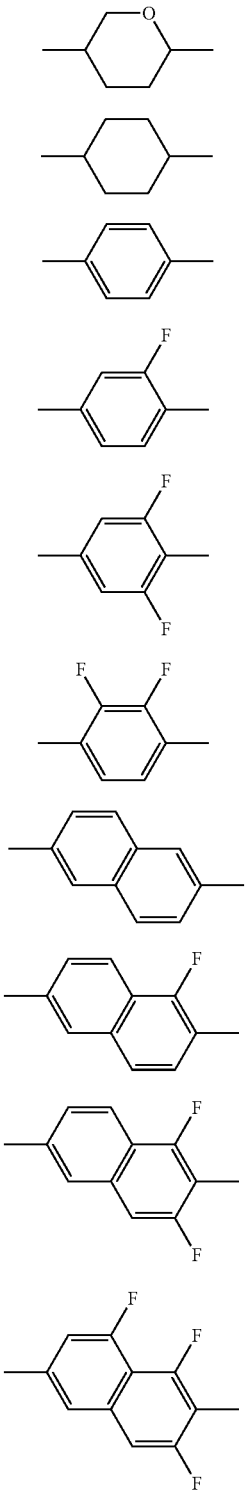

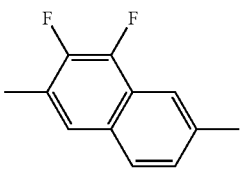 Np4

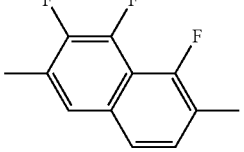 Np5

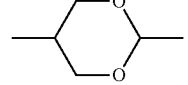 Dy

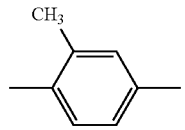 Pa2

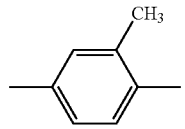 Pa3

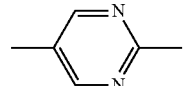 Ma (Side Chain Structures and Linking Structures)

TABLE 2

| Description in formula | Indicated substituent and linking group |
|---|---|
| 1- | $CH_3$— |
| 2- | $C_2H_5$— |
| 3- | $n-C_3H_7$— |
| 4- | $n-C_4H_9$— |
| 5- | $n-C_5H_{11}$— |
| V— | $CH_2=CH$— |
| V2— | $CH_2=CH-CH_2-CH_2$— |
| 1V2— | $CH_3-CH=CH-CH_2-CH_2$— |
| -1 | —$CH_3$ |
| -2 | —$C_2H_5$ |
| -3 | —$n-C_3H_7$ |
| —O2 | —$OC_2H_5$ |
| —V0 | —$CH=CH_2$ |
| —V1 | —$CH=CH-CH_3$ |
| —2V | —$CH_2-CH_2-CH=CH_2$ |
| —F | —F |
| —OCF3 | —$OCF_3$ |
| —CN | —CN |
| — | Single bond |
| —E— | —COO— |
| —CH2CH2— | —$CH_2CH_2$— |
| —CFFO— | —$CF_2O$— |
| —T— | —C≡C— |
| —O1— | —$OCH_2$— |
| —1O— | —$CH_2O$— |

The following characteristics were measured in the examples. Unless otherwise specified, the measurements followed methods specified in JEITA ED-2521B.

Tni: nematic phase-isotropic liquid phase transition temperature (° C.)
  Δn: refractive index anisotropy at 25° C.
  Δε: dielectric constant anisotropy at 25° C.
  K11: elastic constant K11 (pN) at 25° C.
  K33: elastic constant K33 (pN) at 25° C.
  γ1: rotational viscosity (mPa·s) at 25° C.

Low-temperature storage stability evaluation test: A liquid crystal composition was filtered, and dissolved air was removed in a vacuum. The liquid crystal composition was charged into a thoroughly washed container and was left standing at −20° C. for 240 hours. After that, the liquid crystal composition was visually inspected for precipitation and was rated in the following two grades.
  ○: No precipitation is observed.
  x: Precipitation is observed.

Vertical alignment evaluation test: A first substrate (a common electrode substrate) and a second substrate (a pixel electrode substrate) were produced. The first substrate had a transparent electrode layer compose of a transparent common electrode, had a color filter layer, and had no alignment film. The second substrate had a pixel electrode layer including a transparent pixel electrode to be driven by an active device and had no alignment film. A liquid crystal composition was dropped onto the first substrate and was held between the first substrate and the second substrate. A sealing material was cured to form a liquid crystal cell. Vertical alignment was examined with a polarizing microscope and were rated in the following four grades.
  ⊙: Uniform vertical alignment
  ○: Acceptable few alignment defects
  Δ: Unacceptable alignment defects
  x: Very poor alignment Pretilt angle stability evaluation test: While 10 V, 100 Hz rectangular alternating waves were applied to the liquid crystal cell used in the (vertical alignment evaluation test), the liquid crystal cell was irradiated for 200 seconds with UV light from a high-pressure mercury lamp at an illuminance of 100 m/cm2 measured at 365 nm. Subsequently, while 10 V, 100 Hz rectangular alternating waves were applied to the liquid crystal cell, an external force was physically applied to the cell. The white display stability was rated in the following four grades.
  ⊙: Uniform alignment
  ○: Acceptable few alignment defects
  Δ: Unacceptable alignment defects
  x: Very poor alignment Examples 11 to 28, Comparative Example 6

Liquid crystal compositions LC-3 to LC-20 in the following tables were prepared, and some physical properties of the liquid crystal compositions were measured. The tables show the physical properties.

TABLE 3

|  | LC-3 | LC-4 | LC-5 | LC-6 | LC-7 | LC-8 |
|---|---|---|---|---|---|---|
| 3-Cy-Cy-2 | 21 |  | 21 |  | 21.5 |  |
| 3-Cy-Cy-4 | 6.5 |  | 6.5 |  | 6.5 |  |
| 3-Cy-Cy-5 |  |  |  |  |  |  |
| 3-Cy-Cy-V |  | 32 |  | 31.5 |  | 32 |
| 3-Cy-Cy-V1 |  |  |  |  |  |  |
| 3-Cy-Ph-01 |  |  |  |  |  |  |
| 3-Ph—Ph-1 | 12 | 10 | 12 | 10 | 12 | 10 |
| 3-C—C—Ph-1 | 7.5 | 5 | 6 | 4 | 2 |  |
| 3-C—C—Ph-3 |  |  |  |  |  |  |

TABLE 3-continued

|  | LC-3 | LC-4 | LC-5 | LC-6 | LC-7 | LC-8 |
|---|---|---|---|---|---|---|
| 3-C—Ph—Ph-2 |  |  |  |  |  |  |
| 3-Ph—Ph5-02 |  |  |  |  |  |  |
| 3-Cy-Ph5-02 | 10 | 10 | 10 | 10 | 10 | 10 |
| 5-Cy-Ph5-02 | 5 | 5 | 5 | 5 | 5 | 5 |
| 3-Cy-1O—Ph5-01 |  |  |  |  |  |  |
| 3-Cy-1O—Ph5-02 |  |  |  |  |  |  |
| 3-Cy-Cy-Ph5-02 |  |  | 7.5 | 7.5 | 10 | 10 |
| 3-Cy-Cy-Ph5-04 |  |  |  |  | 9 | 9 |
| 4-Cy-Cy-Ph5-02 |  |  |  |  |  |  |
| 2-Cy-Cy-1O—Ph5-02 |  |  |  |  |  |  |
| 3-Cy-Cy-1O—Ph5-02 | 14 | 14 | 8 | 8 |  |  |
| 2-Cy-Ph—Ph5-02 | 7 | 7 | 7 | 7 | 7 | 7 |
| 3-Cy-Ph—Ph5-02 | 8 | 8 | 8 | 8 | 8 | 8 |
| 3-Cy-Ph—Ph5-03 |  |  |  |  |  |  |
| 3-Cy-Ph—Ph5-04 | 9 | 9 | 9 | 9 | 9 | 9 |
| $T_{NI}$ [° C.] | 75.3 | 74.3 | 74.9 | 75.5 | 75.4 | 74.7 |
| Δn | 0.103 | 0.103 | 0.103 | 0.103 | 0.104 | 0.103 |
| γ₁ [mPa · s] | 88 | 77 | 90 | 79 | 91 | 80 |
| Δε | −2.8 | −2.8 | −2.8 | −2.9 | −2.8 | −2.8 |
| K11 [pN] | 14.4 | 13.4 | 14.4 | 13.4 | 14.5 | 13.3 |
| K33 [pN] | 13.5 | 14.0 | 13.3 | 13.8 | 13.0 | 13.6 |
| γ1 / K33 | 6.5 | 5.5 | 6.8 | 5.7 | 7.0 | 5.9 |

TABLE 4

|  | LC-9 | LC-10 | LC-11 | LC-12 | LC-13 | LC-14 |
|---|---|---|---|---|---|---|
| 3-Cy-Cy-2 | 21.5 |  | 21 |  | 12 |  |
| 3-Cy-Cy-4 | 8.5 |  | 9.5 |  | 8 |  |
| 3-Cy-Cy-5 |  |  |  |  | 7 |  |
| 3-Cy-Cy-V |  | 31 |  | 32 |  | 31.5 |
| 3-Cy-Cy-V1 |  |  |  |  |  |  |
| 3-Cy-Ph-01 | 12 |  |  |  | 4.5 |  |
| 3-Ph—Ph-1 |  | 13 | 2.5 | 2 |  |  |
| 3-C—C—Ph-1 |  |  | 8 | 10 | 5 | 5 |
| 3-C—C—Ph-3 |  |  |  |  |  |  |
| 3-C—Ph—Ph-2 |  |  | 3 |  | 2.5 | 2.5 |
| 3-Ph—Ph5-02 | 15 | 15 | 10 | 10 |  |  |
| 3-Cy-Ph5-02 |  |  | 10 | 10 | 8 | 8 |
| 5-Cy-Ph5-02 |  |  | 5 | 5 |  |  |
| 3-Cy-1O—Ph5-01 |  |  |  |  |  |  |
| 3-Cy-1O—Ph5-02 |  |  |  |  |  |  |
| 3-Cy-Cy-Ph5-02 | 10 | 10 | 7 | 7 | 12 | 12 |
| 3-Cy-Cy-Ph5-04 | 9 | 12 |  |  | 12 | 12 |
| 4-Cy-Cy-Ph5-02 |  |  |  |  | 10 | 10 |
| 2-Cy-Cy-1O—Ph5-02 |  |  |  |  |  |  |
| 3-Cy-Cy-1O—Ph5-02 |  |  |  |  |  |  |
| 2-Cy-Ph—Ph5-02 | 7 | 7 | 7 | 7 | 5 | 5 |
| 3-Cy-Ph—Ph5-02 | 8 | 8 | 8 | 8 | 5 | 5 |
| 3-Cy-Ph—Ph5-03 |  |  |  |  | 5 | 5 |
| 3-Cy-Ph—Ph5-04 | 9 | 4 | 9 | 9 | 4 | 4 |
| $T_{NI}$ [° C.] | 76.2 | 73.8 | 75.3 | 74.2 | 110.8 | 108.8 |
| Δn | 0.103 | 0.102 | 0.103 | 0.103 | 0.098 | 0.098 |
| γ₁ [mPa · s] | 92 | 78 | 87 | 76 | 153 | 122 |
| Δε | −3.0 | −3.0 | −2.8 | −2.8 | −3.2 | −3.1 |
| K11 [pN] | 13.7 | 13.0 | 13.8 | 13.3 | 19.5 | 17.4 |
| K33 [pN] | 13.3 | 13.4 | 12.7 | 13.6 | 17.5 | 18.1 |
| γ1 / K33 | 6.9 | 5.8 | 6.9 | 5.6 | 8.7 | 6.7 |

TABLE 5

|  | LC-15 | LC-16 | LC-17 | LC-18 | LC-19 | LC-20 |
|---|---|---|---|---|---|---|
| 3-Cy-Cy-2 | 12 |  | 21.5 |  | 12 |  |
| 3-Cy-Cy-4 | 8 |  | 9.5 |  | 8 |  |
| 3-Cy-Cy-5 | 7 |  |  |  | 7 |  |
| 3-Cy-Cy-V |  | 29 |  | 32 |  | 32 |
| 3-Cy-Cy-V1 |  |  |  |  |  |  |
| 3-Cy-Ph-O1 | 3 |  |  |  | 8 | 3 |
| 3-Ph—Ph-1 |  |  | 13.5 | 11 |  |  |
| 3-C—C—Ph-1 | 7 | 7 | 6 | 8 | 7 | 7 |
| 3-C—C—Ph-3 | 4 | 4 |  |  | 4 | 4 |
| 3-C—Ph—Ph-2 |  |  |  |  | 5 | 5 |
| 3-Ph—Ph5-02 | 10 | 10 |  |  |  |  |
| 3-Cy-Ph5-02 |  |  |  |  |  |  |
| 5-Cy-Ph5-02 |  |  |  | 2 |  |  |
| 3-Cy-1O—Ph5-01 |  |  | 11.5 | 11.5 |  |  |
| 3-Cy-1O—Ph5-02 |  |  |  |  |  |  |
| 3-Cy-Cy-Ph5-02 | 15 | 15 |  | 11.5 |  |  |
| 3-Cy-Cy-Ph5-04 | 15 | 15 |  |  |  |  |
| 4-Cy-Cy-Ph5-02 | 10 | 13 |  |  |  |  |
| 2-Cy-Cy-1O—Ph5-02 |  |  |  |  | 15 | 15 |
| 3-Cy-Cy-1O—Ph5-02 |  |  | 14 |  | 15 | 15 |
| 2-Cy-Ph—Ph5-02 | 5 | 5 | 7 | 7 | 5 | 5 |
| 3-Cy-Ph—Ph5-02 | 4 | 2 | 8 | 8 | 5 | 5 |
| 3-Cy-Ph—Ph5-03 |  |  |  |  | 5 | 5 |
| 3-Cy-Ph—Ph5-04 |  |  | 9 | 9 | 4 | 4 |
| $T_{NI}$ [° C.] | 111.2 | 110.2 | 74.7 | 74.7 | 110.8 | 109.1 |
| Δn | 0.098 | 0.098 | 0.103 | 0.104 | 0.097 | 0.098 |
| $γ_1$ [mPa · s] | 154 | 135 | 84 | 73 | 142 | 125 |
| Δε | −3.1 | −3.1 | −2.8 | −2.9 | −3.1 | −3.0 |
| K11 [pN] | 20.6 | 18.3 | 14.9 | 14.0 | 20.0 | 17.9 |
| K33 [pN] | 18.3 | 18.7 | 13.5 | 14.1 | 18.4 | 18.5 |
| γ1/K33 | 8.4 | 7.2 | 62 | 5.2 | 7.7 | 6.8 |

TABLE 6

|  | Example 11 | Example 12 | Example 13 | Example 14 | Example 15 | Example 16 |
|---|---|---|---|---|---|---|
| Base composition | LC-3 | LC-4 | LC-5 | LC-6 | LC-7 | LC-8 |
| Additive compound 1 | R-1-0 | R-1-0 | R-1-0 | R-1-0 | R-1-0 | R-1-0 |
| Amount of additive compound 1/parts by mass | 0.3 | 0.3 | 0.3 | 0.3 | 0.3 | 0.3 |
| Additive compound 2 | P-1-27 | P-1-27 | P-1-27 | P-1-27 | P-1-27 | P-1-27 |
| Amount of additive compound 2/parts by mass | 0.6 | 0.6 | 0.6 | 0.6 | 0.6 | 0.6 |
| Additive compound 3 |  |  |  | P-1-8 | P-1-8 | P-1-8 |
| Amount of additive compound 3/parts by mass |  |  |  | 0.2 | 0.3 | 0.4 |
| Low-temperature storage stability | ○ | ○ | ○ | ○ | ○ | ○ |
| Vertical alignment | ⊙ | ⊙ | ⊙ | ⊙ | ⊙ | ⊙ |
| Pretilt angle stability | ○ | ○ | ○ | ○ | ○ | ○ |

TABLE 7

|  | Example 17 | Comparative example 18 | Example 19 | Example 20 | Example 21 | Example 22 |
|---|---|---|---|---|---|---|
| Base composition | LC-9 | LC-10 | LC-11 | LC-12 | LC-13 | LC-14 |
| Additive compound 1 | R-1-0 | R-1-0 | R-1-0 | R-1-0 | R-1-0 | R-1-0 |
| Amount of additive compound 1/parts by mass | 0.3 | 0.3 | 0.3 | 0.3 | 0.3 | 0.3 |
| Additive compound 2 | P-1-28 | P-1-28 | P-1-28 | P-1-28 | P-1-29 | P-1-29 |
| Amount of additive compound 2/parts by mass | 0.6 | 0.6 | 0.6 | 0.6 | 0.6 | 0.6 |

TABLE 7-continued

|  | Example 17 | Comparative example 18 | Example 19 | Example 20 | Example 21 | Example 22 |
|---|---|---|---|---|---|---|
| Low-temperature storage stability | ○ | ○ | ○ | ○ | ○ | ○ |
| Vertical alignment | ⊙ | ⊙ | ⊙ | ⊙ | ⊙ | ⊙ |
| Pretilt angle stability | ○ | ○ | ○ | ○ | ○ | ○ |

TABLE 8

|  | Example 23 | Comparative example 24 | Example 25 | Example 26 | Example 27 | Example 28 |
|---|---|---|---|---|---|---|
| Base composition | LC-15 | LC-16 | LC-17 | LC-18 | LC-19 | LC-20 |
| Additive compound 1 | R-1-0 | R-1-0 | R-1-0 | R-1-0 | R-1-0 | R-1-0 |
| Amount of additive compound 1/parts by mass | 0.3 | 0.3 | 0.3 | 0.3 | 0.3 | 0.3 |
| Additive compound 2 | P-1-29 | P-1-29 | P-1-30 | P-1-30 | P-1-30 | P-1-30 |
| Amount of additive compound 2/parts by mass | 0.6 | 0.6 | 0.6 | 0.6 | 0.6 | 0.6 |
| Low-temperature storage stability | ○ | ○ | ○ | ○ | ○ | ○ |
| Vertical alignment | ⊙ | ⊙ | ⊙ | ⊙ | ⊙ | ⊙ |
| Pretilt angle stability | ○ | ○ | ○ | ○ | ○ | ○ |

TABLE 9

|  | Comparative example 6 | Comparative example 7 |
|---|---|---|
| Base composition | LC-3 | LC-3 |
| Additive compound 1 | P-3-1 | P-3-2 |
| Amount of additive compound 1/parts by mass | 0.3 | 0.3 |
| Additive compound 2 | P-3-1 | P-3-2 |
| Amount of additive compound 2/parts by mass | 0.6 | 0.6 |
| Low-temperature storage stability | x | x |
| Vertical alignment | ○ | ○ |
| Pretilt angle stability | Δ | Δ |

A polymerizable compound in an amount listed in the tables was added to 100 parts by mass of each liquid crystal composition to prepare a liquid crystal composition containing the polymerizable compound. The low-temperature storage stability, vertical alignment, and pretilt angle stability were examined. The results showed that polymerizable liquid crystal compositions according to the present invention were superior in these characteristics.

The invention claimed is:

1. A compound represented by a general formula (i):

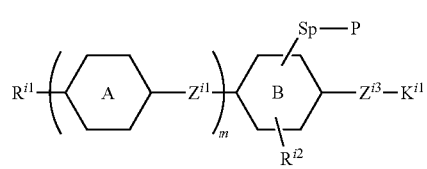

(i)

wherein
$R^{i1}$ denotes a hydrogen atom, an alkyl group having 1 to 30 carbon atoms, or a halogenated alkyl group having 1 to 30 carbon atoms, —$CH_2$— in the alkyl or halogenated alkyl group is optionally replaced with —CH=CH—, —C≡—, —O—, —NH—, —COO—, —OCO—, or —OCOO—, but —O— is not adjacent to another —O—, $R^{i2}$ denotes a linear alkyl group having 2 to 10 carbon atoms, a branched alkyl group having 3 to 10 carbon atoms, a linear halogenated alkyl group having 2 to 10 carbon atoms, or a branched halogenated alkyl group having 3 to 10 carbon atoms, wherein —$CH_2$— in the alkyl or halogenated alkyl group is optionally replaced with —CH=CH—, —O—, —COO—, or —OCO—, but —O— is not adjacent to another —O—, a ring A denotes a divalent aromatic group, a divalent alicyclic group, a divalent heterocyclic compound group, a divalent fused ring, or a divalent fused polycyclic ring, a hydrogen atom in these ring structures is optionally replaced with $L^{i1}$, $L^{i1}$ denotes a halogen atom, a cyano group, a nitro group, P-Sp-, a monovalent organic group having a group represented by a general formula $K^{i1}$, a linear alkyl group having 1 to 10 carbon atoms, a branched alkyl group having 3 to 10 carbon atoms, a linear halogenated alkyl group having 1 to 10 carbon atoms, or a branched halogenated alkyl group having 3 to 10 carbon atoms, wherein —$CH_2$— in the alkyl or halogenated alkyl group is optionally replaced with —CH=CH—, —C≡C—, —O—, —NH—, —COO—, —OCO—, or —OCOO—, but —O— is not adjacent to another —O—, a ring B denotes a formula (B-1),

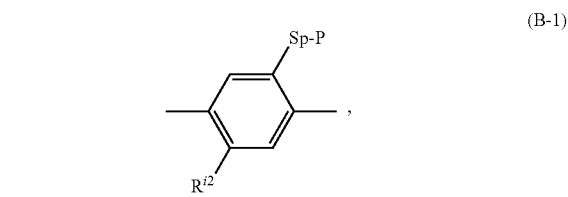

(B-1)

wherein a hydrogen atom in the ring B is optionally replaced with $L^{i2}$, $L^{i2}$ denotes a halogen atom, a monovalent organic group having a group represented by the general formula $K^{i1}$, a linear alkyl group having 1 to 10 carbon atoms, wherein —$CH_2$— in the alkyl or halogenated alkyl group is optionally replaced with —CH═CH—, —C≡—, —O—, —COO—, or —OCO—, but —O— is not adjacent to another —O—, $Z^{i1}$ denotes a single bond, —O—, —CH═CH—, —CF═CF—, —C≡C—, —COO—, —OCO—, —OCOO—, —$CF_2$O—, —$OCF_2$—, —CH═CHCOO—, —OCOCH═CH—, —CH═C($CH_3$)COO—, —OCOC($CH_3$)═CH—, —$CH_2$—CH($CH_3$)COO—, —OCOCH($CH_3$)—$CH_2$—, —$OCH_2CH_2$O—, or an alkylene group having 2 to 10 carbon atoms, and one —$CH_2$— or two or more nonadjacent —$CH_2$— groups in the alkylene group are optionally replaced with —O—, —COO—, or —OCO—, $Z^{i3}$ denotes a single bond, —O—, —CH═CH—, —COO—, —OCO—, —OCOO—, —CH═CHCOO—, —OCOCH═CH—, —CH═C($CH_3$)COO—, —OCOC($CH_3$)═CH—, —$CH_2$—CH($CH_3$)COO—, —OCOCH($CH_3$)—$CH_2$—, or a linear alkylene group having 2 to 20 carbon atoms, a branched alkylene group having 3 to 20 carbon atoms, one —$CH_2$— or two or more nonadjacent —$CH_2$— groups in the alkylene group are optionally replaced with —O—, —COO—, or —OCO—, $K^{i1}$ denotes a group represented by one of general formulae (K-1) to (K-6),

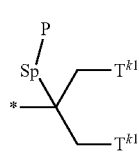
(K-1)

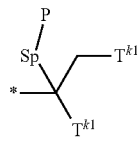
(K-2)

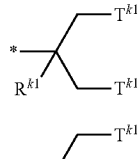
(K-3)

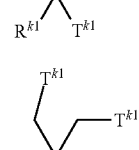
(K-4)

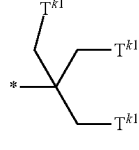
(K-5)

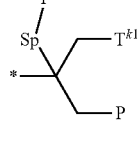
(K-6)

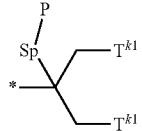
(K-1)

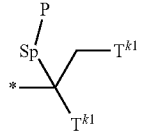
(K-2)

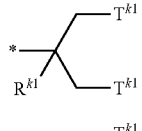
(K-3)

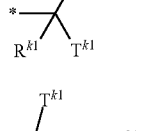
(K-4)

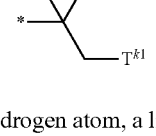
(K-5)

$R^{K1}$ denotes a hydrogen atom, a linear alkyl group having 1 to 6 carbon atoms, or a alkyl group having 3 to 6 carbon atoms, and $T^{K1}$ independently denotes a group represented by one of general formulae (T-1) to (T-6),

——OH (T-1)

——COOH (T-2)

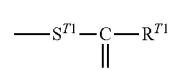
(T-3)

——SH (T-4)

——$NH_2$ (T-5)

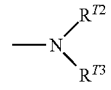
(T-6)

$S^{T1}$ denotes a single bond, a linear alkylene group having 1 to 15 carbon atoms, a branched alkylene group having 3 to 15 carbon atoms, a linear alkenylene group having 2 to 18 carbon atoms, or a branched alkenylene group having 3 to 18 carbon atoms, wherein —$CH_2$— in the alkylene or alkelene group is optionally replaced with —O—, —COO—, —C(═O)—, —C(═$CH_2$)—, or —OCO— such that oxygen atoms are not directly adjacent to each other, $R^{T1}$ denotes an alkyl group having 1 to 5 carbon atoms, —$CH_2$— in the alkyl group is optionally replaced with —O—, —COO—, —C(═O)—, —C(═$CH_2$)—, or —OCO— such that oxygen atoms are not directly adjacent to each other, and $R^{T2}$ and $R^{T3}$ independently denote a hydrogen atom or an alkyl group having 1 to 5 carbon atoms, and P denotes a polymerizable group, Sp denotes a spacer group or a single bond, m denotes an integer in the range of 1 to 4, a plurality of As, if present, may be the same or different, a plurality of $Z^{i1}$s, if present, may be the same or different, a plurality of Ps, if present, may be the same or different, and a plurality of Sps, if present, may be the same or different.

2. The compound according to claim 1, wherein A in the general formula (i) denotes a ring structure selected from a 1,4-phenylene group, a 1,4-cyclohexylene group, an anthracene-2,6-diyl group, a phenanthrene-2,7-diyl group, a pyridine-2,5-diyl group, a pyrimidine-2,5-diyl group, a naphthalene-2,6-diyl group, an indan-2,5-diyl group, a 1,2,3,4-tetrahydronaphthalene-2,6-diyl group, and a 1,3-dioxane-2,5-diyl group, and the ring structure is unsubstituted or denotes a group optionally substituted with an alkyl group having 1 to 12 carbon atoms, a halogenated alkyl group having 1 to 12 carbon atoms, an alkoxy group having 1 to 12 carbon atoms, a halogenated alkoxy group having 1 to 12 carbon atoms, a halogen atom, a cyano group, a nitro group, or P-Sp-.

3. The compound according to claim 1, wherein P in the general formula (i) denotes a substituent selected from a group represented by the following general formulae (P-1) to (P-14).

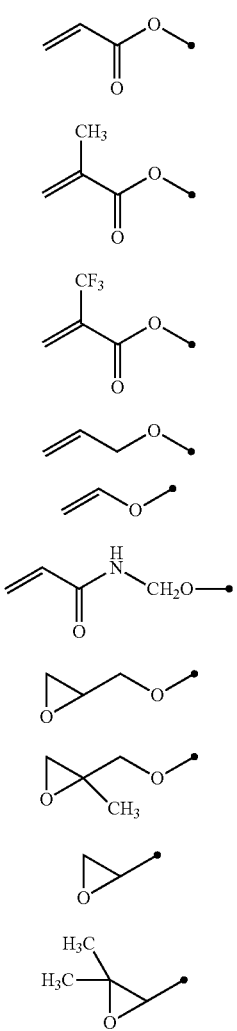

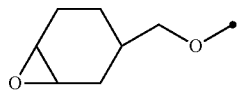

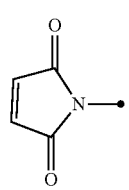

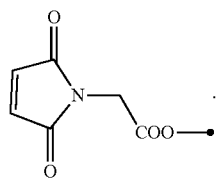

4. The compound according to claim 1, wherein $K^{i1}$ in the general formula (i) is represented by the general formula (K-1) or (K-2).

5. A liquid crystal composition comprising: a compound represented by the general formula (i) according to claim 1; a polymerizable compound different from the compound represented by the general formula (i); and a nonpolymerizable liquid crystal compound.

6. The liquid crystal composition according to claim 5, wherein the polymerizable compound is one or two or more compounds represented by a general formula (P):

$$(R^{p1}-Sp^{p1})_{mp1}(M^{p1})_{mp2}(L^{p1}-M^{p2})_{mp3}(L^{p2}-M^{p3})_{mp4}(Z^{p1})_{mp5} \quad (P)$$

wherein
$Z^{p1}$ denotes a fluorine atom, a cyano group, a hydrogen atom, an alkyl group having 1 to 15 carbon atoms in which a hydrogen atom is optionally replaced with a halogen atom, an alkoxy group having 1 to 15 carbon atoms in which a hydrogen atom is optionally replaced with a halogen atom, an alkenyl group having 2 to 15 carbon atoms in which a hydrogen atom is optionally replaced with a halogen atom, an alkenyloxy group having 2 to 15 carbon atoms in which a hydrogen atom is optionally replaced with a halogen atom, or -Sp$^{p2}$-R$^{p2}$, $R^{p1}$ and $R^{p2}$ denote one of the following formulae (R-I) to (R-VIII),

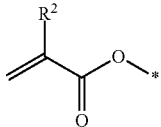

-continued (R-II)

(R-III)

(R-IV)

(R-V)

(R-VI)

(R-VII)

(R-VIII)

wherein
* is bonded to $Sp^{p1}$,
$R^2$ to $R^6$ independently denote a hydrogen atom, an alkyl group having 1 to 5 carbon atoms, or a halogenated alkyl group having 1 to 5 carbon atoms,
W denotes a single bond, —O—, or a methylene group,
T denotes a single bond or —COO—, and
p, t, and q independently denote 0, 1, or 2,
$Sp^{p1}$ and $Sp^{p2}$ denote a spacer group,
$L^{p1}$ and $L^{p2}$ independently denote a single bond, —O—, —S—, —CH$_2$—, —OCH$_2$—, —CH$_2$O—, —CO—, —C$_2$H$_4$—, —COO—, —OCO—, —OCOOCH$_2$—, —CH$_2$OCOO—, —OCH$_2$CH$_2$O—, —CO—NR$^a$—, —NR$^a$—CO—, —SCH$_2$—, —CH$_2$S—, —CH=CR$^a$—COO—, —CH=CR$^a$—OCO—, —COO—CR$^a$=CH—, —OCO—CR$^a$=CH—, —COO—CR$^a$=CH—COO—, —COO—CR$^a$=CH—OCO—, —OCO—CR$^a$=CH—COO—, —OCO—CR$^a$=CH—OCO—, —(CH$_2$)$_z$—C(=O)—O—, —(CH$_2$)$_z$—O—(C=O)—, —O—(C=O)—(CH$_2$)$_z$—, —(C=O)—O—(CH$_2$)$_z$—, —CH$_2$(CH$_3$)C—C(=O)—O—, —CH$_2$(CH$_3$)C—O—(C=O)—, —O—(C=O)—C(CH$_3$)CH$_2$, —(C=O)—O—C(CH$_3$)—CH$_2$, —CH=CH—, —CF=CF—, —CF=CH—, —CH=CF—, —CF$_2$—, —CF$_2$O—, —OCF$_2$—, —CF$_2$CH$_2$—, —CH$_2$CF$_2$—, —CF$_2$CF$_2$—, or —C≡C— (wherein $R^a$ independently denotes a hydrogen atom or an alkyl group having 1 to 4 carbon atoms, and z denotes an integer in the range of 1 to 4,
$M^{p2}$ denotes a 1,4-phenylene group, a 1,4-cyclohexylene group, an anthracene-2,6-diyl group, a phenanthrene-2,7-diyl group, a pyridine-2,5-diyl group, a pyrimidine-2,5-diyl group, a naphthalene-2,6-diyl group, an indan-2,5-diyl group, a 1,2,3,4-tetrahydronaphthalene-2,6-diyl group, a 1,3-dioxane-2,5-diyl group, or a single bond, $M^{p2}$ is unsubstituted or optionally substituted with an alkyl group having 1 to 12 carbon atoms, a halogenated alkyl group having 1 to 12 carbon atoms, an alkoxy group having 1 to 12 carbon atoms, a halogenated alkoxy group having 1 to 12 carbon atoms, a halogen atom, a cyano group, a nitro group, or —R$^{p1}$, $M^{p1}$ denotes one of the following formulae (i-11) to (ix-11), (i-11)

(iv-11)

(vii-11)

(ii-11)

(v-11)

(viii-11)

(iii-11)

(vi-11)

-continued (ix-11)

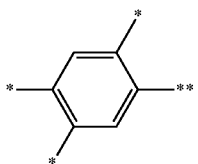

wherein * is bonded to $Sp^{p1}$, and ** is bonded to $L^{p1}$, $L^{p2}$, or $Z^{p1}$, $M^{p3}$ denotes one of the following formulae (i-13) to (ix-13), (i-13)

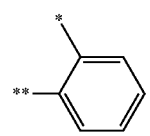

(iv-13)

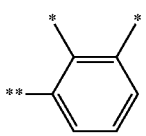

(vii-13)

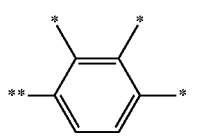

(ii-13)

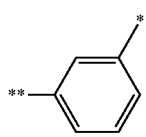

(v-13)

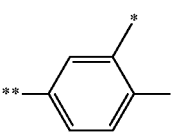

(viii-13)

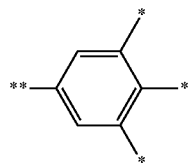

(iii-13)

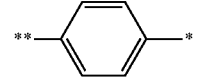

(vi-13)

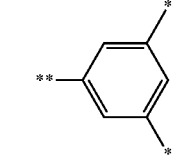

(ix-13)

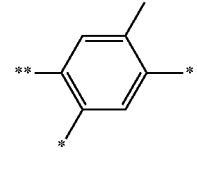

wherein * is bonded to $Z^{p1}$, and ** is bonded to $L^{p2}$, $m^{p2}$ to $m^{p4}$ independently denote 0, 1, 2, or 3, $m^{p1}$ and $m^{p5}$ independently denote 1, 2, or 3, and a plurality of $Z^{p1}$s, if present, may be the same or different, a plurality of $R^{p1}$s, if present, may be the same or different, a plurality of $R^{p2}$s, if present, may be the same or different, a plurality of $Sp^{p1}$s, if present, may be the same or different, a plurality of $Sp^{p2}$s, if present, may be the same or different, a plurality of $L^{p1}$s, if present, may be the same or different, and a plurality of $M^{p2}$s, if present, may be the same or different.

7. A liquid crystal display device in which at least one of two substrates with the liquid crystal compositions according to claim 5 has no alignment film.

* * * * *